US007662565B2

(12) United States Patent
Albino et al.

(10) Patent No.: US 7,662,565 B2

(45) Date of Patent: Feb. 16, 2010

(54) APPROACHES TO IDENTIFY LESS HARMFUL TOBACCO AND TOBACCO PRODUCTS

(75) Inventors: Anthony P. Albino, New York, NY (US); Ellen D. Jorgensen, South Salem, NY (US); Frank Traganos, Katonah, NY (US); Zbigniew Darzynkiewicz, Chappaque, NY (US); Wendy Jin, Chapel Hill, NC (US)

(73) Assignee: Vector Tobacco, Inc., Morrisville, NC (US)

( * ) Notice: Subject to any disclaimer, the term of this patent is extended or adjusted under 35 U.S.C. 154(b) by 55 days.

(21) Appl. No.: 11/596,088

(22) PCT Filed: May 11, 2005

(86) PCT No.: PCT/US2005/016941

§ 371 (c)(1), (2), (4) Date: Apr. 4, 2008

(87) PCT Pub. No.: WO2005/113821

PCT Pub. Date: Dec. 1, 2005

(65) Prior Publication Data

US 2008/0227088 A1 Sep. 18, 2008

Related U.S. Application Data

(60) Provisional application No. 60/570,175, filed on May 12, 2004.

(30) Foreign Application Priority Data

Mar. 29, 2005 (US) ............... PCT/US2005/010733

(51) Int. Cl.
*C12Q 1/68* (2006.01)
*C12Q 1/02* (2006.01)

(52) U.S. Cl. .......................... 435/6; 435/7.21; 435/7.23

(58) Field of Classification Search ....................... None
See application file for complete search history.

(56) References Cited

U.S. PATENT DOCUMENTS

| | | | |
|---|---|---|---|
| 3,586,005 | A | 6/1971 | Lippman et al. |
| 3,812,865 | A | 5/1974 | Anderson |
| 6,362,317 | B1 | 3/2002 | Bonner et al. |
| 6,470,894 | B2 | 10/2002 | Hersh et al. |
| 2002/0132989 | A1 | 9/2002 | Bonner et al. |
| 2003/0108952 | A1 | 6/2003 | Darzynkiewicz et al. |

FOREIGN PATENT DOCUMENTS

| | | | |
|---|---|---|---|
| WO | WO 01/04158 | A1 | 1/2001 |
| WO | WO 03/100417 | A1 | 12/2003 |

OTHER PUBLICATIONS

Wang et al, Journal of Environmental Pathology, Toxicology and Oncology 19 (1 & 2), 13 (2000).*

International Search Report issued on the corresponding International Application No. PCT/US2005/016941, dated Nov. 1, 2005.

Mai, H. et al., "A functional role for nicotine in Bcl2 phosphorylation and suppression of apoptosis," *Journal of Biological Chemistry*, Jan. 17, 2003, Vo. 278, No. 3, pp. 1886-1891.

Wang, Q. et al., "DNA damage and activation of c-ras in human embryo lung cells exposed to chrysotile and cigarette smoking solution," *Chemical Abstracts*, 2002, vol. 133.

Hibi et al., Gene expression in tobacco low-niccotine mutants, The Plant Cell, 1994, 6:723-735.

Office Action for U.S. Appl. No. 11/285,537 dated Feb. 14, 2008.

Banath, Judit P. et al., "Expression of Phosphorylated Histone H2AX as a Surrogate of Cell Killing by Drugs That Create DNA Double-Strand Breaks" Cancer Research, Aug. 1, 2003, pp. 4347-4350, vol. 63.

Brown, Buddy et al., "Comparative studies of DNA adduct formation in mice following dermal application of smoke condensates from cigarettes that burn or primarily heat tobacco" Mutation Research, 1998, pp. 21-30, vol. 414.

Demidenko, Zoya N. et al., "From Cytometry to Cell Cycle—A Protrait of Zbigniew Darzynkiewicz" Cell Cycle, 2003, pp. e94-e97, vol. 3, Issue 5.

Huang, Xuan et al., "DNA Damage Induced by DNA Topoisomerase I- and Topoisomerase II-Inhibitors Detected by Histone H2AXphosphorylation in Relation to the Cell Cycle Phase and Apoptosis" Cell Cycle, 2003, pp. 614-619, vol. 2, Issue 6.

Huang, Xuan et al., "Assessment of Histone H2AX Phosphorylation Induced by DNA Topoisomerase I and II Inhibitors Topotecan and Mitoxantrone and by the DNA Cross-Linking Agent Cisplatin" Cytometry Part A, 2004, pp. 99-110, vol. 58A.

Ingebrethsen, Bradley J. "Aerosol Studies of Cigarette Smoke" Recent Adv. Tob. Sci., 1986, pp. 54-142, vol. 12.

Massey, Eian et al., "Micronucleus induction in V79 cells after direct exposure to whole cigarette smoke" Mutagenesis, 1998, pp. 145-149, vol. 13, No. 2.

Meckley, Daniel et al., "A responsive, sensitive, and reproducible dermal tumor promotion assay for the comparative evaluation of cigarette smoke condensates" Regulatory Toxicology and Pharmacology, 2004, pp. 135-149, vol. 39.

(Continued)

*Primary Examiner*—James Martinell
(74) *Attorney, Agent, or Firm*—Knobbe Martens Olson & Bear LLP

(57) ABSTRACT

Aspects of the invention concern methods for detecting, identifying and evaluating tobacco and tobacco products to determine the potential that these compositions have to contribute to a tobacco-related disease. It is based, at least in part; on the discovery that exposure of pulmonary cells to smoke or smoke condensate obtained from tobacco or tobacco products induces double stranded breaks in cellular DNA, which were efficiently detected using assays that measure the presence, absence, or amount of phosphorylation of the histone, H2AX.

74 Claims, 28 Drawing Sheets

OTHER PUBLICATIONS

Meckley, Daniel R. et al., "Comparative study of smoke condensates from 1R4F cigarettes that burn tobacco versus ECLIPSE cigarettes that primarily heat tobacco in the SENCAR mouse dermal tumor promotion assay" Food and Chemical Toxicology, 2004, pp. 851-863, vol. 42.

Nakayama, Tsutomu et al., "Cigarette smoke induces DNA single-strand break in human cells" Nature, Apr. 1985, pp. 462-464, vol. 314.

Phillips, Jeremy et al., "Exposure of Bronchial Epithelial Cells to Whole Cigarette Smoke: Assessment of Cellular Responses" ATLA, 2005, pp. 239-248, vol. 33.

Putnam, K.P. et al., "Evaluation of eight in vitro assays for assessing the cytotoxicity of cigarette smoke condensate" Toxicology in Vitro, 2002, pp. 599-607, vol. 16.

Singh, Narendra P. et al., "A Simple Technique for Quantitation of Low Levels of DNA Damage in Individual Cells" Experimental Cell Research, 1988, pp. 184-191, vol. 175.

* cited by examiner

Summary of A549 cloning efficiency
5 days post-smoke exposure
(corrected to mock)
IM16 vs Marlboro Cloning efficiency of mock exposed cells is 48.2% (average of 12 experiments)
(#) = number of experiments in group Cloning efficiency of mock exposed A549 cells was 16.3%.

SE-130: Effect of 25mM N-acetyl-L-cysteine (NAC) on cloning efficiency of A549 cells 5 days post-smoke exposure 5 x $10^4$ cells seeded/chamber Cloning efficiency of mock exposed A549 cells was 23.7%.

QPTASE (full-length) RNAi CONSTRUCT

QPTase (fragment) RNAi CONSTRUCT

PMTase (fragment) RNAi CONSTRUCT

A622 (fragment) RNAi CONSTRUCT

QPTase/A622 (fragments) DOUBLE KNOCK-OUT RNAi CONSTRUCT

SMT2/A622 (fragments) DOUBLE KNOCK-OUT RNAi CONSTRUCT

SEQUENCE LISTING

```
<160> NUMBER OF SEQ ID NOS: 36

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 1

Asp Glu Val Asp
 1


<210> SEQ ID NO 2
<211> LENGTH: 1056
<212> TYPE: DNA
<213> ORGANISM: Nicotiana tabacum

<400> SEQUENCE: 2

atgtttagag ctattccttt cactgctaca gtgcatcctt atgcaattac agctccaagg     60

ttggtggtga aaatgtcagc aatagccacc aagaatacaa gagtggagtc attagaggtg    120

aaaccaccag cacacccaac ttatgattta aaggaagtta tgaaacttgc actctctgaa    180

gatgctggga atttaggaga tgtgacttgt aaggcgacaa ttcctcttga tatggaatcc    240

gatgctcatt ttctagcaaa ggaagacggg atcatagcag gaattgcact tgctgagatg    300

atattcgcgg aagttgatcc ttcattaaag gtggagtggt atgtaaatga tggcgataaa    360

gttcataaag gcttgaaatt tggcaaagta caaggaaacg cttacaacat tgttatagct    420

gagagggttg ttctcaattt tatgcaaaga atgagtggaa tagctacact aactaaggaa    480

atggcagatg ctgcacaccc tgcttacatg ttggagacta ggaaaactgc tcctggatta    540

cgtttggtgg ataaatgggc ggtattgatc ggtggggggga agaatcacag aatgggctta    600

tttgatatgg taatgataaa agacaatcac atatctgctg ctggaggtgt cggcaaagct    660

ctaaaatctg tggatcagta tttggagcaa aataaacttc aaataggggt tgaggttgaa    720

accaggacaa ttgaagaagt acgtgaggtt ctagactatg catctcaaac aaagacttcg    780

ttgactagga taatgctgga caatatggtt gttccattat ctaacggaga tattgatgta    840

tccatgctta aggaggctgt agaattgatc aatgggaggt ttgatacgga ggcttcagga    900

aatgttaccc ttgaaacagt acacaagatt ggacaaactg gtgttaccta catttctagt    960

ggtgccctga cgcattccgt gaaagcactt gacatttccc tgaagatcga tacagagctc   1020

gcccttgaag ttggaaggcg tacaaaacga gcatga                             1056


<210> SEQ ID NO 3
<211> LENGTH: 360
<212> TYPE: DNA
<213> ORGANISM: Nicotiana tabacum

<400> SEQUENCE: 3
```

-continued

```
atgtttagag ctattccttt cactgctaca gtgcatcctt atgcaattac agctccaagg      60

ttggtggtga aaatgtcagc aatagccacc aagaatacaa gagtggagtc attagaggtg     120

aaaccaccag cacacccaac ttatgattta aaggaagtta tgaaacttgc actctctgaa     180

gatgctggga atttaggaga tgtgacttgt aaggcgacaa ttcctcttga tatggaatcc     240

gatgctcatt ttctagcaaa ggaagacggg atcatagcag gaattgcact tgctgagatg     300

atattcgcgg aagttgatcc ttcattaaag gtggagtggt atgtaaatga tggcgataaa     360
```

<210> SEQ ID NO 4
<211> LENGTH: 241
<212> TYPE: DNA
<213> ORGANISM: Nicotiana tabacum

<400> SEQUENCE: 4

```
cattttacca tctttcgcca gaagtatgat cgagtcttaa tcaagtgaat aatgaacact      60

ggtagtacaa tcattggacc aagatcgagt cttaatcaag tgaataaata agtgaaatgc     120

gacgtattgt aggagaattc tgcagtaatt atcataattt ccaattcaca atcattgtaa     180

aattctttct ctgtggtgtt tcgtacttta atataaattt tcctgctgaa gttttgaatc     240

g                                                                     241
```

<210> SEQ ID NO 5
<211> LENGTH: 628
<212> TYPE: DNA
<213> ORGANISM: Nicotiana tabacum

<400> SEQUENCE: 5

```
tgatcaagtg aacatcatca aagcaattaa agaagctgga aatatcaaga gatttcttcc      60

ttcagaattt ggatttgatg tggatcatgc tcgtgcaatt gaaccagctg catcactctt     120

cgctctaaag gtaagaatca ggaggatgat agaggcagaa ggaattccat acacatatgt     180

aatctgcaat tggtttgcag atttcttctt gcccaacttg gggcagttag aggccaaaac     240

ccctcctaga gacaaagttg tcatttttgg cgatggaaat cccaaagcaa tatatgtgaa     300

ggaagaagac atagcgacat acactatcga agcagtagat gatccacgga cattgaataa     360

gactcttcac atgagaccac ctgccaatat tctatccttc aacgagatag tgtccttgtg     420

ggaggacaaa attgggaaga ccctcgagaa gttatatcta tcagaggaag atattctcca     480

gattgtacaa gagggacctc tgccattaag gactaatttg gccatatgcc attcagtttt     540

tgttaatgga gattctgcaa actttgaggt tcagcctcct acaggtgtcg aagccactga     600

gctatatcca aaagtgaaat acacaacc                                        628
```

<210> SEQ ID NO 6
<211> LENGTH: 439
<212> TYPE: DNA
<213> ORGANISM: Nicotiana tabacum

<400> SEQUENCE: 6

```
ccacattggg gcttctgtta ctcaatgctt cataaggttt ctcgtagctt tgctctcgtc      60

attcaacaac ttcccgtcga gcttcgtgac gccgtgtgca ttttctattt ggttcttcga     120

gcacttgaca ctgttgagga tgataccagc attcccaccg atgttaaagt acctattctg     180

atctcttttc atcagcatgt ttatgatcgt gaatggcatt tttcatgtgg tacaaaagag     240

tacaaggttc tcatggacca gttccatcat gtttcaactg cttttctgga gcttaggaaa     300

cattatcagc aggcaattga ggatattacc atgaggatgg gtgcaggaat ggcaaaattc     360
```

-continued

```
atatgcaagg aggtggaaac aactgatgat tatgacgaat attgtcacta tgtagctggg    420

cttgttgggc taggattgt                                                 439
```

<210> SEQ ID NO 7
<211> LENGTH: 850
<212> TYPE: DNA
<213> ORGANISM: Nicotiana tabacum

<400> SEQUENCE: 7

```
gaggctgtaa atgatggcaa agacctccat atttcagtaa ctatgccttc tattgaggtt     60

ggcacagttg gtggtggaac tcaacttgca tcacagtcag cttgcttgaa cttattagga    120

gtgaaaggtg caaacaggga ggcagcaggg tcaaatgcaa ggctcttggc cacaatagta    180

gcaggttctg ttcttgctgg tgagttatct ctcatgtctg ctatctcagc agggcagctg    240

gttaagagtc acatgaaata caatagatct agcaaagatg ttactaagat ttcctcttag    300

taaggaaaaa gacaaattta ttatcccaac atcgtgtaca tcaccatcct ttatggacca    360

tcattattaa agaaatggat tacaataaaa gtaggaataa aattttccaa ttagggagag    420

caataagtaa agggtagacc aaaaagttga aaaagtgtaa ggcattagtc atgtggagaa    480

agatcaagaa gaaaaagaca agcaaatcaa gggtggacgt ggatctgtat gtagtgttgt    540

attctttcta tgaaggcatg tgaggaggta gggtcgtatt tttttctgag ttcgtgtaaa    600

aaaacctgca aatatttggt gaagatctac gaaaggtgtt aggtgggatg gtgaccagtg    660

gggttaactt gtaattcaac atttggttaa tttcattcat gcgccaagga agataacccc    720

ttttttttta aataatcttt tctgttgtac tgtctttcgt ttgtttgtta attgtgacta    780

gattgtaatt tagagagaaa tggcatctca aactctttat gtttgctcag aaagtttgct    840

tttgtatatg                                                           850
```

<210> SEQ ID NO 8
<211> LENGTH: 780
<212> TYPE: DNA
<213> ORGANISM: Nicotiana tabacum

<400> SEQUENCE: 8

```
agaagctacc tgccatgcac cagatccatt gggatgctat aaagagattt accgggtgct     60

gaagcctggt caatgtttcg ctgtgtatga gtggtgcatg accgattctt acaaccccaa    120

taacgaagag cacaacagga tcaaggccga aattgagctc ggaaatggcc tccctgaggt    180

tagattgaca acacagtgcc tcgaagcagc caaacaagct ggttttgaag ttgtatggga    240

caaggatctg gctgatgact cacctgttcc atggtacttg cctttggata cgagtcactt    300

ctcgctcagt agcttccgcc taacagcagt tggcagactt ttcaccagaa atctggtttc    360

ggcgcttgaa tacgtgggac ttgctcctaa aggtagtcaa agggttcaag ctttcttaga    420

gaaagctgca gaaggtcttg tcggtggtgc caagaaaggg attttcacac caatgtactt    480

cttcgtggtt cgcaagccca tttcagactc tcagtaatat ggagtttagt cacttagctt    540

tttgctttag ctagcaaatc tgtaagattc ttcgcacaga actttacaca ttgaatatga    600

ccgccctaat taaggtgact acagtttttg gagggcgttg tgggtggagg gtttcttttt    660

ctgtgttgct tgtctggcac aatttgattt catgtcttgc tatttttgcc attgatgtcc    720

ttgttctaag atatatacct attgacaagc tcataaaggt gggcatttgc taatatatgg    780
```

<210> SEQ ID NO 9

-continued

<211> LENGTH: 885
<212> TYPE: DNA
<213> ORGANISM: Nicotiana tabacum

<400> SEQUENCE: 9

```
aagaatatca cgttcttcgt tggcccagaa gtgtcggccc atttctttaa ggccccagaa     60
accgatctca gtcaacaaga ggtttatcag ttcaatgtgc ctacttttgg ccctggtgtg    120
gtttttgacg ttgattatac tatcagacaa gagcaattta ggttctttac tgaatctttg    180
agggtaaata aattgaaggg atatgtggat cagatggtca tggaagctga ggagtacttc    240
tcaaaatggg gtgatagtgg tgaagtggac ttgaagtatg aactggagca tcttatcata    300
ctgacagcta gtagatgtct gttgggagaa gaggttcgca ataaactctt tgaggatgtc    360
tctgctctct tccatgacct ggacaatggg atgcttccta tcagtgtaat ctttccctac    420
cttcccattc cagcccatcg ccgtcgtgac aatgcccgca agaagctcgc ggagatcttt    480
gcaaacatca tagattctag aaaacgtaca ggcaaggcgg agagcgatat gttacaatgc    540
ttcattgact ccaagtacaa agatgggcgg gcaacgacag agtctgagat cacaggtctt    600
ctgattgctg ctcttttcgc tggcaacac accagttcca tcacctccac ttgggcaggg    660
gcataccttc tctgcaacaa caagtacatg tctgccgtcg tagatgaaca gaagaatctg    720
atgaagaaac atgggaataa ggtcgatcat gacatccttt ccgagatgga agtcctctat    780
agatgcataa aggaagccct gagactccat cctccactga taatgcttct acgtagttcg    840
catagtgatt tcactgttaa aaccagggaa ggaaaagagt atgat                   885
```

<210> SEQ ID NO 10
<211> LENGTH: 1701
<212> TYPE: DNA
<213> ORGANISM: Arabidopsis thaliana

<400> SEQUENCE: 10

```
atggttgtgt ttgggaatgt ttctgcggcg aatttgcctt atcaaaacgg gtttttggag     60
gcactttcat ctggaggttg tgaactaatg ggacatagct ttagggttcc cacttctcaa    120
gcgcttaaga caagaacaag gaggaggagt actgctggtc ctttgcaggt agtttgtgtg    180
gatattccaa ggccagagct agagaacact gtcaatttct tggaagctgc tagtttatct    240
gcatccttcc gtagtgctcc tcgtcctgct aagcctttga aagttgtaat tgctggtgct    300
ggattggctg gattgtcaac tgcaaagtac ctggctgatg caggccacaa acctctgttg    360
cttgaagcaa gagatgttct tggtggaaag atagctgcat ggaaggatga agatggggac    420
tggtatgaga ctggtttaca tattttcttc ggtgcttatc cgaatgtgca gaatttattt    480
ggagaacttg ggatcaatga tcggttgcag tggaaggaac actccatgat ttttgctatg    540
ccaagtaaac ctggagaatt tagtagattt gacttcccag atgtcctacc agcaccctta    600
aatggtattt gggctatttt gcggaacaac gagatgctga catggccaga gaaaataaag    660
tttgctattg gacttttgcc agccatggtc ggcggtcagg cttatgttga ggcccaagat    720
ggtttatcag tcaaagaatg gatggaaaag cagggagtac ctgagcgcgt gaccgacgag    780
gtgtttattg ccatgtcaaa ggcgctaaac tttataaacc ctgatgaact gtcaatgcaa    840
tgcattttga tagctttgaa ccggtttctt caggaaaaac atggttccaa gatggcattc    900
ttggatggta atcctccgga aaggctttgt atgccagtag tggatcatat tcgatcacta    960
ggtggggaag tgcaacttaa ttctaggata aagaaaattg agctcaatga cgatggcacg   1020
gttaagagtt tcttactcac taatggaagc actgtcgaag gagacgctta tgtgtttgcc   1080
```

-continued gctccagtcg atatcctgaa gctcctttta ccagatccct ggaaagaaat accgtacttc 1140
aagaaattgg ataaattagt tggagtacca gttattaatg ttcatatatg gtttgatcga 1200
aaactgaaga acacatatga tcacctactc tttagcagaa gtaaccttct gagcgtgtat 1260
gccgacatgt ccttaacttg taaggaatat tacgatccta accggtcaat gctggagcta 1320
gtatttgcac cagcagagga atggatatca cggactgatt ctgacatcat agatgcaaca 1380
atgaaagaac ttgagaaact cttccctgat gaaatctcag ctgaccaaag caaagctaaa 1440
attctgaagt accatgtcgt taagactcca agatctgggt acaagaccat cccaaactgt 1500
gaaccatgtc gtcctctaca aagatcacct attgaaggat tctacttagc tggagattac 1560
acaaaacaga agtacttagc ttccatggaa ggcgctgtcc tctctggcaa attctgctct 1620
cagtctattg ttcaggatta cgagctactg gctgcgtctg gaccaagaaa gttgtcggag 1680
gcaacagtat catcatcatg a 1701

<210> SEQ ID NO 11
<211> LENGTH: 1701
<212> TYPE: DNA
<213> ORGANISM: Arabidopsis thaliana

<400> SEQUENCE: 11
atggttgtgt ttgggaatgt ttctgcggcg aatttgcctt atcaaaacgg gtttttggag 60
gcactttcat ctggaggttg tgaactaatg ggacatagct ttagggttcc cacttctcaa 120
gcgcttaaga caagaacaag gaggaggagt actgctggtc ctttgcaggt agtttgtgtg 180
gatattccaa ggccagagct agagaacact gtcaatttct tggaagctgc tagtttatct 240
gcatccttcc gtagtgctcc tcgtcctgct aagcctttga aagttgtaat tgctggtgct 300
ggattggctg gattgtcaac tgcaaagtac ctggctgatg caggccacaa acctctgttg 360
cttgaagcaa gagatgttct tggtggaaag atagctgcat ggaaggatga agatggggac 420
tggtatgaga ctggtttaca tattttcttc ggtgcttatc cgaatgtgca gaatttattt 480
ggagaacttg ggatcaatga tcggttgcag tggaaggaac actccatgat ttttgctatg 540
ccaagtaaac ctggagaatt tagtagattt gacttcccag atgtcctacc agcaccctta 600
aatggtattt gggctatttt gcggaacaac gagatgctga catggccaga gaaaataaag 660
tttgctattg gacttttgcc agccatggtc ggcggtcagg cttatgttga ggcccaagat 720
ggtttatcag tcaaagaatg gatggaaaag cagggagtac ctgagcgcgt gaccgacgag 780
gtgtttattg ccatgtcaaa ggcgctaaac tttataaacc ctgatgaact gtcaatgcaa 840
tgcattttga tagctttgaa cccgtttctt caggaaaaac atggttccaa gatggcattc 900
ttggatggta atcctccgga aaggctttgt atgccagtag tggatcatat tcgatcacta 960
ggtggggaag tgcaacttaa ttctaggata aagaaaattg agctcaatga cgatggcacg 1020
gttaagagtt tcttactcac taatggaagc actgtcgaag gagacgctta tgtgtttgcc 1080
gctccagtcg atatcctgaa gctcctttta ccagatccct ggaaagaaat accgtacttc 1140
aagaaattgg ataaattagt tggagtacca gttattaatg ttcatatatg gtttgatcga 1200
aaactgaaga acacatatga tcacctactc tttagcagaa gtaaccttct gagcgtgtat 1260
gccgacatgt ccttaacttg taaggaatat tacgatccta accggtcaat gctggagcta 1320
gtatttgcac cagcagagga atggatatca cggactgatt ctgacatcat agatgcaaca 1380
atgaaagaac ttgagaaact cttccctgat gaaatctcag ctgaccaaag caaagctaaa 1440

-continued

```
attctgaagt accatgtcgt taagactcca agatctgtgt acaagaccat cccaaactgt   1500

gaaccatgtc gtcctctaca aagatcacct attgaaggat tctacttagc tggagattac   1560

acaaaacaga agtacttagc ttccatggaa ggcgctgtcc tctctggcaa attctgctct   1620

cagtctattg ttcaggatta cgagctactg gctgcgtctg gaccaagaaa gttgtcggag   1680

gcaacagtat catcatcatg a                                             1701
```

<210> SEQ ID NO 12
<211> LENGTH: 1701
<212> TYPE: DNA
<213> ORGANISM: Arabidopsis thaliana

<400> SEQUENCE: 12

```
atggttgtgt ttgggaatgt ttctgcggcg aatttgcctt atcaaaacgg gtttttggag     60

gcactttcat ctggaggttg tgaactaatg ggacatagct ttagggttcc cacttctcaa    120

gcgcttaaga caagaacaag gaggaggagt actgctggtc ctttgcaggt agtttgtgtg    180

gatattccaa ggccagagct agagaacact gtcaatttct tggaagctgc tagtttatct    240

gcatccttcc gtagtgctcc tcgtcctgct aagcctttga aagttgtaat tgctggtgct    300

ggattggctg gattgtcaac tgcaaagtac ctggctgatg caggccacaa acctctgttg    360

cttgaagcaa gagatgttct tggtggaaag atagctgcat ggaaggatga agatggggac    420

tggtatgaga ctggtttaca tattttcttc ggtgcttatc cgaatgtgca gaatttattt    480

ggagaacttg ggatcaatga tcggttgcag tggaaggaac actccatgat tttgctatg    540

ccaagtaaac ctggagaatt tagtagattt gacttcccag atgtcctacc agcaccctta    600

aatggtattt gggctatttt gcggaacaac gagatgctga catggccaga gaaaataaag    660

tttgctattg gacttttgcc agccatggtc ggcggtcagg cttatgttga ggcccaagat    720

ggtttatcag tcaaagaatg gatggaaaag cagggagtac ctgagcgcgt gaccgacgag    780

gtgtttattg ccatgtcaaa ggcgctaaac tttataaacc ctgatgaact gtcaatgcaa    840

tgcattttga tagctttgaa ccggtttctt caggaaaaac atggttccaa gatggcattc    900

ttggatggta atcctccgga aaggctttgt atgccagtag tggatcatat tcgatcacta    960

ggtggggaag tgcaacttaa ttctaggata aagaaaattg agctcaatga cgatggcacg   1020

gttaagagtt tcttactcac taatggaagc actgtcgaag gagacgctta tgtgtttgcc   1080

gctccagtcg atatcctgaa gctcctttta ccagatccct ggaaagaaat accgtacttc   1140

aagaaattgg ataaattagt tggagtacca gttattaatg ttcatatatg gtttgatcga   1200

aaactgaaga acacatatga tcacccactc tttagcagaa gtaaccttct gagcgtgtat   1260

gccgacatgt ccttaacttg taaggaatat tacgatccta accggtcaat gctggagcta   1320

gtatttgcac cagcagagga atggatatca cggactgatt ctgacatcat agatgcaaca   1380

atgaaagaac ttgagaaact cttccctgat gaaatctcag ctgaccaaag caaagctaaa   1440

attctgaagt accatgtcgt taagactcca agatctgtgt acaagaccat cccaaactgt   1500

gaaccatgtc gtcctctaca aagatcacct attgaaggat tctacttagc tggagattac   1560

acaaaacaga agtacttagc ttccatggaa ggcgctgtcc tctctggcaa attctgctct   1620

cagtctattg ttcaggatta cgagctactg gctgcgtctg gaccaagaaa gttgtcggag   1680

gcaacagtat catcatcatg a                                             1701
```

<210> SEQ ID NO 13
<211> LENGTH: 1061

-continued

<212> TYPE: DNA
<213> ORGANISM: Nicotiana tabacum

<400> SEQUENCE: 13
aatatgaaag gaaacatatt caatacattg tagtttgcta ctcataatcg ctagaatact 60
ttgtgccttg ctaataaaga tacttgaaat agcttagttt aaatataaat agcataatag 120
attttaggaa ttagtatttt gagtttaatt acttattgac ttgtaacagt ttttataatt 180
ccaaggccca tgaaaaattt aatgctttat tagttttaaa cttactatat aaatttttca 240
tatgtaaaat ttaatcggta tagttcgata ttttttcaat ttatttttat aaaataaaaa 300
acttacccta attatcggta cagttataga tttatataaa aatctacggt tcttcagaag 360
aaacctaaaa atcggttcgg tgcggacggt tcgatcggtt tagtcgattt tcaaatattc 420
attgacactc ctagttgttg ttataggtaa aaagcagtta cagagaggta aaatataact 480
taaaaaatca gttctaagga aaaattgact tttatagtaa atgactgtta tataaggatg 540
ttgttacaga gaggtatgag tgtagttggt aaattatgtt cttgacggtg tatgtcacat 600
attatttatt aaaactagaa aaaacagcgt caaaactagc aaaaatccaa cggacaaaaa 660
aatcggctga atttgatttg gttccaacat ttaaaaaagt ttcagtgaga aagaatcggt 720
gactgttgat gatataaaca aagggcacat tggtcaataa ccataaaaaa ttatatgaca 780
gctacagttg gtagcatgtg ctcagctatt gaacaaatct aaagaaggta catctgtaac 840
cggaacacca cttaaatgac taaattaccc tcatcagaaa gcagatggag tgctacaaat 900
aacacactat tcaacaacca taaataaaac gtgttcagct actaaaacaa atataaataa 960
atctatgttt gtaagcactc cagccatgtt aatggagtgc tattgcctgt taactctcac 1020
ttataaaata gtagtagaaa aaatatgaac caaaacacaa c 1061

<210> SEQ ID NO 14
<211> LENGTH: 711
<212> TYPE: DNA
<213> ORGANISM: Nicotiana tabacum

<400> SEQUENCE: 14
gaattcaatg gagaaggaaa atatttccag tgtaaacaca agtgaatgaa gagaagccaa 60
aataatctct atcattcaag ccttaggtgg agattaaaaa aattatttac tttcttatca 120
aagtaatagg tgatcaacag ctttcgtaaa acgtcattag gagaatatta taatctcttt 180
tatgctgaag aacccacata aggaagatca taaaatacat gactttcaga tgacttcttg 240
gagctttatt tttaaagagt ggctagctgg tcagcaaaga ggtgctcgtc agatatcata 300
aaattttact attatttgtt ttaagaggga gatggggcac acatgcttgt gacaaaagta 360
agaggaagaa aggagacaga agaggaaata gatttggggg gggggggggg ggtttcacaa 420
tcaaagaaaa tttttaaaat ggagagagaa atgagcacac acatatacta acaaaatttt 480
actaataatt gcaccgagac aaacttatat tttagttcca aaatgtcagt ctaaccctgc 540
acgttgtaat gaatttttaa ctattatatt atatcgagtt gcgccctcca ctcctcggtg 600
tccaaattgt atttaaatgc atagatgttt attgggagtg tacagcaagc tttcggaaaa 660
tacaaaccat aatactttct cttcttcaat ttgtttagtt taattttgaa a 711

<210> SEQ ID NO 15
<211> LENGTH: 1278
<212> TYPE: DNA
<213> ORGANISM: Nicotiana tabacum -continued

<400> SEQUENCE: 15

```
tgcgtcaaat ggataaacaa aaaaatagca taagttagtt ttgttactcg agagttatgt     60
attataaggt atagggaaat gactcaaaca taccactgaa cttaacgaaa cgacgcatat    120
atatactact taacttaacg aaaaaggggt gagagtggat gggtgctggt aaataatgaa    180
gggtttatat aacgtcacgt gtcaaaattc gatagtagta gtttcgttag ttgtaatagc    240
atatatggcc caaagttata atatagataa tatgtttatg tccaactatt aacgagtgac    300
atagacagtt cattttgtga agttcaatga catatttgag ccctttccct tttattatct    360
ccttttattt gttctaataa aagaatggca tttattatgt acatagacaa ataactattt    420
tctttggaat ataatttgtt tatatatttt aaaatcatgt ctcaatttag tttgttttgt    480
gcatatttca actattcaat tttgtccata tatttattac cttcccccat ttacaagcat    540
tgaaccgctt tgctcaccaa aacttatgca cattgcaaaa atatcatgta aaggttttat    600
gtatgctgta attaaggtct gaactcatcg tgattttatt tttaggcttc attgaccact    660
accaaactct ttgatgctac attttctaat tatattggag ttcgattata tccgaattcg    720
cgttgcgtag ggcccattcg agggaaaaca ctccctatca aggatttttt catacccaga    780
gctcgaactc aagacatctg gttaagggaa gaacagtctc atccactgca ccatatcctt    840
ttgtggtcaa caagtaaatt ttatgtagaa ccaaaaacta tactcgaatt gataaaataa    900
atggtgtaaa atattgtttt ctttcttaca ttttggacag taaatatgta ggacaataat    960
aattagcgtg gggtcttaag aaaattagca tagatttcca gaaattccaa atcaaccggc   1020
agttccaggt ttgaaaacta caactcattc cgacggttca aacttcaaac catgcttgct   1080
gactcggctt cttctttctt tttcaccaag acagagcagt agtcacgtga cacccctcac   1140
gtgcctcccc cctttatatt tcagactgca accctacact ttcgctacat tcactaccat   1200
attcttttca ctaagcaatt ttctctccta cttttcttta aacccctttt ttctccccta   1260
agccatggca tctagatc                                                 1278
```

<210> SEQ ID NO 16
<211> LENGTH: 1079
<212> TYPE: DNA
<213> ORGANISM: Nicotiana tabacum

<400> SEQUENCE: 16

```
atcttattgt ataaatatcc ataaacacat catgaaagac actttctttc acggtctgaa     60
ttaattatga tacaattcta atagaaaacg aattaaatta cgttgaattg tatgaaatct    120
aattgaacaa gccaaccacg acgacgacta acgttgcctg gattgactcg gtttaagtta    180
accactaaaa aaacggagct gtcatgtaac acgcggatcg agcaggtcac agtcatgaag    240
ccatcaaagc aaaagaacta atccaagggc tgagatgatt aattagttta aaaattagtt    300
aacacgaggg aaaaggctgt ctgacagcca ggtcacgtta tctttacctg tggtcgaaat    360
gattcgtgtc tgtcgatttt aattattttt ttgaaaggcc gaaaataaag ttgtaagaga    420
taaacccgcc tatataaatt catatatttt ctctccgctt tgaattgtct cgttgtcctc    480
ctcactttca tcggccgttt ttgaatctcc ggcgacttga cagagaagaa caaggaagaa    540
gactaagaga gaaagtaaga gataatccag gagattcatt ctccgttttg aatcttcctc    600
aatctcatct tcttccgctc tttctttcca aggtaatagg aactttctgg atctacttta    660
tttgctggat ctcgatcttg ttttctcaat ttccttgaga tctggaattc gtttaatttg    720
gatctgtgaa cctccactaa atcttttggt tttactagaa tcgatctaag ttgaccgatc    780
```

-continued

```
agttagctcg attatagcta ccagaatttg gcttgacctt gatggagaga tccatgttca    840

tgttacctgg gaaatgattt gtatatgtga attgaaatct gaactgttga agttagattg    900

aatctgaaca ctgtcaatgt tagattgaat ctgaacactg tttaagttag atgaagtttg    960

tgtatagatt cttcgaaact ttaggatttg tagtgtcgta cgttgaacag aaagctattt   1020

ctgattcaat cagggtttat ttgactgtat tgaactcttt ttgtgtgttt gcagctcat    1079
```

```
<210> SEQ ID NO 17
<211> LENGTH: 1943
<212> TYPE: DNA
<213> ORGANISM: Nicotiana tabacum

<400> SEQUENCE: 17

aagcttttta tttagctttt tcctccctat ttcaatatat aatggctcaa tttttgtcag     60

atagcaataa aaccatacaa gaaaataaaa caaatcacaa aatacaaaaa gaggttatat    120

ctccatgtat gcaatttcat tatatgcata taagcatctt acgtataaaa aaaaagaggg    180

aatcatggac gtgtctttct aatccaagta gggtcaactt tatagggtcg gtgtatgtgt    240

agtttaatcg aaaaagaatt ccatcattag gtaatttaca attagatcct taaattatac    300

aaatatataa gggtataaaa gttgatcaat atttcaggga tattttagtc gttcaacatt    360

tagtataaat tattcgtact tttataataa taaatagata gataaacata gatatagata    420

taaatataga tagataaatg ggggatttgc atctataccc actttttggg tcacgtttta    480

atttgtgccc gctttgcaaa aaaaattgca agcgtacaca ctttttcgcg taacttcagc    540

atacggggct aaagtagcaa agacagtcac gcaaaacttc agcatacttc agtctttgct    600

acttcagccc cgtatgctga agttatgcga aaagcgggta tgcttgtaat ttttttgcaa    660

agcgagcata agttaaaacg tgacacaaaa agcgggtata gatacaaatg gccctttttt    720

ttctagccaa attttattca tttttttgga atacttttc actttatttt aaaattagtg    780

tttggttata aatttttaaa tacaacttgg agttggactc caaagtcttt acatacttat    840

ttttagtttt attaccctat ttttttaac atgagatatt tacttttaca gatctaaaaa    900

tgatattttc ttagttttaa cactataaat agccatgaag gcccatttcc tccctttgca    960

aaaagtatac ccaaacgcaa ctccgtcttc acctccaact ccaacttcat aatttcaatt   1020

aaagtgaaaa ttattttaag agaccatttg gacatgataa ttttttcact ttttccgaac   1080

tttttttac tttttttcaa atcagtgttt ggccataaaa ttttcatttt tcacttgaag   1140

ttgaattttt gaatttttcg agaattcgaa aaaccccaga aagctgtttt tcaaaatttt   1200

cactcggatc ctcacaaaac ttccaaaata acccaaaatt atattcatgt ccaacacaac   1260

tctaattttc aaataccatt ttcacttgaa aaagaaattc accttttttt tttttttgaa   1320

ctttacaatt cttatgtcca aacgccccct tcgaatctac ggccaacgtt tattaagtaa   1380

ggaaagaaaa atggctataa taattatatc cctttttgaag taaatataat tctaccaaat   1440

taattaatat gcttaaaaac aataaaaata atcaaaattg ctagagagga caaccaatta   1500

gccgaagcat tgtcaagatt gagcagggcg cagaatgaag aaagtagttt tttatctttt   1560

gatgccctac gccttttgta ttaaaatact atatacaaga tttgaaaaag acgagttcca   1620

ttcaaaacag ttcccttgtc ccgaaatgtt cattgatgaa gtaatatgca cttttaaaat   1680

tatttttttc cagtttatcc taaaaaaaat attattttta taatcacata gaaataatat   1740

atatcaaata acaaagggaa aaagaaagta gggaaagaaa ataataattg aagtgggctg   1800
```

-continued

```
ggctttgaca tggaaaggaa tggcttagta ataattgaag ttagcatcgg atctatttga   1860

agtgccactc atccctcaga aaaacagtgt tagtattttc tctcacaaat tgattctgtg   1920

gtccgaattg gagttcctaa atc                                           1943
```

<210> SEQ ID NO 18
<211> LENGTH: 690
<212> TYPE: DNA
<213> ORGANISM: Arabidopsis thaliana

<400> SEQUENCE: 18

```
ttcgttgaaa aatcatcgaa attttcgacg gattccaatg atcaaaaatt cgtcaataat     60

ttccaacgat attctgacta aactaaatct gatgaaatat ttttgacggc tttccaacca    120

aaatatttcg ttgtgacttg tcaaaaatcc gttagaatac taagcaactt ttcgacagat    180

tttcagcaaa aatattcggt aatataacgt gttaaaaata tgataaaaaa aaaaacttga    240

tgaatctact aaaactaaat tttcaatcat atatatctat tattcatata tttcattcat    300

tttattattt ttctcttaac aattatttag ttattctggt atcgtgtaat tatattcata    360

tgatttattc tgatattgat tcggttagca tccggataaa tctgggttgg gctttttaac    420

ttggtttttc taagaaaaat tctaatatga tttggttagc atccggatta gtctagtttg    480

gtaggcctgc ctttgtgatt cttaactcgg tcttttgtat gggtttgaac aattactaca    540

ccatttagat tcttctgacc catatcaaat aaagatccac ttaggcccat tagggttaga    600

acaaacatga ggttgcagaa taaaaagggt tcattttcct cactctcaag ttggatctca    660

aaaccctaat atctgaactt cgccgtcgag                                     690
```

<210> SEQ ID NO 19
<211> LENGTH: 995
<212> TYPE: DNA
<213> ORGANISM: Arabidopsis thaliana

<400> SEQUENCE: 19

```
ttctgttcgt atatttgtaa ctattatgtg tatttttatt ttgttagtat tactaattca     60

agtggtttaa gttgttgaga ctctttaaaa tctaagcatt ttataaacaa taatatataa    120

ttattgttta ggctaaattt gtcactaatt aaggtttgga tacatagtgt ctaaactaag    180

ctaataatat cacttaacgt ttacttgtaa cgctaggtga tgatgtcgtc aagtcaattg    240

gtacaaggaa taaacgagtg gtcatatgac attatgacca tatgaattca aactccagta    300

atccaatggt aattggattc aatgatcaag acttgaacca cgtaatccac ccttatcctt    360

agaagctcat aaatatcact aaagggacag gcaacactta accagtagtt gtccaataat    420

ttagttttcc aaaatgaaaa attattgttg tcatctattt taggtgtttt agttcaatgt    480

ggattcctcg tcctaacaaa tacttgacga atatatctag actataaaat tggttatgag    540

ttctactttt ttttgtttgt gaaattatca aaatttgtta tatttattta tttattctca    600

ttaatttgag tactaatttt taaattattt atactaaaaa caattactaa gatacaaaaa    660

tggataagag catggtgtat agatatttaa tgggatagaa tatttcccat aattgtatgt    720

gtgtgagagg ttttgttttc gtaaggaaag aaacaaaaac catttgacca aagaaaagca    780

aaagaaggca aggaatcaaa caacaaatgt tgcaaggcag aaataatgga cgttatgtta    840

atgtagtgtc gtcacacgtg acttaaaaga gacgagtctg cgtgtcaaac taaaaatgta    900

tgcaactata aaaatgggat ttgattatct ttttagtacc gaagcctacc aaccacatgc    960

acactaattc tactcgccaa ataaagtgaa aagag                               995
```

-continued

<210> SEQ ID NO 20
<211> LENGTH: 1017
<212> TYPE: DNA
<213> ORGANISM: Arabidopsis thaliana

<400> SEQUENCE: 20
aagtaacttt tagaattgat tcaatctttt tagaatagat ttttttttt ttttttttg 60 gatttcgctg aggttttacc attttgttac tcagcatatt ttaacgatgt tgcatttgtg 120
tcccatatac gttattgtta gtgaaaaata taatgtaaga ataatttata taactatcct 180
actagcaaag ctaacgcaaa ttttgaactc gaactttagt taccgtgaat gaaaataaca 240
gacttgaact ttataatact cgtagtatac gtaatttttg ctttttgcag atatgcttgc 300
cactaataaa gtcataaatt ttatattttc ataaactata gttatacact tttgactaaa 360
caaacaaaat cggtttagca aaagaaaaag ttacttttct gatgaactag gataaggaat 420
tcggaactga attttgctac gttctctctg gaccacacac actgaacacc cttttaagat 480
tttctccttc tctttttcaa cgtaatttat cttttgatca gaaacgacaa aaaagaagtc 540
taacaatatc aaacaatttt tttatagata tttttagata tttttcctgc taattttatc 600
tagtgtagac aaacccaaat atacgattat tataaaaaca cgaaatacca agtggacgac 660
tgaggttaat agatctagcc gtagaataaa gatctgcatg aaaggcggtg agaatctaaa 720
cggtgataag accataacac acggaacatc ggtacgctct cgaacgtaca agaatcgacg 780
acacacaaac actccacaat tatttgaaca ctggacaatt attgaaccga cgtacgagaa 840
tcaatgcgct gagggtaaag acgtaaatga agaactagtt ttggagataa gagcggagaa 900
agattgcgac acatgtatgg tcaatattaa tctcatttag cttataaatt tgggagcttc 960
ctctatcatt aattttcatt cataaatttt tcttcaattt gaattttctc gagaaaa 1017

<210> SEQ ID NO 21
<211> LENGTH: 273
<212> TYPE: DNA
<213> ORGANISM: Arabidopsis thaliana

<400> SEQUENCE: 21
gcaagtgtgt tgcctttgtg tggaaatgaa gaggtacttg cgaggacttt gcgtttatca 60
gtttatgtgt ttgtatatct atttgatcca gttattatgg attatatacg cttgaaactc 120
attttaagcc attgttattg aacgtttatc aaatacttta ttatgccaag caagtcaaac 180
acatgcttgt tgattgaaat caagctatag aaatctcttc ttcacataca gcagtttaga 240
ttcacaatac aacaagcgaa acgataaagt ttc 273

<210> SEQ ID NO 22
<211> LENGTH: 1131
<212> TYPE: DNA
<213> ORGANISM: Arabidopsis thaliana

<400> SEQUENCE: 22
gtccgtcgct tctcttccat ttcttctcat tttcgatttt gattcttatt tctttccagt 60
agctcctgct ctgtgaattt ctccgctcac gatagatctg cttatactcc ttacattcaa 120
ccttagatct ggtctcgatt ctctgtttct ctgttttttt cttttggtcg agaatctgat 180
gtttgtttat gttctgtcac cattaataat aatgaactct ctcattcata caatgattag 240
tttctctcgt ctacaaaacg atatgttgca ttttcacttt tcttcttttt ttctaagatg 300

-continued

```
atttgctttg accaatttgt ttagatcttt attttatttt attttctggt gggttggtgg    360

aaattgaaaa aaaaaaaaac agcataaatt gttatttgtt aatgtattca tttttggct     420

atttgttctg ggtaaaaatc tgcttctact attgaatctt tcctggattt tttactccta    480

ttgggttttt atagtaaaaa tacataataa aaggaaaaca aaagttttat agattctctt    540

aaacccctta cgataaaagt tggaatcaaa ataattcagg atcagatgct ctttgattga    600

ttcagatgcg attacagttg catggcaaat tttctagatc cgtcgtcaca ttttattttc    660

tgtttaaata tctaaatctg atatatgatg tcgacaaatt ctggtggctt atacatcact    720

tcaactgttt tcttttggct ttgtttgtca acttggtttt caatacgatt tgtgatttcg    780

atcgctgaat ttttaataca agcaaactga tgttaaccac aagcaagaga tgtgacctgc    840

cttattaaca tcgtattact tactactagt cgtattctca acgcaatcgt ttttgtattt    900

ctcacattat gccgcttctc tactctttat tccttttggt ccacgcattt tctatttgtg    960

gcaatccctt tcacaacctg atttcccact ttggatcatt tgtctgaaga ctctcttgaa   1020

tcgttaccac ttgtttcttg tgcatgctct gttttttaga attaatgata aaactattcc   1080

atagtcttga gttttcagct tgttgattct tttgcttttg gttttctgca g            1131
```

```
<210> SEQ ID NO 23
<211> LENGTH: 5688
<212> TYPE: DNA
<213> ORGANISM: Artificial Sequence
<220> FEATURE:
<223> OTHER INFORMATION: Artificially created chimeric nucleic acid
      sequence

<400> SEQUENCE: 23

ctcgaggatc taaattgtga gttcaatctc ttccctattg gattgattat cctttctttt     60

cttccaattt gtgtttcttt ttgcctaatt tattgtgtta tccccttttat cctattttgt   120

ttctttactt atttatttgc ttctatgtct ttgtacaaag atttaaactc tatggcacat    180

attttaaagt tgttagaaaa taaattcttt caagattgat gaaagaactt tttaattgta    240

gatatttcgt agattttatt ctcttactac caatataacg cttgaattga cgaaaatttg    300

tgtccaaata tctagcaaaa aggtatccaa tgaaaatata tcatatgtga tcttcaaatc    360

ttgtgtctta tgcaagattg atactttgtt caatggaaga gattgtgtgc atatttttaa    420

aatttttatt agtaataaag attctatata gctgttatag agggataatt ttacaaagaa    480

cactataaat atgattgttg ttgttagggt gtcaatggtt cggttcgact ggttatttta    540

taaaatttgt accataccat ttttttcgat attctatttt gtataaccaa aattagactt    600

ttcgaaatcg tcccaatcat gtcggtttca cttcggtatc ggtaccgttc ggttaatttt    660

catttttttt taaatgtcat taaaattcac tagtaaaaat agaatgcaat aacatacgtt    720

cttttatagg acttagcaaa agctctctag acatttttac tgtttaaagg ataatgaatt    780

aaaaaacatg aaagatggct agagtataga tacacaacta ttcgacagca acgtaaaaga    840

aaccaagtaa aagcaaagaa aatataaatc acacgagtgg aaagatatta accaagttgg    900

gattcaagaa taaagtctat attaaatatt caaaaagata aatttaaata atatgaaagg    960

aaacatattc aatacattgt agtttgctac tcataatcgc tagaatactt tgtgccttgc   1020

taataaagat acttgaaata gcttagttta aatataaata gcataataga ttttaggaat   1080

tagtattttg agtttaatta cttattgact tgtaacagtt tttataattc caaggcccat   1140

gaaaaattta atgctttatt agttttaaac ttactatata aatttttcat atgtaaaatt   1200
```

-continued

```
taatcggtat agttcgatat tttttcaatt tatttttata aaataaaaaa cttaccctaa   1260
ttatcggtac agttatagat ttatataaaa atctacggtt cttcagaaga aacctaaaaa   1320
tcggttcggt gcggacggtt cgatcggttt agtcgatttt caaatattca ttgacactcc   1380
tagttgttgt tataggtaaa aagcagttac agagaggtaa aatataactt aaaaaatcag   1440
ttctaaggaa aaattgactt ttatagtaaa tgactgttat ataaggatgt tgttacagag   1500
aggtatgagt gtagttggta aattatgttc ttgacggtgt atgtcacata ttatttatta   1560
aaactagaaa aaacagcgtc aaaactagca aaaatccaac ggacaaaaaa atcggctgaa   1620
tttgatttgg ttccaacatt taaaaaagtt tcagtgagaa agaatcggtg actgttgatg   1680
atataaacaa agggcacatt ggtcaataac cataaaaaat tatatgacag ctacagttgg   1740
tagcatgtgc tcagctattg aacaaatcta aagaaggtac atctgtaacc ggaacaccac   1800
ttaaatgact aaattaccct catcagaaag cagatggagt gctacaaata acacactatt   1860
caacaaccat aaataaaacg tgttcagcta ctaaaacaaa tataaataaa tctatgtttg   1920
taagcactcc agccatgtta atggagtgct attgcctgtt aactctcact tataaaatag   1980
tagtagaaaa aatatgaacc aaaacacaac aacatctcaa aatatttgaa gtaacacaga   2040
attttacata caccaaactt ataaatcaag tattttcatt gtaacaaatt ccatgaaaca   2100
tgaaaacaaa gctataatga aattaccaac tcaagcaata aggttggaaa agagccatct   2160
gagatattcc agcaatttac atctttttgt ttgattacac agtgaaggat cttttgtttg   2220
acaactagta aaatgattct tatttgcacc tttcagctat tcagctgctt ttactccaac   2280
cctatagcag aagtaatggc gctcatgctc gttttgtacg ccttccaact tcaagggcga   2340
gctctgtatc gatcttcagg gaaatgtcaa gtgctttcac ggaatgcgtc agggcaccac   2400
tagaaatgta ggtaacacca gtttgtccaa tcttgtgtac tgtttcaagg gtaacatttc   2460
ctgaagcctc cgtatcaaac ctcccattga tcaattctac agcctcctta agcatggata   2520
catcaatatc tccgttagat aatggaacaa ccatattgtc cagcattatc ctagtcaacg   2580
aagtctttgt ttgagatgca tagtctagaa cctcacgtac ttcttcaatt gtcctggttt   2640
caacctcaac ccctatttga agtttatttt gctccaaata ctgatccaca gattttagag   2700
ctttgccgac acctccagca gcagatatgt gattgtcttt tatcattacc atatcaaata   2760
agcccattct gtgattcttc cccccaccga tcaataccgc ccatttatcc accaaacgta   2820
atccaggagc agttttccta gtctccaaga tgtaagcagg gtgtgcagca tctgccattt   2880
ccttagttag tgtagctatt ccactcattc tttgcataaa attgagaaca accctctcag   2940
ctataacaat gttgtaagcg tttccttgta ctttgccaaa tttcaagcct ttatgaactt   3000
tatcgccatc atttacatac cactccacct ttaatgaagg atcaacttcc gcgaatatca   3060
tctcagcaag tgcaattcct gctatgatcc cgtcttcctt tgctagaaaa tgagcatcgg   3120
attccatatc aagaggaatt gtcgccttac aagtcacatc tcctaaattc ccagcatctt   3180
cagagagtgc aagtttcata acttccttta aatcataagt tgggtgtgct ggtggtttca   3240
cctctaatga ctccactctt gtattcttgg tggctattgc tgacattttc accaccaacc   3300
ttggagctgt aattgcataa ggatgcactg tagcagtgaa aggaatagct ctaaacatgg   3360
tttttttttg ggggggttgt gaaatgaatt ttgtggaaaa tagtttttgg ggcacatcaa   3420
tcctgcggtg acattcggaa tgtttctaac aagaaagata tcgttggtcc gagccttgct   3480
ctacatcata gctcagtgca taggggccct gtgcgggtgc gccttagtca agacattgca   3540
gcgagatcat tacaaccact atggcggtgg cgctaaccag ctcgttgatg gttatagccg   3600
```

-continued

```
aggcactggc cttgctgttg agattatggg cacctttatt cttctgtata ctgtcttctc   3660
cgccactgat cccaaacgca atgctagaga ttcccatgtt cctgtcttgg ctccactccc   3720
cattggcttt gctgtcttca ttgttcacct cgccaccatt cccgtcaccg gcactggcat   3780
caacccagcg agcaaaaact attttccaca aaattcattt cacaaccccc ccaaaaaaaa   3840
accatgttta gagctattcc tttcactgct acagtgcatc cttatgcaat tacagctcca   3900
aggttggtgg tgaaaatgtc agcaatagcc accaagaata caagagtgga gtcattagag   3960
gtgaaaccac cagcacaccc aacttatgat ttaaaggaag ttatgaaact tgcactctct   4020
gaagatgctg ggaatttagg agatgtgact tgtaaggcga caattcctct tgatatggaa   4080
tccgatgctc attttctagc aaaggaagac gggatcatag caggaattgc acttgctgag   4140
atgatattcg cggaagttga tccttcatta aaggtggagt ggtatgtaaa tgatggcgat   4200
aaagttcata aaggcttgaa atttggcaaa gtacaaggaa acgcttacaa cattgttata   4260
gctgagaggg ttgttctcaa ttttatgcaa agaatgagtg gaatagctac actaactaag   4320
gaaatggcag atgctgcaca ccctgcttac atcttggaga ctaggaaaac tgctcctgga   4380
ttacgtttgg tggataaatg ggcggtattg atcggtgggg ggaagaatca cagaatgggc   4440
ttatttgata tggtaatgat aaaagacaat cacatatctg ctgctggagg tgtcggcaaa   4500
gctctaaaat ctgtggatca gtatttggag caaaataaac ttcaaatagg ggttgaggtt   4560
gaaaccagga caattgaaga agtacgtgag gttctagact atgcatctca aacaaagact   4620
tcgttgacta ggataatgct ggacaatatg gttgttccat tatctaacgg agatattgat   4680
gtatccatgc ttaaggaggc tgtagaattg atcaatggga ggtttgatac ggaggcttca   4740
ggaaatgtta cccttgaaac agtacacaag attggacaaa ctggtgttac ctacatttct   4800
agtggtgccc tgacgcattc cgtgaaagca cttgacattt ccctgaagat cgatacagag   4860
ctcgcccttg aagttggaag gcgtacaaaa cgagcatgag cgccattact tctgctatag   4920
ggttggagta aaagcagctg aatagctgaa aggtgcaaat aagaatcatt ttactagttg   4980
tcaaacaaaa gatccttcac tgtgtaatca aacaaaaaga tgtaaattgc tggaatatct   5040
cagatggctc ttttccaacc ttattgcttg agttggtaat ttcattatag ctttgttttc   5100
atgtttcatg gaatttgtta caatgaaaat acttgattta taagtttggt gtatgtaaaa   5160
ttctgtgtta cttcaaatat tttgagatgt tgagctcgtg aaatggcctc tttagttttt   5220
gattgaatca taggggtatt agttttctat ggccgggagt ggtcttcttg cttaattgta   5280
atggaataac cagagaggaa ctactgtgtt atctttgagg aatgttgggc tttttttcgtt  5340
tgaattatca tgaatgaaat tttacttttt cccaatacaa gtttgttttc gtttcttggt   5400
ttttgttatc ccttggttta tgtcttggtt tggcttaaat gattgaagat tacactacct   5460
atgtttctgc tattcctgtt gaagatcaca tttgataata atgcatcgaa tgcattaaag   5520
tttcttattg gctctgtcaa aagtattgaa ggtggatttt tctaattggc aagagaaagt   5580
attaaagagg tgatttatta gtacttatat ttttctcagc atctctcttt cagtgttgga   5640
gcttcataaa attagcactt cagagtttca gtcgggagct gaattcga                5688
```

<210> SEQ ID NO 24
<211> LENGTH: 4134
<212> TYPE: DNA
<213> ORGANISM: Artificial Sequence
<220> FEATURE:
<223> OTHER INFORMATION: Artificially created chimeric nucleic acid sequence -continued

<400> SEQUENCE: 24

```
ctcgaggatc taaattgtga gttcaatctc ttccctattg gattgattat cctttctttt     60
cttccaattt gtgtttcttt ttgcctaatt tattgtgtta tcccctttat cctattttgt    120
ttctttactt atttatttgc ttctatgtct ttgtacaaag atttaaactc tatggcacat    180
attttaaagt tgttagaaaa taaattcttt caagattgat gaaagaactt tttaattgta    240
gatatttcgt agattttatt ctcttactac caatataacg cttgaattga cgaaaatttg    300
tgtccaaata tctagcaaaa aggtatccaa tgaaaatata tcatatgtga tcttcaaatc    360
ttgtgtctta tgcaagattg atactttgtt caatggaaga gattgtgtgc atatttttaa    420
aatttttatt agtaataaag attctatata gctgttatag agggataatt ttacaaagaa    480
cactataaat atgattgttg ttgttagggt gtcaatggtt cggttcgact ggttatttta    540
taaaatttgt accataccat ttttttcgat attctatttt gtataaccaa aattagactt    600
ttcgaaatcg tcccaatcat gtcggtttca cttcggtatc ggtaccgttc ggttaatttt    660
catttttttt taaatgtcat taaaattcac tagtaaaaat agaatgcaat aacatacgtt    720
cttttatagg acttagcaaa agctctctag acatttttac tgtttaaagg ataatgaatt    780
aaaaaacatg aaagatggct agagtataga tacacaacta ttcgacagca acgtaaaaga    840
aaccaagtaa aagcaaagaa aatataaatc acacgagtgg aaagatatta accaagttgg    900
gattcaagaa taaagtctat attaaatatt caaaaagata aatttaaata atatgaaagg    960
aaacatattc aatacattgt agtttgctac tcataatcgc tagaatactt tgtgccttgc   1020
taataaagat acttgaaata gcttagttta aatataaata gcataataga ttttaggaat   1080
tagtattttg agtttaatta cttattgact tgtaacagtt tttataattc caaggcccat   1140
gaaaaattta atgctttatt agttttaaac ttactatata aatttttcat atgtaaaatt   1200
taatcggtat agttcgatat tttttcaatt tatttttata aaataaaaaa cttaccctaa   1260
ttatcggtac agttatagat ttatataaaa atctacggtt cttcagaaga aacctaaaaa   1320
tcggttcggt gcggacggtt cgatcggttt agtcgatttt caaatattca ttgacactcc   1380
tagttgttgt tataggtaaa aagcagttac agagaggtaa aatataactt aaaaaatcag   1440
ttctaaggaa aaattgactt ttatagtaaa tgactgttat ataaggatgt tgttacagag   1500
aggtatgagt gtagttggta aattatgttc ttgacggtgt atgtcacata ttatttatta   1560
aaactagaaa aaacagcgtc aaaactagca aaaatccaac ggacaaaaaa atcggctgaa   1620
tttgatttgg ttccaacatt taaaaaagtt tcagtgagaa agaatcggtg actgttgatg   1680
atataaacaa agggcacatt ggtcaataac cataaaaaat tatatgacag ctacagttgg   1740
tagcatgtgc tcagctattg aacaaatcta aagaaggtac atctgtaacc ggaacaccac   1800
ttaaatgact aaattaccct catcagaaag cagatggagt gctacaaata acacactatt   1860
caacaaccat aaataaaacg tgttcagcta ctaaaacaaa tataaataaa tctatgtttg   1920
taagcactcc agccatgtta atggagtgct attgcctgtt aactctcact tataaaatag   1980
tagtagaaaa aatatgaacc aaaacacaac tttatcgcca tcatttacat accactccac   2040
ctttaatgaa ggatcaactt ccgcgaatat catctcagca agtgcaattc ctgctatgat   2100
cccgtcttcc tttgctagaa aatgagcatc ggattccata tcaagaggaa ttgtcgcctt   2160
acaagtcaca tctcctaaat tcccagcatc ttcagagagt gcaagtttca taacttcctt   2220
taaatcataa gttgggtgtg ctggtggttt cacctctaat gactccactc ttgtattctt   2280
```

```
ggtggctatt gctgacattt tcaccaccaa ccttggagct gtaattgcat aaggatgcac    2340

tgtagcagtg aaaggaatag ctctaaacat gtccgtcgct tctcttccat ttcttctcat    2400

tttcgatttt gattcttatt tctttccagt agctcctgct ctgtgaattt ctccgctcac    2460

gatagatctg cttatactcc ttacattcaa ccttagatct ggtctcgatt ctctgtttct    2520

ctgttttttt cttttggtcg agaatctgat gtttgtttat gttctgtcac cattaataat    2580

aatgaactct ctcattcata caatgattag tttctctcgt ctacaaaacg atatgttgca    2640

ttttcacttt tcttcttttt ttctaagatg atttgctttg accaatttgt ttagatcttt    2700

attttatttt attttctggt gggttggtgg aaattgaaaa aaaaaaaaac agcataaatt    2760

gttatttgtt aatgtattca ttttttggct atttgttctg ggtaaaaatc tgcttctact    2820

attgaatctt tcctggattt tttactccta ttgggttttt atagtaaaaa tacataataa    2880

aaggaaaaca aaagttttat agattctctt aaacccctta cgataaaagt tggaatcaaa    2940

ataattcagg atcagatgct ctttgattga ttcagatgcg attacagttg catggcaaat    3000

tttctagatc cgtcgtcaca ttttattttc tgtttaaata tctaaatctg atatatgatg    3060

tcgacaaatt ctggtggctt atacatcact tcaactgttt tcttttggct ttgtttgtca    3120

acttggtttt caatacgatt tgtgatttcg atcgctgaat ttttaataca agcaaactga    3180

tgttaaccac aagcaagaga tgtgacctgc cttattaaca tcgtattact tactactagt    3240

cgtattctca acgcaatcgt ttttgtattt ctcacattat gccgcttctc tactctttat    3300

tccttttggt ccacgcattt tctatttgtg gcaatccctt tcacaacctg atttcccact    3360

ttggatcatt tgtctgaaga ctctcttgaa tcgttaccac ttgtttcttg tgcatgctct    3420

gtttttttaga attaatgata aaactattcc atagtcttga gttttcagct tgttgattct    3480

tttgcttttg gttttctgca gatgtttaga gctattcctt tcactgctac agtgcatcct    3540

tatgcaatta cagctccaag gttggtggtg aaaatgtcag caatagccac caagaataca    3600

agagtggagt cattagaggt gaaaccacca gcacacccaa cttatgattt aaaggaagtt    3660

atgaaacttg cactctctga agatgctggg aatttaggag atgtgacttg taaggcgaca    3720

attcctcttg atatggaatc cgatgctcat tttctagcaa aggaagacgg gatcatagca    3780

ggaattgcac ttgctgagat gatattcgcg gaagttgatc cttcattaaa ggtggagtgg    3840

tatgtaaatg atggcgataa agcaagtgtg ttgcctttgt gtggaaatga agaggtactt    3900

gcgaggactt tgcgtttatc agtttatgtg tttgtatatc tatttgatcc agttattatg    3960

gattatatac gcttgaaact cattttaagc cattgttatt gaacgtttat caaatacttt    4020

attatgccaa gcaagtcaaa cacatgcttg ttgattgaaa tcaagctata gaaatctctt    4080

cttcacatac agcagtttag attcacaata caacaagcga aacgataaag tttc           4134
```

<210> SEQ ID NO 25
<211> LENGTH: 3896
<212> TYPE: DNA
<213> ORGANISM: Artificial Sequence
<220> FEATURE:
<223> OTHER INFORMATION: Artificially created chimeric nucleic acid
      sequence

<400> SEQUENCE: 25

```
ctcgaggatc taaattgtga gttcaatctc ttccctattg gattgattat cctttctttt      60

cttccaattt gtgtttcttt ttgcctaatt tattgtgtta tcccctttat cctattttgt     120

ttctttactt atttatttgc ttctatgtct ttgtacaaag atttaaactc tatggcacat     180
```

-continued

```
attttaaagt tgttagaaaa taaattcttt caagattgat gaaagaactt tttaattgta    240
gatatttcgt agattttatt ctcttactac caatataacg cttgaattga cgaaaatttg    300
tgtccaaata tctagcaaaa aggtatccaa tgaaaatata tcatatgtga tcttcaaatc    360
ttgtgtctta tgcaagattg atactttgtt caatggaaga gattgtgtgc atatttttaa    420
aatttttatt agtaataaag attctatata gctgttatag agggataatt ttacaaagaa    480
cactataaat atgattgttg ttgttagggt gtcaatggtt cggttcgact ggttatttta    540
taaaatttgt accataccat ttttttcgat attctatttt gtataaccaa aattagactt    600
ttcgaaatcg tcccaatcat gtcggtttca cttcggtatc ggtaccgttc ggttaatttt    660
catttttttt taaatgtcat taaaattcac tagtaaaaat agaatgcaat aacatacgtt    720
cttttatagg acttagcaaa agctctctag acatttttac tgtttaaagg ataatgaatt    780
aaaaaacatg aaagatggct agagtataga tacacaacta ttcgacagca acgtaaaaga    840
aaccaagtaa aagcaaagaa aatataaatc acacgagtgg aaagatatta accaagttgg    900
gattcaagaa taaagtctat attaaatatt caaaaagata aatttaaata atatgaaagg    960
aaacatattc aatacattgt agtttgctac tcataatcgc tagaatactt tgtgccttgc   1020
taataaagat acttgaaata gcttagttta aatataaata gcataataga ttttaggaat   1080
tagtattttg agtttaatta cttattgact tgtaacagtt tttataattc caaggcccat   1140
gaaaaattta atgctttatt agttttaaac ttactatata aatttttcat atgtaaaatt   1200
taatcggtat agttcgatat tttttcaatt tatttttata aaataaaaaa cttaccctaa   1260
ttatcggtac agttatagat ttatataaaa atctacggtt cttcagaaga aacctaaaaa   1320
tcggttcggt gcggacggtt cgatcggttt agtcgatttt caaatattca ttgacactcc   1380
tagttgttgt tataggtaaa aagcagttac agagaggtaa aatataactt aaaaaatcag   1440
ttctaaggaa aaattgactt ttatagtaaa tgactgttat ataaggatgt tgttacagag   1500
aggtatgagt gtagttggta aattatgttc ttgacggtgt atgtcacata ttatttatta   1560
aaactagaaa aaacagcgtc aaaactagca aaaatccaac ggacaaaaaa atcggctgaa   1620
tttgatttgg ttccaacatt taaaaaagtt tcagtgagaa agaatcggtg actgttgatg   1680
atataaacaa agggcacatt ggtcaataac cataaaaaat tatatgacag ctacagttgg   1740
tagcatgtgc tcagctattg aacaaatcta aagaaggtac atctgtaacc ggaacaccac   1800
ttaaatgact aaattaccct catcagaaag cagatggagt gctacaaata acacactatt   1860
caacaaccat aaataaaacg tgttcagcta ctaaaacaaa tataaataaa tctatgtttg   1920
taagcactcc agccatgtta atggagtgct attgcctgtt aactctcact tataaaatag   1980
tagtagaaaa aatatgaacc aaaacacaac cgattcaaaa cttcagcagg aaaatttata   2040
ttaaagtacg aaacaccaca gagaaagaat tttacaatga ttgtgaattg gaaattatga   2100
taattactgc agaattctcc tacaatacgt cgcatttcac ttatttattc acttgattaa   2160
gactcgatct tggtccaatg attgtactac cagtgttcat tattcacttg attaagactc   2220
gatcatactt ctggcgaaag atggtaaaat ggtccgtcgc ttctcttcca tttcttctca   2280
ttttcgattt tgattcttat ttctttccag tagctcctgc tctgtgaatt tctccgctca   2340
cgatagatct gcttatactc cttacattca accttagatc tggtctcgat tctctgtttc   2400
tctgtttttt tcttttggtc gagaatctga tgtttgttta tgttctgtca ccattaataa   2460
taatgaactc tctcattcat acaatgatta gtttctctcg tctacaaaac gatatgttgc   2520
attttcactt ttcttctttt tttctaagat gatttgcttt gaccaatttg tttagatctt   2580
```

-continued

```
tattttattt tattttctgg tgggttggtg gaaattgaaa aaaaaaaaaa cagcataaat   2640
tgttatttgt taatgtattc attttttggc tatttgttct gggtaaaaat ctgcttctac   2700
tattgaatct ttcctggatt ttttactcct attgggtttt tatagtaaaa atacataata   2760
aaaggaaaac aaaagtttta tagattctct taaacccctt acgataaaag ttggaatcaa   2820
aataattcag gatcagatgc tctttgattg attcagatgc gattacagtt gcatggcaaa   2880
ttttctagat ccgtcgtcac attttatttt ctgtttaaat atctaaatct gatatatgat   2940
gtcgacaaat tctggtggct tatacatcac ttcaactgtt ttcttttggc tttgtttgtc   3000
aacttggttt tcaatacgat ttgtgatttc gatcgctgaa tttttaatac aagcaaactg   3060
atgttaacca caagcaagag atgtgacctg ccttattaac atcgtattac ttactactag   3120
tcgtattctc aacgcaatcg tttttgtatt tctcacatta tgccgcttct ctactcttta   3180
ttccttttgg tccacgcatt ttctatttgt ggcaatccct ttcacaacct gatttcccac   3240
tttggatcat ttgtctgaag actctcttga atcgttacca cttgtttctt gtgcatgctc   3300
tgttttttag aattaatgat aaaactattc catagtcttg agttttcagc ttgttgattc   3360
ttttgctttt ggtttttctgc agcattttac catctttcgc cagaagtatg atcgagtctt   3420
aatcaagtga ataatgaaca ctggtagtac aatcattgga ccaagatcga gtcttaatca   3480
agtgaataaa taagtgaaat gcgacgtatt gtaggagaat tctgcagtaa ttatcataat   3540
ttccaattca caatcattgt aaaattcttt ctctgtggtg tttcgtactt taatataaat   3600
tttcctgctg aagttttgaa tcggcaagtg tgttgccttt gtgtggaaat gaagaggtac   3660
ttgcgaggac tttgcgttta tcagtttatg tgtttgtata tctatttgat ccagttatta   3720
tggattatat acgcttgaaa ctcattttaa gccattgtta ttgaacgttt atcaaatact   3780
ttattatgcc aagcaagtca aacacatgct tgttgattga aatcaagcta tagaaatctc   3840
ttcttcacat acagcagttt agattcacaa tacaacaagc gaaacgataa agtttc       3896
```

<210> SEQ ID NO 26
<211> LENGTH: 4670
<212> TYPE: DNA
<213> ORGANISM: Artificial Sequence
<220> FEATURE:
<223> OTHER INFORMATION: Artificially created chimeric nucleic acid sequence

<400> SEQUENCE: 26

```
ctcgaggatc taaattgtga gttcaatctc ttccctattg gattgattat cctttctttt     60
cttccaattt gtgtttcttt ttgcctaatt tattgtgtta tcccctttat cctattttgt    120
ttctttactt atttatttgc ttctatgtct ttgtacaaag atttaaactc tatggcacat    180
attttaaagt tgttagaaaa taaattcttt caagattgat gaaagaactt tttaattgta    240
gatatttcgt agattttatt ctcttactac caatataacg cttgaattga cgaaaatttg    300
tgtccaaata tctagcaaaa aggtatccaa tgaaaatata tcatatgtga tcttcaaatc    360
ttgtgtctta tgcaagattg atactttgtt caatggaaga gattgtgtgc atatttttaa    420
aatttttatt agtaataaag attctatata gctgttatag agggataatt ttacaaagaa    480
cactataaat atgattgttg ttgttagggt gtcaatggtt cggttcgact ggttatttta    540
taaaatttgt accataccat ttttttcgat attctatttt gtataaccaa aattagactt    600
ttcgaaatcg tcccaatcat gtcggtttca cttcggtatc ggtaccgttc ggttaatttt    660
cattttttttt taaatgtcat taaaattcac tagtaaaaat agaatgcaat aacatacgtt    720
```

-continued

```
cttttatagg acttagcaaa agctctctag acatttttac tgtttaaagg ataatgaatt    780
aaaaaacatg aaagatggct agagtataga tacacaacta ttcgacagca acgtaaaaga    840
aaccaagtaa aagcaaagaa aatataaatc acacgagtgg aaagatatta accaagttgg    900
gattcaagaa taaagtctat attaaatatt caaaaagata aatttaaata atatgaaagg    960
aaacatattc aatacattgt agtttgctac tcataatcgc tagaatactt tgtgccttgc   1020
taataaagat acttgaaata gcttagttta aatataaata gcataataga ttttaggaat   1080
tagtattttg agtttaatta cttattgact tgtaacagtt tttataattc caaggcccat   1140
gaaaaattta atgctttatt agttttaaac ttactatata aatttttcat atgtaaaatt   1200
taatcggtat agttcgatat tttttcaatt tatttttata aaataaaaaa cttaccctaa   1260
ttatcggtac agttatagat ttatataaaa atctacggtt cttcagaaga aacctaaaaa   1320
tcggttcggt gcggacggtt cgatcggttt agtcgatttt caaatattca ttgacactcc   1380
tagttgttgt tataggtaaa aagcagttac agagaggtaa aatataactt aaaaaatcag   1440
ttctaaggaa aaattgactt ttatagtaaa tgactgttat ataaggatgt tgttacagag   1500
aggtatgagt gtagttggta aattatgttc ttgacggtgt atgtcacata ttatttatta   1560
aaactagaaa aaacagcgtc aaaactagca aaaatccaac ggacaaaaaa atcggctgaa   1620
tttgatttgg ttccaacatt taaaaaagtt tcagtgagaa agaatcggtg actgttgatg   1680
atataaacaa agggcacatt ggtcaataac cataaaaaat tatatgacag ctacagttgg   1740
tagcatgtgc tcagctattg aacaaatcta aagaaggtac atctgtaacc ggaacaccac   1800
ttaaatgact aaattaccct catcagaaag cagatggagt gctacaaata acacactatt   1860
caacaaccat aaataaaacg tgttcagcta ctaaaacaaa tataaataaa tctatgtttg   1920
taagcactcc agccatgtta atggagtgct attgcctgtt aactctcact tataaaatag   1980
tagtagaaaa aatatgaacc aaaacacaac ggttgtgtat ttcacttttg gatatagctc   2040
agtggcttcg acacctgtag gaggctgaac ctcaaagttt gcagaatctc cattaacaaa   2100
aactgaatgg catatggcca aattagtcct taatggcaga ggtccctctt gtacaatctg   2160
gagaatatct tcctctgata gatataactt ctcgagggtc ttcccaattt tgtcctccca   2220
caaggacact atctcgttga aggatagaat attggcaggt ggtctcatgt gaagagtctt   2280
attcaatgtc cgtggatcat ctactgcttc gatagtgtat gtcgctatgt cttcttcctt   2340
cacatatatt gctttgggat ttccatcgcc aaaaatgaca actttgtctc taggaggggt   2400
tttggcctct aactgcccca agttgggcaa gaagaaatct gcaaaccaat tgcagattac   2460
atatgtgtat ggaattcctt ctgcctctat catcctcctg attcttacct ttagagcgaa   2520
gagtgatgca gctggttcaa ttgcacgagc atgatccaca tcaaatccaa attctgaagg   2580
aagaaatctc ttgatatttc cagcttcttt aattgctttg atgatgttca cttgatcagt   2640
ccgtcgcttc tcttccattt cttctcattt tcgattttga ttcttatttc tttccagtag   2700
ctcctgctct gtgaatttct ccgctcacga tagatctgct tatactcctt acattcaacc   2760
ttagatctgg tctcgattct ctgtttctct gttttttttct tttggtcgag aatctgatgt   2820
ttgtttatgt tctgtcacca ttaataataa tgaactctct cattcataca atgattagtt   2880
tctctcgtct acaaaacgat atgttgcatt ttcacttttc ttcttttttt ctaagatgat   2940
ttgctttgac caatttgttt agatctttat tttattttat tttctggtgg gttggtggaa   3000
attgaaaaaa aaaaaaacag cataaattgt tatttgttaa tgtattcatt ttttggctat   3060
```

-continued

```
ttgttctggg taaaaatctg cttctactat tgaatctttc ctggattttt tactcctatt   3120

gggtttttat agtaaaaata cataataaaa ggaaaacaaa agttttatag attctcttaa   3180

accccttacg ataaaagttg gaatcaaaat aattcaggat cagatgctct ttgattgatt   3240

cagatgcgat tacagttgca tggcaaattt tctagatccg tcgtcacatt ttattttctg   3300

tttaaatatc taaatctgat atatgatgtc gacaaattct ggtggcttat acatcacttc   3360

aactgttttc ttttggcttt gtttgtcaac ttggttttca atacgatttg tgatttcgat   3420

cgctgaattt ttaatacaag caaactgatg ttaaccacaa gcaagagatg tgacctgcct   3480

tattaacatc gtattactta ctactagtcg tattctcaac gcaatcgttt ttgtatttct   3540

cacattatgc cgcttctcta ctctttattc cttttggtcc acgcattttc tatttgtggc   3600

aatccctttc acaacctgat ttcccacttt ggatcatttg tctgaagact ctcttgaatc   3660

gttaccactt gtttcttgtg catgctctgt tttttagaat taatgataaa actattccat   3720

agtcttgagt tttcagcttg ttgattcttt tgcttttggt tttctgcagt gatcaagtga   3780

acatcatcaa agcaattaaa gaagctggaa atatcaagag atttcttcct tcagaatttg   3840

gatttgatgt ggatcatgct cgtgcaattg aaccagctgc atcactcttc gctctaaagg   3900

taagaatcag gaggatgata gaggcagaag gaattccata cacatatgta atctgcaatt   3960

ggtttgcaga tttcttcttg cccaacttgg ggcagttaga ggccaaaacc cctcctagag   4020

acaaagttgt catttttggc gatggaaatc ccaaagcaat atatgtgaag gaagaagaca   4080

tagcgacata cactatcgaa gcagtagatg atccacggac attgaataag actcttcaca   4140

tgagaccacc tgccaatatt ctatccttca acgagatagt gtccttgtgg gaggacaaaa   4200

ttgggaagac cctcgagaag ttatatctat cagaggaaga tattctccag attgtacaag   4260

agggacctct gccattaagg actaatttgg ccatatgcca ttcagttttt gttaatggag   4320

attctgcaaa ctttgaggtt cagcctccta caggtgtcga agccactgag ctatatccaa   4380

aagtgaaata cacaaccgca agtgtgttgc ctttgtgtgg aaatgaagag gtacttgcga   4440

ggactttgcg tttatcagtt tatgtgtttg tatatctatt tgatccagtt attatggatt   4500

atatacgctt gaaactcatt ttaagccatt gttattgaac gtttatcaaa tactttatta   4560

tgccaagcaa gtcaaacaca tgcttgttga ttgaaatcaa gctatagaaa tctcttcttc   4620

acatacagca gtttagattc acaatacaac aagcgaaacg ataaagtttc              4670
```

<210> SEQ ID NO 27
<211> LENGTH: 5390
<212> TYPE: DNA
<213> ORGANISM: Artificial Sequence
<220> FEATURE:
<223> OTHER INFORMATION: Artificially created chimeric nucleic acid sequence

<400> SEQUENCE: 27

```
ctcgaggatc taaattgtga gttcaatctc ttccctattg gattgattat cctttctttt     60

cttccaattt gtgtttcttt ttgcctaatt tattgtgtta tcccctttat cctattttgt    120

ttctttactt atttatttgc ttctatgtct ttgtacaaag atttaaactc tatggcacat    180

attttaaagt tgttagaaaa taaattcttt caagattgat gaaagaactt tttaattgta    240

gatatttcgt agattttatt ctcttactac caatataacg cttgaattga cgaaaatttg    300

tgtccaaata tctagcaaaa aggtatccaa tgaaaatata tcatatgtga tcttcaaatc    360

ttgtgtctta tgcaagattg atactttgtt caatggaaga gattgtgtgc atatttttaa    420
```

-continued

```
aatttttatt agtaataaag attctatata gctgttatag agggataatt ttacaaagaa    480
cactataaat atgattgttg ttgttagggt gtcaatggtt cggttcgact ggttatttta    540
taaaatttgt accataccat ttttttcgat attctatttt gtataaccaa aattagactt    600
ttcgaaatcg tcccaatcat gtcggtttca cttcggtatc ggtaccgttc ggttaatttt    660
catttttttt taaatgtcat taaaattcac tagtaaaaat agaatgcaat aacatacgtt    720
cttttatagg acttagcaaa agctctctag acatttttac tgtttaaagg ataatgaatt    780
aaaaaacatg aaagatggct agagtataga tacacaacta ttcgacagca acgtaaaaga    840
aaccaagtaa aagcaaagaa aatataaatc acacgagtgg aaagatatta accaagttgg    900
gattcaagaa taaagtctat attaaatatt caaaaagata aatttaaata atatgaaagg    960
aaacatattc aatacattgt agtttgctac tcataatcgc tagaatactt tgtgccttgc   1020
taataaagat acttgaaata gcttagttta aatataaata gcataataga ttttaggaat   1080
tagtattttg agtttaatta cttattgact tgtaacagtt tttataattc caaggcccat   1140
gaaaaattta atgctttatt agttttaaac ttactatata aatttttcat atgtaaaatt   1200
taatcggtat agttcgatat tttttcaatt tatttttata aaataaaaaa cttaccctaa   1260
ttatcggtac agttatagat ttatataaaa atctacggtt cttcagaaga aacctaaaaa   1320
tcggttcggt gcggacggtt cgatcggttt agtcgatttt caaatattca ttgacactcc   1380
tagttgttgt tataggtaaa aagcagttac agagaggtaa aatataactt aaaaaatcag   1440
ttctaaggaa aaattgactt ttatagtaaa tgactgttat ataaggatgt tgttacagag   1500
aggtatgagt gtagttggta aattatgttc ttgacggtgt atgtcacata ttatttatta   1560
aaactagaaa aaacagcgtc aaaactagca aaaatccaac ggacaaaaaa atcggctgaa   1620
tttgatttgg ttccaacatt taaaaaagtt tcagtgagaa agaatcggtg actgttgatg   1680
atataaacaa agggcacatt ggtcaataac cataaaaaat tatatgacag ctacagttgg   1740
tagcatgtgc tcagctattg aacaaatcta aagaaggtac atctgtaacc ggaacaccac   1800
ttaaatgact aaattaccct catcagaaag cagatggagt gctacaaata acacactatt   1860
caacaaccat aaataaaacg tgttcagcta ctaaaacaaa tataaataaa tctatgtttg   1920
taagcactcc agccatgtta atggagtgct attgcctgtt aactctcact tataaaatag   1980
tagtagaaaa aatatgaacc aaaacacaac tttatcgcca tcatttacat accactccac   2040
ctttaatgaa ggatcaactt ccgcgaatat catctcagca agtgcaattc ctgctatgat   2100
cccgtcttcc tttgctagaa aatgagcatc ggattccata tcaagaggaa ttgtcgcctt   2160
acaagtcaca tctcctaaat tcccagcatc ttcagagagt gcaagtttca taacttcctt   2220
taaatcataa gttgggtgtg ctggtggttt cacctctaat gactccactc ttgtattctt   2280
ggtggctatt gctgacattt tcaccaccaa ccttggagct gtaattgcat aaggatgcac   2340
tgtagcagtg aaaggaatag ctctaaacat ggttgtgtat ttcacttttg gatatagctc   2400
agtggcttcg acacctgtag gaggctgaac ctcaaagttt gcagaatctc cattaacaaa   2460
aactgaatgg catatggcca aattagtcct taatggcaga ggtccctctt gtacaatctg   2520
gagaatatct tcctctgata gatataactt ctcgagggtc ttcccaattt tgtcctccca   2580
caaggacact atctcgttga aggatagaat attggcaggt ggtctcatgt gaagagtctt   2640
attcaatgtc cgtggatcat ctactgcttc gatagtgtat gtcgctatgt cttcttcctt   2700
cacatatatt gctttgggat ttccatcgcc aaaaatgaca actttgtctc taggaggggt   2760
tttggcctct aactgcccca agttgggcaa gaagaaatct gcaaaccaat tgcagattac   2820
```

-continued atatgtgtat ggaattcctt ctgcctctat catcctcctg attcttacct ttagagcgaa 2880
gagtgatgca gctggttcaa ttgcacgagc atgatccaca tcaaatccaa attctgaagg 2940
aagaaatctc ttgatatttc cagcttcttt aattgctttg atgatgttca cttgatcagt 3000
ccgtcgcttc tcttccattt cttctcattt tcgattttga ttcttatttc tttccagtag 3060
ctcctgctct gtgaatttct ccgctcacga tagatctgct tatactcctt acattcaacc 3120
ttagatctgg tctcgattct ctgtttctct gttttttct tttggtcgag aatctgatgt 3180
ttgtttatgt tctgtcacca ttaataataa tgaactctct cattcataca atgattagtt 3240
tctctcgtct acaaaacgat atgttgcatt ttcactttc ttcttttttt ctaagatgat 3300
ttgctttgac caatttgttt agatctttat tttattttat tttctggtgg gttggtggaa 3360
attgaaaaaa aaaaaaacag cataaattgt tatttgttaa tgtattcatt ttttggctat 3420
ttgttctggg taaaaatctg cttctactat tgaatctttc ctggattttt tactcctatt 3480
gggtttttat agtaaaaata cataataaaa ggaaaacaaa agttttatag attctcttaa 3540 acccottacg ataaaagttg gaatcaaaat aattcaggat cagatgctct ttgattgatt 3600
cagatgcgat tacagttgca tggcaaattt tctagatccg tcgtcacatt ttattttctg 3660
tttaaatatc taaatctgat atatgatgtc gacaaattct ggtggcttat acatcacttc 3720 aactgtttc ttttggcttt gtttgtcaac ttggttttca atacgatttg tgatttcgat 3780
cgctgaattt ttaatacaag caaactgatg ttaaccacaa gcaagagatg tgacctgcct 3840
tattaacatc gtattactta ctactagtcg tattctcaac gcaatcgttt ttgtatttct 3900
cacattatgc cgcttctcta ctctttattc cttttggtcc acgcattttc tatttgtggc 3960
aatccctttc acaacctgat ttcccacttt ggatcatttg tctgaagact ctcttgaatc 4020
gttaccactt gtttcttgtg catgctctgt tttttagaat taatgataaa actattccat 4080
agtcttgagt tttcagcttg ttgattcttt tgcttttggt tttctgcagt gatcaagtga 4140
acatcatcaa agcaattaaa gaagctggaa atatcaagag atttcttcct tcagaatttg 4200
gatttgatgt ggatcatgct cgtgcaattg aaccagctgc atcactcttc gctctaaagg 4260
taagaatcag gaggatgata gaggcagaag gaattccata cacatatgta atctgcaatt 4320
ggtttgcaga tttcttcttg cccaacttgg ggcagttaga ggccaaaacc cctcctagag 4380
acaaagttgt catttttggc gatggaaatc ccaaagcaat atatgtgaag gaagaagaca 4440
tagcgacata cactatcgaa gcagtagatg atccacggac attgaataag actcttcaca 4500
tgagaccacc tgccaatatt ctatccttca acgagatagt gtccttgtgg gaggacaaaa 4560
ttgggaagac cctcgagaag ttatatctat cagaggaaga tattctccag attgtacaag 4620
agggacctct gccattaagg actaatttgg ccatatgcca ttcagttttt gttaatggag 4680
attctgcaaa ctttgaggtt cagcctccta caggtgtcga agccactgag ctatatccaa 4740
aagtgaaata cacaaccatg tttagagcta ttcctttcac tgctacagtg catccttatg 4800
caattacagc tccaaggttg gtggtgaaaa tgtcagcaat agccaccaag aatacaagag 4860
tggagtcatt agaggtgaaa ccaccagcac acccaactta tgatttaaag gaagttatga 4920
aacttgcact ctctgaagat gctgggaatt taggagatgt gacttgtaag gcgacaattc 4980
ctcttgatat ggaatccgat gctcattttc tagcaaagga agacgggatc atagcaggaa 5040
ttgcacttgc tgagatgata ttcgcggaag ttgatccttc attaaaggtg gagtggtatg 5100
taaatgatgg cgataaagca agtgtgttgc ctttgtgtgg aaatgaagag gtacttgcga 5160

-continued ggactttgcg tttatcagtt tatgtgtttg tatatctatt tgatccagtt attatggatt 5220
atatacgctt gaaactcatt ttaagccatt gttattgaac gtttatcaaa tactttatta 5280
tgccaagcaa gtcaaacaca tgcttgttga ttgaaatcaa gctatagaaa tctcttcttc 5340
acatacagca gtttagattc acaatacaac aagcgaaacg ataaagtttc 5390

<210> SEQ ID NO 28
<211> LENGTH: 3773
<212> TYPE: DNA
<213> ORGANISM: Artificial Sequence
<220> FEATURE:
<223> OTHER INFORMATION: Artificially created chimeric nucleic acid sequence

<400> SEQUENCE: 28
gacggtccga tgtgagactt ttcaacaaag ggtaatatcc ggaaacctcc tcggattcca 60
ttgcccagct atctgtcact ttattgtgaa gatagtggaa aaggaaggtg gctcctacaa 120
atgccatcat tgcgataaag gaaaggccat cgttgaagat gcctctgccg acagtggtcc 180
caaagatgga cccccaccca cgaggagcat cgtggaaaaa gaagacgttc caaccacgtc 240
ttcaaagcaa gtggattgat gtgatggtcc gatgtgagac ttttcaacaa agggtaatat 300
ccggaaacct cctcggattc cattgcccag ctatctgtca ctttattgtg aagatagtgg 360
aaaaggaagg tggctcctac aaatgccatc attgcgataa aggaaaggcc atcgttgaag 420
atgcctctgc cgacagtggt cccaaagatg gacccccacc cacgaggagc atcgtggaaa 480
aagaagacgt tccaaccacg tcttcaaagc aagtggattg atgtgatatc tccactgacg 540
taagggatga cgcacaatcc cactatcctt cgcaagaccc ttcctctata taaggaagtt 600
catttcattt ggagaggaat catactcttt tccttccctg gttttaacag tgaaatcact 660
atgcgaacta cgtagaagca ttatcagtgg aggatggagt ctcagggctt cctttatgca 720
tctatagagg acttccatct cggaaaggat gtcatgatcg accttattcc catgtttctt 780
catcagattc ttctgttcat ctacgacggc agacatgtac ttgttgttgc agagaaggta 840
tgcccctgcc caagtggagg tgatggaact ggtgtgttgc ccagcgaaaa gagcagcaat 900
cagaagacct gtgatctcag actctgtcgt tgcccgccca tctttgtact tggagtcaat 960
gaagcattgt aacatatcgc tctccgcctt gcctgtacgt tttctagaat ctatgatgtt 1020
tgcaaagatc tccgcgagct tcttgcgggc attgtcacga cggcgatggg ctggaatggg 1080
aaggtaggga aagattacac tgataggaag catcccattg tccaggtcat ggaagagagc 1140
agagacatcc tcaaagagtt tattgcgaac ctcttctccc aacagacatc tactagctgt 1200
cagtatgata agatgctcca gttcatactt caagtccact tcaccactat caccccattt 1260
tgagaagtac tcctcagctt ccatgaccat ctgatccaca tatcccttca atttatttac 1320
cctcaaagat tcagtaaaga acctaaattg ctcttgtctg atagtataat caacgtcaaa 1380
aaccacacca gggccaaaag taggcacatt gaactgataa acctcttgtt gactgagatc 1440
ggtttctggg gccttaaaga aatgggccga cacttctggg ccaacgaaga acgtgatatt 1500
cttgtccgtc gcttctcttc catttcttct cattttcgat tttgattctt atttctttcc 1560
agtagctcct gctctgtgaa tttctccgct cacgatagat ctgcttatac tccttacatt 1620
caaccttaga tctggtctcg attctctgtt tctctgtttt tttcttttgg tcgagaatct 1680
gatgtttgtt tatgttctgt caccattaat aataatgaac tctctcattc atacaatgat 1740
tagtttctct cgtctacaaa acgatatgtt gcattttcac ttttcttctt tttttctaag 1800

-continued

```
atgatttgct ttgaccaatt tgtttagatc tttattttat tttattttct ggtgggttgg   1860

tggaaattga aaaaaaaaaa aacagcataa attgttattt gttaatgtat tcatttttttg   1920

gctatttgtt ctgggtaaaa atctgcttct actattgaat ctttcctgga tttttttactc   1980

ctattgggtt tttatagtaa aaatacataa taaaaggaaa acaaaagttt tatagattct   2040

cttaaacccc ttacgataaa agttggaatc aaaataattc aggatcagat gctctttgat   2100

tgattcagat gcgattacag ttgcatggca aattttctag atccgtcgtc acattttatt   2160

ttctgtttaa atatctaaat ctgatatatg atgtcgacaa attctggtgg cttatacatc   2220

acttcaactg ttttcttttg gctttgtttg tcaacttggt tttcaatacg atttgtgatt   2280

tcgatcgctg aatttttaat acaagcaaac tgatgttaac cacaagcaag agatgtgacc   2340

tgccttatta acatcgtatt acttactact agtcgtattc tcaacgcaat cgtttttgta   2400

tttctcacat tatgccgctt ctctactctt tattcctttt ggtccacgca ttttctattt   2460

gtggcaatcc ctttcacaac ctgatttccc actttggatc atttgtctga agactctctt   2520

gaatcgttac cacttgtttc ttgtgcatgc tctgtttttt agaattaatg ataaaactat   2580

tccatagtct tgagttttca gcttgttgat tcttttgctt ttggttttct gcagaagaat   2640

atcacgttct tcgttggccc agaagtgtcg gcccatttct ttaaggcccc agaaaccgat   2700

ctcagtcaac aagaggttta tcagttcaat gtgcctactt ttggccctgg tgtggttttt   2760

gacgttgatt atactatcag acaagagcaa tttaggttct ttactgaatc tttgagggta   2820

aataaattga agggatatgt ggatcagatg gtcatggaag ctgaggagta cttctcaaaa   2880

tggggtgata gtggtgaagt ggacttgaag tatgaactgg agcatcttat catactgaca   2940

gctagtagat gtctgttggg agaagaggtt cgcaataaac tctttgagga tgtctctgct   3000

ctcttccatg acctggacaa tggatgcttt cctatcagtg taatctttcc ctaccttccc   3060

attccagccc atcgccgtcg tgacaatgcc cgcaagaagc tcgcggagat ctttgcaaac   3120

atcatagatt ctagaaaacg tacaggcaag gcggagagcg atatgttaca atgcttcatt   3180

gactccaagt acaaagatgg gcgggcaacg acagagtctg agatcacagg tcttctgatt   3240

gctgctcttt tcgctgggca acacaccagt tccatcacct ccacttgggc aggggcatac   3300

cttctctgca acaacaagta catgtctgcc gtcgtagatg aacagaagaa tctgatgaag   3360

aaacatggga ataaggtcga tcatgacatc ctttccgaga tggaagtcct ctatagatgc   3420

ataaaggaag ccctgagact ccatcctcca ctgataatgc ttctacgtag ttcgcatagt   3480

gatttcactg ttaaaaccag ggaaggaaaa gagtatgatg atcgttcaaa catttggcaa   3540

taaagtttct taagattgaa tcctgttgcc ggtcttgcga tgattatcat ataatttctg   3600

ttgaattacg ttaagcatgt aataattaac atgtaatgca tgacgttatt tatgagatgg   3660

gtttttatga ttagagtccc gcaattatac atttaatacg cgatagaaaa caaaatatag   3720

cgcgcaaact aggataaatt atcgcgcgcg gtgtcatcta tgttactaga tcg          3773
```

<210> SEQ ID NO 29
<211> LENGTH: 3563
<212> TYPE: DNA
<213> ORGANISM: Artificial Sequence
<220> FEATURE:
<223> OTHER INFORMATION: Artificially created chimeric nucleic acid sequence

<400> SEQUENCE: 29

```
gacggtccga tgtgagactt ttcaacaaag ggtaatatcc ggaaacctcc tcggattcca     60
```

-continued

```
ttgcccagct atctgtcact ttattgtgaa gatagtggaa aaggaaggtg gctcctacaa    120
atgccatcat tgcgataaag gaaaggccat cgttgaagat gcctctgccg acagtggtcc    180
caaagatgga cccccaccca cgaggagcat cgtggaaaaa gaagacgttc caaccacgtc    240
ttcaaagcaa gtggattgat gtgatggtcc gatgtgagac ttttcaacaa agggtaatat    300
ccggaaacct cctcggattc cattgcccag ctatctgtca ctttattgtg aagatagtgg    360
aaaaggaagg tggctcctac aaatgccatc attgcgataa aggaaaggcc atcgttgaag    420
atgcctctgc cgacagtggt cccaaagatg gacccccacc cacgaggagc atcgtggaaa    480
aagaagacgt tccaaccacg tcttcaaagc aagtggattg atgtgatatc tccactgacg    540
taagggatga cgcacaatcc cactatcctt cgcaagaccc ttcctctata taaggaagtt    600
catttcattt ggagaggacc atatattagc aaatgcccac ctttatgagc ttgtcaatag    660
gtatatatct tagaacaagg acatcaatgg caaaaatagc aagacatgaa atcaaattgt    720
gccagacaag caacacagaa aaagaaaccc tccacccaca acgccctcca aaaactgtag    780
tcaccttaat tagggcggtc atattcaatg tgtaaagttc tgtgcgaaga atcttacaga    840
tttgctagct aaagcaaaaa gctaagtgac taaactccat attactgaga gtctgaaatg    900
ggcttgcgaa ccacgaagaa gtacattggt gtgaaaatcc ctttcttggc accaccgaca    960
agaccttctg cagctttctc taagaaagct tgaacccttt gactaccttt aggagcaagt   1020
cccacgtatt caagcgccga aaccagattt ctggtgaaaa gtctgccaac tgctgttagg   1080
cggaagctac tgagcgagaa gtgactcgta tccaaaggca agtaccatgg aacaggtgag   1140
tcatcagcca gatccttgtc ccatacaact tcaaaaccag cttgtttggc tgcttcgagg   1200
cactgtgttg tcaatctaac ctcagggagg ccatttccga gctcaatttc ggccttgatc   1260
ctgttgtgct cttcgttatt ggggttgtaa gaatcggtca tgcaccactc atacacagcg   1320
aaacattgac caggcttcag cacccggtaa atctctttat agcatcccaa tggatctggt   1380
gcatggcagg tagcttctgt ccgtcgcttc tcttccattt cttctcattt tcgattttga   1440
ttcttatttc tttccagtag ctcctgctct gtgaatttct ccgctcacga tagatctgct   1500
tatactcctt acattcaacc ttagatctgg tctcgattct ctgtttctct gttttttct    1560
tttggtcgag aatctgatgt ttgtttatgt tctgtcacca ttaataataa tgaactctct   1620
cattcataca atgattagtt tctctcgtct acaaaacgat atgttgcatt ttcacttttc   1680
ttcttttttt ctaagatgat ttgctttgac caatttgttt agatctttat tttattttat   1740
tttctggtgg gttggtggaa attgaaaaaa aaaaaaacag cataaattgt tatttgttaa   1800
tgtattcatt ttttggctat ttgttctggg taaaaatctg cttctactat tgaatctttc   1860
ctggattttt tactcctatt gggtttttat agtaaaaata cataataaaa ggaaaacaaa   1920
agttttatag attctcttaa accccttacg ataaaagttg gaatcaaaat aattcaggat   1980
cagatgctct ttgattgatt cagatgcgat tacagttgca tggcaaattt tctagatccg   2040
tcgtcacatt ttattttctg tttaaatatc taaatctgat atatgatgtc gacaaattct   2100
ggtggcttat acatcacttc aactgttttc ttttggcttt gtttgtcaac ttggttttca   2160
atacgatttg tgatttcgat cgctgaattt ttaatacaag caaactgatg ttaaccacaa   2220
gcaagagatg tgacctgcct tattaacatc gtattactta ctactagtcg tattctcaac   2280
gcaatcgttt ttgtatttct cacattatgc cgcttctcta ctctttattc cttttggtcc   2340
acgcattttc tatttgtggc aatccctttc acaacctgat ttcccacttt ggatcatttg   2400
tctgaagact ctcttgaatc gttaccactt gtttcttgtg catgctctgt tttttagaat   2460
```

-continued taatgataaa actattccat agtcttgagt tttcagcttg ttgattcttt tgcttttggt 2520
tttctgcaga gaagctacct gccatgcacc agatccattg ggatgctata aagagattta 2580
ccgggtgctg aagcctggtc aatgtttcgc tgtgtatgag tggtgcatga ccgattctta 2640
caaccccaat aacgaagagc acaacaggat caaggccgaa attgagctcg gaaatggcct 2700
ccctgaggtt agattgacaa cacagtgcct cgaagcagcc aaacaagctg gttttgaagt 2760
tgtatgggac aaggatctgg ctgatgactc acctgttcca tggtacttgc ctttggatac 2820
gagtcacttc tcgctcagta gcttccgcct aacagcagtt ggcagacttt tcaccagaaa 2880
tctggtttcg gcgcttgaat acgtgggact tgctcctaaa ggtagtcaaa gggttcaagc 2940
tttcttagag aaagctgcag aaggtcttgt cggtggtgcc aagaaaggga ttttcacacc 3000
aatgtacttc ttcgtggttc gcaagcccat ttcagactct cagtaatatg gagtttagtc 3060
acttagcttt ttgctttagc tagcaaatct gtaagattct tcgcacagaa ctttacacat 3120
tgaatatgac cgccctaatt aaggtgacta cagtttttgg agggcgttgt gggtggaggg 3180
tttctttttc tgtgttgctt gtctggcaca atttgatttc atgtcttgct atttttgcca 3240
ttgatgtcct tgttctaaga tatataccta ttgacaagct cataaaggtg ggcatttgct 3300
aatatatggg atcgttcaaa catttggcaa taaagtttct taagattgaa tcctgttgcc 3360
ggtcttgcga tgattatcat ataatttctg ttgaattacg ttaagcatgt aataattaac 3420
atgtaatgca tgacgttatt tatgagatgg gtttttatga ttagagtccc gcaattatac 3480
atttaatacg cgatagaaaa caaaatatag cgcgcaaact aggataaatt atcgcgcgcg 3540
gtgtcatcta tgttactaga tcg 3563

<210> SEQ ID NO 30
<211> LENGTH: 2881
<212> TYPE: DNA
<213> ORGANISM: Artificial Sequence
<220> FEATURE:
<223> OTHER INFORMATION: Artificially created chimeric nucleic acid sequence

<400> SEQUENCE: 30
gacggtccga tgtgagactt ttcaacaaag ggtaatatcc ggaaacctcc tcggattcca 60
ttgcccagct atctgtcact ttattgtgaa gatagtggaa aaggaaggtg gctcctacaa 120
atgccatcat tgcgataaag gaaaggccat cgttgaagat gcctctgccg acagtggtcc 180
caaagatgga cccccaccca cgaggagcat cgtggaaaaa gaagacgttc caaccacgtc 240
ttcaaagcaa gtggattgat gtgatggtcc gatgtgagac ttttcaacaa agggtaatat 300
ccggaaacct cctcggattc cattgcccag ctatctgtca ctttattgtg aagatagtgg 360
aaaaggaagg tggctcctac aaatgccatc attgcgataa aggaaaggcc atcgttgaag 420
atgcctctgc cgacagtggt cccaaagatg gacccccacc cacgaggagc atcgtggaaa 480
aagaagacgt tccaaccacg tcttcaaagc aagtggattg atgtgatatc tccactgacg 540
taagggatga cgcacaatcc cactatcctt cgcaagaccc ttcctctata taaggaagtt 600
catttcattt ggagaggaac aatcctagcc caacaagccc agctacatag tgacaatatt 660
cgtcataatc atcagttgtt tccacctcct tgcatatgaa ttttgccatt cctgcaccca 720
tcctcatggt aatatcctca attgcctgct gataatgttt cctaagctcc agaaaagcag 780
ttgaaacatg atggaactgg tccatgagaa ccttgtactc ttttgtacca catgaaaaat 840
gccattcacg atcataaaca tgctgatgaa aagagatcag aataggtact ttaacatcgg 900

-continued tgggaatgct ggtatcatcc tcaacagtgt caagtgctcg aagaaccaaa tagaaaatgc 960
acacggcgtc acgaagctcg acgggaagtt gttgaatgac gagagcaaag ctacgagaaa 1020
ccttatgaag cattgagtaa cagaagcccc aatgtgggtc cgtcgcttct cttccatttc 1080
ttctcatttt cgattttgat tcttatttct ttccagtagc tcctgctctg tgaatttctc 1140
cgctcacgat agatctgctt atactcctta cattcaacct tagatctggt ctcgattctc 1200
tgtttctctg ttttttttctt ttggtcgaga atctgatgtt tgtttatgtt ctgtcaccat 1260
taataataat gaactctctc attcatacaa tgattagttt ctctcgtcta caaaacgata 1320
tgttgcattt tcacttttct tcttttttttc taagatgatt tgctttgacc aatttgttta 1380
gatctttatt ttattttatt ttctggtggg ttggtggaaa ttgaaaaaaa aaaaaaacagc 1440 ataaattgtt atttgttaat gtattcattt tttggctatt tgttctgggt aaaaatctgc 1500
ttctactatt gaatctttcc tggatttttt actcctattg ggtttttata gtaaaaatac 1560
ataataaaag gaaaacaaaa gttttataga ttctcttaaa ccccttacga taaaagttgg 1620
aatcaaaata attcaggatc agatgctctt tgattgattc agatgcgatt acagttgcat 1680
ggcaaatttt ctagatccgt cgtcacattt tattttctgt ttaaatatct aaatctgata 1740
tatgatgtcg acaaattctg gtggcttata catcacttca actgttttct tttggctttg 1800
tttgtcaact tggttttcaa tacgatttgt gatttcgatc gctgaatttt taatacaagc 1860
aaactgatgt taaccacaag caagagatgt gacctgcctt attaacatcg tattacttac 1920
tactagtcgt attctcaacg caatcgtttt tgtatttctc acattatgcc gcttctctac 1980
tctttattcc ttttggtcca cgcattttct atttgtggca atccctttca caacctgatt 2040
tcccactttg gatcatttgt ctgaagactc tcttgaatcg ttaccacttg tttcttgtgc 2100
atgctctgtt ttttagaatt aatgataaaa ctattccata gtcttgagtt ttcagcttgt 2160
tgattctttt gcttttggtt ttctgcagcc acattggggc ttctgttact caatgcttca 2220
taaggtttct cgtagctttg ctctcgtcat tcaacaactt cccgtcgagc ttcgtgacgc 2280
cgtgtgcatt ttctatttgg ttcttcgagc acttgacact gttgaggatg ataccagcat 2340
tcccaccgat gttaaagtac ctattctgat ctcttttcat cagcatgttt atgatcgtga 2400
atggcatttt tcatgtggta caaaagagta caaggttctc atggaccagt tccatcatgt 2460
ttcaactgct tttctggagc ttaggaaaca ttatcagcag gcaattgagg atattaccat 2520
gaggatgggt gcaggaatgg caaaattcat atgcaaggag gtggaaacaa ctgatgatta 2580
tgacgaatat tgtcactatg tagctgggct tgttgggcta ggattgtgat cgttcaaaca 2640
tttggcaata aagtttctta agattgaatc ctgttgccgg tcttgcgatg attatcatat 2700
aatttctgtt gaattacgtt aagcatgtaa taattaacat gtaatgcatg acgttattta 2760
tgagatgggt ttttatgatt agagtcccgc aattatacat ttaatacgcg atagaaaaca 2820
aaatatagcg cgcaaactag gataaattat cgcgcgcggt gtcatctatg ttactagatc 2880
g 2881

<210> SEQ ID NO 31
<211> LENGTH: 3703
<212> TYPE: DNA
<213> ORGANISM: Artificial Sequence
<220> FEATURE:
<223> OTHER INFORMATION: Artificially created chimeric nucleic acid sequence

<400> SEQUENCE: 31

-continued

```
gacggtccga tgtgagactt ttcaacaaag ggtaatatcc ggaaacctcc tcggattcca     60
ttgcccagct atctgtcact ttattgtgaa gatagtggaa aaggaaggtg gctcctacaa    120
atgccatcat tgcgataaag gaaaggccat cgttgaagat gcctctgccg acagtggtcc    180
caaagatgga cccccaccca cgaggagcat cgtggaaaaa gaagacgttc caaccacgtc    240
ttcaaagcaa gtggattgat gtgatggtcc gatgtgagac ttttcaacaa agggtaatat    300
ccggaaacct cctcggattc cattgcccag ctatctgtca ctttattgtg aagatagtgg    360
aaaaggaagg tggctcctac aaatgccatc attgcgataa aggaaaggcc atcgttgaag    420
atgcctctgc cgacagtggt cccaaagatg gacccccacc cacgaggagc atcgtggaaa    480
aagaagacgt tccaaccacg tcttcaaagc aagtggattg atgtgatatc tccactgacg    540
taagggatga cgcacaatcc cactatcctt cgcaagaccc ttcctctata taaggaagtt    600
catttcattt ggagaggaca tatacaaaag caaactttct gagcaaacat aaagagtttg    660
agatgccatt tctctctaaa ttacaatcta gtcacaatta acaaacaaac gaaagacagt    720
acaacagaaa agattattta aaaaaaaagg ggttatcttc cttggcgcat gaatgaaatt    780
aaccaaatgt tgaattacaa gttaacccca ctggtcacca tcccacctaa cacctttcgt    840
agatcttcac caaatatttg caggtttttt tacacgaact cagaaaaaaa tacgacccta    900
cctcctcaca tgccttcata gaaagaatac aacactacat acagatccac gtccaccctt    960
gatttgcttg tctttttctt cttgatcttt ctccacatga ctaatgcctt acactttttc   1020
aactttttgg tctacccttt acttattgct ctccctaatt ggaaaatttt attcctactt   1080
ttattgtaat ccatttcttt aataatgatg gtccataaag gatggtgatg tacacgatgt   1140
tgggataata aatttgtctt tttccttact aagaggaaat cttagtaaca tctttgctag   1200
atctattgta tttcatgtga ctcttaacca gctgccctgc tgagatagca gacatgagag   1260
ataactcacc agcaagaaca gaacctgcta ctattgtggc caagagcctt gcatttgacc   1320
ctgctgcctc cctgtttgca cctttcactc ctaataagtt caagcaagct gactgtgatg   1380
caagttgagt tccaccacca actgtgccaa cctcaataga aggcatagtt actgaaatat   1440
ggaggtcttt gccatcattt acagcctcgt ccgtcgcttc tcttccattt cttctcattt   1500
tcgattttga ttcttatttc tttccagtag ctcctgctct gtgaatttct ccgctcacga   1560
tagatctgct tatactcctt acattcaacc ttagatctgg tctcgattct ctgtttctct   1620
gttttttct tttggtcgag aatctgatgt ttgtttatgt tctgtcacca ttaataataa    1680
tgaactctct cattcataca atgattagtt tctctcgtct acaaaacgat atgttgcatt   1740
ttcactttc ttcttttttt ctaagatgat ttgctttgac caatttgttt agatctttat    1800
tttattttat tttctggtgg gttggtggaa attgaaaaaa aaaaaaacag cataaattgt   1860
tatttgttaa tgtattcatt ttttggctat ttgttctggg taaaaatctg cttctactat   1920
tgaatctttc ctggattttt tactcctatt gggtttttat agtaaaaata cataataaaa   1980
ggaaaacaaa agttttatag attctcttaa accccttacg ataaaagttg gaatcaaaat   2040
aattcaggat cagatgctct ttgattgatt cagatgcgat tacagttgca tggcaaattt   2100
tctagatccg tcgtcacatt ttattttctg tttaaatatc taaatctgat atatgatgtc   2160
gacaaattct ggtggcttat acatcacttc aactgttttc ttttggcttt gtttgtcaac   2220
ttggttttca atacgatttg tgatttcgat cgctgaattt ttaatacaag caaactgatg   2280
ttaaccacaa gcaagagatg tgacctgcct tattaacatc gtattactta ctactagtcg   2340
```

-continued

```
tattctcaac gcaatcgttt ttgtatttct cacattatgc cgcttctcta ctctttattc   2400

cttttggtcc acgcattttc tatttgtggc aatccctttc acaacctgat ttcccacttt   2460

ggatcatttg tctgaagact ctcttgaatc gttaccactt gtttcttgtg catgctctgt   2520

tttttagaat taatgataaa actattccat agtcttgagt tttcagcttg ttgattcttt   2580

tgcttttggt tttctgcagg aggctgtaaa tgatggcaaa gacctccata tttcagtaac   2640

tatgccttct attgaggttg gcacagttgg tggtggaact caacttgcat cacagtcagc   2700

ttgcttgaac ttattaggag tgaaaggtgc aaacagggag gcagcagggt caaatgcaag   2760

gctcttggcc acaatagtag caggttctgt tcttgctggt gagttatctc tcatgtctgc   2820

tatctcagca gggcagctgg ttaagagtca catgaaatac aatagatcta gcaaagatgt   2880

tactaagatt tcctcttagt aaggaaaaag acaaatttat tatcccaaca tcgtgtacat   2940

caccatcctt tatggaccat cattattaaa gaaatggatt acaataaaag taggaataaa   3000

attttccaat tagggagagc aataagtaaa gggtagacca aaaagttgaa aaagtgtaag   3060

gcattagtca tgtggagaaa gatcaagaag aaaaagacaa gcaaatcaag ggtggacgtg   3120

gatctgtatg tagtgttgta ttctttctat gaaggcatgt gaggaggtag ggtcgtattt   3180

ttttctgagt tcgtgtaaaa aaacctgcaa atatttggtg aagatctacg aaaggtgtta   3240

ggtgggatgg tgaccagtgg ggttaacttg taattcaaca tttggttaat ttcattcatg   3300

cgccaaggaa gataacccct tttttttttaa ataatctttt ctgttgtact gtctttcgtt   3360

tgtttgttaa ttgtgactag attgtaattt agagagaaat ggcatctcaa actctttatg   3420

tttgctcaga aagtttgctt ttgtatatgg atcgttcaaa catttggcaa taaagtttct   3480

taagattgaa tcctgttgcc ggtcttgcga tgattatcat ataatttctg ttgaattacg   3540

ttaagcatgt aataattaac atgtaatgca tgacgttatt tatgagatgg gtttttatga   3600

ttagagtccc gcaattatac atttaatacg cgatagaaaa caaaatatag cgcgcaaact   3660

aggataaatt atcgcgcgcg gtgtcatcta tgttactaga tcg                     3703
```

<210> SEQ ID NO 32
<211> LENGTH: 4286
<212> TYPE: DNA
<213> ORGANISM: Artificial Sequence
<220> FEATURE:
<223> OTHER INFORMATION: Artificially created chimeric nucleic acid sequence

<400> SEQUENCE: 32

```
ttctgttcgt atatttgtaa ctattatgtg tatttttatt ttgttagtat tactaattca     60

agtggtttaa gttgttgaga ctctttaaaa tctaagcatt ttataaacaa taatatataa    120

ttattgttta ggctaaattt gtcactaatt aaggtttgga tacatagtgt ctaaactaag    180

ctaataatat cacttaacgt ttacttgtaa cgctaggtga tgatgtcgtc aagtcaattg    240

gtacaaggaa taaacgagtg gtcatatgac attatgacca tatgaattca aactccagta    300

atccaatggt aattggattc aatgatcaag acttgaacca cgtaatccac ccttatcctt    360

agaagctcat aaatatcact aaagggacag gcaacactta accagtagtt gtccaataat    420

ttagttttcc aaaatgaaaa attattgttg tcatctattt taggtgtttt agttcaatgt    480

ggattcctcg tcctaacaaa tacttgacga atatatctag actataaaat tggttatgag    540

ttctactttt ttttgtttgt gaaattatca aaatttgtta tatttattta tttattctca    600

ttaatttgag tactaatttt taaattattt atactaaaaa caattactaa gatacaaaaa    660
```

-continued

```
tggataagag catggtgtat agatatttaa tgggatagaa tatttcccat aattgtatgt    720
gtgtgagagg ttttgttttc gtaaggaaag aaacaaaaac catttgacca aagaaaagca    780
aaagaaggca aggaatcaaa caacaaatgt tgcaaggcag aaataatgga cgttatgtta    840
atgtagtgtc gtcacacgtg acttaaaaga gacgagtctg cgtgtcaaac taaaaatgta    900
tgcaactata aaaatgggat ttgattatct ttttagtacc gaagcctacc aaccacatgc    960
acactaattc tactcgccaa ataaagtgaa aagagccata tattagcaaa tgcccacctt   1020
tatgagcttg tcaataggta tatatcttag aacaaggaca tcaatggcaa aaatagcaag   1080
acatgaaatc aaattgtgcc agacaagcaa cacagaaaaa gaaaccctcc acccacaacg   1140
ccctccaaaa actgtagtca ccttaattag ggcggtcata ttcaatgtgt aaagttctgt   1200
gcgaagaatc ttacagattt gctagctaaa gcaaaaagct aagtgactaa actccatatt   1260
actgagagtc tgaaatgggc ttgcgaacca cgaagaagta cattggtgtg aaaatccctt   1320
tcttggcacc accgacaaga ccttctgcag ctttctctaa gaaagcttga accctttgac   1380
tacctttagg agcaagtccc acgtattcaa gcgccgaaac cagatttctg gtgaaaagtc   1440
tgccaactgc tgttaggcgg aagctactga gcgagaagtg actcgtatcc aaaggcaagt   1500
accatggaac aggtgagtca tcagccagat ccttgtccca tacaacttca aaaccagctt   1560
gtttggctgc ttcgaggcac tgtgttgtca atctaacctc agggaggcca tttccgagct   1620
caatttcggc cttgatcctg ttgtgctctt cgttattggg gttgtaagaa tcggtcatgc   1680
accactcata cacagcgaaa cattgaccag gcttcagcac ccggtaaatc tctttatagc   1740
atcccaatgg atctggtgca tggcaggtag cttctgtaag ttcctgtttt cacctgcacc   1800
atgaaaaata tactattact attatttttc atttatttgt gtggtccata ttgctatgtg   1860
tgaaatgaaa aaatattttt tttctcaaac tacaatattg tcagaaagaa aggaattaat   1920
attccgaatt tataccaaaa aattaatttc ttttttctct ttggtaagct ggattctgtt   1980
attctttggt aaaacggaga ataattttgt ttatcaactt ctgttgattt tatgaacaat   2040
tctcaattaa ttgaaggggt agtttaaggc tgatgaatct tttggatgag ttacttgagc   2100
agtatggatt gactcacatg actaactgct tcactagctt ccaatatttt ttagttatta   2160
catgttgtgt atgttgatta ttgtgctcta agcaatcgga ttctcttgtt aaataaaaac   2220
tatcatagtt tatttattca ataatcgagt ttgagctaac actcctgtct atctggaata   2280
caaaaggaaa gataataaaa gtttttggta ccttgaaaac tagaagtatc aggaagggga   2340
gccttgaaca aaggtcaagt tgtctccgtt tgacctacat gtcatgttcg agccattgat   2400
gcttgcatca ggatagactg cctacatcac cccctcttgc ggtacggccc ttccccggac   2460
ctgcgtgaac gcgggatact ttgtgcaccg gaaaactaca agtatcccta acacatatca   2520
ggattttagt gatatccctt cactgccgtg ttcgataaag gttacataaa gttttaaatt   2580
tatgggtgct aaatatcaca gctaaatata cacattaaag atattactgc atccatatat   2640
gttgccatga ccatacatca agtatacatc cacccctaat ttttgagtgt ttttgagatg   2700
cagcaaagtt gaaggagatt ataatagttt gatgtggaga gactaatttt ttttttaaca   2760
tcactttcta agggtgctat cttttcacca ccatcactgg tggcttgttg atttgtagct   2820
aatcattatc ttttgatgaa aacaaggaca ttctttagtg cactaagatt gttaaacgtt   2880
cgtgcttcat tgtaaatgta atatactcgc gcttgttggc atgaacactt ggaattgttt   2940
actggaacac tgcagagaag ctacctgcca tgcaccagat ccattgggat gctataaaga   3000
gatttaccgg gtgctgaagc ctggtcaatg tttcgctgtg tatgagtggt gcatgaccga   3060
```

-continued

```
ttcttacaac cccaataacg aagagcacaa caggatcaag gccgaaattg agctcggaaa   3120

tggcctccct gaggttagat tgacaacaca gtgcctcgaa gcagccaaac aagctggttt   3180

tgaagttgta tgggacaagg atctggctga tgactcacct gttccatggt acttgccttt   3240

ggatacgagt cacttctcgc tcagtagctt ccgcctaaca gcagttggca gacttttcac   3300

cagaaatctg gtttcggcgc ttgaatacgt gggacttgct cctaaaggta gtcaaagggt   3360

tcaagctttc ttagagaaag ctgcagaagg tcttgtcggt ggtgccaaga aagggatttt   3420

cacaccaatg tacttcttcg tggttcgcaa gcccatttca gactctcagt aatatggagt   3480

ttagtcactt agctttttgc tttagctagc aaatctgtaa gattcttcgc acagaacttt   3540

acacattgaa tatgaccgcc ctaattaagg tgactacagt tttggaggg cgttgtgggt   3600

ggagggtttc tttttctgtg ttgcttgtct ggcacaattt gatttcatgt cttgctattt   3660

ttgccattga tgtccttgtt ctaagatata tacctattga caagctcata aaggtgggca   3720

tttgctaata tatggtttcc ctttgctttt gtgtaaacct caaaacttta tcccccatct   3780

ttgattttat cccttgtttt tctgcttttt tcttctttct tgggttttaa tttccggact   3840

taacgtttgt tttccggttt gcgagacata ttctatcgga ttctcaactg tctgatgaaa   3900

taaatatgta atgttctata agtctttcaa tttgatatgc atatcaacaa aaagaaaata   3960

ggacaatgcg gctacaaata tgaaatttac aagtttaaga accatgagtc gctaaagaaa   4020

tcattaagaa aattagtttc acattcaatt cttgtcacat gattaacgag cttgagaggt   4080

ttagagtaac aatatcttga agcaaaagat gacccacttg aaatctagtg atggatacat   4140

aagtggacgt gccttgttta ggataggatt ctggataaga gtctcgaata ttcattttta   4200

ccaagtatat tcaaggatct tgtggatcat atatttcctc aatcaaaggg acttgaccca   4260

aattcacata aagatatttt ggagtc                                       4286
```

```
<210> SEQ ID NO 33
<211> LENGTH: 8956
<212> TYPE: DNA
<213> ORGANISM: Artificial Sequence
<220> FEATURE:
<223> OTHER INFORMATION: Artificially created chimeric nucleic acid
      sequence

<400> SEQUENCE: 33

ctcgaggatc taaattgtga gttcaatctc ttccctattg gattgattat cctttctttt     60

cttccaattt gtgtttcttt ttgcctaatt tattgtgtta tcccctttat cctattttgt    120

ttctttactt atttatttgc ttctatgtct ttgtacaaag atttaaactc tatggcacat    180

attttaaagt tgttagaaaa taaattcttt caagattgat gaaagaactt tttaattgta    240

gatatttcgt agattttatt ctcttactac caatataacg cttgaattga cgaaaatttg    300

tgtccaaata tctagcaaaa aggtatccaa tgaaaatata tcatatgtga tcttcaaatc    360

ttgtgtctta tgcaagattg atactttgtt caatggaaga gattgtgtgc atatttttaa    420

aatttttatt agtaataaag attctatata gctgttatag agggataatt ttacaaagaa    480

cactataaat atgattgttg ttgttagggt gtcaatggtt cggttcgact ggttatttta    540

taaaatttgt accataccat ttttttcgat attctatttt gtataaccaa aattagactt    600

ttcgaaatcg tcccaatcat gtcggtttca cttcggtatc ggtaccgttc ggttaatttt    660

catttttttt taaatgtcat taaaattcac tagtaaaaat agaatgcaat aacatacgtt    720

cttttatagg acttagcaaa agctctctag acatttttac tgtttaaagg ataatgaatt    780
```

-continued

```
aaaaaacatg aaagatggct agagtataga tacacaacta ttcgacagca acgtaaaaga    840
aaccaagtaa aagcaaagaa aatataaatc acacgagtgg aaagatatta accaagttgg    900
gattcaagaa taaagtctat attaaatatt caaaaagata aatttaaata atatgaaagg    960
aaacatattc aatacattgt agtttgctac tcataatcgc tagaatactt tgtgccttgc   1020
taataaagat acttgaaata gcttagttta aatataaata gcataataga ttttaggaat   1080
tagtattttg agtttaatta cttattgact tgtaacagtt tttataattc caaggcccat   1140
gaaaaattta atgctttatt agttttaaac ttactatata aatttttcat atgtaaaatt   1200
taatcggtat agttcgatat tttttcaatt tattttata aaataaaaaa cttaccctaa    1260
ttatcggtac agttatagat ttatataaaa atctacggtt cttcagaaga aacctaaaaa   1320
tcggttcggt gcggacggtt cgatcggttt agtcgatttt caaatattca ttgacactcc   1380
tagttgttgt tataggtaaa aagcagttac agagaggtaa aatataactt aaaaaatcag   1440
ttctaaggaa aaattgactt ttatagtaaa tgactgttat ataaggatgt tgttacagag   1500
aggtatgagt gtagttggta aattatgttc ttgacggtgt atgtcacata ttatttatta   1560
aaactagaaa aaacagcgtc aaaactagca aaaatccaac ggacaaaaaa atcggctgaa   1620
tttgatttgg ttccaacatt taaaaaagtt tcagtgagaa agaatcggtg actgttgatg   1680
atataaacaa agggcacatt ggtcaataac cataaaaaat tatatgacag ctacagttgg   1740
tagcatgtgc tcagctattg aacaaatcta aagaaggtac atctgtaacc ggaacaccac   1800
ttaaatgact aaattaccct catcagaaag cagatggagt gctacaaata acacactatt   1860
caacaaccat aaataaaacg tgttcagcta ctaaaacaaa tataaataaa tctatgtttg   1920
taagcactcc agccatgtta atggagtgct attgcctgtt aactctcact tataaaatag   1980
tagtagaaaa aatatgaacc aaaacacaac ggttgtgtat ttcacttttg gatatagctc   2040
agtggcttcg acacctgtag gaggctgaac ctcaaagttt gcagaatctc cattaacaaa   2100
aactgaatgg catatggcca aattagtcct taatggcaga ggtccctctt gtacaatctg   2160
gagaatatct tcctctgata gatataactt ctcgagggtc ttcccaattt tgtcctccca   2220
caaggacact atctcgttga aggatagaat attggcaggt ggtctcatgt gaagagtctt   2280
attcaatgtc cgtggatcat ctactgcttc gatagtgtat gtcgctatgt cttcttcctt   2340
cacatatatt gctttgggat ttccatcgcc aaaaatgaca actttgtctc taggaggggt   2400
tttggcctct aactgcccca agttgggcaa gaagaaatct gcaaaccaat tgcagattac   2460
atatgtgtat ggaattcctt ctgcctctat catcctcctg attcttacct ttagagcgaa   2520
gagtgatgca gctggttcaa ttgcacgagc atgatccaca tcaaatccaa attctgaagg   2580
aagaaatctc ttgatatttc cagcttcttt aattgctttg atgatgttca cttgatcagt   2640
ccgtcgcttc tcttccattt cttctcattt tcgattttga ttcttatttc tttccagtag   2700
ctcctgctct gtgaatttct ccgctcacga tagatctgct tatactcctt acattcaacc   2760
ttagatctgg tctcgattct ctgtttctct gttttttttct tttggtcgag aatctgatgt   2820
ttgtttatgt tctgtcacca ttaataataa tgaactctct cattcataca atgattagtt   2880
tctctcgtct acaaaacgat atgttgcatt ttcacttttc ttctttttttt ctaagatgat   2940
ttgctttgac caatttgttt agatctttat tttattttat tttctggtgg gttggtggaa   3000
attgaaaaaa aaaaaaacag cataaattgt tatttgttaa tgtattcatt ttttggctat   3060
ttgttctggg taaaaatctg cttctactat tgaatctttc ctggattttt tactcctatt   3120
```

-continued

```
gggtttttat agtaaaaata cataataaaa ggaaaacaaa agttttatag attctcttaa   3180
acccccttacg ataaaagttg gaatcaaaat aattcaggat cagatgctct ttgattgatt   3240
cagatgcgat tacagttgca tggcaaattt tctagatccg tcgtcacatt ttattttctg   3300
tttaaatatc taaatctgat atatgatgtc gacaaattct ggtggcttat acatcacttc   3360
aactgttttc ttttggcttt gtttgtcaac ttggttttca atacgatttg tgatttcgat   3420
cgctgaattt ttaatacaag caaactgatg ttaaccacaa gcaagagatg tgacctgcct   3480
tattaacatc gtattactta ctactagtcg tattctcaac gcaatcgttt ttgtatttct   3540
cacattatgc cgcttctcta ctctttattc cttttggtcc acgcattttc tatttgtggc   3600
aatccctttc acaacctgat ttcccacttt ggatcatttg tctgaagact ctcttgaatc   3660
gttaccactt gtttcttgtg catgctctgt tttttagaat taatgataaa actattccat   3720
agtcttgagt tttcagcttg ttgattcttt tgcttttggt tttctgcagt gatcaagtga   3780
acatcatcaa agcaattaaa gaagctggaa atatcaagag atttcttcct tcagaatttg   3840
gatttgatgt ggatcatgct cgtgcaattg aaccagctgc atcactcttc gctctaaagg   3900
taagaatcag gaggatgata gaggcagaag gaattccata cacatatgta atctgcaatt   3960
ggtttgcaga tttcttcttg cccaacttgg ggcagttaga ggccaaaacc cctcctagag   4020
acaaagttgt catttttggc gatggaaatc ccaaagcaat atatgtgaag gaagaagaca   4080
tagcgacata cactatcgaa gcagtagatg atccacggac attgaataag actcttcaca   4140
tgagaccacc tgccaatatt ctatccttca acgagatagt gtccttgtgg gaggacaaaa   4200
ttgggaagac cctcgagaag ttatatctat cagaggaaga tattctccag attgtacaag   4260
agggacctct gccattaagg actaatttgg ccatatgcca ttcagttttt gttaatggag   4320
attctgcaaa ctttgaggtt cagcctccta caggtgtcga agccactgag ctatatccaa   4380
aagtgaaata cacaaccgca agtgtgttgc ctttgtgtgg aaatgaagag gtacttgcga   4440
ggactttgcg tttatcagtt tatgtgtttg tatatctatt tgatccagtt attatggatt   4500
atatacgctt gaaactcatt ttaagccatt gttattgaac gtttatcaaa tactttatta   4560
tgccaagcaa gtcaaacaca tgcttgttga ttgaaatcaa gctatagaaa tctcttcttc   4620
acatacagca gtttagattc acaatacaac aagcgaaacg ataaagtttc ttctgttcgt   4680
atatttgtaa ctattatgtg tatttttatt ttgttagtat tactaattca agtggtttaa   4740
gttgttgaga ctctttaaaa tctaagcatt tttataaacaa taatatataa ttattgttta   4800
ggctaaattt gtcactaatt aaggtttgga tacatagtgt ctaaactaag ctaataatat   4860
cacttaacgt ttacttgtaa cgctaggtga tgatgtcgtc aagtcaattg gtacaaggaa   4920
taaacgagtg gtcatatgac attatgacca tatgaattca aactccagta atccaatggt   4980
aattggattc aatgatcaag acttgaacca cgtaatccac ccttatcctt agaagctcat   5040
aaatatcact aaagggacag gcaacactta accagtagtt gtccaataat ttagttttcc   5100
aaaatgaaaa attattgttg tcatctattt taggtgtttt agttcaatgt ggattcctcg   5160
tcctaacaaa tacttgacga atatatctag actataaaat tggttatgag ttctactttt   5220
ttttgtttgt gaaattatca aaatttgtta tatttattta tttattctca ttaatttgag   5280
tactaatttt taaattattt atactaaaaa caattactaa gatacaaaaa tggataagag   5340
catggtgtat agatatttaa tgggatagaa tatttcccat aattgtatgt gtgtgagagg   5400
ttttgttttc gtaaggaaag aaacaaaaac catttgacca aagaaaagca aaagaaggca   5460
aggaatcaaa caacaaatgt tgcaaggcag aaataatgga cgttatgtta atgtagtgtc   5520
```

-continued

```
gtcacacgtg acttaaaaga gacgagtctg cgtgtcaaac taaaaatgta tgcaactata   5580
aaaatgggat ttgattatct ttttagtacc gaagcctacc aaccacatgc acactaattc   5640
tactcgccaa ataaagtgaa aagagccata tattagcaaa tgcccacctt tatgagcttg   5700
tcaataggta tatatcttag aacaaggaca tcaatggcaa aaatagcaag acatgaaatc   5760
aaattgtgcc agacaagcaa cacagaaaaa gaaaccctcc acccacaacg ccctccaaaa   5820
actgtagtca ccttaattag ggcggtcata ttcaatgtgt aaagttctgt gcgaagaatc   5880
ttacagattt gctagctaaa gcaaaaagct aagtgactaa actccatatt actgagagtc   5940
tgaaatgggc ttgcgaacca cgaagaagta cattggtgtg aaaatccctt tcttggcacc   6000
accgacaaga ccttctgcag ctttctctaa gaaagcttga accctttgac tacctttagg   6060
agcaagtccc acgtattcaa gcgccgaaac cagatttctg gtgaaaagtc tgccaactgc   6120
tgttaggcgg aagctactga gcgagaagtg actcgtatcc aaaggcaagt accatggaac   6180
aggtgagtca tcagccagat ccttgtccca tacaacttca aaccagctt gtttggctgc   6240
ttcgaggcac tgtgttgtca atctaacctc agggaggcca tttccgagct caatttcggc   6300
cttgatcctg ttgtgctctt cgttattggg gttgtaagaa tcggtcatgc accactcata   6360
cacagcgaaa cattgaccag gcttcagcac ccggtaaatc tctttatagc atcccaatgg   6420
atctggtgca tggcaggtag cttctgtaag ttcctgtttt cacctgcacc atgaaaaata   6480
tactattact attattttc atttatttgt gtggtccata ttgctatgtg tgaaatgaaa   6540
aaatattttt tttctcaaac tacaatattg tcagaaagaa aggaattaat attccgaatt   6600
tataccaaaa aattaatttc ttttttctct ttggtaagct ggattctgtt attctttggt   6660
aaaacggaga ataattttgt ttatcaactt ctgttgattt tatgaacaat tctcaattaa   6720
ttgaaggggt agtttaaggc tgatgaatct tttggatgag ttacttgagc agtatggatt   6780
gactcacatg actaactgct tcactagctt ccaatatttt ttagttatta catgttgtgt   6840
atgttgatta ttgtgctcta agcaatcgga ttctcttgtt aaataaaaac tatcatagtt   6900
tatttattca ataatcgagt ttgagctaac actcctgtct atctggaata caaaaggaaa   6960
gataataaaa gtttttggta ccttgaaaac tagaagtatc aggaagggga gccttgaaca   7020
aaggtcaagt tgtctccgtt tgacctacat gtcatgttcg agccattgat gcttgcatca   7080
ggatagactg cctacatcac cccctcttgc ggtacggccc ttccccggac ctgcgtgaac   7140
gcgggatact ttgtgcaccg gaaaactaca agtatcccta acacatatca ggattttagt   7200
gatatccctt cactgccgtg ttcgataaag gttacataaa gttttaaatt tatgggtgct   7260
aaatatcaca gctaaatata cacattaaag atattactgc atccatatat gttgccatga   7320
ccatacatca agtatacatc cacccctaat ttttgagtgt ttttgagatg cagcaaagtt   7380
gaaggagatt ataatagttt gatgtggaga gactaatttt ttttttaaca tcactttcta   7440
agggtgctat cttttcacca ccatcactgg tggcttgttg atttgtagct aatcattatc   7500
ttttgatgaa aacaaggaca ttctttagtg cactaagatt gttaaacgtt cgtgcttcat   7560
tgtaaatgta atatactcgc gcttgttggc atgaacactt ggaattgttt actggaacac   7620
tgcagagaag ctacctgcca tgcaccagat ccattgggat gctataaaga gatttaccgg   7680
gtgctgaagc ctggtcaatg tttcgctgtg tatgagtggt gcatgaccga ttcttacaac   7740
cccaataacg aagagcacaa caggatcaag gccgaaattg agctcggaaa tggcctccct   7800
gaggttagat tgacaacaca gtgcctcgaa gcagccaaac aagctggttt tgaagttgta   7860
```

-continued

```
tgggacaagg atctggctga tgactcacct gttccatggt acttgccttt ggatacgagt   7920

cacttctcgc tcagtagctt ccgcctaaca gcagttggca gacttttcac cagaaatctg   7980

gtttcggcgc ttgaatacgt gggacttgct cctaaaggta gtcaaagggt tcaagctttc   8040

ttagagaaag ctgcagaagg tcttgtcggt ggtgccaaga aagggatttt cacaccaatg   8100

tacttcttcg tggttcgcaa gcccatttca gactctcagt aatatggagt ttagtcactt   8160

agctttttgc tttagctagc aaatctgtaa gattcttcgc acagaacttt acacattgaa   8220

tatgaccgcc ctaattaagg tgactacagt tttggaggg cgttgtgggt ggagggtttc    8280

tttttctgtg ttgcttgtct ggcacaattt gatttcatgt cttgctattt ttgccattga   8340

tgtccttgtt ctaagatata tacctattga caagctcata aaggtgggca tttgctaata   8400

tatggtttcc ctttgctttt gtgtaaacct caaaacttta tcccccatct ttgattttat   8460

cccttgtttt tctgcttttt tcttctttct tgggttttaa tttccggact taacgtttgt   8520

tttccggttt gcgagacata ttctatcgga ttctcaactg tctgatgaaa taaatatgta   8580

atgttctata agtctttcaa tttgatatgc atatcaacaa aaagaaaata ggacaatgcg   8640

gctacaaata tgaaatttac aagtttaaga accatgagtc gctaaagaaa tcattaagaa   8700

aattagtttc acattcaatt cttgtcacat gattaacgag cttgagaggt ttagagtaac   8760

aatatcttga agcaaaagat gacccacttg aaatctagtg atggatacat aagtggacgt   8820

gccttgttta ggataggatt ctggataaga gtctcgaata ttcattttta ccaagtatat   8880

tcaaggatct tgtggatcat atatttcctc aatcaaaggg acttgaccca aattcacata   8940

aagatatttt ggagtc                                                   8956
```

<210> SEQ ID NO 34
<211> LENGTH: 3600
<212> TYPE: DNA
<213> ORGANISM: Artificial Sequence
<220> FEATURE:
<223> OTHER INFORMATION: Artificially created chimeric nucleic acid sequence

<400> SEQUENCE: 34

```
tctagaatgt tcgtgcgtca aatggataaa caaaaaaata gcataagtta gttttgttac     60

tcgagagtta tgtattataa ggtataggga aatgactcaa acataccact gaacttaacg    120

aaacgacgca tatatatact acttaactta acgaaaaagg ggtgagagtg gatgggtgct    180

ggtaaataat gaagggttta tataacgtca cgtgtcaaaa ttcgatagta gtagtttcgt    240

tagttgtaat agcatatatg gcccaaagtt ataatataga taatatgttt atgtccaact    300

attaacgagt gacatagaca gttcattttg tgaagttcaa tgacatattt gagccctttc    360

ccttttatta tctcctttta tttgttctaa taaaagaatg gcatttatta tgtacataga    420

caaataacta ttttctttgg aatataattt gtttatatat tttaaaatca tgtctcaatt    480

tagtttgttt tgtgcatatt tcaactattc aattttgtcc atatatttat taccttcccc    540

catttacaag cattgaaccg ctttgctcac caaaacttat gcacattgca aaaatatcat    600

gtaaaggttt tatgtatgct gtaattaagg tctgaactca tcgtgatttt atttttaggc    660

ttcattgacc actaccaaac tctttgatgc tacattttct aattatattg gagttcgatt    720

atatccgaat tcgcgttgcg tagggcccat tcgagggaaa acactcccta tcaaggattt    780

tttcataccc agagctcgaa ctcaagacat ctggttaagg gaagaacagt ctcatccact    840

gcaccatatc cttttgtggt caacaagtaa attttatgta gaaccaaaaa ctatactcga    900
```

-continued

```
attgataaaa taaatggtgt aaaatattgt tttctttctt acattttgga cagtaaatat    960
gtaggacaat aataattagc gtggggtctt aagaaaatta gcatagattt ccagaaattc   1020
caaatcaacc ggcagttcca ggtttgaaaa ctacaactca ttccgacggt tcaaacttca   1080
aaccatgctt gctgactcgg cttcttcttt ctttttcacc aagacagagc agtagtcacg   1140
tgacacccct cacgtgcctc ccccctttat atttcagact gcaaccctac actttcgcta   1200
cattcactac catattcttt tcactaagca attttctctc ctacttttct ttaaacccct   1260
tttttctccc ctaagccatg gcatctagat catgttacgt cctgtagaaa ccccaacccg   1320
tgaaatcaaa aaactcgacg gcctgtgggc attcagtctg gatcgcgaaa actgtggaat   1380
tgatcagcgt tggtgggaaa gcgcgttaca agaaagccgg gcaattgctg tgccaggcag   1440
ttttaacgat cagttcgccg atgcagatat tcgtaattat gcgggcaacg tctggtatca   1500
gcgcgaagtc tttataccga aaggttgggc aggccagcgt atcgtgctgc gtttcgatgc   1560
ggtcactcat tacggcaaag tgtgggtcaa taatcaggaa gtgatggagc atcagggcgg   1620
ctatacgcca tttgaagccg atgtcacgcc gtatgttatt gccgggaaaa gtgtacgtat   1680
caccgtttgt gtgaacaacg aactgaactg gcagactatc ccgccgggaa tggtgattac   1740
cgacgaaaac ggcaagaaaa agcagtctta cttccatgat ttctttaact atgccggaat   1800
ccatcgcagc gtaatgctct acaccacgcc gaacacctgg gtggacgata tcaccgtggt   1860
gacgcatgtc gcgcaagact gtaaccacgc gtctgttgac tggcaggtgg tggccaatgg   1920
tgatgtcagc gttgaactgc gtgatgcgga tcaacaggtg gttgcaactg gacaaggcac   1980
tagcgggact ttgcaagtgg tgaatccgca cctctggcaa ccgggtgaag gttatctcta   2040
tgaactgtgc gtcacagcca aaagccagac agagtgtgat atctacccgc ttcgcgtcgg   2100
catccggtca gtggcagtga agggcgaaca gttcctgatt aaccacaaac cgttctactt   2160
tactggcttt ggtcgtcatg aagatgcgga cttgcgtggc aaaggattcg ataacgtgct   2220
gatggtgcac gaccacgcat taatggactg gattggggcc aactcctacc gtacctcgca   2280
ttacccttac gctgaagaga tgctcgactg ggcagatgaa catggcatcg tggtgattga   2340
tgaaactgct gctgtcggct ttaacctctc tttaggcatt ggtttcgaag cgggcaacaa   2400
gccgaaagaa ctgtacagcg aagaggcagt caacggggaa actcagcaag cgcacttaca   2460
ggcgattaaa gagctgatag cgcgtgacaa aaaccaccca agcgtggtga tgtggagtat   2520
tgccaacgaa ccggataccc gtccgcaagg tgcacgggaa tatttcgcgc cactggcgga   2580
agcaacgcgt aaactcgacc cgacgcgtcc gatcacctgc gtcaatgtaa tgttctgcga   2640
cgctcacacc gataccatca gcgatctctt tgatgtgctg tgcctgaacc gttattacgg   2700
atggtatgtc caaagcggcg atttggaaac ggcagagaag gtactggaaa aagaacttct   2760
ggcctggcag gagaaactgc atcagccgat tatcatcacc gaatacggcg tggatacgtt   2820
agccgggctg cactcaatgt acaccgacat gtggagtgaa gagtatcagt gtgcatggct   2880
ggatatgtat caccgcgtct ttgatcgcgt cagcgccgtc gtcggtgaac aggtatggaa   2940
tttcgccgat tttgcgacct cgcaaggcat attgcgcgtt ggcggtaaca agaaagggat   3000
cttcactcgc gaccgcaaac cgaagtcggc ggcttttctg ctgcaaaaac gctggactgg   3060
catgaacttc ggtgaaaaac cgcagcaggg aggcaaacaa tgagagctcg tgaaatggcc   3120
tctttagttt ttgattgaat cataggggta ttagttttct atggccggga gtggtcttct   3180
tgcttaattg taatggaata accagagagg aactactgtg ttatctttga ggaatgttgg   3240
gctttttttcg tttgaattat catgaatgaa attttacttt ttcccaatac aagtttgttt   3300
```

tcgtttcttg gtttttgtta tcccttggtt tatgtcttgg tttggcttaa atgattgaag 3360
attacactac ctatgtttct gctattcctg ttgaagatca catttgataa taatgcatcg 3420
aatgcattaa agtttcttat tggctctgtc aaaagtattg aaggtggatt tttctaattg 3480
gcaagagaaa gtattaaaga ggtgatttat tagtacttat atttttctca gcatctctct 3540
ttcagtgttg gagcttcata aaattagcac ttcagagttt cagtcgggag ctgaattcga 3600

<210> SEQ ID NO 35
<211> LENGTH: 3387
<212> TYPE: DNA
<213> ORGANISM: Artificial Sequence
<220> FEATURE:
<223> OTHER INFORMATION: Artificially created chimeric nucleic acid sequence

<400> SEQUENCE: 35
cgttttgacg agttcggatg tagtagtagc cattatttaa tgtacatact aatcgtgaat 60
agtgaatatg atgaaacatt gtatcttatt gtataaatat ccataaacac atcatgaaag 120
acactttctt tcacggtctg aattaattat gatacaattc taatagaaaa cgaattaaat 180
tacgttgaat tgtatgaaat ctaattgaac aagccaacca cgacgacgac taacgttgcc 240
tggattgact cggtttaagt taaccactaa aaaaacggag ctgtcatgta acacgcggat 300
cgagcaggtc acagtcatga agccatcaaa gcaaaagaac taatccaagg gctgagatga 360
ttaattagtt taaaaattag ttaacacgag ggaaaaggct gtctgacagc caggtcacgt 420
tatctttacc tgtggtcgaa atgattcgtg tctgtcgatt ttaattattt ttttgaaagg 480
ccgaaaataa agttgtaaga gataaacccg cctatataaa ttcatatatt ttctctccgc 540
tttgaattgt ctcgttgtcc tcctcacttt catcggccgt ttttgaatct ccggcgactt 600
gacagagaag aacaaggaag aagactaaga gagaaagtaa gagataatcc aggagattca 660
ttctccgttt tgaatcttcc tcaatctcat cttcttccgc tctttctttc caaggtaata 720
ggaactttct ggatctactt tatttgctgg atctcgatct tgttttctca atttccttga 780
gatctggaat tcgtttaatt tggatctgtg aacctccact aaatcttttg gttttactag 840
aatcgatcta agttgaccga tcagttagct cgattatagc taccagaatt tggcttgacc 900
ttgatggaga gatccatgtt catgttacct gggaaatgat ttgtatatgt gaattgaaat 960
ctgaactgtt gaagttagat tgaatctgaa cactgtcaat gttagattga atctgaacac 1020
tgtttaagtt agatgaagtt tgtgtataga ttcttcgaaa ctttaggatt tgtagtgtcg 1080
tacgttgaac agaaagctat ttctgattca atcagggttt atttgactgt attgaactct 1140
ttttgtgtgt ttgcagctca tatggttgtg tttgggaatg tttctgcggc gaatttgcct 1200
tatcaaaacg ggtttttgga ggcactttca tctggaggtt gtgaactaat gggacatagc 1260
tttagggttc ccacttctca agcgcttaag acaagaacaa ggaggaggag tactgctggt 1320
cctttgcagg tagtttgtgt ggatattcca aggccagagc tagagaacac tgtcaatttc 1380
ttggaagctg ctagtttatc tgcatccttc cgtagtgctc ctcgtcctgc taagcctttg 1440
aaagttgtaa ttgctggtgc tggattggct ggattgtcaa ctgcaaagta cctggctgat 1500
gcaggccaca aacctctgtt gcttgaagca agagatgttc ttggtggaaa gatagctgca 1560
tggaaggatg aagatgggga ctggtatgag actggtttac atattttctt cggtgcttat 1620
ccgaatgtgc agaatttatt tggagaactt gggatcaatg atcggttgca gtggaaggaa 1680
cactccatga tttttgctat gccaagtaaa cctggagaat ttagtagatt tgacttccca 1740

-continued

```
gatgtcctac cagcaccctt aaatggtatt tgggctattt tgcggaacaa cgagatgctg   1800
acatggccag agaaaataaa gtttgctatt ggacttttgc cagccatggt cggcggtcag   1860
gcttatgttg aggcccaaga tggtttatca gtcaaagaat ggatggaaaa gcagggagta   1920
cctgagcgcg tgaccgacga ggtgtttatt gccatgtcaa aggcgctaaa ctttataaac   1980
cctgatgaac tgtcaatgca atgcattttg atagctttga accggtttct tcaggaaaaa   2040
catggttcca agatggcatt cttggatggt aatcctccgg aaaggctttg tatgccagta   2100
gtggatcata ttcgatcact aggtggggaa gtgcaactta attctaggat aaagaaaatt   2160
gagctcaatg acgatggcac ggttaagagt ttcttactca ctaatggaag cactgtcgaa   2220
ggagacgctt atgtgtttgc cgctccagtc gatatcctga agctcctttt accagatccc   2280
tggaaagaaa taccgtactt caagaaattg gataaattag ttggagtacc agttattaat   2340
gttcatatat ggtttgatcg aaaactgaag aacacatatg atcacctact ctttagcaga   2400
agtaaccttc tgagcgtgta tgccgacatg tccttaactt gtaaggaata ttacgatcct   2460
aaccggtcaa tgctggagct agtatttgca ccagcagagg aatggatatc acggactgat   2520
tctgacatca tagatgcaac aatgaaagaa cttgagaaac tcttccctga tgaaatctca   2580
gctgaccaaa gcaaagctaa aattctgaag taccatgtcg ttaagactcc aagatctggg   2640
tacaagacca tcccaaactg tgaaccatgt cgtcctctac aaagatcacc tattgaagga   2700
ttctacttag ctggagatta cacaaaacag aagtacttag cttccatgga aggcgctgtc   2760
ctctctggca aattctgctc tcagtctatt gttcaggatt acgagctact ggctgcgtct   2820
ggaccaagaa agttgtcgga ggcaacagta tcatcatcat gagaaaaggg cgaattcgtt   2880
aaccgcagac gagctcgtga aatggcctct ttagtttttg attgaatcat aggggtatta   2940
gttttctatg gccgggagtg gtcttcttgc ttaattgtaa tggaataacc agagaggaac   3000
tactgtgtta tctttgagga atgttgggct tttttcgttt gaattatcat gaatgaaatt   3060
ttactttttc ccaatacaag tttgttttcg tttcttggtt tttgttatcc cttggtttat   3120
gtcttggttt ggcttaaatg attgaagatt acactaccta tgtttctgct attcctgttg   3180
aagatcacat ttgataataa tgcatcgaat gcattaaagt ttcttattgg ctctgtcaaa   3240
agtattgaag gtggattttt ctaattggca agagaaagta ttaaagaggt gatttattag   3300
tacttatatt tttctcagca tctctctttc agtgttggag cttcataaaa ttagcacttc   3360
agagtttcag tcgggagctg aattcga                                        3387
```

<210> SEQ ID NO 36
<211> LENGTH: 1701
<212> TYPE: DNA
<213> ORGANISM: Arabidopsis thaliana

<400> SEQUENCE: 36

```
atggttgtgt ttgggaatgt ttctgcggcg aatttgcctt atcaaaacgg gtttttggag     60
gcactttcat ctggaggttg tgaactaatg ggacatagct ttagggttcc cacttctcaa    120
gcgcttaaga caagaacaag gaggaggagt actgctggtc ctttgcaggt agtttgtgtg    180
gatattccaa ggccagagct agagaacact gtcaatttct tggaagctgc tagtttatct    240
gcatccttcc gtagtgctcc tcgtcctgct aagcctttga aagttgtaat tgctggtgct    300
ggattggctg gattgtcaac tgcaaagtac ctggctgatg caggccacaa acctctgttg    360
cttgaagcaa gagatgttct tggtggaaag atagctgcat ggaaggatga agatggggac    420
```

-continued

```
tggtatgaga ctggtttaca tattttcttc ggtgcttatc cgaatgtgca gaatttattt    480
ggagaacttg ggatcaatga tcggttgcag tggaaggaac actccatgat ttttgctatg    540
ccaagtaaac ctggagaatt tagtagattt gacttcccag atgtcctacc agcaccctta    600
aatggtattt gggctatttt gcggaacaac gagatgctga catggccaga gaaaataaag    660
tttgctattg gacttttgcc agccatggtc ggcggtcagg cttatgttga ggcccaagat    720
ggtttatcag tcaaagaatg gatggaaaag cagggagtac ctgagcgcgt gaccgacgag    780
gtgtttattg ccatgtcaaa ggcgctaaac tttataaacc ctgatgaact gtcaatgcaa    840
tgcattttga tagctttgaa ccggtttctt caggaaaaac atggttccaa gatggcattc    900
ttggatggta atcctccgga aaggctttgt atgccagtag tggatcatat tcgatcacta    960
ggtggggaag tgcaacttaa ttctaggata aagaaaattg agctcaatga cgatggcacg   1020
gttaagagtt tcttactcac taatggaagc actgtcgaag gagacgctta tgtgtttgcc   1080
gctccagtcg atatcctgaa gctcctttta ccagatccct ggaaagaaat accgtacttc   1140
aagaaattgg ataaattagt tggagtacca gttattaatg ttcatatatg gtttgatcga   1200
aaactgaaga acacatatga tcacctactc tttagcagaa gtaaccttct gagcgtgtat   1260
gccgacatgt ccttaacttg taaggaatat tacgatccta accggtcaat gctggagcta   1320
gtatttgcac cagcagagga atggatatca cggactgatt ctgacatcat agatgcaaca   1380
atgaaagaac ttgagaaact cttccctgat gaaatctcag ctgaccaaag caaagctaaa   1440
attctgaagt accatgtcgt taagactcca agatctgtgt acaagaccat cccaaactgt   1500
gaaccatgtc gtcctctaca aagatcacct attgaaggat tctacttagc tggagattac   1560
acaaaacaga agtacttagc ttccatggaa ggcgctgtcc tctctggcaa attctgctct   1620
cagtctattg ttcaggatta cgagctactg gctgcgtctg gaccaagaaa gttgtcggag   1680
gcaacagtat catcatcatg a                                             1701
```

APPROACHES TO IDENTIFY LESS HARMFUL TOBACCO AND TOBACCO PRODUCTS

This application is the U.S. National Phase under 35 U.S.C. §371 of International Application No. PCT/US2005/016941, filed May 11, 2005, which claims priority to the U.S. Provisional Patent Application No. 60/570,175, filed May 12, 2004 and the International Application No. PCT/US2005/010733, filed Mar. 29, 2005. The corresponding International Application was published in English under PCT Article 21(2) on Dec. 1, 2005. The above-referenced applications are hereby expressly incorporated by reference in their entireties.

GRANT INFORMATION

The subject matter of this provisional application was developed in part using funds from NIH, NCI grant CA28704 (Probes for Cytometry, to Z. Darzynkiewicz, P. I.) so that the United States Government has certain rights herein.

FIELD OF THE INVENTION

Aspects of the invention relate to methods for detecting, identifying and evaluating tobacco and tobacco products to determine the potential that these compositions have to contribute to a tobacco-related disease. It is based, at least in part; on the discovery that exposure of pulmonary cells to smoke or smoke condensate obtained from tobacco or tobacco products induces double stranded breaks in cellular DNA, which were efficiently detected using assays that measure the presence, absence, or amount of phosphorylation of the histone, H2AX.

BACKGROUND OF THE INVENTION

The leading preventable cause of death and disability in the United States is the chronic use of tobacco products, in particular, cigarettes. In addition to lung cancers, tobacco use plays important direct and indirect roles in the etiology of a wide range of other cancers, including those of the upper aerodigestive tract (i.e., oral cavity, pharynx, larynx, and esophagus), bladder, stomach, kidney, pancreas, uterine cervix, and blood (myeloid leukemia). Exposure to tobacco carcinogens and toxins is also a major cause of other diseases of the pulmonary system (e.g., bronchitis, emphysema, and chronic obstructive pulmonary disease), the cardiovascular system (e.g., stroke, atherosclerosis, and myocardial infarction), and the female reproductive system (e.g., increased risk of miscarriage, premature delivery, low birth weight, and stillbirth). While numerous studies have elucidated some of the biological effects of cigarette smoke that result in its ability to induce this range of pathologies in smokers, little is known about the nature and temporal association of molecular events that drive specific stages in the multi-step processes that result in clinically evident disease. This is due to the fact that cigarette smoke is a complex chemical mixture of gases and suspended particulate material that consists of a wide variety of condensed organic compounds (i.e., 'tar') that collectively contain a large number of toxins, carcinogens, co-carcinogens, mutagens, and reactive organic and inorganic molecules. To date, only a limited number of these individual tobacco constituents such as benzo[a]pyrene have been assessed for genetic impact in model systems.

Conventional approaches to evaluate the effects of cigarette smoke do not have sufficient sensitivity, specificity, and robustness to be useful in deciphering specific qualitative and quantitative relationships between tobacco smoke constituents and cellular processes. Thus, there is a pressing need to develop novel approaches to accurately evaluate both the genotoxic and biologic effects of tobacco smoke in a rapid and sensitive manner. In particular, since genetic instability is a critical step towards the eventual evolution of a malignant tumor, assessing the various types of chromosomal damage caused by tobacco smoke is a priority. The present methods meet this need and provide additional advantages as well.

SUMMARY OF THE INVENTION

Aspects of the invention concern several approaches to determine the extent that a tobacco or tobacco product induces cellular damage. Some of the embodiments described herein evaluate the potential for a tobacco or tobacco product to induce DNA damage (e.g., double strand DNA breaks) or modulate cell homeostasis (e.g., inhibit apoptosis and/or inhibit cell proliferation). The assays described herein are useful for identifying tobacco and tobacco products that are reduced risk in that they are less likely or have a lower potential to contribute to a tobacco related disease. The assays described herein can also be used to identify components in tobacco and tobacco products that induce cellular damage. Further, the assays described herein can be used to develop reduced risk tobacco and tobacco products that have a reduced potential to contribute to a tobacco related disease.

Several embodiments, for example, concern methods of identifying a tobacco or a tobacco product that induces a double-strand DNA break by providing a tobacco or tobacco product, obtaining smoke or a smoke condensate from the tobacco or tobacco product, contacting a cell with the smoke or smoke condensate, and identifying the presence or absence of a double strand DNA break in the cell after contact with the smoke or smoke condensate. In some methods provided herein, the tobacco comprises a genetic modification, a chemical modification, a biotic modification, or said tobacco has been extracted, expanded, or reconstituted. In some methods provided herein, the genetic modification reduces the amount of alkaloid in the tobacco to less than or equal to 5,000 ppm 3,000 ppm, 1,000 ppm, or 500 ppm. In such methods, the genetic modification reduces the expression of a gene encoding a quinolate phosphoribosyl transferase, a putrescene methyl transferase, or an A622 protein. In some methods, the genetic modification of tobacco reduces the amount of nornicotine in the tobacco without reducing the amount of nicotine in the tobacco. In some methods, wherein the genetic modification of tobacco reduces the amount of nornicotine in the tobacco without reducing the amount of nicotine in the tobacco, the genetic modification reduces the expression of an A622 protein. In some methods, the genetic modification reduces the expression of a gene that regulates production of a sterol. In some methods provided herein, the chemical modification comprises palladium. In some methods provided herein, the chemical modification comprises an auxin, auxin analog, or jasmonate antagonist. In some methods provided herein, the tobacco is reconstituted tobacco. In some methods provided herein, the tobacco is extracted or expanded tobacco. In some methods provided herein, the tobacco comprises a biotic modification. In some methods provided herein, the biotic modification comprises bacteria. In some methods provided herein, the tobacco or tobacco product is processed to remove the presence of a microbe. In such methods the processing can comprise sterilization, pasteurization, or radiation. In some methods provided herein, exogenous nicotine or a nicotine analog has been added to the tobacco or tobacco product.

In some methods provided herein, smoke is obtained from the tobacco or tobacco product. In some methods provided herein, the smoke is contacted with the cells for greater than, less than, or equal to 5 minutes, 15 minutes, 20 minutes, 30 minutes, 40 minutes, or one hour. In some methods provided herein, the presence or absence of a phosphorylation of histone H2AX is identified. In some methods provided herein, the presence or absence of phosphorylation of histone H2AX is identified immunocytochemically, with an antibody or fragment thereof, which binds to phosphorylated H2AX but not unphosphorylated H2AX. In some methods provided herein, activation of one or more protein kinases that are responsible for histone H2AX phosphorylation are detected or identified. In some methods provided herein, the appearance of nuclear foci that are induced by histone H2AX phosphorylation and contain several proteins involved in DNA repair are immunocytochemically identified. In some methods provided herein, activation of one or more protein components of nuclear "foci" induced by H2AX phosphorylation that are associated with DNA repair, is identified. In some methods provided herein, the presence or absence of a chromosomal translocation is identified. In some methods provided herein, the tobacco is provided in a cigarette and the smoke or smoke condensate is obtained from the cigarette. Some methods provided herein further include contacting the smoke or smoke concentrate with a filter. In some such methods, the smoke or smoke condensate is obtained from the cigarette after passing through a filter (e.g., a charcoal, paper, or acetate filter) attached to the tobacco product, such as a cigarette. In some such methods, the filter comprises an antioxidant or a radical scavenger. In some methods provided herein, a plurality of cells are contacted with the smoke or smoke condensate and the presence or absence of a double strand break in the plurality of cells is identified. In some methods provided herein, the plurality of cells are at least, greater than, or equal to a 50%, 60%, 70%, 75%, 80%, 85%, 90%, 95%, or a 100% population of cells in $G_0$, $G_1$, S, $G_2$, or M phase. In some methods provided herein, the first cell is a cell obtained from a human. In some methods provided herein, the cell is a A549 cell, a normal human bronchial epithelial ("NHBE") cell, or a cell obtained from a human primary culture. In some methods provided herein, the first cell is a cell of the oral mucosa of the human. In some methods provided herein, the cell is a cheek cell. In some methods provided herein, the first cell is a cell of the pulmonary system of the human. In some methods provided herein, the cell is a lung or bronchial cell. In some methods provided herein, the cell is a lymphocyte, monocyte, neutrophil, eosinophil or basophil. In some methods provided herein, the first cell is obtained from a human after the human consumes a cigarette. In some methods provided herein, the first cell is obtained from a human after the human consumes a cigarette. Some methods provided herein further include the step of identifying the tobacco or tobacco product to be provided as a composition for an analysis of the potential to induce a double strand DNA break. Some methods provided herein further include the step of measuring the amount of double strand DNA breaks induced after exposure of the cell to the smoke or smoke condensate. In some methods provided herein, double strand DNA breaks can be identified immunocytochemically by detection of (i) histone H2AX phosphorylation; (ii) activation of one or more of the protein kinases that are responsible for H2AX phosphorylation; (iii) appearance of nuclear foci that are induced by histone H2AX phosphorylation; or (iv) activation of one or more protein components of nuclear "foci" induced by H2AX phosphorylation that are associated with DNA repair. In some methods provided herein activation of one or more protein kinases (e.g., ATR, ATM or DNA-dependent—DNA-PK) that phosphorylate H2AX is identified immunocytochemically using an antibody that binds to the activated (e.g. phosphorylated) but not to inactive kinase. ATM, for example undergoes autophosphorylation on serine-1981 and, thus, an antibody to Ser-1981-P-ATM can be used in the methods provided herein. In some methods provided herein activation of one or more proteins, the components of nuclear "foci" induced by H2AX phosphorylation that are associated with DNA repair, is immunocytochemically detected.

The methods provided herein also can be used to identify one or more biomarkers in a biological sample or fluid indicative of a tobacco-related disease. A biological fluid or sample such as urine or blood or a tissue sample can contain one or more molecules such as a as protein mutant that is indicative of a tobacco-related disease. Exemplary fluids that can be used include, but are not limited to, sputum, saliva, tears, cerebro-spinal fluid, blood, lymph, serum, plasma, interstitial fluid, lavage fluid (e.g., lung or breast lavage), urine, semen, seminal fluid, amniotic fluid, cervicovaginal fluid, feces, and secretions of the digestive tract. Exemplary biological samples include but are not limited to a tissue sample or a swab, including a sample or swab or lung tissue, breast tissue or fetal tissue.

Also provided herein are methods of identifying a tobacco or tobacco product that induces an inhibition of apoptosis comprising, providing a tobacco or tobacco product, obtaining smoke or a smoke condensate from the tobacco or tobacco product, contacting a cell with the smoke or smoke condensate, identifying an inhibition of apoptosis in the cell after contact with the smoke or smoke condensate. In some methods provided herein, the tobacco comprises a genetic modification. In some methods provided herein, the genetic modification reduces the amount of alkaloid in the tobacco to less than or equal to 5,000 ppm 3,000 ppm, 1,000 ppm, or 500 ppm. In some methods provided herein, the genetic modification reduces the expression of a gene encoding a quinolate phosphoribosyl transferase, a putrescene methyl transferase, or an A622 protein. In some embodiments, the genetic modification reduces the amount of nornicotine in the tobacco without reducing the amount of nicotine in the tobacco. In some such embodiments, the genetic modification reduces the expression of an A622 protein. In some methods provided herein, the genetic modification reduces the expression of a gene that regulates production of a sterol. In some methods provided herein, the tobacco comprises a chemical modification. In some methods provided herein, the chemical modification comprises palladium. In some methods provided herein, the chemical modification comprises an auxin, auxin analog, or jasmonate antagonist. In some methods provided herein, the tobacco is reconstituted tobacco. In some methods provided herein, the tobacco is extracted or expanded tobacco. In some methods provided herein, the tobacco comprises a biotic modification. In some methods provided herein, the biotic modification comprises bacteria. In some methods provided herein, the tobacco or tobacco product is processed to remove the presence of a microbe. In some methods provided herein, the processing comprises sterilization, pasteurization, or radiation. In some methods provided herein, exogenous nicotine or a nicotine analog has been added to the tobacco or tobacco product. Some methods provided herein include a step of comparing the extent of apoptosis in two or more populations of cells upon exposure of each population of cells to smoke or smoke condensate of different tobaccos, where the exposure induces the same degree of DNA damage (e.g., DNA strand breaks) to each population of cells. In some methods provided herein, different chemopreventive agents, such as antioxidants can be administered to the cells prior to, during, or subsequent to exposure of the cells to smoke or smoke condensate.

In some methods provided herein, smoke is obtained from the tobacco. In some methods provided herein, the smoke is contacted with the cells for greater than, less than, or equal to 5 minutes, 15 minutes, 20 minutes, 30 minutes, 40 minutes, or one hour. In some methods provided herein, the presence or absence of caspase activation is identified. In some methods provided herein, the presence or absence of caspase activation is identified with an antibody or fragment thereof, which binds to activated caspase but not inactive caspase. In some methods provided herein, the tobacco is provided in a cigarette and the smoke or smoke condensate is obtained from the cigarette. Some embodiments further include contacting the smoke or smoke concentrate with a filter. In some methods provided herein, the smoke or smoke condensate is obtained from the cigarette after passing through a filter attached to the cigarette. In some methods provided herein, the filter comprises an antioxidant or a radical scavenger. In some methods provided herein, a plurality of cells is contacted with the smoke or smoke condensate and the presence or absence of an inhibition of apoptosis is identified. In some methods provided herein, the plurality of cells are at least, greater than, or equal to a 50%, 60%, 70%, 75%, 80%, 85%, 90%, 95%, or a 100% population of cells in $G_0$, $G_1$, S, $G_2$, or M phase. In some methods provided herein, the first cell is a cell obtained from a human. In some methods provided herein, the cell is an A549 cell, a NHBE cell, or a cell obtained from a human primary culture. In some methods provided herein, the first cell is a cell of the oral mucosa of the human. In some methods provided herein, the cell is a cheek cell. In some methods provided herein, the first cell is a cell of the pulmonary system of the human. In some methods provided herein, the cell is a lung or bronchial cell. In some methods provided herein, the first cell is obtained from a human after the human consumes a cigarette. In some methods provided herein, the first cell is obtained from a human after the human consumes a cigarette. Some methods provided herein further include the step of identifying the tobacco or tobacco product to be provided as a composition for an analysis of the potential to inhibit apoptosis. Some methods provided herein further include the step of measuring the amount of inhibition of apoptosis induced after exposure of the cell to the smoke or smoke condensate.

Also provided herein are methods of identifying a tobacco or tobacco product that induces an inhibition of cell proliferation comprising, providing a tobacco or tobacco product, obtaining smoke or a smoke condensate from the tobacco or tobacco product, contacting a cell with the smoke or smoke condensate, identifying an inhibition of proliferation of the cell after contact with the smoke or smoke condensate. In some methods provided herein, the tobacco comprises a genetic modification. In some methods provided herein, the genetic modification reduces the amount of alkaloid in the tobacco to less than or equal to 5,000 ppm 3,000 ppm, 1,000 ppm, or 500 ppm. In some methods provided herein, the genetic modification reduces the expression of a gene encoding a quinolate phosphoribosyl transferase, a putrescene methyl transferase, or an A622 protein. In some methods provided herein, the genetic modification reduces the amount of nornicotine in the tobacco without reducing the amount of nicotine in the tobacco. In some methods provided herein, wherein the genetic modification reduces the amount of nornicotine in the tobacco without reducing the amount of nicotine in the tobacco, the genetic modification reduces the expression of an A622 protein. In some methods provided herein, the genetic modification reduces the expression of a gene that regulates production of a sterol. In some methods provided herein, the tobacco comprises a chemical modification. In some methods provided herein, the chemical modification comprises palladium. In some methods provided herein, the chemical modification comprises an auxin, auxin analog, or jasmonate antagonist. In some methods provided herein, the tobacco is reconstituted tobacco. In some methods provided herein, the tobacco is extracted or expanded tobacco. In some methods provided herein, the tobacco comprises a biotic modification. In some methods provided herein, the biotic modification comprises bacteria. In some methods provided herein, the tobacco or tobacco product is processed to remove the presence of a microbe. In some methods provided herein, the processing comprises sterilization, pasteurization, or radiation. In some methods provided herein, exogenous nicotine or a nicotine analog has been added to the tobacco or tobacco product. Some methods provided herein include a step of comparing the extent of modulation of cell proliferation in two or more populations of cells upon exposure of each population of cells to smoke or smoke condensate of different tobaccos, where the exposure induces the same degree of DNA damage (e.g., DNA strand breaks) to each population of cells. In some methods provided herein, different chemopreventive agents, such as antioxidants can be administered to the cells prior to, during, or subsequent to exposure of the cells to smoke or smoke condensate.

In some methods provided herein, smoke is obtained from the tobacco or tobacco product. In some methods provided herein, the smoke is contacted with the cells for greater than, less than, or equal to 5 minutes, 15 minutes, 20 minutes, 30 minutes, 40 minutes, or one hour. In some methods provided herein, the number of surviving cells after contact with the smoke or smoke condensate are identified. In some methods provided herein, the incorporation of a metabolic label into a nucleic acid or protein is identified. In some methods provided herein, the incorporation of a labeled nucleotide is identified. In some methods provided herein, the tobacco is provided in a cigarette and the smoke or smoke condensate is obtained from the cigarette. Some methods provided herein further include contacting the smoke or smoke concentrate with a filter. In some methods provided herein, the smoke or smoke condensate is obtained from the cigarette after passing through a filter (e.g., a charcoal, paper, or acetate filter) attached to the cigarette. In some methods provided herein, the filter comprises an antioxidant or a radical scavenger. In some methods provided herein, a plurality of cells are contacted with the smoke or smoke condensate and the presence or absence of an inhibition of cell proliferation is identified. In some methods provided herein, the plurality of cells is at least, greater than, or equal to a 50%, 60%, 70%, 75%, 80%, 85%, 90%, 95%, or a 100% population of cells in $G_0$, $G_1$, S, $G_2$, or M phase. In some methods provided herein, the first cell is a cell obtained from a human. In some methods provided herein, the cell is an A549 cell, a NHBE cell, or a cell obtained from a human primary culture. In some methods provided herein, the first cell is a cell of the oral mucosa of the human. In some methods provided herein, the cell is a cheek cell. In some methods provided herein, the first cell is a cell of the pulmonary system of the human. In some methods provided herein, the cell is a lung or bronchial cell. In some methods provided herein, the first cell is obtained from a human after the human consumes a cigarette. In some methods provided herein, the first cell is obtained from a human after the human consumes a cigarette. Some methods provided herein further include the step of identifying the tobacco or tobacco product to be provided as a tobacco for an analysis of the potential to inhibit cell proliferation. Some methods provided herein further include the step of measuring the amount of inhibition of cell proliferation induced after exposure of the cell to the smoke or smoke condensate.

Also provided herein are methods of identifying a compound in tobacco or tobacco product that induces a double-strand DNA break in a cell, an inhibition of apoptosis, or an inhibition of cell proliferation by providing a first tobacco or tobacco product, obtaining smoke or a smoke condensate from the first tobacco or tobacco product, contacting a first population of cells with the smoke or smoke condensate from the first tobacco or tobacco product, identifying the presence or absence of a double strand DNA break, an inhibition of apoptosis, or an inhibition of cell proliferation in the first population of cells after contact with the smoke or smoke condensate from the first tobacco or tobacco product, providing a second tobacco or tobacco product that has been genetically modified to reduce the expression of at least one gene that regulates production of a compound in the second tobacco or tobacco product, obtaining smoke or a smoke condensate from the second tobacco or tobacco product, contacting a second population of cells with the smoke or smoke condensate from the second tobacco or tobacco product, and identifying the presence or absence of a double strand DNA break, an inhibition of apoptosis, or an inhibition of cell proliferation in the second population of cells after contact with the smoke or smoke condensate from the second tobacco or tobacco product, where an identification of a reduction in the amount of double strand DNA breaks, inhibition of apoptosis, or inhibition of cell proliferation in the second population of cells after contact with the smoke or smoke condensate from the second tobacco or tobacco product identifies the compound as one that induces the double strand DNA breaks, inhibition of apoptosis, or inhibition of cell proliferation. In some methods provided herein, the identification steps comprise identifying the presence or absence of phosphorylation of histone H2AX, activation of caspase, or incorporation of a labeled nucleotide or amino acid. In some methods provided herein, the tobacco is provided in a cigarette and the smoke or smoke condensate is obtained from the cigarette. Some methods provided herein further include contacting the smoke or smoke concentrate with a filter. In some methods provided herein, the smoke or smoke condensate is obtained from the cigarette after passing through a filter attached to the cigarette. In some methods provided herein, the filter comprises an antioxidant or a radical scavenger. In some methods provided herein, smoke is obtained from the first and second tobaccos or tobacco products. In some methods provided herein, the identification steps comprise identifying the presence or absence of a double strand DNA break. In some methods provided herein, the presence or absence of phosphorylation of histone H2AX is identified with an antibody or fragment thereof, which binds to phosphorylated H2AX but not unphosphorylated H2AX. In some methods provided herein, the genetic modification reduces the expression of a gene that regulates nicotine or sterol biosynthesis. In some methods provided herein, the gene is selected from the group consisting of quinolate phosphoribosyl transferase, putrescine methyl transferase, and A622. In some methods provided herein, the second tobacco or tobacco product is processed to remove the presence of a microbe. In some methods provided herein, the processing comprises sterilization, pasteurization, or radiation. In some methods provided herein, exogenous nicotine or a nicotine analog has been added to the second tobacco. In some methods provided herein, the smoke is contacted with the cells for greater than, less than, or equal to 5 minutes, 15 minutes, 20 minutes, 30 minutes, 40 minutes, or one hour. In some methods provided herein, the number of surviving cells after contact with the smoke or smoke condensate are identified. In some methods provided herein, the first and second populations of cells are at least, greater than, or equal to a 50%, 60%, 70%, 75%, 80%, 85%, 90%, 95%, or a 100% population of cells in $G_0$, $G_1$, S, $G_2$, or M phase. In some methods provided herein, the first and second populations of cells are obtained from a human. In some methods provided herein, the first and second populations of cells are A549 cells, NHBE cells, or cells obtained from a human primary culture. In some methods provided herein, the first and second populations of cells are cells of the oral mucosa of the human. In some methods provided herein, the first and second populations of cells are cheek cells. In some methods provided herein, the first and second populations of cells are cells of the pulmonary system of the human. In some methods provided herein, the first and second populations of cells are lung or bronchial cells. In some methods provided herein, the first and second populations of cells are obtained from a human after the human consumes a cigarette. Some methods provided herein further include the step of identifying the second tobacco as a tobacco for an analysis of the potential to induce a double strand DNA break. Some methods provided herein further include the step of measuring the amount of double strand DNA breaks induced after contact of the first and second populations of cells to the smoke or smoke condensate. Some methods provided herein further include the step of identifying the second tobacco or tobacco product as a composition for an analysis of the potential to inhibit apoptosis. Some methods provided herein further include the step of measuring the amount of inhibition of apoptosis induced after contact of the first and second populations of cells to the smoke or smoke condensate. Some methods provided herein further include the step of identifying the tobacco or tobacco product to be provided as a composition for an analysis of the potential to inhibit cell proliferation. Some methods provided herein further include the step of measuring the amount of inhibition of cell proliferation induced after exposure of the first and second populations of cells to the smoke or smoke condensate. In some methods, a plurality of compounds are removed from said tobacco through modification (e.g., chemical treatment and/or genetic modification) and each compound is added back to the modified tobacco incrementally (e.g., by replacement of the removed compounds, such as by application of exogenous compound, in the tobacco one at a time followed by analysis of the effect on cell homeostasis after each compound is added) so as to identify the individual contribution to tobacco related disease provided by each of the compounds that were removed.

Also provided herein are methods of identifying a tobacco product that has a reduced potential to contribute to a tobacco-related disease by providing a first tobacco product, obtaining smoke or a smoke condensate from the first tobacco product, contacting a first population of cells with the smoke or smoke condensate from the first tobacco product, identifying the presence or absence of a double strand DNA break, an inhibition of apoptosis, or an inhibition of cell proliferation in the first population of cells after contact with the smoke or smoke condensate from the first tobacco product, providing a second tobacco product, obtaining smoke or a smoke condensate from the second tobacco product, contacting a second population of cells with the smoke or smoke condensate from the second tobacco product, and identifying the presence or absence of a double strand DNA break, an inhibition of apoptosis, or an inhibition of cell proliferation in the second population of cells after contact with the smoke or smoke condensate from the second tobacco product, where an identification of a reduction in the amount of double strand DNA breaks, inhibition of apoptosis, or inhibition of cell proliferation in the second population of cells after contact with the smoke or smoke condensate from the second tobacco product, as compared to the amount of double strand DNA breaks, inhibition of apoptosis, or inhibition of cell proliferation identified in the first population of cells identifies the second tobacco product as one that has a reduced potential to contribute to a tobacco-related disease. In some methods provided herein, the identification steps comprise identifying the presence or absence of phosphorylation of histone H2AX, activation of caspase, incorporation of a labeled nucleotide, incorporation of a labeled amino acid, or cell lysis. In some methods provided herein, the first and second tobacco products are cigarettes. Some methods provided herein further include contacting the smoke or smoke concentrate with a filter. In some methods provided herein, the smoke or smoke condensate is obtained from the cigarettes after passing through a filter attached to the cigarettes. In some methods provided herein, the filter comprises an antioxidant or a radical scavenger. In some methods provided herein, smoke is obtained from the first and second tobaccos. In some methods provided herein, the identification steps comprise identifying the presence or absence of a double strand DNA break. In some methods provided herein, the presence or absence of phosphorylation of histone H2AX is identified with an antibody or fragment thereof, which binds to phosphorylated H2AX but not unphosphorylated H2AX. In some methods provided herein, the second tobacco product comprises a genetically modified tobacco comprising a reduced amount of a compound. In some methods provided herein, the second tobacco product comprises a reduced amount of nicotine and/or a sterol and a collective content of tobacco specific nitrosamines less than or equal to 0.5 μg/g. In some methods provided herein, the second tobacco product comprises a reduced amount of alkaloid or sterol. In some methods provided herein, the genetically modified tobacco comprises a reduced expression of a gene selected from the group consisting of quinolate phosphoribosyl transferase, putrescine methyl transferase, and A622. In some methods provided herein, the second tobacco is processed to remove the presence of a microbe. In some methods provided herein, the processing comprises sterilization, pasteurization, or radiation. In some methods provided herein, exogenous nicotine or a nicotine analog has been added to the second tobacco. In some methods provided herein, the smoke is contacted with the cells for greater than, less than, or equal to 5 minutes, 15 minutes, 20 minutes, 30 minutes, 40 minutes, or one hour. In some methods provided herein, the number of surviving cells after contact with the smoke or smoke condensate are identified. In some methods provided herein, the first and second populations of cells are at least, greater than, or equal to a 50%, 60%, 70%, 75%, 80%, 85%, 90%, 95%, or a 100% population of cells in $G_0$, $G_1$, S, $G_2$, or M phase. In some methods provided herein, the first and second populations of cells are obtained from a human. In some methods provided herein, the first and second populations of cells are A549 cells, NHBE cells, or cells obtained from a human primary culture. In some methods provided herein, the first and second populations of cells are cells of the oral mucosa of the human. In some methods provided herein, the first and second populations of cells are cheek cells. In some methods provided herein, the first and second populations of cells are cells of the pulmonary system of the human. In some methods provided herein, the first and second populations of cells are lung or bronchial cells. In some methods provided herein, the first and second populations of cells are obtained from a human after the human consumes a cigarette. Some methods provided herein further include the step of identifying the second tobacco as a tobacco for an analysis of the potential to induce a double strand DNA break. Some methods provided herein further include the step of measuring the amount of double strand DNA breaks induced after contact of the first and second populations of cells to the smoke or smoke condensate. Some methods provided herein further include the step of identifying the second tobacco as a tobacco for an analysis of the potential to inhibit apoptosis. Some methods provided herein further include the step of measuring the amount of inhibition of apoptosis induced after contact of the first and second populations of cells to the smoke or smoke condensate. Some methods provided herein further include the step of identifying the tobacco or tobacco product to be provided as a tobacco for an analysis of the potential to inhibit cell proliferation. Some methods provided herein further include the step of measuring the amount of inhibition of cell proliferation induced after exposure of the first and second populations of cells to the smoke or smoke condensate.

Also provided herein are methods of making a tobacco product that has a reduced potential to contribute to a tobacco-related disease by providing a first tobacco, obtaining smoke or a smoke condensate from the first tobacco, contacting a first population of cells with the smoke or smoke condensate from the first tobacco, identifying the presence or absence of a double strand DNA break, an inhibition of apoptosis, or an inhibition of cell proliferation in the first population of cells after contact with the smoke or smoke condensate from the first tobacco, providing a second tobacco that is genetically modified to reduce the expression of at least one gene that regulates production of a compound in the second tobacco, obtaining smoke or a smoke condensate from the second tobacco, contacting a second population of cells with the smoke or smoke condensate from the second tobacco, identifying the presence or absence of a double strand DNA break, an inhibition of apoptosis, or an inhibition of cell proliferation in the second population of cells after contact with the smoke or smoke condensate from the second tobacco, where an identification of a reduction in the amount of double strand DNA breaks, inhibition of apoptosis, or inhibition of cell proliferation in the second population of cells after contact with the smoke or smoke condensate from the second tobacco, as compared to the amount of double strand DNA breaks, inhibition of apoptosis, or inhibition of cell proliferation identified in the first population of cells identifies the second tobacco as one that has a reduced potential to contribute to a tobacco-related disease, and incorporation of the second tobacco, which has a reduced potential to contribute to a tobacco-related disease, into a tobacco product. In some of the methods provided herein, the identification steps comprise identifying the presence or absence of phosphorylation of histone H2AX, activation of caspase, incorporation of a labeled nucleotide, incorporation of a labeled amino acid, or cell lysis. In some of the methods provided herein, the first and second tobaccos are present in cigarettes. Some of the methods provided herein further include contacting the smoke or smoke concentrate with a filter. In some of the methods provided herein, the smoke or smoke condensate is obtained from the cigarettes after passing through a filter attached to the cigarettes. In some of the methods provided herein, the filter comprises an antioxidant or a radical scavenger. In some of the methods provided herein, the filter comprises an interceptor of an aromatic carcinogen, where the carcinogen associates with interceptor forming a complex that is retained in the filter. In some of the methods provided herein, smoke is obtained from the first and second tobaccos. In some of the methods provided herein, the identification steps comprise identifying the presence or absence of a double strand DNA break. In some of the methods provided herein, the presence or absence of phosphorylation of histone H2AX is identified with an antibody or fragment thereof, which binds to phosphorylated H2AX but not unphosphorylated H2AX. In some of the methods provided herein, the second tobacco product comprises a genetically modified tobacco comprising a reduced amount of a compound. In some of the methods provided herein, the second tobacco product comprises a reduced amount of nicotine and/or sterol and a collective content of tobacco specific nitrosamines less than or equal to 0.5 μg/g. In some of the methods provided herein, the second tobacco product comprises a reduced amount of alkaloid or sterol or both. In some of the methods provided herein, the genetically modified tobacco comprises a reduced expression of a gene selected from the group consisting of quinolate phosphoribosyl transferase, putrescine methyl transferase, and A622. In some of the methods provided herein, the second tobacco is processed to remove the presence of a microbe. In some of the methods provided herein, the processing comprises sterilization, pasteurization, or radiation. In some of the methods provided herein, exogenous nicotine or a nicotine analog has been added to the second tobacco. In some of the methods provided herein, the smoke is contacted with the cells for greater than, less than, or equal to 5 minutes, 15 minutes, 20 minutes, 30 minutes, 40 minutes, or one hour. In some of the methods provided herein, the number of surviving cells after contact with the smoke or smoke condensate are identified. In some of the methods provided herein, the first and second populations of cells are at least, greater than, or equal to a 50%, 60%, 70%, 75%, 80%, 85%, 90%, 95%, or a 100% population of cells in $G_0$, $G_1$, S, $G_2$, or M phase. In some of the methods provided herein, the first and second populations of cells are obtained from a human. In some of the methods provided herein, the first and second populations of cells are A549 cells, NHBE cells, or cells obtained from a human primary culture. In some of the methods provided herein, the first and second populations of cells are cells of the oral mucosa of the human. In some of the methods provided herein, the first and second populations of cells are cheek cells. In some of the methods provided herein, the first and second populations of cells are cells of the pulmonary system of the human. In some of the methods provided herein, the first and second populations of cells are lung or bronchial cells. In some of the methods provided herein, the first and second populations of cells are obtained from a human after the human consumes a cigarette. Some methods provided herein further include the step of identifying the second tobacco as a tobacco for an analysis of the potential to induce a double strand DNA break. Some methods provided herein further include the step of measuring the amount of double strand DNA breaks induced after contact of the first and second populations of cells to the smoke or smoke condensate. Some methods provided herein further include the step of identifying the second tobacco as a tobacco for an analysis of the potential to inhibit apoptosis. Some methods provided herein further include the step of measuring the amount of inhibition of apoptosis induced after contact of the first and second populations of cells to the smoke or smoke condensate. Some methods provided herein further include the step of identifying the tobacco or tobacco product to be provided as a composition for an analysis of the potential to inhibit cell proliferation. Some methods provided herein further include the step of measuring the amount of inhibition of cell proliferation induced after exposure of the first and second populations of cells to the smoke or smoke condensate.

Also provided herein are tobacco products made by any of the methods of making a tobacco product provided herein.

Also provided herein are efficient assays that can be used to assess and compare the harmful potential of tobacco products as well as to identify harmful smoke components and thereby develop new tobacco products without such components that pose a reduced risk to a consumer. The assays provided herein are based, at least in part, on the discovery that short-term exposure of (i) A549 pulmonary adenocarcinoma cells to tobacco smoke and (ii) NHBE to smoke condensate, induced DSBs in a dose-dependent manner. DSBs can be detected using, for example, an antibody specifically directed to the phosphorylated form of the DSB-associated histone, H2AX, and were manifested as an increased degree of phosphorylation of H2AX. Also provided herein are methods of detecting DSBs using antibodies to the activated (e.g., phosphorylated) form of protein kinases ATR, ATM or DNA-PK, that are involved in H2AX phosphorylation. DSBs can also be detected by revealing the presence of characteristic "foci" in cell nucleus that comprise of several proteins associated with DNA repair.

Accordingly, provided herein are methods and kits for identifying and/or detecting harmful agents found in or derived from tobacco products in a variety of contexts, including smoke or smoke concentrates applied in a laboratory setting or arising in the environment. These methods and kits can be used to determine whether a tobacco-derived test composition promotes the formation of DSBs in chromosomal DNA, preferably using a γH2AX-based assay. The kits provided herein can be based on either detection of γH2AX or of activated protein kinases ATR, ATM or DNA-PK, or of protein components of the nuclear "foci" detected immunocytochemically.

In specific non-limiting embodiments, the assays provided herein can be used to identify harmful components arising from tobacco product use. Steps can then be taken to eliminate, decrease, or neutralize these components in the tobacco products themselves, in the environment, or in vivo. Further provided herein are assay systems to determine whether modified tobacco products are indeed "reduced risk" as compared to traditional tobacco products.

DETAILED DESCRIPTION OF THE INVENTION

Figure 1A:
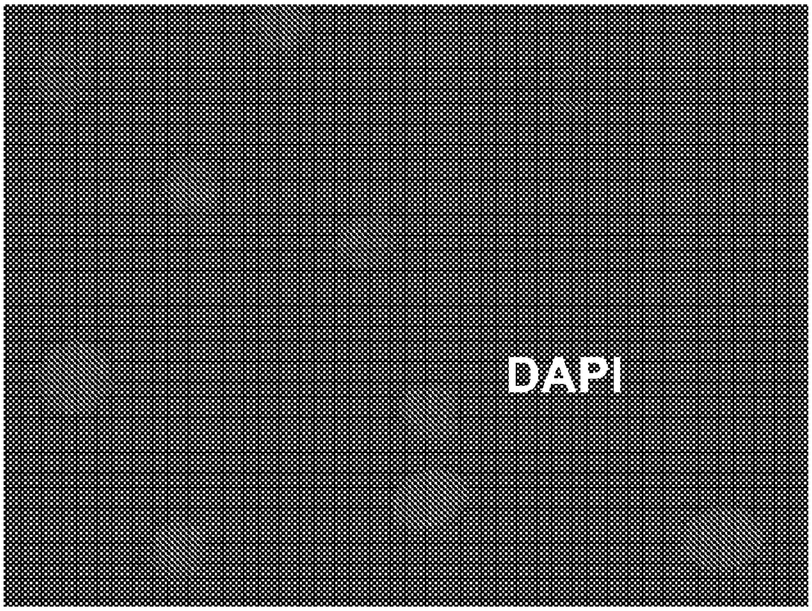
FIG. 1A-B. Fluorescence photomicrographs of NHBE cells exposed to 25 μg/ml of tobacco smoke condensate for 24 h. The cells stained with DAPI and immuno-stained with γH2AX Ab were examined under UV light—(A) or blue light—(B) fluorescence excitation (Nikon Microphot FXA, 60× Objective.).

Several approaches to determine the extent that a tobacco or tobacco product induces cellular damage have been developed. In some embodiments, a tobacco or a tobacco product is analyzed for its ability to induce DNA damage (e.g., double strand DNA breaks) or modulate cell homeostasis (e.g., inhibit apoptosis and/or inhibit cell proliferation). These assays are particularly useful for identifying tobacco and tobacco products that have a reduced potential to contribute to a tobacco related disease, as compared to a reference tobacco (e.g., the industry standard reference tobacco IM16 (Philip Morris® USA) or the full-flavor low tar reference cigarette 2R4F or the ultra low tar cigarette 1R5F, which are Kentucky reference cigarettes that can be obtained from the Tobacco and Health Institute at the University of Kentucky), a conventional tobacco (e.g., a commercially available tobacco of the same class (e.g., "full-flavor" or "light" or "ultra-light")), or a non-transgenic tobacco or wild-type tobacco (e.g., a tobacco of the same variety, such as Burley, Virginia Flue, or Oriental, or strain, such as LA Burley 21, K326, Tn90, Djebel174). That is, the assays provided herein can be used to confirm that a tobacco or tobacco product is a reduced risk tobacco or tobacco product, as compared to a reference tobacco or tobacco product (e.g., IM16, 2R4F or 1R5F), a conventional, commercially available, or traditional tobacco product or a wild-type tobacco. The assays described herein can also be used to identify components in tobacco and tobacco products that induce cellular damage. Further, the assays described herein can be used to develop reduced risk tobacco and tobacco products that have a lower potential to contribute to a tobacco related disease than a reference tobacco or tobacco product (e.g., IM16, 2R4F or 1R5F), a conventional, commercially available, or traditional tobacco product or a wild-type tobacco.

Some of the embodiments described herein compare the effects/damage (e.g., effects on DNA damage, apoptosis, or cell proliferation) of smoke generated from a transgenic tobacco or a tobacco product containing transgenic tobacco to a reference tobacco or reference tobacco product (e.g., IM16, 2R4F or 1R5F), a commercially available tobacco product of the same class (e.g., full-flavor, lights, and ultra-lights), or, preferably, a tobacco of the same variety (e.g., Burley, Virginia Flue, or Oriental) or strain (e.g., LA Burley 21, K326, Tn90, Djebel174). Reduced risk tobacco products developed according to the methods described herein include "full-flavor," "lights," and "ultra light" cigarettes with both reduced levels of alkaloids and/or sterols and levels of alkaloids and/or sterols that are commensurate with amounts of these compounds common to the particular class of cigarette (i.e., a conventional amount of nicotine).

The term "tobacco products" includes, but is not limited to, smoking materials (e.g., cigarettes, cigars, pipe tobacco), snuff, chewing tobacco, gum, and lozenges. The term "reduced risk tobacco product" or "reduced risk tobacco" includes, but is not limited to, a tobacco product or tobacco comprising a modified tobacco (e.g., chemically or genetically modified tobacco) that has a reduced amount of a compound that contributes to a tobacco-related disease (e.g., nicotine, nornicotine, a sterol, or the metabolites thereof including, but not limited to, a tobacco specific nitrosamine (TSNA), an acrolein, an aldehyde, polycyclic aromatic hydrocarbon (PAH), benz[a]pyrene (BAP), a heterocyclic hydrocarbon, or an aromatic amine), as compared to a reference tobacco or reference tobacco product (e.g., IM16, 2R4F or 1R5F), a commercially available tobacco product of the same class (e.g., full-flavor, lights, and ultra-lights), or, preferably, a tobacco of the same variety (e.g., Burley, Virginia Flue, or Oriental) or strain (e.g., LA Burley 21, K326, Tn90, Djebel174) as the modified tobacco prior to modification. Exemplary reference tobaccos that can be used in the methods provided herein include IM16, 2R4F, and 1R5F, where 2R4F (full flavor low tar) and 1R5F (ultra low tar) Kentucky reference cigarettes can be obtained from the Tobacco and Health Institute at the University of Kentucky, and IM16 reference cigarettes can be obtained from Phillip Morris® USA.

In other contexts, a reduced risk tobacco or a reduced risk tobacco product refers to a modified tobacco or tobacco product comprising a modified tobacco (e.g., transgenic tobacco or a tobacco product comprising transgenic tobacco) that induces less cellular damage (e.g., fewer double strand DNA breaks, or less modulation of cell homeostasis (e.g., a reduced amount of inhibition of apoptosis or less inhibition of cell proliferation) than a reference tobacco or reference tobacco product (e.g., IM16, 2R4F or 1R5F), a commercially available tobacco product of the same class (e.g., full-flavor, lights, and ultra-lights), or, preferably, a tobacco of the same variety (e.g., Burley, Virginia Flue, or Oriental) or strain (e.g., LA Burley 21, K326, Tn90, Djebel174) as the modified tobacco prior to modification). In still other contexts, a reduced risk tobacco or a reduced risk tobacco product refers to a modified tobacco or tobacco product comprising a modified tobacco (e.g., transgenic tobacco or a tobacco product comprising transgenic tobacco) that up-regulates fewer genes associated with a tobacco-related disease as compared to a reference tobacco or reference tobacco product (e.g., IM16, 2R4F or 1R5F), a commercially available tobacco product of the same class (e.g., full-flavor, lights, and ultra-lights), or, preferably, a tobacco of the same variety (e.g., Burley, Virginia Flue, or Oriental) or strain (e.g., LA Burley 21, K326, Tn90, Djebel174) as the as the modified tobacco prior to modification).

In still other contexts, a reduced risk tobacco or a reduced risk tobacco product refers to a modified tobacco or tobacco product (e.g., a transgenic tobacco or a tobacco product comprising transgenic tobacco) that down-regulates fewer genes associated with the repair of tobacco-induced damage (e.g., oxidative damage), as compared to a reference tobacco or reference tobacco product (e.g., IM16, 2R4F or 1R5F), a commercially available tobacco product of the same class (e.g., full-flavor, lights, and ultra-lights), or, preferably, a tobacco of the same variety (e.g., Burley, Virginia Flue, or Oriental) or strain (e.g., LA Burley 21, K326, Tn90, Djebel174) as the as the modified tobacco prior to modification). Accordingly, aspects of the invention provide several assays to determine whether a tobacco or tobacco product has a reduced potential to contribute to a tobacco-related disease (i.e., that a reduced risk tobacco has been identified) by identifying tobacco-induced changes in cell homeostasis. That is, the degree of tobacco product-induced change in expression levels in contacted cells relative to expression levels in homeostatic cells can be compared (or the expression levels in two or more populations of contacted cells can be compared), and the tobacco associated with expression levels that differ less or differ the least from homeostatic levels can be a tobacco has a reduced potential to contribute to a tobacco-related disease.

It should also be emphasized that the word "reduced," or the phrase "a reduced amount" is intended to refer to an amount of a harmful compound (e.g., total alkaloid, nicotine, nornicotine, a sterol, or the metabolites thereof including, but not limited to, a TSNA, an acrolein, an aldehyde, PAH, BAP, a heterocyclic hydrocarbon, or an aromatic amine) in or produced by a modified tobacco plant, tobacco, or tobacco product (e.g., a genetically modified tobacco plant, tobacco, or a tobacco product containing said tobacco) that is less than the amount of said harmful compound found or produced, preferably, in a tobacco plant, tobacco, or a tobacco product from the same class of tobacco product (e.g., full-flavor, light, ultra-light), same variety of tobacco (e.g. the parental strain of tobacco prior to genetic modification), or in comparison to a reference cigarette (e.g., IM16, 2R4F or 1R5F), which has not been modified (e.g., genetically modified tobacco). Thus, in some contexts and embodiments, wild-type tobacco of the same variety that has been grown and processed in the same manner as the modified tobacco (e.g., genetically modified tobacco) is used as a control by which to measure whether a reduction in a harmful compound has been obtained by the inventive methods described herein. In other embodiments, the determination of whether a reduced amount of a harmful compound in a transgenic tobacco has been obtained is made by comparing the amount of a harmful compound in the transgenic tobacco to a commercially available cigarette and/or a reference cigarette (e.g., IM16, 2R4F or 1R5F). The section below describes approaches to characterize the tobacco and tobacco products described herein in greater detail.

Methods for Determining the Risk Potential of Tobacco and Tobacco Products

Provided herein are several methods for characterizing a tobacco or tobacco product to determine the potential for said tobacco or tobacco product to contribute to a tobacco related disease. Generally, these approaches are practiced by providing a tobacco, obtaining smoke or a smoke condensate from the tobacco, contacting a cell with the smoke or smoke condensate, and identifying one or more attributes of the contacted cell. Tobacco products contain a number of compounds that induce various types of cell damage including mutations, chromosomal aberrations, aberrant sister chromatid exchanges and micronuclei. Attributes of contacted cells indicative of such tobacco-induced cell damage can be identified in the methods provided herein, and such attributes include induction of a double-strand DNA break, inhibition of apoptosis, or inhibition of cell proliferation. Accordingly, the methods provided herein can be used to characterize a tobacco by assay methods including assay for induction of damage of cellular genetic material or modulation of cell homeostasis. For example, the methods provided herein can be used to characterize a tobacco by assay methods including an assay for the induction of a double-strand DNA break, inhibition of apoptosis, or inhibition of cell proliferation.

Several other assays have classically been used to analyze tobacco for the risk of adverse health effects. Traditionally, the first manner of testing consists of analysis of cigarette smoke for various components that can relate to health effects associated with smoking. A second manner of testing includes testing cigarette smoke tar on living cells. One of these tests detects changes in the genetic material of bacteria. Another test uses mouse cells grown in Petri dishes to detect potential cancer-causing activity. A third manner of testing seeks to determine if people smoke the tested tobacco cigarettes differently than the comparable brand or type currently on the market. If the way the cigarettes are smoked is different, then the other manners of testing can be repeated with the smoking machines set to reflect the change in smoking behavior. A fourth manner of testing examines the response of animals to cigarette smoke or tar. One test looks for inflammation in the lungs of mice in response to cigarette smoke. A second test looks for tumor formation in the upper respiratory tract of hamsters exposed to smoke. A third test looks for the cancer producing ability of cigarette smoke tar by applying the tar to the skin of mice. Each manner of testing can include comparing tobacco cigarettes and both the effects of mainstream and sidestream smoke can be tested.

During smoking, both mainstream smoke (inhaled by the smoker) and sidestream smoke (mainly: from the burning end of the cigarette) are generated. While mainstream and sidestream smoke are qualitatively similar the quantity of specific components differs between the two. Additionally, modifications to the cigarette can independently affect the composition of sidestream and mainstream smoke. It is concluded, therefore, that testing of tobacco or cigarettes can be assayed for both mainstream and sidestream smoke.

Epidemiology is not a practical approach for addressing the issue of the health effects of changes in a cigarette composition. Because people can smoke cigarettes differently (ex. longer or faster puffs) it can be important to consider whether these changes affect smoke chemistry and therefore toxicity. For example, a new, cigarette type can result in a smoker taking longer puffs, which can then change the smoke chemistry and toxicity.

Testing, however, can examine the effects on toxicity of a single design change in a cigarette or can examine the effects of a set of design changes compared to an unchanged control. Testing protocols can follow either a screening or a tradeoff approach. In the screening approach new designs can be subjected to a series of tests each with criteria for passing or failing. Designs that fail are eliminated from further testing, while those passing are subjected to additional scrutiny. In the tradeoff approach the relative changes in each test would be assessed in light of other information about the particular design. Changing cigarette additives can complicate toxicity testing. This is because new additives might introduce entirely new toxic endpoints which are not associated with current products.

The FTC method describes: how cigarettes are to be prepared for smoking, the type of smoking machine to use, the way the smoking machine should be operated, the method for collecting smoke products, and ways to measure moisture content, nicotine, carbon monoxide and tar. Typically in the methods provided herein, the FTC protocol for studies of cigarette smoke chemistry and toxicity are used. There is capability to make six runs per day at the Tobacco Institute Laboratory.

Toxicity of cigarette smoke is directly related to the composition of the smoke and the composition of smoke can be changed if the way the cigarettes are smoked is changed.

There are a variety of chemical analyses that can be done to aid in the determination of the change in toxicity of a tobacco. These relate to the chemical composition of tobacco smoke. The following lists the chemical composition analysis and the health effect associated with the component or property measured Analysis Total Particulate Matter (TPM; carcinogen), pH (effect on nicotine toxicity), Redox Potential (influence toxicity of whole smoke), Carbon Monoxide (reduces ability of blood to carry oxygen) Nitrogen Oxides (NOx; increases nitrosamine formation, inhibits enzyme function) Hydrogen Cyanide (inhibits lung clearance, lowers ability of body to use oxygen), Hydrocarbons (benzene, butadiene; suspected or known carcinogens) Aldehydes (ex. formaldehyde, acrolein; inhibit lung clearance, animal carcinogens) Volatile nitrosamines (strong animal carcinogens), Tobacco-specific nitrosamines (strong animal carcinogens), Nicotine (associated with cardiovascular disease); Phenols (enhance carcinogen action) Catechol (major carcinogen), Polynuclear Aromatic Hydrocarbons (PNAs; major tumor initiators).

There are also a variety of known cell toxicity tests that can be performed in a relatively short time scale: bacterial mutagenicity test, animal cell test to detect potential carcinogens, and lung inflammation test in animals. One test, the Ames test, uses certain types of *Salmonella* bacteria to quantitatively assess the ability of a material to cause mutations, such as mutations involved in the process of carcinogenesis.

In this test a solution of collected smoke particulates is mixed with the bacteria. Bacteria with the ability to grow in the absence of a particular nutrient are scored as mutants.

The potential cancer-causing ability of chemicals can also be evaluated using a cell transformation assay. In this assay solutions of smoke particulates are given to animal cells grown in Petri dishes in the laboratory. After several weeks the cells are examined under the microscope. At this time the cells are scored for abnormal growth patterns. The number of clusters of abnormally growing cells is then compared among cigarette types.

In animal studies, inflammation of the lungs can be assessed. The changes measured in this test can be related to the development of chronic obstructive pulmonary disease. In these tests mice can be exposed to whole smoke two times per day, for any number of days according to the experimental design. At the end of the exposure period the animals would be killed and their lungs washed out to collect inflammatory cells. The numbers and kinds of the cells would be measured.

Two long-term animal tests for cancer causing ability of tobacco can be performed. In the first, test cigarette tar is applied to the back skin of mice. Skin tumors are then scored over the life of the animals. The use of this test is based on two observations: (1) in studies of tumor formation by smoke in hamsters whole smoke is active but smoke free of particulates is not and (2) a large number of known carcinogens are contained in the particulate portion of cigarette smoke.

The second test examines the tumor forming ability, of whole smoke in hamsters. A positive response can be observed in the larynx of hamsters exposed over their lifetime to whole cigarette smoke. In this test the animals are exposed twice daily to the diluted smoke of one cigarette every day for their entire lives. Tumor formation is the endpoint measured in this assay. Because the test is so labor intensive it is recommended only as a last step in a series of tests.

These known methods for assaying tobacco toxicity can have limitations in terms of time length and/or expense relative to the assay methods provided herein. Accordingly, there is a long felt need for more rapid and less costly methods of analysis of tobacco products of different compositions. Despite the inefficiencies of the approaches above, it is contemplated herein that these methods for assaying tobacco toxicity can be used in conjunction with the methods provided herein so as to provide additional information regarding the properties of the tobacco being characterized.

The methods provided herein can be applied to any tobacco or tobacco product, including, but not limited to pipe, cigar and cigarette tobacco and chewing tobacco in any form including leaf tobacco, shredded tobacco or cut tobacco. The term "tobacco product" includes, but is not limited to, smoking materials (e.g., cigarettes, cigars, pipe tobacco), snuff, chewing tobacco, gum, and lozenges.

In the methods provided herein, one or more cells can be contacted with a tobacco composition such as tobacco smoke (TS), or a tobacco smoke condensate (TSC), where exemplary TS and TSC are cigarette smoke (CS) and cigarette smoke condensate (CSC). Preparation of the Tobacco Composition Used in the Methods Provided Herein can be performed in accordance with the teachings herein and the knowledge and skill in the art. For example, TS can be collected using a smoking machine such as an INBIFO-Condor smoking machine, and TSC can be collected using cold traps, as is known in the art. For example, CSC for testing can be prepared by passing smoke through a series of cold traps containing glass beads upon which CSC condenses; the CSC can then be collected by washing the beads with acetone as described in Mathewson, H. D. Beitrage zur Tabforschung. 3(6):430-7. September 1966. In addition, cells can be contacted with smoke provided in diluted form, where diluted smoke can be produced in a dilution chamber, as known in the art. For example, a smoking setup can contain a dilution chamber where the concentration of the smoke being applied to the cells can be varied by dilution with air in order to produce different dosages and intensities of smoke. The dilution chamber can be located between the burning cigarette and the cell exposure chamber. In addition, cigarette particulate matter for testing can be prepared by passing smoke through a glass fiber filter which is subsequently washed with solvent to collect the sample as described in Coresta Recommended Method No. 23 (August 1991). Although the description herein provides several methods in the context of characterizing tobacco and tobacco products that undergo pyrolysis (e.g., cigarettes, pipe tobacco, and cigars), similar approaches can be applied to the evaluate snuff, chew, and other tobacco products that do not undergo pyrolysis. Accordingly, the methods provided herein are not limited to smoke or smoke condensate, but can be applied to any tobacco composition known in the art. The preparation and analysis of compositions from such non-pyrolysis tobacco products is straightforward given the teachings provided herein or otherwise known in the art. Methods for contacting cells with compositions from such non-pyrolysis tobacco products also is straightforward given the teachings provided herein or otherwise known in the art.

The tobacco derived composition (i) can originate in a tobacco product, which can be either pure tobacco or a tobacco formulation (such as a cigarette, cigar, pipe or chewing tobacco) having multiple compositional elements, for example but not limited to structural elements, flavor chemicals and/or other additives, and (ii) can have multiple components (e.g., smoke or a smoke condensate, also referred to collectively as "smoke products") or can be a single known or unidentified component (e.g., a single chemical compound). The composition can be "derived" from tobacco or a tobacco formulation (i) by simple physical separation; (ii) as a product of combustion or heating, (iii) by solvent extraction, (iv) by chemical reaction(s) or (v) by enzyme activity (e.g., smoke concentrate treated with a microsomal cellular fraction or purified cytochrome P450).

In some methods provided herein, cells are contacted with TS, such as CS. The contacting of the cells with the CS, CSC, TS, or TSC can be accomplished using any method known to one of skill in the art, including but not limited to, placing said cells into a smoking machine or smoke chamber (e.g., CULTEX®) for a period of time to allow the cells to be contacted with smoke, and/or providing a CSC or TSC to the media for a designated period of time (e.g., in beeswax or other formulation). The contacting can be for any amount of time, however, preferably the cells are contacted for an amount of time that does not result in nonviability of more than 40% of the cells. In some embodiments, the amount of time can be varied and the results are compared. In a further embodiment, the cells are treated for an amount of time in which the gene expression is modulated, but the majority of cells are still viable. That is, in some embodiments, the cells are treated to a point in which the cells are at least, equal to, or more than 1% viable, including but not limited to 1%, 5%, 10%, 15%, 20%, 25%, 30%, 35%, 40%, 45%, 50%, 55%, 60%, 65%, 70%, 75%, 80%, 85%, 90%, 95%, 99%, and 100% viable.

In a another embodiment, the amount of time for contacting a cell with the CS, CSC, TS, or TSC is any amount selected from the group consisting of about at least, equal to, or more than 1 seconds to about 24 hours, including but not limited to at least, equal to, or more than 1 second, 15 seconds, 30 seconds, 45 seconds, 1 minute, 3 minutes, 5 minutes, 10 minutes, 15 minutes, 20 minutes, 25 minutes, 30 minutes, 35 minutes, 40 minutes, 45 minutes, 60 minutes, 1.5 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 10.5 hours, 11 hours, 11.5 hours, 12 hours, 12.5 hours, 13 hours, 13.5 hours, 14 hours, 14.5 hours, 15 hours, 15.5 hours, 16 hours, 16.5 hours, 17 hours, 17.5 hours, 18 hours, 18.5 hours, 19 hours, 19.5 hours, 20 hours, 20.5 hours, 21 hours, 22 hours 23 hours and 24 hours. In a further embodiment, the cells are contacted for less than and including about 20 minutes. In yet another embodiment, the cells are contacted for about 2 to about 20 minutes.

The amount of smoke with which the cells are contacted can be any of a variety of amounts according to the desired level of exposure. For example, smoke exposure can be performed in accordance with FTC parameters: 2.0 second puff duration, 35 mL puff every 60 seconds. Puff duration, volume and frequency can be increased or decreased to achieve different levels of smoke exposure, as desired. Similarly, smoke condensate or other tobacco compositions can be contacted with cells at a variety of different concentrations and for a variety of different durations, as desired. For example, smoke condensate at 20 mg/mL can be contacted with cells for any of the above-provided amounts of time, as desired.

Tobacco smoke or smoke products can be treated prior to contacting the cells with the smoke or smoke product. For example, the smoke or smoke concentrate can be contacted with a filter, for example by obtaining smoke or smoke condensate from a cigarette after passing through a filter attached to the tobacco product, such as a cigarette. The filters that can be used can be any of a variety of known filters, including commercially available filters provided in cigarette products, and other filters known in the art, such as charcoal and/or paper-containing filters. One exemplary filter can be a filter containing an antioxidant or a radical scavenger. Filters containing antioxidants or radical scavengers can be prepared according to known methods, as exemplified in U.S. Pat. Nos. 6,832,612 and 6,415,798, herein expressly incorporated by reference in their entireties. Other filters can be a filter that can sequester or intercept harmful components that generate DNA breaks, or enhance DNA breakage, thereby yielding a filter that removes harmful smoke components. For example, a filter can contain flat aromatic compounds that can scavenge potential carcinogens (e.g., components of tar), where exemplary flat aromatic compounds include caffeine and pontoxyfyllen. In some of the methods provided herein the filter comprises an interceptor of the carcinogen that has aromatic chemical structure: the carcinogen associates then with interceptor forming a complex that is retained in the filter.

A tobacco composition used in the methods provided herein, such as TS, TSC, CS or CSC can be derived from any of a variety of different tobacco products, where the tobacco products can be formed from any of a variety of tobaccos known in the art, including modified tobacco. As used herein, "modified tobacco" refers to a tobacco that has been subjected to one or more genetic, chemical or processing steps that is different than the conventional treatment or processing of traditional "wild-type" tobacco products. In one example, a tobacco product can be genetically modified, by, for example, administering to a tobacco plant a nucleic acid molecule that modulates expression of one or more genes in the tobacco plant that produce a compound. Genetically modified tobacco and methods of preparing same are provided elsewhere herein. In another example, a tobacco product can be chemically modified, by, for example, extracting or chemically altering one or more components of tobacco, according to methods known in the art as exemplified in U.S. Pat. Nos. 6,789,548, 4,557,280; 4,561,452; 4,848,373; 4,183,364; 4,215,706; 4,257,430; 4,248,251; 4,235,251; 4,216,784; 4,177,822; 4,055,191 (all of which are herein expressly incorporated by reference in their entireties) or by adding one or more compounds to a tobacco plant prior to harvesting the tobacco, as known in the art and exemplified in U.S. Pat. Pub. No. 20050072047, herein expressly incorporated by reference in its entirety. Additional modified tobaccos contemplated herein include reconstituted tobacco, extracted tobacco, and expanded or puffed tobacco. In some embodiments, the tobacco is modified to have a reduced amount of a compound that contributes to a tobacco-related disease, including, but not limited to, a compound associated with a tobacco-related disease or a metabolite thereof (e.g., tobacco sterols, nicotine, a TSNA, and a gene product that is involved in the production of a compound associated with a tobacco-related disease or a metabolite thereof.

Several genetically modified tobacco plants, tobaccos, and tobacco products comprising said tobaccos are described in the sections that follow. The genetically modified tobacco plants described herein are suitable for conventional growing and harvesting techniques (e.g. topping or no topping, bagging the flowers or not bagging the flowers, cultivation in manure rich soil or without manure) and the harvested leaves and stems are suitable for use in any traditional tobacco product including, but not limited to, pipe, cigar and cigarette tobacco and chewing tobacco in any form including leaf tobacco, shredded tobacco or cut tobacco. It is also contemplated that the transgenic tobacco (e.g., reduced nicotine/TSNA and/or sterol tobacco) described herein can be processed and blended with conventional tobacco so as to create a wide-range of tobacco products with varying amounts of nicotine, nitrosamines, and/or sterols.

The cells suitable for use in the methods provided herein include human as well as non-human cells, but are preferably human pulmonary cells (e.g., lung or bronchial cell), although cells of other systems impacted by smoking, including but not limited to cells of the upper aerodigestive tract (e.g., oral cavity including cheek, pharynx, larynx, and esophagus), bladder, stomach, kidney, pancreas, and blood (e.g., lymphocytes, monocytes, neutrophils, esoinophils or basophils, or neoplastic blood cells such as myeloid leukemia cells); cells of the cardiovascular system (including endothelial cells, smooth muscle cells (e.g. from vessel walls, myocardial cells, etc.) and cells of the female reproductive system (e.g. cells of the uterus, cervix, fallopian tubes, ovary, and placenta), can also be used. The cells can be normal or can be neoplastic, metaplastic, dysplastic or malignant. The cells can be collected from a living organism (e.g., a pulmonary lavage specimen, tissue section such as a lung or bronchial section, oral mucosa sample, cheek swab, or sputum sample) or can be established cell cultures. In some embodiments, the cells can be obtained from a living organism, including a human, after the organism is contacted with a tobacco composition, for example, after a human consumes a cigarette. Cells collected from a living organism can be collected using any of a variety of known methods known in the art, according to the cell type to be collected (e.g., a cheek scrape or lung lavage). In specific, non-limiting embodiments, the cells can be NHBE cells, or can be human epithelian pulmonary type II cells, such as A549 cells, or can be cells obtained from a human primary culture.

Many embodiments described herein employ NHBE cells that are maintained in culture, and other embodiments employ human lung carcinoma cells (A549 cells). Although NHBE and A549 cells are preferred for the methods described herein, it should be understood that many other cells that are typically contacted with tobacco or TS during the process of smoking (e.g., lung cells, bronchial cells, cells of the oral mucosa, pharynx, larynx, and tongue) can also be used. Additionally, many immortal cell lines can be used with the methods described herein. Preferred cells for use with the embodied approaches include, but are not limited to, human bronchial cells (e.g., BEP2D or 16HBE140 cells), human bronchial epithelial cells (e.g., HBEC cells, 1198, or 1170-I cells), NHBE cells, BEAS cells (e.g., BEAS-2B), NCI-H292 cells, non-small cell lung cancer (NSCLC) cells or human alveolar cells (e.g., H460, H1792, SK-MES-1, Calu, H292, H157, H1944, H596, H522, A549, and H226), tongue cells (e.g., CAL 27), and mouth cells (e.g., Ueda-1)). Many of such cultures are available commercially or through a public repository (e.g., ATCC). Further, several techniques exist that allow for one to generate primary cultures of said cells and these primary cultures can be used with the methods described herein.

Conventional approaches in tissue culture can be used to establish and maintain said cells in preparation for the methods described herein. That is, the cells may be grown in culture by any method known to one of skill in the art and with the appropriate media and conditions. The cells grown in culture may require feeder layers, for example. The cells may be grown to confluence or may be grown to less than confluence before, during, or after treatment. In some embodiments the cells are grown to between about 10% and about 90% confluence, including but not limited to, at least, equal to, or more than 15%, 20%, 25%, 30%, 35%, 40%, 45%, 50%, 55%, 60%, 65%, 70%, 75%, 80%, 85%, 90%, 95%, and 99% confluence before contact with CS, CSC, TS, or TSC.

In some embodiments, the cells contacted and assayed in accordance with the methods provided herein are manipulated to control and/or modify the percentage of cells that are in one or more phases of the cell cycle. For example, the cells can be manipulated such that at least 50% of the cells of the population of cells are in the S phase. The cells used herein can be manipulated to control the population of cells in one or more of $G_0$, $G_1$, S, $G_2$, or M phases of the cell cycle. For example, cells can be manipulated such that at least 50%, 60%, 70%, 75%, 80%, 85%, 90%, 95%, or 100%, of the population of cells are in $G_0$, $G_1$, S, $G_2$, or M phase. In another example, cells can be manipulated such that greater than 50%, 60%, 70%, 75%, 80%, 85%, 90%, 95%, or 100%, of the population of cells are in $G_0$, $G_1$, S, $G_2$, or M phase. In another example, cells can be manipulated such that 50%, 60%, 70%, 75%, 80%, 85%, 90%, 95%, or 100%, of the population of cells are in $G_0$, $G_1$, S, $G_2$, or M phase. The section below describes several preferred methods for characterizing tobacco and tobacco products in greater detail.

Exemplary Assays

The methods provided herein for characterizing tobacco can be used in a variety of applications, including, but not limited to, the comparison of two or more tobaccos, identifying induction of damage of cellular genetic material or modulation of cell homeostasis, identifying a tobacco product that has a reduced potential to contribute to a tobacco-related disease, and making a tobacco product that has a reduced potential to contribute to a tobacco-related disease. In addition to methods provided herein for characterizing tobacco or a tobacco product, additional methods known in the art for characterizing tobacco can be used in conjunction with the methods provided herein.

The methods of identifying a tobacco, identifying a compound in tobacco, identifying a tobacco product, and making a tobacco product provided herein, can in addition be utilized in methods of identifying two or more tobaccos, identifying a compound in two or more tobaccos, identifying a tobacco product by comparing two or more tobacco products, and making a tobacco product by comparing two or more tobacco products. In some embodiments, the two or more tobaccos can be compared for their effect on damage to genetic material of cells. In some embodiments, at least one tobacco can be a reduced risk tobacco. In some embodiments, at least one tobacco can be a modified tobacco, such as a chemically modified tobacco or a genetically modified tobacco. In one example, two or more tobaccos can be compared to identify a compound in tobacco that induces a double-strand DNA break, an inhibition of apoptosis, or an inhibition of cell proliferation.

In some embodiments, a second tobacco product (e.g., a cigarette) is compared to a first tobacco product (e.g., a cigarette) using the methods above so as to identify which of the two tobacco products is less likely to contribute to a tobacco-related disease. For example, a first population of isolated human cells of the mouth, tongue, oral cavity, or lungs (e.g., NHBE cells), is contacted with a CS from a first tobacco product (e.g., a "reduced risk full flavor" cigarette) in an amount and for a time sufficient to induce damage of cellular genetic material or modulate cell homeostasis. A second population of isolated human cells of the mouth, tongue, oral cavity, or lungs (e.g., NHBE cells), preferably the same type of cell as used in the analysis of the first tobacco product, is also contacted with a CS from a second tobacco product (e.g., a cigarette) in an amount and for the same amount of time as used with the first product or for a time sufficient to induce damage of cellular genetic material or modulate cell homeostasis.

The data obtained from the analysis of the first tobacco product can be compared to the data obtained from the analysis of the second tobacco product so as to identify, for example, an increased risk tobacco or a compound in tobacco. The data also can be used to identify a decreased risk tobacco. Thus, by analyzing the differences between the tobacco products, one can identify a tobacco product that has less potential to contribute to a tobacco related disease or to identify, for example, a first tobacco product that has a reduced risk to contribute to a tobacco-related disease, as compared to a second tobacco product or vice versa. By one technique, a tobacco product that is less likely to contribute to a tobacco-related disease is identified because it induces less damage to cellular genetic material. In another technique, a tobacco product that is less likely to contribute to a tobacco-related disease is identified because it causes less modulation of cell homeostasis. By another technique, a tobacco product that is less likely to contribute to a tobacco-related disease is identified because it causes less modulation of cell homeostasis under the same level of damage induced to cellular genetic material.

The methods provided herein can be used not only to identify a tobacco product that has a reduced potential to contribute to a tobacco-related disease, as compared to a second tobacco product, but also to develop tobacco products that have a reduced potential to contribute to a tobacco-related disease, as compared to a second tobacco product. That is, by screening modified tobacco (e.g., chemically or genetically modified tobacco) in accordance with the methods disclosed herein, one can rapidly determine whether the modified tobacco has an increased or decreased potential to contribute to a tobacco-related disease, as compared to the tobacco that is not modified.

More embodiments concern methods to identify components of a tobacco product that contribute to a tobacco-related disease, the selective removal or inhibition of production of these components, and the determination that the removal of the component(s) modulates expression of a gene that is associated with a tobacco-related disease in a manner that reduces the potential for the tobacco product to contribute to a tobacco related disease. It is contemplated that particular components of tobacco products are the factors that modulate responses in human cells that contribute to tobacco-related disease. It is further contemplated that modification of genes that contribute to the production of these toxic components in tobacco (e.g., genetic engineering or chemical treatment) will, concomitantly, result in a modulation of the response in human cells contacted with the smoke from said modified tobacco, which modulates the likelihood to contribute to a tobacco-related disease relative to tobacco prior to modification of the component-producing gene. Accordingly, by selectively removing the components that induce the events that contribute to tobacco-related disease in a human, one can develop tobacco products that are less likely to contribute to a tobacco-related disease.

By one approach, for example, CS is generated using a smoking machine from a first tobacco product that has been genetically modified to have a reduced amount of a compound. A first population of NHBE cells is contacted with said CS obtained from the modified tobacco, and the cells contacted with CS are assayed for double-strand DNA breaks. A second population of NHBE cells is then contacted with CS generated from the parental variety of tobacco. That is, the parental variety of tobacco is the unmodified tobacco variety used to generate the modified tobacco variety, wherein the unmodified tobacco retains the component that was removed or inhibited in the modified tobacco. The second population of cells contacted with CS is then assayed for double-strand DNA breaks. A comparison of the data obtained from the analysis of the first and second tobacco products will reveal that the difference in double-strand DNA breaks caused by the modified tobacco relative to the unmodified tobacco. By this approach, one can effectively identify the contribution of individual components of a tobacco product to double-strand DNA breaks, or other assay conditions provided herein. These methods can thereby be used to identify the contribution of individual components of a tobacco product to a tobacco-related disease. This approach can be used to develop tobacco products that are less likely to contribute to a tobacco-related disease and reduced risk tobacco products identified by these methods are aspects of the invention. Further, tobacco products prepared by these approaches can be prepared according to good manufacturing processes (GMP) (e.g., suitable for or accepted by a governmental regulatory body, such as the Federal Drug Administration (FDA), and containers that house said tobacco products can comprise a label or other indicia, with or without structure-function indicia, which reflects approval of said tobacco product from said regulatory body.

Thus, the methods provided herein can be used to characterize a first and a second tobacco by providing the first and second tobaccos, obtaining a first and second tobacco composition from the first and second tobaccos, respectively, contacting a first cell with the first tobacco composition and contacting the second cell with the second tobacco composition, and identifying one or more attributes of the contacted cells. Different tobacco products can contain different levels of carcinogens that can induce various types of cell damage including mutations, chromosomal aberrations, aberrant sister chromatid exchanges and micronuclei. Comparison of attributes of cells contacted with different tobacco compositions can be performed in the methods provided herein, and such attributes include induction of damage of cellular genetic material or modulation of cell homeostasis. Accordingly, the methods provided herein can be used to compare two or more tobaccos by assay methods including assay for induction of damage of cellular genetic material or modulation of cell homeostasis. Exemplary assay methods include assays of a double-strand DNA break, inhibition of apoptosis, or inhibition of cell proliferation.

In some embodiments, the first and second smoke products are prepared using essentially equivalent protocols. The phrase, "wherein the first and second smoke products are prepared using essentially equivalent protocols," as used herein, means that the two smoke products can be validly compared. For example, both products can be smoke or both products can be smoke concentrates.

The methods provided herein include methods of identifying a compound in tobacco that induces damage of cellular genetic material or modulates cell homeostasis by providing a first tobacco, obtaining smoke or a smoke condensate from the first tobacco, contacting a first population of cells with the smoke or smoke condensate from the first tobacco, identifying induction of damage of cellular genetic material or modulation of cell homeostasis in the first population of cells after contact with the smoke or smoke condensate from the first tobacco, providing a second tobacco that has been modified to reduce a compound in the second tobacco, obtaining smoke or a smoke condensate from the second tobacco, contacting a second population of cells with the smoke or smoke condensate from the second tobacco, and identifying an induction of damage of cellular genetic material or modulation of cell homeostasis in the second population of cells after contact with the smoke or smoke condensate from the second tobacco, where an identification of a reduction in the induction of damage of cellular genetic material or modulation of cell homeostasis in the second population of cells after contact with the smoke or smoke condensate from the second tobacco identifies the compound as one that induces damage of cellular genetic material or modulates cell homeostasis. Compounds identified in accordance with the methods provided herein can be, for example, compounds that induce the double strand DNA breaks, inhibit apoptosis, or inhibit cell proliferation. In some embodiments, the second tobacco can be genetically modified to reduce the expression of at least one gene that regulates production of the compound.

The compound in tobacco that induces damage of cellular genetic material or modulates cell homeostasis identified by the methods provided herein can be a tobacco-derived substance associated with double-strand DNA breaks (DSBs). The tobacco-derived substance associated with DSBs can be detected in the context of comparing the harmful potential of two different tobacco or smoke products (as provided herein elsewhere) or can be detected in an environmental context, such as TS in a business office, train car, or restaurant. The ability to detect the tobacco derived substance can depend on not only its presence, but also its concentration in the "tobacco test composition" (which can be smoke, a smoke concentrate, or, for example, an air sample containing or potentially containing TS). To that end, useful parameters for assessing the degree of harmfulness can include, for example, not only the degree of phosphorylation of H2AX (or accumulation of another DSB marker), but also the initial rate of DSB accumulation, the period of time required to reach a plateau and the degree of phosphorylated DSB at the plateau level where a rapid rise in the degree of H2AX phosphorylation, a protracted period of time to reach a plateau, and a high plateau level can be correlated with increased harmful potential (for example, see FIGS. 3 and 4 and accompanying text). Note that where assay conditions are relatively prolonged (for example, longer than 55 minutes) it can be desirable to include, in the assay, a phosphatase inhibitor such as calyculin A or okadaic acid to inhibit and/or prevent possible dephosphorylation of H2AX molecules.

Also provided herein are methods of identifying a tobacco product that has a reduced potential to contribute to a tobacco-related disease by providing a first tobacco product, obtaining smoke or a smoke condensate from the first tobacco product, contacting a first population of cells with the smoke or smoke condensate from the first tobacco product, identifying the presence or absence of an induction of damage of cellular genetic material or modulation of cell homeostasis in the first population of cells after contact with the smoke or smoke condensate from the first tobacco product, providing a second tobacco product, obtaining smoke or a smoke condensate from the second tobacco product, contacting a second population of cells with the smoke or smoke condensate from the second tobacco product, and identifying the presence or absence of an induction of damage of cellular genetic material or modulation of cell homeostasis in the second population of cells after contact with the smoke or smoke condensate from the second tobacco product, where an identification of a reduction in the amount or the absence of an induction of damage of cellular genetic material or modulation of cell homeostasis in the second population of cells after contact with the smoke or smoke condensate from the second tobacco product, as compared to the amount or presence of an induction of damage of cellular genetic material or modulation of cell homeostasis identified in the first population of cells identifies the second tobacco product as one that has a reduced potential to contribute to a tobacco-related disease. Tobacco products identified as having a reduced potential to contribute to a tobacco-related disease in accordance with the methods provided herein can be, for example, tobacco products that are characterized by a reduced induction of double strand DNA breaks, a lower level of inhibition of apoptosis, or a lower level of inhibition of cell proliferation.

Also provided herein are methods of making a tobacco product that has a reduced potential to contribute to a tobacco-related disease by providing a first tobacco, obtaining smoke or a smoke condensate from the first tobacco, contacting a first population of cells with the smoke or smoke condensate from the first tobacco, identifying the presence or absence or amount of induction of damage of cellular genetic material or modulation of cell homeostasis in the first population of cells after contact with the smoke or smoke condensate from the first tobacco, providing a second tobacco that is genetically modified to reduce the expression of at least one gene that regulates production of a compound in the second tobacco, obtaining smoke or a smoke condensate from the second tobacco, contacting a second population of cells with the smoke or smoke condensate from the second tobacco, identifying the presence or absence or amount of induction of damage of cellular genetic material or modulation of cell homeostasis in the second population of cells after contact with the smoke or smoke condensate from the second tobacco, where an identification of a reduction in the presence or amount of induction of damage of cellular genetic material or modulation of cell homeostasis in the second population of cells after contact with the smoke or smoke condensate from the second tobacco, as compared to the presence or amount of induction of damage of cellular genetic material or modulation of cell homeostasis identified in the first cell population identifies the second tobacco as one that has a reduced potential to contribute to a tobacco-related disease, and incorporation of the second tobacco, which has a reduced potential to contribute to a tobacco-related disease, into a tobacco product. Tobacco products identified as having a reduced potential to contribute to a tobacco-related disease in accordance with the methods provided herein, which are incorporated into a tobacco product, can be, for example, tobacco products that are characterized by a lower induction of double strand DNA breaks, lower level of inhibition of apoptosis, or lower level of inhibition of cell proliferation. The following section describes several methods for identifying a tobacco or tobacco product that induces genetic damage.

Methods for Identifying a Tobacco that Induces Genetic Damage

Provided herein are methods of identifying a tobacco that induces genetic damage by providing a tobacco, obtaining a tobacco composition from the tobacco, contacting a cell with the tobacco composition, and identifying the presence or absence of damage of cellular genetic material in the cell after contact with the tobacco composition. In some embodiments, the methods provided herein can be used to identify a tobacco that induces a double-strand DNA break. In some embodiments, the tobacco composition can be smoke or smoke condensate.

Also provided herein are methods of identifying a compound in tobacco that induces damage of cellular genetic material by providing a first tobacco, obtaining a tobacco composition from the first tobacco, contacting a first population of cells with the tobacco composition from the first tobacco, identifying the amount of damage of cellular genetic material in the first population of cells after contact with the tobacco composition from the first tobacco, providing a second tobacco that has been modified to reduce a compound in the second tobacco, obtaining a tobacco composition from the second tobacco, contacting a second population of cells with the tobacco composition from the second tobacco, and identifying the amount of damage of cellular genetic material after contact with the tobacco composition from the second tobacco, where an identification of a reduction in the amount of damage of cellular genetic material after contact with the tobacco composition from the second tobacco identifies the compound as one that induces the damage of cellular genetic material. In some embodiments, the methods provided herein can be used to identify a compound in tobacco that induces a double-strand DNA break. In some embodiments, the tobacco composition can be smoke or smoke condensate.

Also provided herein are methods of identifying a tobacco product that has a reduced potential to contribute to a tobacco-related disease by providing a first tobacco product, obtaining a tobacco composition from the first tobacco product, contacting a first population of cells with the tobacco composition from the first tobacco product, identifying the amount of damage of cellular genetic material in the first population of cells after contact with the tobacco composition from the first tobacco product, providing a second tobacco product, obtaining a tobacco composition from the second tobacco product, contacting a second population of cells with the tobacco composition from the second tobacco product, and identifying the amount of damage of cellular genetic material after contact with the tobacco composition from the second tobacco product, where an identification of a reduction in the amount of damage of cellular genetic material after contact with the tobacco composition from the second tobacco product as compared to the amount of damage of cellular genetic material after contact with the tobacco composition from the first tobacco product identifies the second tobacco product as one that has a reduced potential to contribute to a tobacco-related disease. In some embodiments, the second tobacco product has been modified to reduce a compound in the second tobacco. In some embodiments, the second tobacco product can be genetically modified to reduce the expression of at least one gene that regulates production of the compound. In some embodiments of the methods provided herein, the amount of damage of cellular genetic material can be determined by identifying the induction of double-strand DNA breaks. In some embodiments, the tobacco composition can be smoke or smoke condensate.

Also provided herein are methods of making a tobacco product that has a reduced potential to contribute to a tobacco-related disease by providing a first tobacco, obtaining a tobacco composition from the first tobacco, contacting a first population of cells with the tobacco composition from the first tobacco, identifying the amount of damage of cellular genetic material in the first population of cells after contact with the tobacco composition from the first tobacco, providing a second tobacco, obtaining a tobacco composition from the second tobacco, contacting a second population of cells with the tobacco composition from the second tobacco, identifying the amount of damage of cellular genetic material after contact with the tobacco composition from the second tobacco product, where an identification of a reduction in the amount of damage of cellular genetic material after contact with the tobacco composition from the second tobacco as compared to the amount of damage of cellular genetic material after contact with the tobacco composition from the first tobacco identifies the second tobacco as one that has a reduced potential to contribute to a tobacco-related disease, and incorporating the second tobacco, which has a reduced potential to contribute to a tobacco-related disease, into a tobacco product. In some embodiments, the second tobacco has been modified to reduce a compound in the second tobacco. In some embodiments, the second tobacco can be genetically modified to reduce the expression of at least one gene that regulates production of the compound. In some embodiments of the methods provided herein, the amount of damage of cellular genetic material can be determined by identifying the induction of double-strand DNA breaks. In some embodiments, the tobacco composition can be smoke or smoke condensate.

Also provided herein are methods, compositions and kits for evaluating the ability of a tobacco-derived substance to produce DSBs in chromosomal DNA. The presence of DSBs is detected using an appropriate marker, which, in preferred embodiments of the invention, is phosphorylated histone H2AX (also referred to herein as "γH2AX"). The presence of DSBs also can be detected by detecting (i) activation of one or more of the protein kinases that are responsible for H2AX phosphorylation (e.g., ATM, ATR and/or DNA-PK); (ii) appearance of nuclear foci that are induced by histone H2AX phosphorylation; or (iii) activation of one or more protein components of nuclear "foci" induced by H2AX phosphorylation that are associated with DNA repair. The term "activation" in regard to proteins activated by DSBs refers to a chemical modification such as phosphorylation, acetylation, ubiquitinylation or poly(ADP)ribosylation, and/or a change in protein conformation, occurring in response to formation of DSBs. Activated proteins can be detected, for example, immunocytochemically.

Some of the assays provided concern methods of detecting, quantifying, identifying and/or evaluating (e.g., for harmfulness) a tobacco-derived substance in the course of research or in the environment via its promotion of DSBs in the chromosomal DNA of a test cell. A correlation with harmful potential is drawn based upon the known relationship between DSBs and genetic mutations (including cancer-causing and teratogenic mutations) as well as cell damage and death.

Accordingly, one set of preferred embodiments provided herein are methods of detecting a harmful tobacco-derived substance comprising the steps of (a) exposing a test cell (or test cell population) to a tobacco test composition; (b) measuring the degree of H2AX phosphorylation in the test cell or cell population; and (c) comparing the degree of H2AX phosphorylation determined in the test cell or cell population to the degree of H2AX phosphorylation in a control cell or control cell population; wherein a higher degree of H2AX phosphorylation in the test cell compared to the control cell indicates the presence of a harmful tobacco derived substance in the tobacco test composition. The presence of DSBs also can be detected by detecting (i) activation of one or more of the protein kinases that are responsible for H2AX phosphorylation (e.g., ATM, ATR and/or DNA-PK); (ii) appearance of nuclear foci that are induced by histone H2AX phosphorylation; or (iii) activation of one or more protein components of nuclear "foci" induced by H2AX phosphorylation that are associated with DNA repair.

Another set of non-limiting embodiments, provided herein include methods for identifying one or more harmful components of TS comprising the steps of: (a) exposing a first test cell population to a first smoke product generated from a first tobacco composition; (b) exposing a second test cell population to a second smoke product generated from a second tobacco composition, wherein the first and second smoke products are prepared using essentially equivalent protocols; (c) measuring the degree of H2AX phosphorylation in the first and second test cell populations; and (d) comparing the degree of H2AX phosphorylation in the first and second test cell populations; (e) identifying the tobacco composition associated with a greater degree of H2AX phosphorylation in steps (a)-(d); and (f) comparing the components of the first and second tobacco composition to identify one or more component present in the tobacco composition of step (e) but absent in the other tobacco composition. Methods for detecting activation of protein kinases such as ATM, ATR and/or DNA-PK as well as formation of nuclear "foci" and protein components of the nuclear foci can be performed according to the same steps. According to such embodiments, the first tobacco composition can differ from the second tobacco composition in its ingredients and/or in the way it was processed. The information obtained by this method can be used to develop a tobacco product that lacks or has lower levels of the identified harmful component(s), which can render the product lower-risk. Alternatively, the information can be used in an environmental context: for example, air purifiers can be modified to extract the harmful component from smoke-contaminated air.

Another set of non-limiting embodiments provided herein concern methods for identifying one or more harmful components of TS comprising the steps of: (a) exposing a first test cell population to a first smoke product generated from a tobacco composition; (b) exposing a second test cell population to a second smoke product generated from the tobacco composition, wherein the first and second smoke products are prepared differently; (c) measuring the degree of H2AX phosphorylation in the first and second test cell populations; (d) comparing the degree of H2AX phosphorylation in the first and second test cell populations; and (e) identifying the method of smoke product preparation associated with a greater degree of H2AX phosphorylation in steps (a)-(d); wherein the method of smoke product preparation identified in step (e) has greater harmful potential. Methods for detecting activation of protein kinases such as ATM, ATR and/or DNA-PK as well as formation of nuclear "foci" and protein components of the nuclear foci can be performed according to the same steps. In such embodiments, the methods of smoke product preparation can differ in the rate of combustion of the tobacco composition (including whether the tobacco composition is burned or heated), or can differ in the filtering of the smoke product (e.g., unfiltered, filtered with a traditional filter, or filtered with a filter containing an antioxidant), or can differ by other known methods of altering tobacco smoke products. The components of the different smoke products can be compared to identify one or more harmful components. As above, the identification of a harmful component can facilitate the development of lower-risk tobacco products and/or environmental safeguards.

Also provided herein are methods for comparing the harmful potentials of a first and a second tobacco composition comprising the steps of: (a) exposing a first test cell population to a first smoke product generated from the first tobacco composition; (b) exposing a second test cell population to a second smoke product generated from the second tobacco composition, wherein the first and second smoke products are prepared using essentially equivalent protocols; (c) measuring the degree of H2AX phosphorylation in the first and second test cell populations; and (d) comparing the degree of H2AX phosphorylation in the first and second test cell populations; wherein the tobacco composition which generated the smoke product that produced a higher degree of H2AX phosphorylation has greater harmful potential. Methods for detecting activation of protein kinases such as ATM, ATR and/or DNA-PK as well as formation of nuclear "foci" and protein components of the nuclear foci can be performed according to the same steps.

Accordingly, the methods provided herein include one or more steps of determining whether damage of cellular genetic material has occurred. Typically, such methods include assays for damage to the genomic DNA of the cell. Any of a variety of methods known in the art for assaying damage of cellular genetic material, such as genomic DNA, can be used in the methods provided herein. Exemplary known assays include assays for double-strand DNA breaks, assays for single-strand DNA breaks, and assays for modulated properties of DNA resultant from damage, such as assays for micronuclei and assays for chromosome exchange. Assays for DNA breaks are known in the art, as exemplified in U.S. Pat. Pub. No. 20040132004 and U.S. Pat. No. 6,309,838, all of which are hereby expressly incorporated by reference in their entireties.

In one example, the methods provided herein can include detection of double-strand DNA breaks by detection of phosphorylation of histone H2AX. Mammalian cells respond to agents that introduce DNA double-stranded breaks with the immediate and substantial phosphorylation of histone H2AX. While not wishing to be bound to the following theory, which is only offered to explain one possible mechanism, H2AX is thought to be involved in the recognition of regions of chromatin containing a DNA double-stranded break. Formation of the phosphorylated H2AX protein, termed gamma-H2AX, can be detected as an indicator of DNA double-stranded breaks. Known antibodies or antigenically-reactive fragments thereof that specifically bind to a C-terminal phosphorylated serine in an H2AX histone protein can be used for the detection of gamma-H2AX, and, thus can be used to indicate the presence of double stranded breaks in a cell. Thus, in the methods provided herein, the presence or absence of DNA damage can be detected by detecting the presence or absence of phosphorylation of histone H2AX. For example, the presence or absence of phosphorylation of histone H2AX can be identified with an antibody or fragment thereof, which binds to phosphorylated H2AX but not unphosphorylated H2AX. Antibodies and fragments thereof, and related methods for selectively detecting gamma-H2AX, are known in the art, as exemplified in U.S. Pat. Nos. 6,362,317 and 6,884,873, all of which hereby expressly incorporated by reference in their entireties.

In some embodiments provided herein, the methods include assaying a cell for double-strand DNA breaks (DSBs). DSBs are generated by a variety of genotoxic agents, and are among the most critical lesions that lead either to apoptosis, mutations or the loss of significant sections of chromosomal material. Detection of DSBs upon cell exposure to a potential carcinogen, therefore, provides the means to assess the potential hazard of the exposure in terms of cancer induction. In one embodiment, a sensitive assay of DSBs detection based on analysis of histone H2AX phosphorylation can be used. Histone H2AX, a variant of a family of at least eight protein species of the nucleosome core histone H2AX, becomes phosphorylated in live cells upon induction of DNA double strand breaks (DSBs). The phosphorylation of H2AX on Ser 139 at sites flanking the DSBs is carried out by ATM-, ATR-, and/or DNA-dependent protein kinases (DNA-PKs). The phosphorylated form of H2AX is denoted γH2AX.

The availability of antibodies to γH2AX allow for immunocytochemical detection of DSBs. After induction of DSBs, the appearance of γH2AX in chromatin manifests in the form of discrete foci, each focus considered to represent a single DSB. Checkpoint and DNA repair proteins such as Rad50, Rad51 and Brca1 co-localize with γH2AX. The intensity of γH2AX immunofluorescence (IF) measured by cytometry was reported to strongly correlate with the dose of ionizing radiation and thus with the number of the induced DSBs. However, because untreated cells, particularly cells replicating DNA, express γH2AX, to obtain a stoichiometric relationship between DSBs and the intensity of γH2AX IF, it is necessary to compensate for the extent of this "programmed" H2AX phosphorylation. Following compensation, the γH2AX IF measured by cytometry offers a sensitive and convenient means to detect and measure DSBs in individual cells following radiation. In fact, γH2AX IF can be a surrogate for cell killing in viability assays of radiated cells.

γH2AX antibody ("Ab") in conjunction with multiparameter flow- and laser scanning cytometry can be used in assays of DSBs, to detect and measure their induction in individual, live cancer cells exposed to antitumor drugs in vitro. The intensity of γH2AX IF correlates well with the drug concentration and duration of cell exposure to the drug, indicating a relationship between the incidence of DSBs induced by these drugs and γH2AX IF intensity. Multiparameter analysis of γH2AX IF and cellular DNA content made it possible to relate the abundance of DSBs (extent of DNA damage) to the position of the cell in the cycle.

The ability of the tobacco-derived substance to promote the formation of DSBs is measured using an appropriate DSB marker, which is preferably γH2AX (phosphorylated histone H2AX), but which can be another associated molecule, such as, but not limited to, Rad50, Rad51 and Brca1, and other proteins that are characteristic of nuclear "foci" formation. Formation of DSBs also can be detected by detecting activate protein kinases associated with DSBs such as ATM, ATR or DNA-PK. The presence of such markers can be determined using a marker-specific antibody (or derivative or fragment thereof), preferably an antibody (or fragment or derivative thereof) specific for γH2AX, or an antibody (or fragment or derivative thereof) specific for Rad50, Rad51 or Brca1, or ATM, ATR or DNA-PK. The presence of such markers can be determined using a marker-specific antibody (or derivative or fragment thereof), preferably an antibody (or fragment or derivative thereof) specific for a polypeptide encoded by a gene provided in Tables 1 and 2. The genes provided in Table 1 encode polypeptides that are involved in homologous recombination processes in the cell, and these genes can be activated in response to cellular damage of genetic material. Accordingly, detection of one or more products of the genes of Table 1 can be indicative of cellular damage of genetic material, for example, double-strand DNA breaks. The genes provided in Table 2 encode polypeptides that are involved in non-homologous nucleic acid end-joining processes in the cell, and these genes can be activated in response to cellular damage of genetic material. Accordingly, detection of one or more products of the genes of Table 2 can be indicative of cellular damage of genetic material, for example, double-strand DNA breaks. Provided herein is an exemplary use of antibody directed to γH2AX; analogous methods can be applied using antibodies directed to Rad50, Rad51, Brca1, ATM, ATR or DNA-PK, or the products of the genes listed in Tables 1 and 2. In preferred non-limiting embodiments of the invention, antibody binding can be detected by immunofluorescence-based techniques. Various antibodies for Rad50, Rad51, Brca1, ATM, ATR, DNA-PK, and the products of the genes listed in Tables 1 and 2 are known in the art and can be readily obtained for use in accordance with the methods provided herein; for example, Anti-phospho-ATM (Ser1981), is available from Upstate USA as clone 10H11.E12. Such techniques can optionally be used in conjunction with automated cytometry, such as, for example, flow and/or laser scanning cytometry.

TABLE 1

| Homologous recombination | | | Top of Page |
|---|---|---|---|
| RAD51 | Homologous pairing | 15q15.1 | NM_002875 |
| RAD51L1 (RAD51B) | Rad51 homolog | 14q24.1 | NM_002877 |
| RAD51C | Rad51 homolog | 17q23.2 | NM_002876 |
| RAD51L3 (RAD51D) | Rad51 homolog | 17q12 | NM_002878 |
| DMC1 | Rad51 homolog, meiosis | 22q13.1 | NM_007068 |
| XRCC2 | DNA break and crosslink repair | 7q36.1 | NM_005431 |
| XRCC3 | XRCC2, XRCC3 | 14q32.33 | NM_005432 |
| RAD52 | Accessory factors for | 12p13.33 | NM_002879 |
| RAD54L | recombination | 1p34.1 | NM_003579 |
| RAD54B | RAD52, RAD54L, RAD54B | 8q22.1 | NM_012415 |
| BRCA1 | Accessory factor for transcription and recombination, E3 Ubiquitin ligase | 17q21.31 | NM_007295 |
| BRCA2 | Cooperation with RAD51, essential function | 13q13.1 | NM_000059 |
| SHFM1 (DSS1) | BRCA2 associated | 7q21.3 | NM_006304 |
| RAD50 | ATPase in complex with MRE11A, NBS1 | 5q23.3 | NM_005732 |
| MRE11A | 3' exonuclease | 11q21 | NM_005590 |
| NBS1 | Mutated in Nijmegen breakage syndrome | 8q21.3 | NM_002485 |
| MUS81 | A structure-specific DNA | 11q13.1 | NM_025128 |
| EME1 (MMS4L) | nuclease MUS81, MMS4 | 17q21.33 | NM_152463 |

TABLE 2

| Non-homologous end-joining | | |
|---|---|---|
| G22P1 (Ku70) | 22q13.2 | NM_001469 |
| XRCC5 (Ku80) | 2q35 | NM_021141 |
| PRKDC | 8q11.21 | NM_006904 |
| LIG4 | 13q33.3 | NM_002312 |
| XRCC4 | 5q14.2 | NM_003401 |
| DCLRE1C (Artemis) | 10p13 | NM_022487 |

The term “immunofluorescence-based techniques” or “immunocytochemical-based techniques” encompasses various forms of such assays, as are known in the art. For example, and not by way of limitation, an immunofluorescence-based technique can use an unlabelled primary antibody and a fluorescently labeled secondary antibody (as illustrated, for example, in Example 1); or can use a primary antibody that carries a fluorescent tag to detect the phosphorylated H2AX molecule directly; or the primary antibody can carry a biotin molecule while the secondary antibody can carry both an avidin molecule (which binds specifically to biotin) and a fluorescence molecule. In the biotin/avidin approach, the binding of the secondary antibody is based on binding of biotin by avidin rather than the binding of an antibody of one species directed against a protein of another species. Other variations of such techniques that would be known to the skilled artisan as “immunofluorescence-based techniques” or “immunocytochemical-based techniques” can be used according to the invention. Likewise, detection can be made using analogous methods that utilize a modality other than fluorescence, such as chromogenic or colorimetric assays, radiologic assays, and so forth.

Techniques such as immunocytochemical-based techniques can be used in conjunction with methods for counting cells, sorting cells, or other method for further characterizing cells. Exemplary methods include, but are not limited to, flow cytometry, laser scanning cytometry, fluorescence image analysis, chromogenic product imaging, fluorescence microscopy or transmission microscopy.

The “degree of phosphorylation of H2AX” as used herein refers to the relative, rather than absolute, amount of γH2AX. This is because γH2AX is produced during normal progression of the cell cycle. As discussed in Example 1, allowance can be made for normally occurring phosphorylation of H2AX. For example, the data can preferably be subjected to two normalization processes. First, allowance can be made for the normally occurring “programmed” phosphorylation of H2AX. Second, correction can be made for the fact that histone content is exactly doubled over the course of a cell cycle, doubling the size of the target (histone). In a specific non-limiting embodiment, a data value from cells with twice the DNA content (e.g., $G_2$ and mitotic cells) with twice the histone target can be divided by 2 while a data value from cells in S phase having an intermediate in histone content can be divided by 1.5. In this manner, the amount of γH2AX detected beyond what occurs in an untreated control cell or cell population is normalized to a unit of histone so that one can refer to the “degree of histone H2AX phosphorylation” on a per unit of histone basis.

In another example, the methods provided herein can include detection of DNA breaks and other forms of genomic damage by Comet assay. Comet assay can be used to detect damaged DNA pulled from the nucleus of cells exposed to an electric field. Comet assay is a fluorescent microscopic method to examine DNA damage and repair at individual cell level. For example, cells can be embedded in agarose on a microscope slide and lysed with detergent and high salt to form nucleoids containing supercoiled loops of DNA linked to the nuclear matrix, and electrophoresis at high pH can result in structures resembling comets, observed by fluorescence microscopy. The intensity of the comet tail relative to the head reflects the number of DNA breaks. This assay can be used for detecting various forms of DNA damage (e.g., single- and double-strand breaks, oxidative DNA base damage, and DNA-DNA/DNA-protein/DNA-Drug cross-linking) and DNA repair in many eukaryotic cell types. Comet assay not only provides an estimate of how much damage is present in cells, but what form it takes. Although it is primarily a method for measuring DNA breaks, modifications of the methods, for example, by introducing lesion-specific endonucleases, allows detection of, for example, pyrimidine dimers, oxidized bases, and alkylation damage. Thus, in the methods provided herein, the presence or absence of DNA damage can identified by, for example, detecting the presence or absence of comet-like nuclei in cells. Various methods for performing Comet assays are known in the art, as exemplified in Collins, (2004) Mol. Biotechnology 26:249-261, Tice, et al. (2000) Environ. Mol. Mutagen. 35:206-221 and Gichner et al. (2004) Mutation Res. 559:49-57, all of which are hereby expressly incorporated by reference in their entireties.

In another example, the methods provided herein can include detection of double-strand DNA breaks by TUNEL assay. TUNEL assay can be used to measure double-strand breaks by incorporation of labeled nucleotides at the site of double-strand breaks using terminal transferase. The labeled nucleotides can then be detected with antibodies. TUNEL assay is frequently used to detect apoptosis-induced DNA fragmentation through a quantitative fluorescence assay. In one exemplary protocol, terminal deoxynucleotidyl transferase (TdT) catalyzes the incorporation of bromo-deoxyuridine (BrdU) residues into the fragmenting nuclear DNA at the 3'-hydroxyl ends by nicked end labeling. A TRITC-conjugated anti-BrdU antibody can then label the 3'-hydroxyl ends for detection. The TUNEL assay distinguishes two populations of cells: non-apoptotic cells (TUNEL-negative) and apoptotic cells (TUNEL-positive). Thus, in the methods provided herein, the presence or absence of DNA damage can identified by, for example, detecting the presence or absence of labeled nucleotides at the site of double-strand breaks, incorporated by, for example, terminal transferase. A variety of methods of performing TUNEL assays is known in the art, as exemplified in Doolin et al., J. Bum Care Rehabil. 20: 374-376, 1999; Kalyuzhny (2002) Methods Mol. Biol. 203: 219-34; Lawry, Methods Mol. Med. (2004) 88:183-90; U.S. Pat. No. 6,506,609 and U.S. Pat. Pub. No. 20030017462, all of which are hereby expressly incorporated by reference in their entireties.

In another example, the methods provided herein can include detection of double-strand DNA breaks by sister chromatid exchange assay. Sister chromatid exchange assays detect late damage when genetic material is exchanged between sister chromatids. Sister chromatid exchange refers to a reciprocal interchange of the two chromatid arms within a single chromosome. This exchange can be visualized during the metaphase portion of the cell cycle and can be mediated by the enzymatic incision, translocation and ligation of at least two DNA helices. Thus, in the methods provided herein, the presence or absence of DNA damage can identified by, for example, detecting the presence or absence of interchange of chromatid arms within a single chromosome by, for example, sister chromatid exchange assay. A variety of methods for performing sister chromatid exchange assays are known in the art, as exemplified in 40 C.F.R. §79.65, 40 C.F.R. §798.5915, Renqing et al., (2000) Toxicology Letters 115:23-32, Deen et al. and Cancer Res. (1986) 46:1599-602, all of which are hereby expressly incorporated by reference in their entireties.

In another example, the methods provided herein can include detection of double-strand DNA breaks by micronuclei assays. Micronuclei assays can be used to detect late damage occurring after cells attempt to divide so that non-centromeric DNA forms as micronuclei in daughter cells. The test is based on the observation that a secondary nucleus (micronucleus) is formed around a chromosomal fragment, outside the main nucleus of a dividing cell. A micronucleus may also be produced due to a lagging whole chromosome formed as a result of a chromosome loss at anaphase. Thus, in the methods provided herein, the presence or absence of micronuclei can be identified. Micronuclei can be detected by microscopic methods, flow cytometric methods and automated image recognition methods, as known in the art and exemplified in Offer et al., FASEB J. (2005) 19:485-7; Smolewski et al., Cytometry (2001) 45:19-26; Driessens et al., Ann NY Acad Sci. (2003) 1010:775-9; and U.S. Pat. Pub. No. 20050002552, all of which are hereby expressly incorporated by reference in their entireties.

In another example, the methods provided herein can include detection of chromosomal translocations. Chromosomal translocations can occur as a result of DNA damage. Methods for detecting chromosomal translocations can include fluorescence in situ hybridization methods (FISH), in which probe hybridization patterns in cells containing chromosomal translocation are altered relative to wild type. Thus, in the methods provided herein, the presence or absence of DNA damage can identified by, for example, detecting the presence or absence of chromosomal translocations by, for example, FISH. Methods for detecting chromosomal translocations are known in the art, as exemplified by U.S. Pat. Nos. 5,997,869, 6,576,421, and 6,416,948, and U.S. Pat. Pub. Nos. 20040235039 and 20020192692, all of which are hereby expressly incorporated by reference in their entireties.

Working Example 1 herein provides one non-limiting specific example of the DSB detection methods and materials. Variations of the assay method used in terms of materials, assay times, instrumentation and protocols would be apparent to the skilled artisan for detecting and/or quantifying DSBs, for example via γH2AX.

EXAMPLE 1

Preparation of Cigarette Smoke Condensates

Smoke was generated from a commercially available nationally sold brand of American cigarettes (non-menthol, full-flavor type with averaged FTC measured values of 14.5 mg tar/1.04 mg nicotine) using an INBIFO-Condor smoking machine under Federal Trade Commission (FTC) smoking parameters (2.0 second puff duration 35 milliliter puff every 60 seconds). The cigarettes had been equilibrated at 23.9° C.±1.1° C. and 60%±2% relative humidity for a minimum of 24 hours and a maximum of 14 days. CSC was collected from the smoke via a series of three cold traps (−10° C., −40° C., and −70° C.) onto impingers filled with glass beads. The smoke condensate was dissolved in acetone, which was then removed by rotary evaporation at 35° C. The resulting smoke condensate was weighed and dissolved in dimethylsulfoxide (DMSO) to make a stock solution at a concentration of 20 mg/mL, which was stored at −20° C. prior to use.

NHBE Cell Culture and Smoke Condensate Treatment

NHBE cells were purchased from Cambrex Corporation, East Rutherford, N.J. The cells were cultured in complete Bronchial Epithelial Cell Growth Medium (BEGM), prepared by supplementing Bronchial Epithelial Basal Medium with retinoic acid, human epidermal growth factor, epinephrine, transferrin, triiodothyronine, insulin, hydrocortisone, bovine pituitary extract and gentamicin by addition of SingleQuots™, (both medium and the supplements were purchased from Cambrex Corporation, East Rutherford, N.J.). Dual-chambered slides (Nunc Lab-Tek II, Fisher Scientific, Pittsburgh, Pa.) were seeded with 1 ml of $8\times10^4$ cells/ml cell suspension per chamber. All incubations were at 37° C. in a humidified atmosphere of 5% $CO_2$ in air. Cells were grown to 50% confluency, at which time they were treated with medium containing smoke condensate. Appropriate dilutions of the 20 mg/ml smoke condensate in DMSO stock solution were used to prepare culture medium containing 10, 25, or 50 µg/mL smoke condensate. The final DMSO concentration was 0.5%. Cells were treated by carefully aspirating the culture medium from each chamber and replacing it with 1 ml per chamber of smoke condensate-containing medium at 37° C. For control slides, the medium was replaced with 1 mL of either fresh medium (mock-treated control) or medium containing 0.5% DMSO (vehicle control). Slides were immediately returned to the incubator for up to 24 hours. At the end of the treatment, medium from each chamber was carefully aspirated and 1 ml of 1% fresh paraformaldehyde in 1× Dulbecco's PBS was added to each chamber and the cells fixed by gently rocking the slides at room temperature for 15 minutes. Following aspiration of the fixative, the chamber slides were disassembled and the slides submerged in 50 ml conical tubes filled with 70% ethanol. The fixed slides were stored at 4° C. prior to analysis.

A549 Cell Culture and Smoke Treatment

A549 cells were purchased from American Type Culture Collection (ATCC #CCL-185, Manassas, Va.). The cells were cultured in Ham's F12K medium with 2 mM L-glutamine adjusted to contain 1.5 g/L sodium bicarbonate (ATCC, Manassas, Va.) and supplemented with 10% fetal bovine serum (ATCC, Manassas, Va.). Dual-chambered slides (Nunc Lab-Tek II) were seeded with 1 ml of $10^5$ cells/ml cell suspension per chamber 48 hours before exposure. All incubations were at 37° C. in a humidified atmosphere of 5% $CO_2$ in air. Cells were grown to 70% confluency, at which time they were treated with smoke. The cell culture medium was replaced with 37° C. Dulbecco's PBS (D-PBS) containing calcium and magnesium (Sigma, St. Louis, Mo.) for the smoke exposure. Slide chamber covers were removed and the slides were placed in a smoke exposure chamber (20.6 cm×6.7 cm×6.3 cm—L×W×H). Smoke was generated from IM16 (Industry Monitor #16, Philip-Morris, Richmond Va.) cigarettes under FTC smoking conditions using a KC 5 Port Smoker (KC Automation, Richmond, Va.). The smoke was diluted by drawing it through a 250 mL round-bottom flask prior to its reaching the exposure chamber. The time and distance that the smoke traveled from the end of the cigarette to the exposure chamber was minimized by using the shortest lengths of tubing possible between the parts of the apparatus. Cigarettes were smoked to within 3 mm of the filter tip. Cells were exposed to smoke for up to 40 minutes. Mock-exposed (control) cells were treated under identical conditions as the exposed cells except for the absence of a cigarette in the smoking port. They were mock-exposed for 10 minutes. Following treatment or mock treatment, the D-PBS was aspirated and replaced with 1 ml per chamber of fresh culture medium at 37° C. The slides were placed in the 37° C., 5% $CO_2$ incubator and incubated for 15 minutes. Following incubation, the medium was aspirated and the cells fixed as described above for the NHBE experiment.

Immunocytochemical Detection of Phosphorylated Histone H2AX and Caspase-3 Activation Cells were treated with smoke (i.e., A549) or smoke condensate (i.e., NHBE) and fixed as described above, then rinsed twice in PBS and immersed in 0.2% Triton X-100 (Sigma) in a solution of 1% (w/v) bovine serum albumin (BSA; Sigma) in PBS for 30 min to suppress non-specific antibody binding. The cells were then incubated in 100 µl volume of 1% BSA containing 1:200 dilution of anti-phosphorylated histone H2AX (γH2AX) rabbit polyclonal Ab (Trevigen, Gaithersburg, Md.). After overnight incubation at 4° C., the slides were washed twice with PBS and then incubated in 100 µl of 1:200 dilution of Alexa Fluor 488 goat anti-rabbit IgG (H+L) (Molecular Probes, Eugene, Oreg.) for 45 min at room temperature in the dark. Parallel samples were incubated with 1:100 diluted anti-cleaved (activated) caspase-3 rabbit polyclonal Ab (Cell Signaling Technology, Beverly, Mass.) overnight at 4° C., washed twice with PBS and incubated with 1:30 diluted FITC-conjugated F(ab')2 fragment of swine anti-rabbit immunoglobulin (DAKO, Carpinteria, Calif.) for 30 min in room temperature in the dark. The cells were then counterstained with 1 µg/ml 4,6-diamidino-2-phenylindole (DAPI, Molecular Probes, Eugene, Oreg.) in PBS for 5 min. Each experiment was performed with an IgG control in which cells were labeled only with secondary antibody, Alexa Fluor 488 goat anti-rabbit IgG (H+L) or FITC-conjugated F(ab')2 fragment of goat anti-mouse immunoglobulins, without primary antibody incubation to estimate the extent of nonspecific binding of the secondary antibody to the cells.

Measurement of Cell Fluorescence by Laser Scanning Cytometry

Cellular green (phosphorylated histone H2AX and cleaved caspase 3), and blue (DNA-bound DAPI) fluorescence emission was measured using a Laser Scanning Cytometer (LSC; CompuCyte, Cambridge, Mass.), utilizing standard filter settings; fluorescence was excited with 488-nm argon ion and violet diode lasers, respectively. The intensities of maximal pixel and integrated fluorescence were measured and recorded for each cell. At least 3,000 cells were measured per sample.

Statistical Analysis

To compare the changes in immunofluorescence intensity, the mean fluorescence intensity (integral values of individual cells) was calculated for cells in each phase of the cycle by gating $G_1$, S and $G_2$/M cells based on differences in DNA content. The means of the fluorescence value for $G_1$, S and $G_2$/M populations of cells in the IgG control groups were then subtracted from the respective means of the smoke condensate or smoke-treated cells. All experiments were run under identical instrument settings. Data is presented as mean γH2AX fluorescence of each cell cycle compartment or where not indicated, of the entire population ($G_1$, S and $G_2$M). Each experiment was run in duplicate or triplicate. All experiments were repeated at least three times.

Figure 1B:
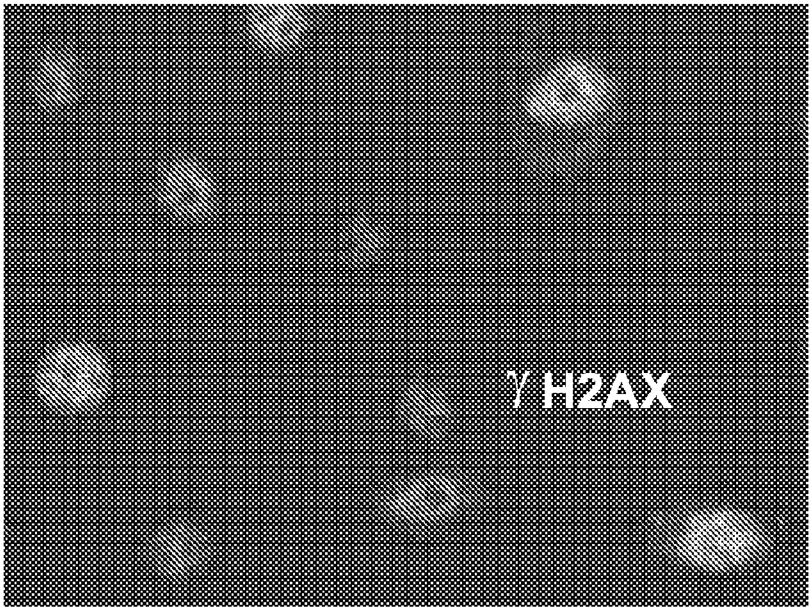

Exposure of A549 cells to TS induces H2AX phosphorylation, which can be detected immunocytochemically (FIG. 1). Though the intensity of green γH2AX IF varies from cell to cell, its distribution is nuclear and punctate. Mock-treated cells have minimal, but still detectable levels of γH2AX IF.

Figure 2:
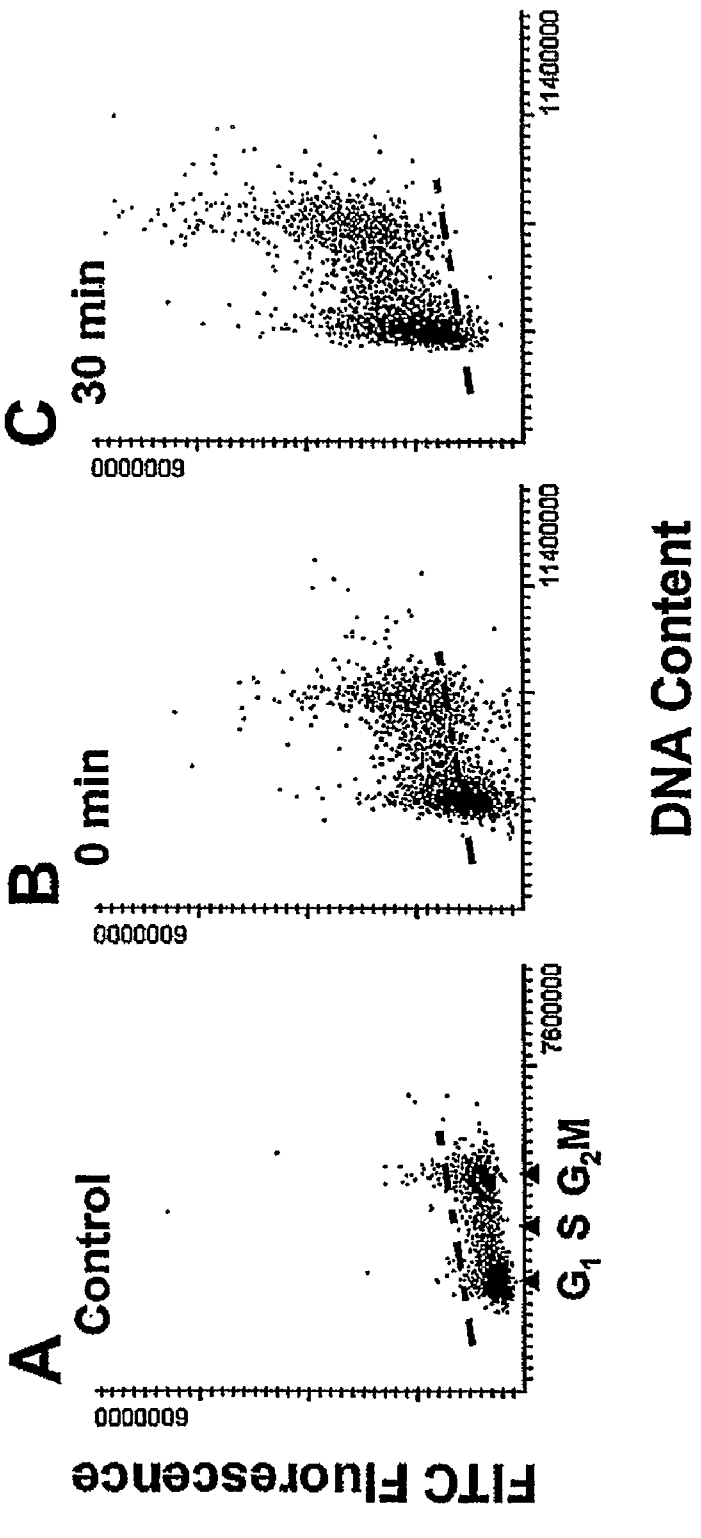
FIG. 2A-C. Bivariate (cellular DNA content vs cell immunofluorescence) distributions (scatterplots) of A549 cells, mock-treated (B) or exposed for 30 min to tobacco smoke (A, C), immuno-stained either with γH2AX Ab (B, C) or with an isotype control IgG (A). The dashed-line represents the maximal fluorescence level (for 99% cells) of the IgG control.

FIG. 2 illustrates the raw data in the form of scattergrams of the A549 cells untreated (0 time) and exposed to TS for 30 min. A scattergram representing cells immunostained with an irrelevant isotype control IgG is also included in the figure. The intensity of fluorescence of the mock-exposed cells is distinctly higher than that of the isotype control. This is a reflection of the "programmed" phosphorylation of H2AX, known to occur during normal progression through the cell cycle. Exposure of A549 cells to smoke, in this instance, markedly increased cellular γH2AX IF. The increase, however, was proportional for the cells in each phase of the cell cycle.

Figure 3:
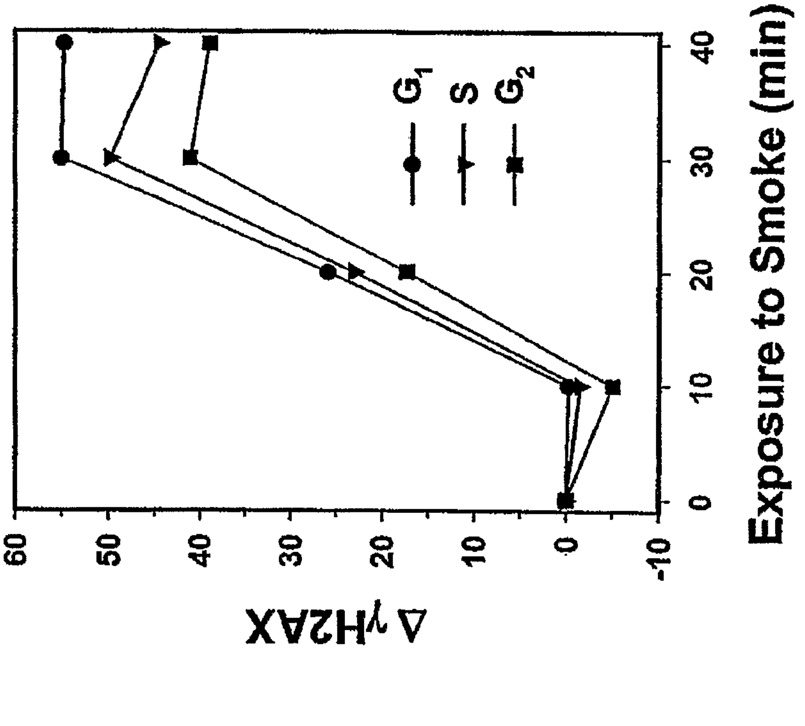
FIG. 3. Plots showing the percent increase (Δ) in mean γH2AX immunofluorescence of A549 cells (per unit of DNA) exposed to smoke for different time intervals, calculated for cells in particular phases of the cell cycle, as described in Example 1. The value for mock-exposed cells was subtracted from those exposed to smoke.
Figure 4:
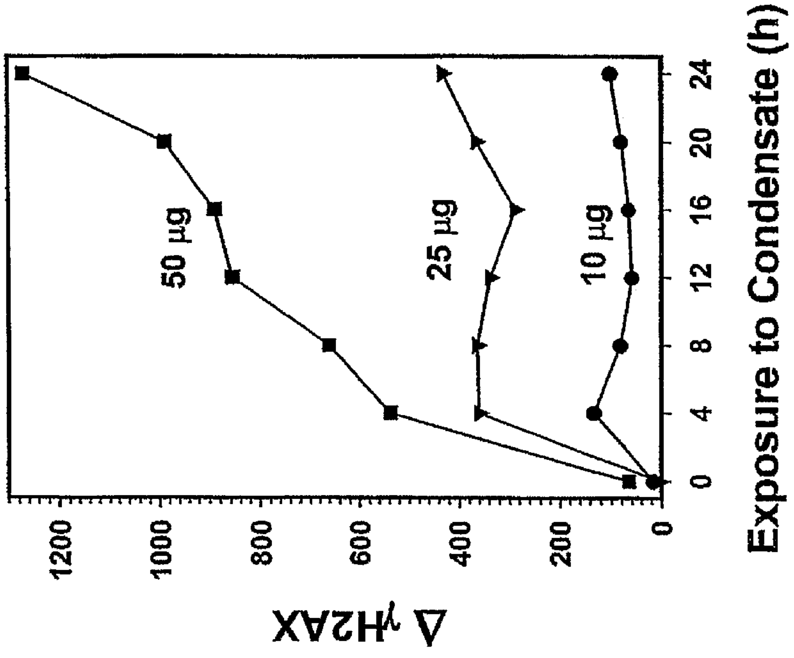
FIG. 4. Plots showing percent increase (Δ) in mean γH2AX immunofluorescence of NHBE cells treated with 10, 25 or 50 μg/ml concentrations of smoke condensate for different periods of time. As in FIG. 3, the γH2AX value for the mock-exposed cells was subtracted from the values of the cells exposed to different concentrations of condensate.

As noted above, the mean "programmed" H2AX IF was subtracted from the mean γH2AX IF of the cells exposed to either smoke or smoke condensate, separately for cells in each phase of the cell cycle, for each data-point shown in the FIGS. 3 and 4. In addition, since the amount of histone doubles as cells proceed from $G_1$ to $G_2$ phase, γH2AX IF was normalized to DNA/histone content by dividing the mean γH2AX IF of the S and $G_2$M phase cells by 1.5 and 2, respectively. The normalized data, therefore, does not represent the total amount of phosphorylated H2AX per cells but rather the degree of H2AX phosphorylation, independent of the increase in total H2AX IF that occurs during progression through S.

During the initial 10 min exposure of A549 cells to smoke, no change in γH2AX IF was apparent (FIG. 3). However, between 10 and 20 min exposure to smoke, γH2AX IF increased by 71%, 67.5% and 45.7% for $G_1$, S and $G_2$M phase cells, respectively. An additional 10 min of exposure to smoke (30 min in total) resulted in an additional increase in γH2AX IF compared to mock-exposed cells: 151.2%, 132.2% and 109.3% for $G_1$, S or $G_2$M phase cells.

Figure 5:
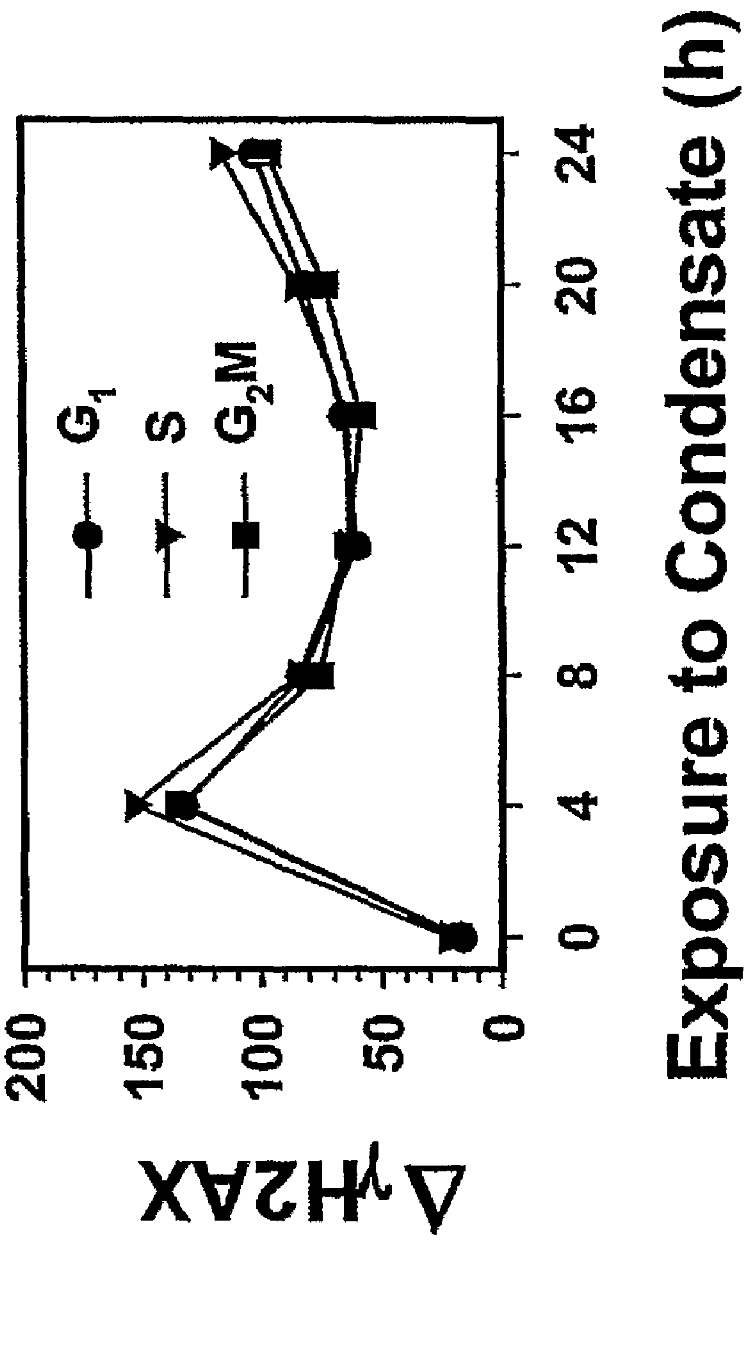
FIG. 5. Percent increase (Δ) in mean γH2AX immunofluorescence of NHBE cells treated with 10 μg/ml of smoke condensate for different intervals of time, in relation to cell cycle phase. As in FIG. 3, the γH2AX value for the mock-exposed cells was subtracted from the values of the cells exposed to condensate.

The plots shown in FIG. 4 display the increase in the level of H2AX phosphorylation as a function of length of exposure of NHBE cells to 10, 25 or 50 μg/ml concentrations of smoke condensate. At each concentration, the maximal rate of increase in H2AX IF was seen during the initial 4 h of cell treatment. However, whereas at 10 and 25 μg/ml of smoke condensate the peak of H2AX phosphorylation occurred at 4 h, followed by a plateau up to 24 h, at a smoke condensate concentration of 50 μg/ml, H2AX phosphorylation increased during the entire 24 h time course of the experiment. No cell cycle phase specificity was apparent in H2AX phosphorylation when cells were exposed to 10 μg/ml smoke condensate (FIG. 5). The same was true for these cells exposed to 25 or 50 μg/ml.

Activation of caspase-3 was measured in samples parallel to those that were subjected to analysis of H2AX phosphorylation, by detecting the presence of activated caspase-3 immunocytochemically. Exposure of A549 cells to smoke for up to 40 min followed by their fixation at 15 minutes had no effect on caspase-3 activation: less than 0.5% of the cells demonstrated the presence of activated caspase-3 in either mock-exposed or smoke treated cultures (Table 3). Caspase-3 activation could be shown, however, if A549 cells exposed to smoke for 20 min were allowed to grow in culture for an extended period of time (24 h) at which point virtually half the cells were positive for activated caspase-3 (Table 1).

TABLE 3

Effect of Smoke on Caspase-3 Activation

| Exposure to smoke (min) | Time in culture following exposure (h) | % Caspase-3 positive cells (%)* |
|---|---|---|
| 0 | 0.25 | 0.1 |
| 10 | 0.25 | 0.4 |
| 20 | 0.25 | 0.1 |
| 30 | 0.25 | 0.4 |
| 40 | 0.25 | 0.1 |

TABLE 3-continued

Effect of Smoke on Caspase-3 Activation

| Exposure to smoke (min) | Time in culture following exposure (h) | % Caspase-3 positive cells (%)* |
|---|---|---|
| 0 | 24 | 0.2 |
| 20 | 24 | 49.9 |

*Caspase-3 positive cells were detected immunocytochemically, as described elsewhere.

The present results demonstrate that exposure of A549 cells to TS or NHBE cells to TSC induces phosphorylation of H2AX. The extent of H2AX phosphorylation is concentration-dependent. It also correlated with the duration of exposure. In the case of NHBE cells, while at lower smoke condensate concentrations (10 and 25 μg/ml), a plateau is achieved after 4 h, at 50 μg/ml concentration, progressive phosphorylation continues for up to 24 h. H2AX phosphorylation in the A549 cells exposed to smoke also progresses with time of exposure, although it appears to plateau after 30 min. Phosphorylation of H2AX is a specific marker of induction of DSBs; the present data indicate that TS and TSC both induce such breaks in A549 cells and NHBE cells in a dose and time dependent manner.

It should be noted that H2AX is intensely phosphorylated in response to DNA fragmentation that occurs upon induction of apoptosis. Caspase activation, however, is required to trigger apoptosis-related DNA fragmentation. In fact, inhibition of caspase-3 activity (e.g. by z-VAD-FMK) can prevent the apoptosis-associated H2AX phosphorylation. In the present study, no caspase-3 activation was detected in the cells exposed for up to 40 min to smoke (Table 3). Thus, apoptosis-associated phosphorylation of H2AX did not contribute to the γH2AX IF measured in A549 cells exposed to smoke for up to 40 min, when the cells were collected within 15 min of exposure.

The present assay provides quantitative results. Specifically, the number of H2AX phosphorylation foci is considered to correspond to the number of DSBs. Assuming that the individual foci have comparable intensity of IF, the integrated value H2AX IF, as presently measured, would be expected to correspond to the number of foci, hence, to the number of DSBs. Furthermore, the mean γH2AX IF of the mock-exposed cells was subtracted from each mean of cells exposed to smoke or smoke condensate, to ensure that the measurement was not affected by the level of "programmed" H2AX phosphorylation in these cells (see FIG. 2). Though not applicable in the present instance in which the time between exposure to smoke or smoke condensate and harvesting of the cells was relatively short (55 min or less), a phosphatase inhibitor such as calyculin A or okadaic acid can be included in the culture to prevent possible dephosphorylation of H2AX molecules. The data presented in the plots, therefore, represent the smoke-induced differential γH2AX IF. Furthermore, since the H2AX content increases as cells traverse through S phase, the mean values γH2AX IF for S and $G_2$/M cells were compensated for the H2AX increase. The intensity of γH2AX IF so compensated, thus, reflects the degree of H2AX phosphorylation in the cell, i.e. is unrelated to H2AX content.

There is little evidence that CS and specific smoke constituents can cause single strand breaks (SSBs) in the normal human genome 40-45, but no evidence for the induction of DSBs. DSBs are among the most deleterious types of DNA damage in mammalian cells. A cell that incurs DSBs is at major risk for developing genomic instability, which can result in an array of specific defects such as chromosome fragmentation, translocation, rearrangement and loss. More importantly, each of these chromosomal abnormalities can play a pivotal role in the etiology or progression of a wide range of human cancers. Consequently, in order to ensure the faithful repair of DSBs and maintain genomic integrity, the cell has evolved sensitive DNA damage-activated checkpoint control pathways that are coupled to an interconnected web of efficient repair mechanisms, the most prominent of which are homologous recombination and non-homologous end joining. Individuals who either have debilitating alterations or deletions of the genes involved in detecting and repairing DSBs tend to manifest the dual syndromes of chromosome instability and higher incidence of various cancers. Clearly, therefore, the induction of DSBs by an exogenous agent like TS can be a potentially hazardous genetic event in the long-term smoker. In particular, if overall repair efficiencies of DSBs are not as efficient as for other types of DNA damage, e.g., single strand breaks (SSBs), and/or if an individual smoker has specific polymorphisms in the relevant genes that reduce their effectiveness, then cells chronically exposed to TS can manifest the genetically dangerous combination of increased levels of DSBs and compromised repair capacities. Furthermore, in addition to DSB level and repair capacity, the genomic positioning of DSBs can be another factor that determines how successfully a cell responds to this type of damage. For example, the probability that a DSB break is inaccurately rejoined is relatively low when DSBs are spatially separated but increases considerably when multiple breaks coincide.

The successful repair of DSBs appears also to depend on cell cycle position. The data, however, show no obvious cell cycle specificity in terms of accumulation of DSBs. Thus, if proliferating cells exposed to TS experience similar levels of DSBs during each phase of the cell cycle but dissimilar repair rates, they can be particularly susceptible to accumulating deleterious DNA defects during that specific phase. It is relevant to point out that although the rates of DSB induction and repair in noncycling cells, which are one of the initial primary target cells in lungs exposed to CS, can be different than in cycling cells, the lungs of persistent smokers undergo a significant increase in the number of proliferating cells due to smoke-induced damage. Moreover, cells actively dividing at the time of carcinogen exposure are at particular risk for transformation-related events.

The methods of identifying a tobacco, identifying a compound in tobacco, identifying a tobacco product, and making a tobacco product provided herein, can additionally be used to compare two or more tobaccos so as to identify a toxic compound, evaluate the potential risk posed by the tobacco products, or to develop reduced risk tobacco products. In some embodiments, the two or more tobaccos are compared for their ability to induce damage to the genetic material of cells. In some embodiments, at least one tobacco is a reduced risk tobacco or identified as a reduced risk tobacco. In some embodiments, at least one tobacco is a modified tobacco, such as a chemically modified tobacco or a genetically modified tobacco.

Working Example 2 herein provides one non-limiting specific example of methods for comparing tobaccos in accordance with the methods provided herein. Variations of the assay method used in terms of assay methodologies (e.g., assay for apoptosis or for cell proliferation) would be apparent to the skilled artisan for comparing tobaccos.

EXAMPLE 2

A549 cells were exposed to whole smoke from IM 16 cigarettes for various lengths of time, washed and allowed to grow for an additional hour before being harvested for analysis. DNA damage was identified as an increase in phosphorylation of histone H2AX denoted as γH2AX.

In order to compare DNA damage as a function of the cell's position in the cell cycle, γH2AX values were normalized to DNA content since histone content doubles as cells proceed from $G_1$ to $G_2$ phase. Thus, in order to determine any change in histone H2AX phosphorylation independent of changes in histone/DNA content or DNA ploidy, the values for S and $G_2M$ phase populations, gated according to DNA content, were multiplied by 0.75 and 0.5, respectively. In instances where "normalized" values of γH2AX are presented, these values were obtained by subtracting the mean values of each cell cycle population (or the total population) from the mean of the mock-treated population whose γH2AX values represent "scheduled" γH2AX expression. In all instances, the values presented represent the mean γH2AX fluorescence of the population; typically 3-5×$10^3$ cells were analyzed for each condition.

Figure 6:
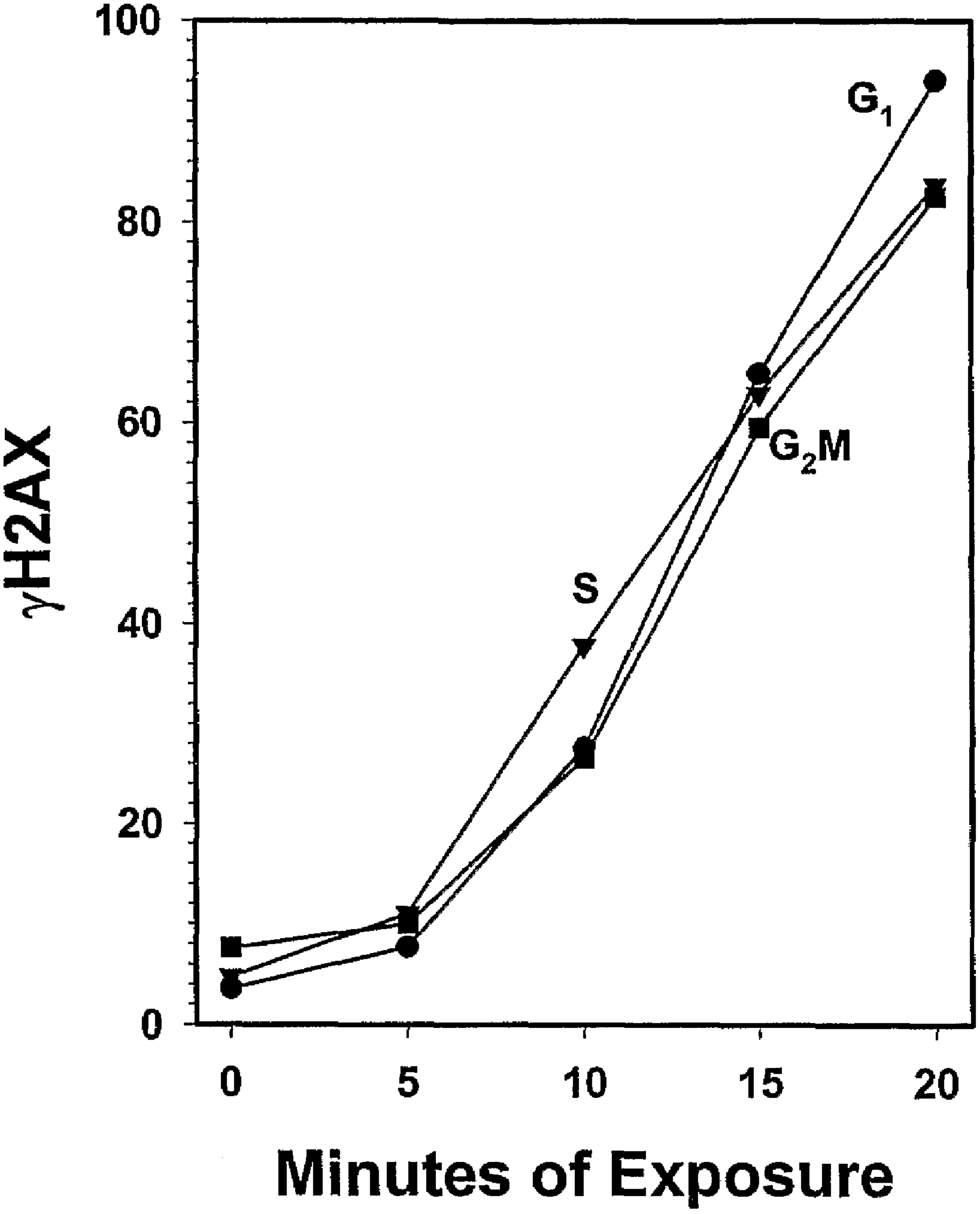
FIG. 6. Plots showing the percent increase (Δ) in mean γH2AX immunofluorescence of A549 cells (per unit of DNA) exposed to smoke of IM 16 cigarettes for different time intervals, calculated for cells in particular phases of the cell cycle, as described in Example 2.

As illustrated in FIG. 6, there was little or no change in γH2AX when exposure of A549 cells to whole smoke was limited to 5 min. However, as the time of exposure exceeded 5 min there was a more or less linear increase in γH2AX. Initially, S phase cells appeared most sensitive to DNA damage expressing approximately 37% higher levels of γH2AX than $G_1$ phase cells following 10 min of exposure to smoke. When the length of exposure was increased to 20 min, $G_1$ phase cells invariably expressed 10-20% higher levels of γH2AX-associated fluorescence.

In another set of experiments it was determined that the extent of DNA damage varied with the length of time of recovery following exposure to whole smoke. Previous studies have shown that following exposure to whole smoke for times in excess of 20 min leads to a significant increase in apoptotic cells in the population depending upon when the assay is performed. Apoptotic cells contained significantly increased levels γH2AX compared to what one sees when assessing the primary breaks due to DNA damaging agents. Based on the absence of activation of caspase 3, there is little or no induction of apoptosis in A549 cells within the first 3 h following 20 min exposure to whole smoke from IM 16.

Figure 7:
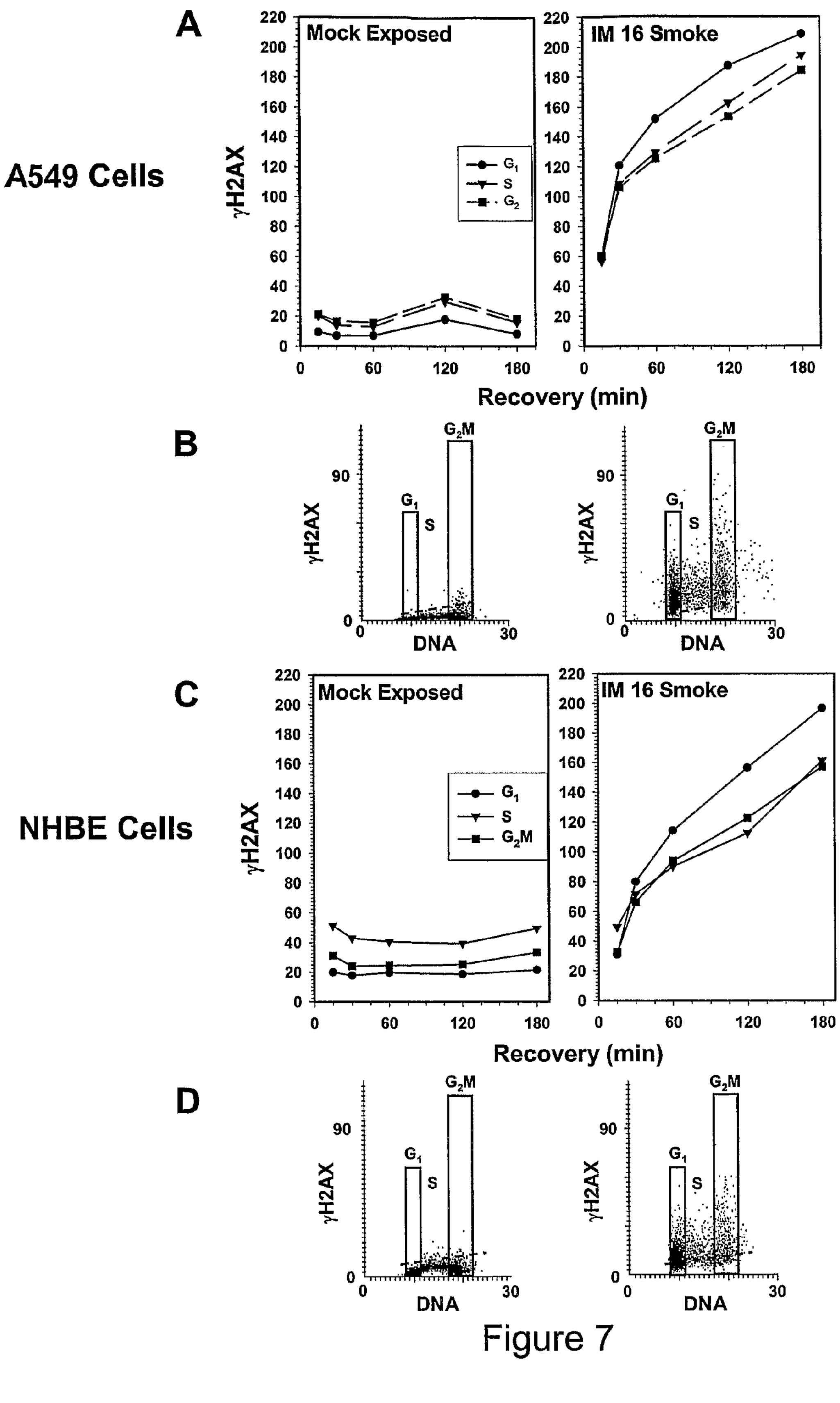
FIG. 7A-D. (A) Plot showing increase (Δ) in mean γH2AX immunofluorescence of A549 cells exposed to smoke of IM 16 cigarettes for 15 minutes, calculated for cells in particular phases of the cell cycle. (B) Scatter plot relative increase in γH2AX following 60 min of recovery of the A549 cells in particular phases of the cell cycle. (C) Plot showing increase (Δ) in mean γH2AX immunofluorescence of NHBE cells exposed to smoke of IM 16 cigarettes for 20 minutes, calculated for cells in particular phases of the cell cycle. (B) Scatter plot relative increase in γH2AX following 60 min of recovery of the NHBE cells in particular phases of the cell cycle.

Within 15 min of exposure to whole smoke, A549 cells already displayed a dramatic increase in γH2AX (FIG. 7A). Increasing the recovery time following exposure led to continued increase in DNA damage. As noted above, $G_1$ cells appear to be the most sensitive to smoke especially when the cells are harvested 30 min or longer after exposure to whole smoke. The relative increase in γH2AX following 60 min of recovery is illustrated in FIG. 7B where it can be observed that virtually all cells express levels of γH2AX in excess to mock-treated cells (e.g., are above the dotted line).

The response of NHBE cells to whole smoke from IM 16 cigarettes was more or less identical to that observed for A549 cells (FIG. 7C). The one difference between the two cell lines was that S phase cells in NHBE cultures always expressed higher "scheduled" amounts of γH2AX. Nevertheless, as with A549 cells, $G_1$ cells are the most sensitive to smoke-induced DNA damage in these cultures. FIG. 7D demonstrates both the increased basal level of γH2AX in mock-treated cultures and the extensive increase in γH2AX expression observed 60 min following a 20 min exposure to whole smoke.

Figure 8:
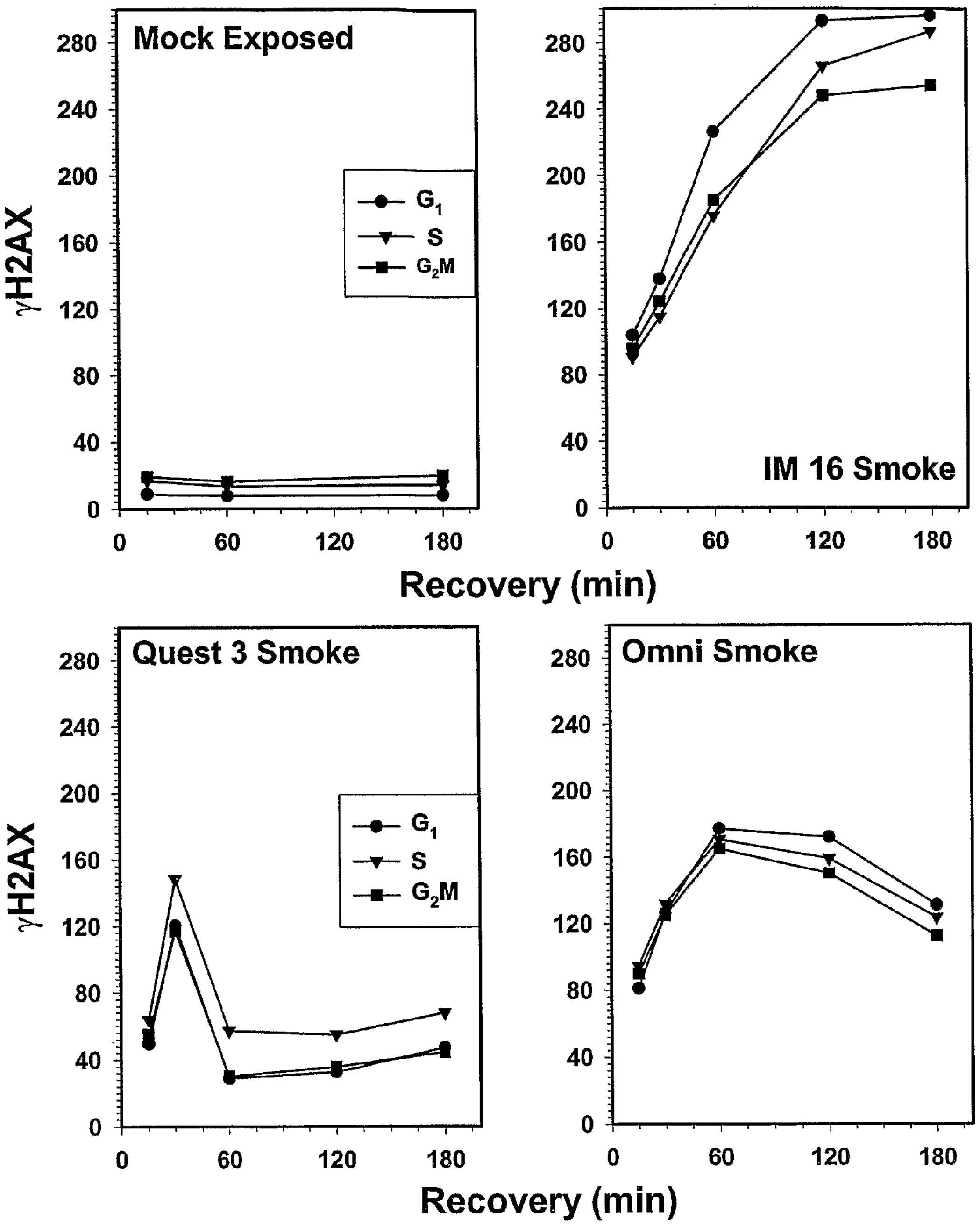
FIG. 8. Plots showing the increase (Δ) in mean γH2AX immunofluorescence during different time points of the recovery of A549 cells (per unit of DNA) after exposure to smoke of IM 16, Quest 3®, and Omni® cigarettes for 20 minutes, calculated for cells in particular phases of the cell cycle.

In the next series of experiments, the DNA damage caused by whole smoke from different sources was compared. Using an exposure time of 20 min, damage due to whole smoke from two other cigarettes could be compared to that caused by IM 16 following various recovery times. The curves of γH2AX following exposure of A549 cells to IM 16 (FIG. 8, top right) were comparable to that displayed in FIG. 7A. Exposure of the same cells to whole smoke from Quest 3® on the other hand resulted in an initial increase in γH2AX at 30 min that returned to near background levels when assayed after longer recovery times (FIG. 8, bottom left). Whole smoke from Omni® cigarettes caused damage intermediate between that of Quest 3® and IM 16 (FIG. 8, bottom right). The DNA damage caused by Omni® increased until 60 min after which it more or less plateaued. Smoke from Quest 3® cigarettes affects S phase cells to a greater extent than any other phase while $G_1$ cells are invariably most sensitive to smoke from IM 16 and Omni®. Importantly, these data demonstrate that tobacco products containing modified tobacco (i.e., Omni® and Quest 3®) induced less DNA damage than a reference tobacco product (i.e., IM16). Accordingly, the modified tobacco products Omni®, and Quest 3® have a reduced potential to contribute to a tobacco related disease (i.e., Omni®, and Quest 3® are reduced risk tobacco products) according to the double strand break assay.

In the next series of experiments, it was determined that DNA damage caused by whole smoke can be mitigated by the presence of NAC. Using a standardized set of conditions (20 min of exposure followed by a 1 h recovery), DNA damage caused by whole smoke from IM 16 cigarettes was assayed in both A549 and NHBE cells. NAC at a concentration of 25 mM was either absent or present during exposure and absent or present during the 1 h recovery time. In this instance, the background or "scheduled" γH2AX expression observed in Mock-treated cells was subtracted from each measurement. The remaining fluorescence should be indicative of the level of DNA DSBs under each set of conditions.

In A549 cells (FIG. 9, top), IM 16 caused a dramatic increase in H2AX phosphorylation in the absence of NAC (PBS, PBS). Applying NAC to the media following exposure to smoke did nothing to mitigate the DNA damage caused by whole smoke. However, if NAC was present during exposure to smoke, DNA damage was suppressed by greater than 80% for the entire population; the suppression was greatest for $G_1$ cells (91%), intermediate for $G_2M$ (88%) and least for S (82%) phase cells. The presence of NAC both during exposure to smoke and during the 1 h recovery period provided slightly more protection increasing suppression of γH2AX to 90% for the entire population.

Figure 9:
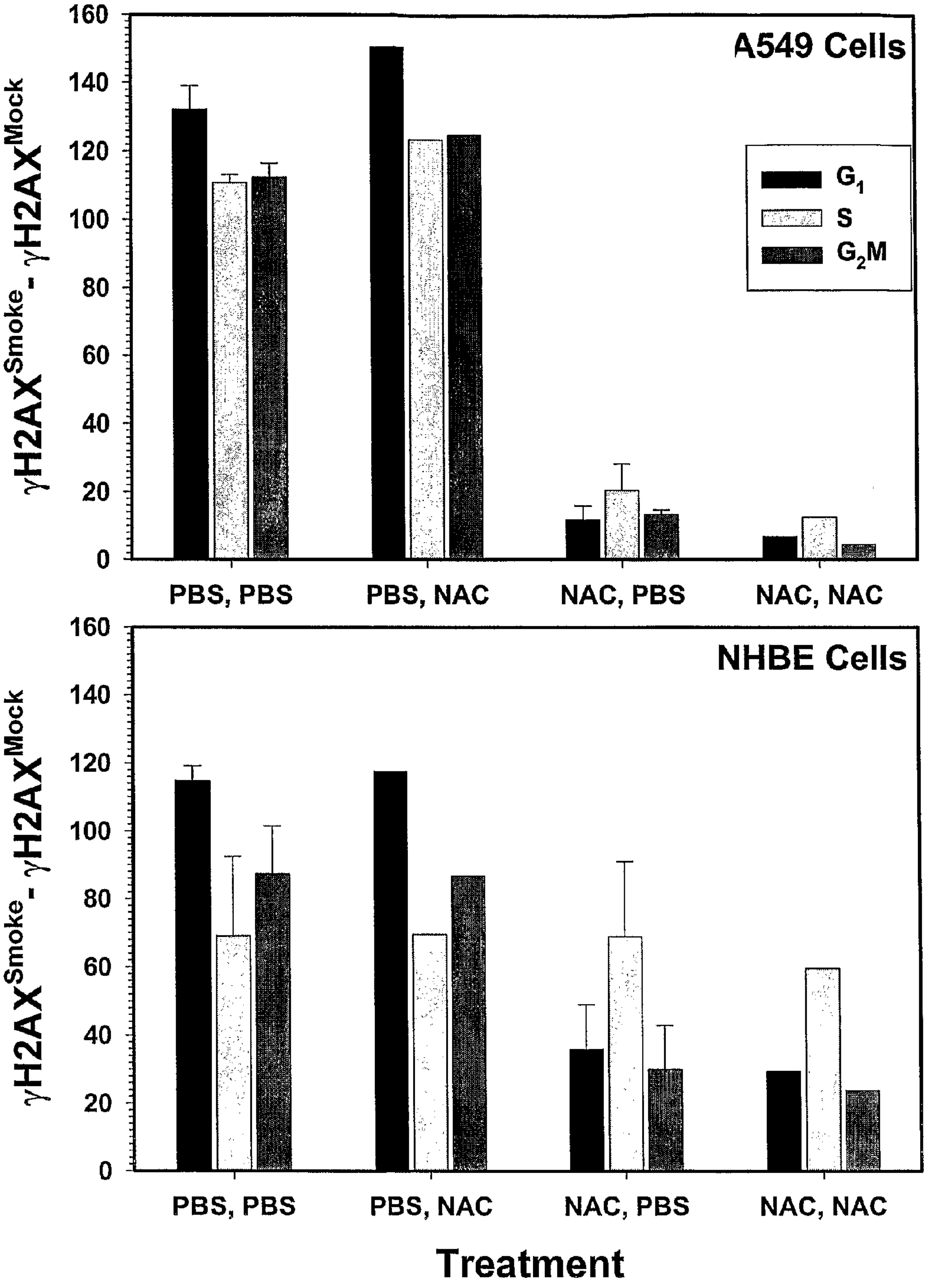
FIG. 9. Bar plots showing the increase (Δ) in mean γH2AX immunofluorescence of A549 cells (top) and NHBE cells (bottom) exposed to smoke of IM 16 cigarettes for 20 minutes, followed by a 1 hour recovery, for cells treated with phosphate-buffered saline (PBS) or N-acetyl-L-cysteine (NAC) during exposure (first value) and during recovery (second value).

As with A549 cells, when NHBE cells were exposed to whole smoke form IM 16 cigarettes, the cells in $G_1$ phase were the most sensitive. However, since the S phase cells express somewhat higher levels of "scheduled" γH2AX and are not as sensitive as $G_1$ cells to smoke (FIG. 7C), the value for S phase cell DNA damage was considerably less than for cells in $G_1$ or $G_2M$ phase (FIG. 9, bottom). Addition of NAC only during recovery had little effect on the level of DNA damage induced by whole smoke. NAC present during exposure diminished the damage observed in $G_1$ cells by nearly 69%; the decrease was about 65% for $G_2M$ cells but S phase cells were afforded no protection. NAC present both during exposure and recovery provided a small degree of additional protection.

Figure 10:
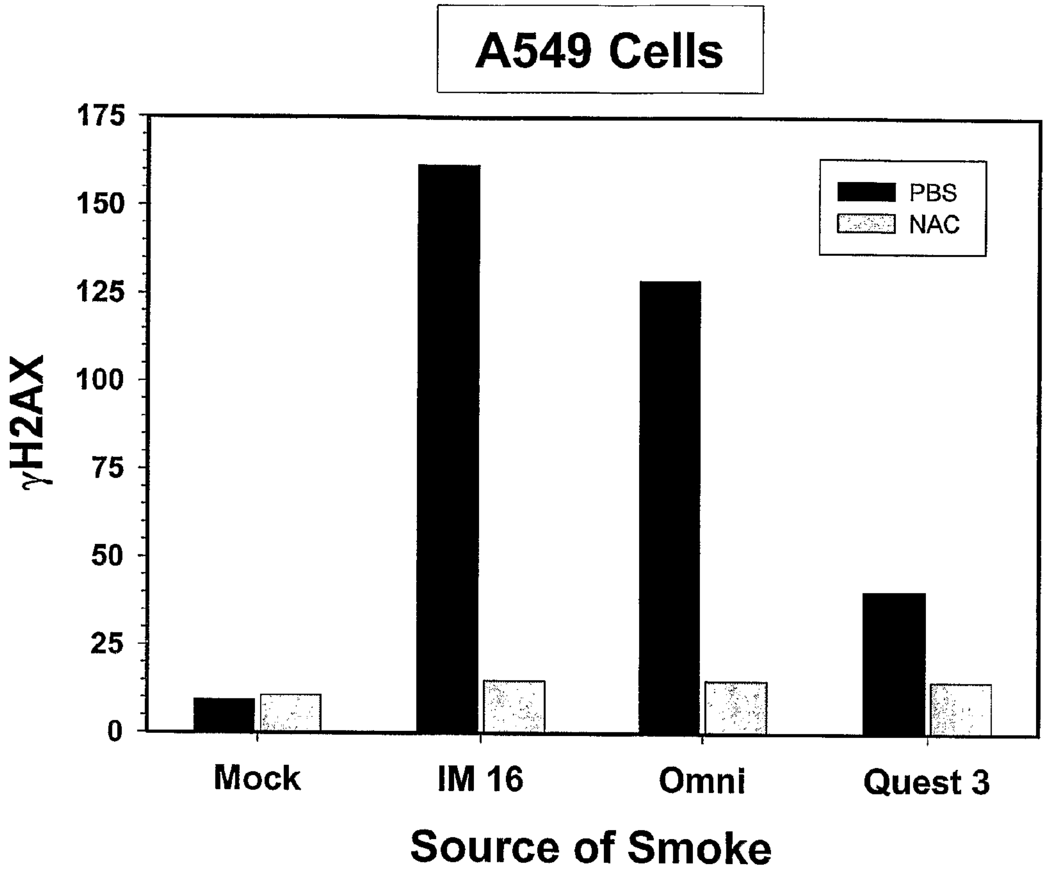
FIG. 10. Bar plot showing the increase (Δ) in mean γH2AX immunofluorescence of A549 cells exposed to smoke from IM 16, Omni® and Quest 3® in the presence of PBS or NAC.

Next, the effect of NAC on DNA damage caused by whole smoke from various sources was evaluated. A549 cells were exposed to smoke from IM 16, Omni® and Quest 3® cigarettes in the presence and absence of NAC during exposure. As illustrated in FIG. 10, NAC dramatically reduced the effects of smoke from IM 16 cells. Omni® produced less damage than IM 16 but NAC reduced the damage to near background levels. Quest 3® smoke caused the least amount of damage which could also be reduced to background levels by the presence of 25 mM NAC during exposure. In all instances, the level of damage following exposure to smoke in the presence of NAC was approximately the same, just slightly more than the background or scheduled level of γH2AX expression. As above, the data from this assay demonstrates that tobacco products containing modified tobacco (i.e., Omni® and Quest 3®) induced less DNA damage than a reference tobacco product (i.e., IM16). Again, the double strand break assay has shown that the modified tobacco products Omni®, and Quest 3® have a reduced potential to contribute to a tobacco related disease (i.e., Omni®, and Quest 3® are reduced risk tobacco products).

In more experiments, the cell cycle specific inhibition of whole smoke-induced DNA damage by NAC was analyzed. A549 cells were exposed to whole smoke in the presence and absence of various concentrations of NAC. Exposure was always for 20 min and recovery was 1 h. In each instance, the background or "scheduled" expression of γH2AX was subtracted from the value obtained for each population in each cell cycle phase. Since $G_1$ phase cells were the most sensitive and had the highest value, all other measurements were normalized to that of $G_1$ phase cells exposed to IM 16 smoke in the absence of NAC (plotted as 0.1 mM NAC on the log plot).

Figure 11:
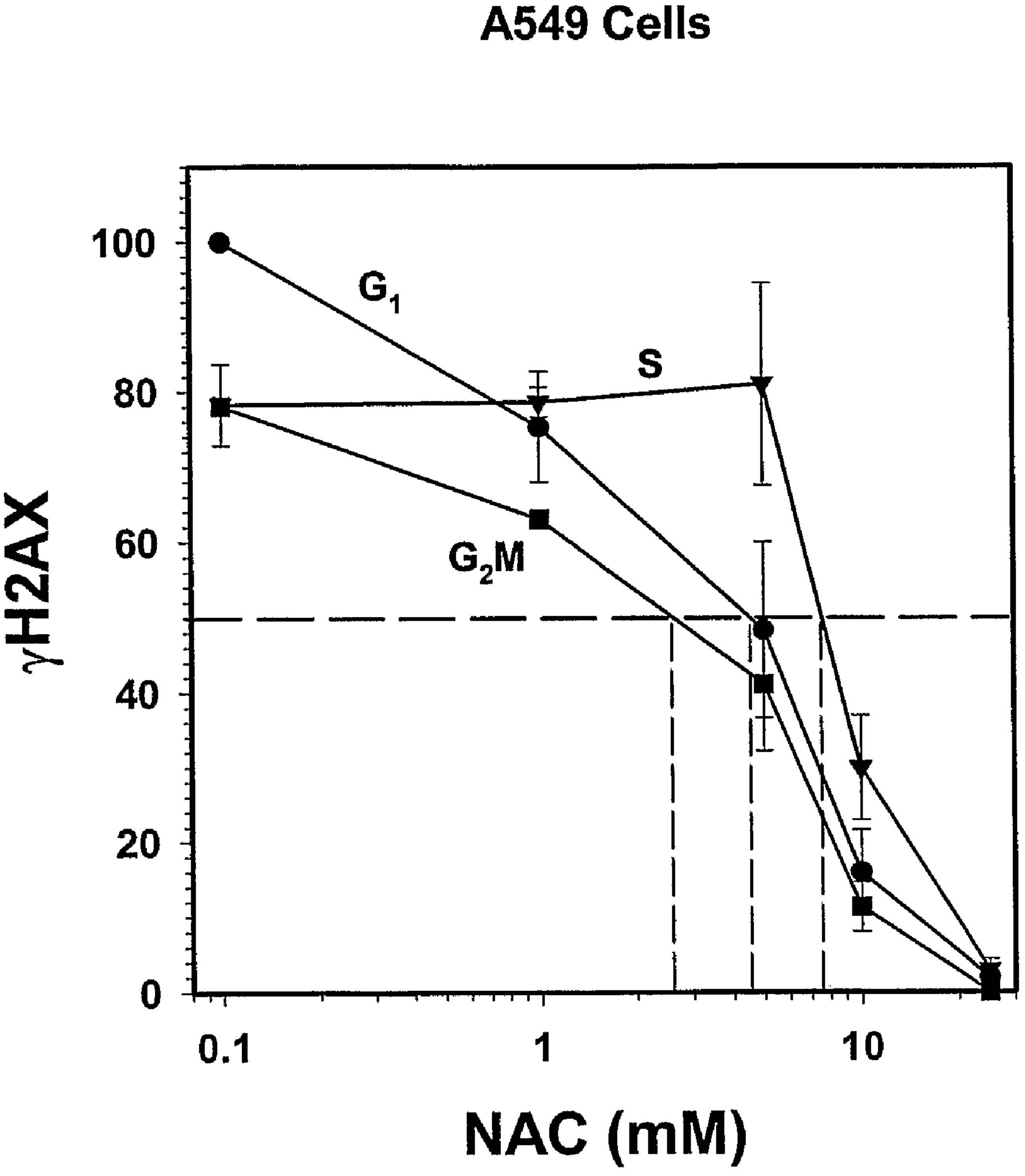
FIG. 11. Plot of the relative amount of mean γH2AX immunofluorescence of A549 cells exposed to smoke from IM 16 as a function of different concentrations of NAC, calculated for cells in particular phases of the cell cycle. Horizontal dashed line indicates 50% reduction in γH2AX immunofluorescence. Vertical dashed lines indicate the estimated NAC concentration for each cell type at 50% reduction.

As can be seen in FIG. 11, damage by whole smoke from IM 16 to S phase A549 cells was unaffected by the presence of NAC up to a concentration of 5 mM. In contrast, damage caused to both $G_1$ and $G_2M$ cells began to decrease when as little as 1 mM NAC was present during exposure. The damage caused to S phase cells decreased sharply as the NAC concentration was increased to 10 mM and, by 25 mM, there was little difference in residual γH2AX expression between cells in any phase of the cycle.

The concentration of NAC that reduced DNA damage by 50% for each cell cycle phase can be determined from the graph in FIG. 11. For $G_1$, S and $G_2M$ phase cells the values were approximately 4.5, 2.6 and 7.5 mM NAC.

Figure 12:
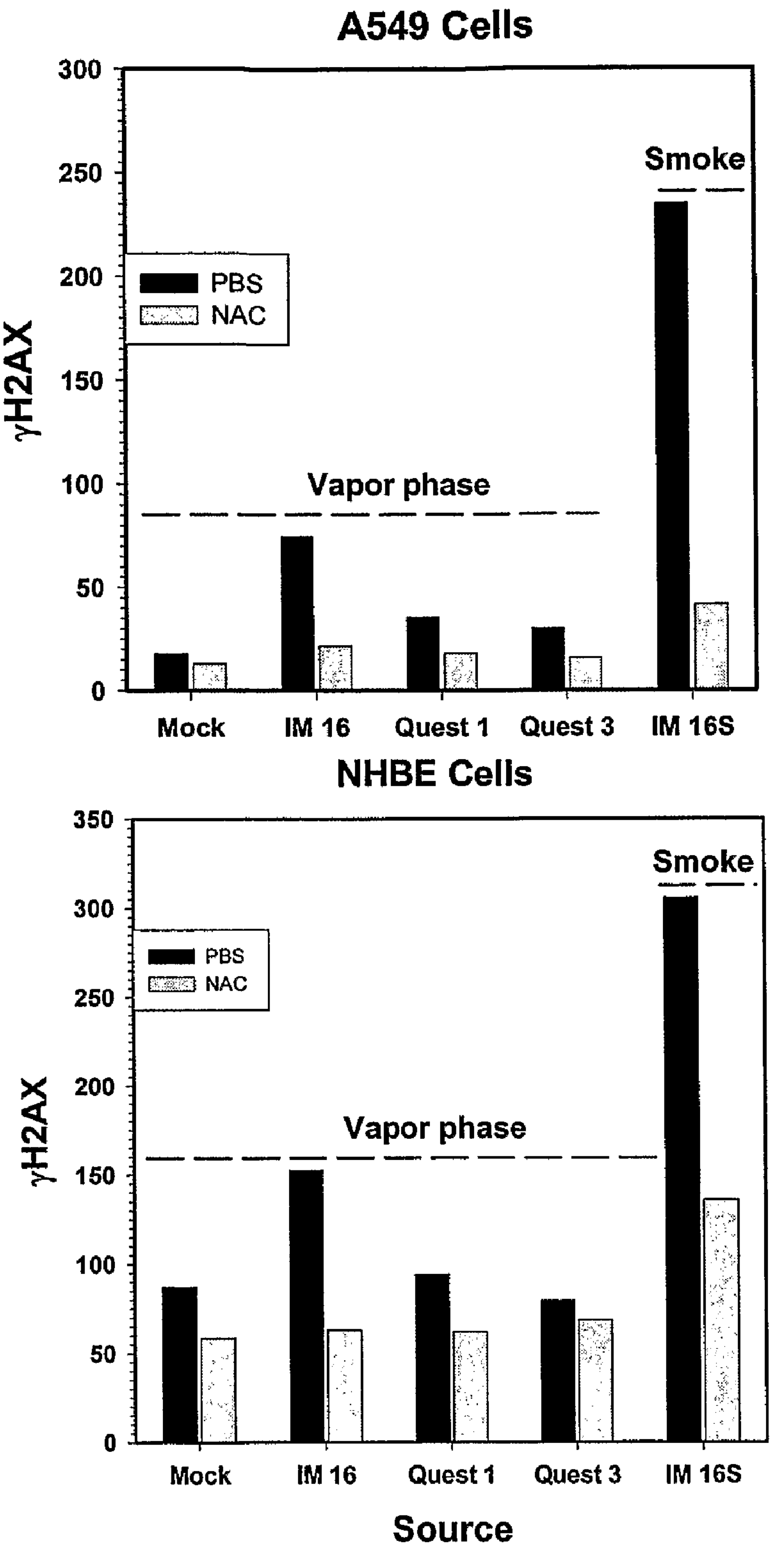
FIG. 12. Bar plots showing the increase (Δ) in mean γH2AX immunofluorescence of A549 cells (upper plot) and NHBE cells (lower plot) exposed to the vapor phase of smoke from IM 16, Quest 1® and Quest 3®, and smoke from IM 16 in the presence of PBS or NAC.

In more experiments, it was determined that the vapor phase of smoke induces damage that is abrogated by the presence of NAC. FIG. 12 (top) illustrates the ability of the vapor phase of smoke from various tobacco sources to cause DNA damage to A549 cells in comparison to whole smoke from IM 16 cigarettes. Thus, the vapor phase from IM 16 cigarettes using standard conditions of exposure and recovery caused only about 26% of the DNA damage (γH2AX) as whole smoke from the same source. In the same comparison, the vapor phase from Quest 1® and Quest 3® caused only 8.1% and 5.6% of the damage caused by whole smoke from IM 16. As a direct comparison, the vapor phase of smoke from Quest 1® and Quest® caused 68.8% and 78.5%, respectively, less damage than the vapor phase of smoke from IM 16.

The presence of 25 mM NAC during exposure of A549 cells to whole smoke form IM 16 cigarettes reduced γH2AX by nearly 90% (89.1%) compared to cells exposed to whole smoke in the absence of NAC. NAC present during cell exposure to the vapor phase of smoke from IM 16, Quest 1® and Quest 3®, reduced γH2AX by 93.2%, 98.9% and 100%, respectively compared to the damage caused by the vapor phase of smoke in the absence of NAC.

The same experiment performed on NHBE cells resulted in more or less comparable results (FIG. 12, bottom). Whole smoke from IM 16 cells produced less damage in NHBE cells under standard conditions compared to A549 cells (note the greater background observed in NHBE cells). The vapor phase from IM 16 CS cause only about 30% (29.7%) of the damage caused by whole smoke whereas the vapor phase of smoke from Quest 1® caused 97% less damage than whole smoke from IM 16 cigarettes. The vapor phase of smoke from Quest 3® produced no increase in γH2AX over background in NHBE cells.

The presence of NAC during exposure of NHBE cells to whole smoke from IM 16 cigarettes reduced γH2AX by about 78% (77.9%). The presence of NAC during exposure of cells the vapor phase of IM 16, Quest 1® or Quest 3® abolished virtually all DNA damage relative to mock-treated cells; i.e., γH2AX was reduced to background levels or below.

Figure 13:
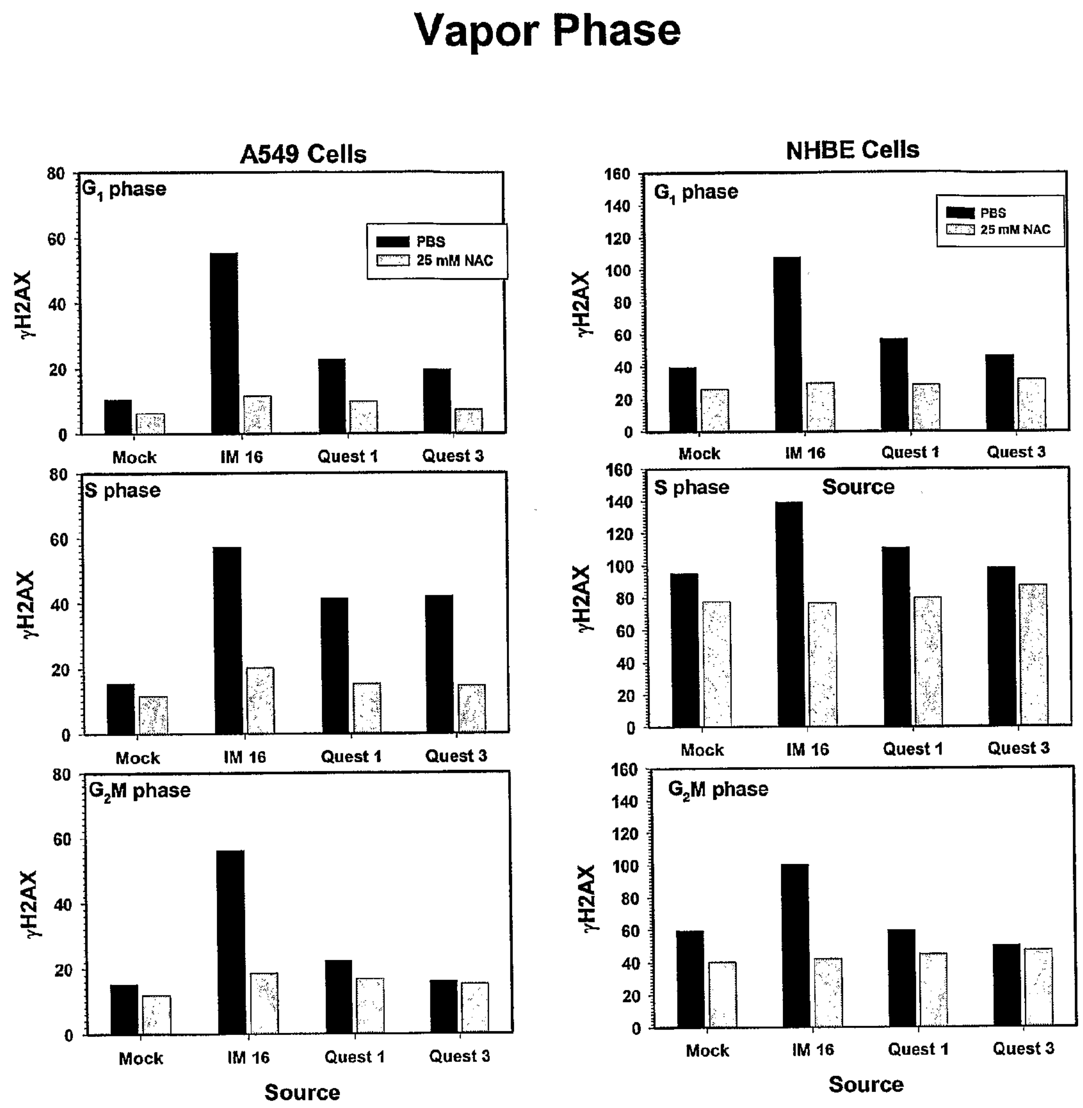
FIG. 13. Bar plots showing the increase (Δ) in mean γH2AX immunofluorescence of $G_1$, S and $G_2M$ phase A549 cells (left plots) and $G_1$, S and $G_2M$ phase NHBE cells (right plots) exposed to the vapor phase of smoke from IM 16, Quest 1® and Quest 3® in the presence of PBS or NAC.

The cell cycle phase specific results are comparable to that for the whole populations (FIG. 13). The vapor phase of smoke from IM 16 caused comparable amounts of damage in each cell cycle phase in A549 cells though the reduction of damage in $G_1$ phase by NAC was somewhat higher than it was for S and $G_2M$ phase; 98.5% versus 89.0% and 92.2%, respectively. The vapor phase from both Quest 1® and Quest 3® caused more damage to S phase cells though in each instance, the presence of NAC reduced damage to background levels for each cell cycle phase.

NHBE cells as noted earlier have higher γH2AX levels in S phase of mock-treated cells as can be seen in FIG. 13. The largest increase in damage caused by the vapor phase of smoke from IM 16 occurred in $G_1$ phase cells (54.4% and 66.9% greater than for cells in S or $G_2M$, respectively). The presence of NAC reduced the damage caused by the vapor phase of smoke from IM 16 to background levels or below. The vapor phase of smoke from Quest 1® and Quest 3® cigarettes had only a small effect on DNA damage in cells in $G_1$ or S but not $G_2M$ phase. All damage caused by the vapor phase of smoke from Quest® cigarettes in NHBE cells was inhibited in the presence of NAC. Importantly, this data provide more evidence that the tobacco products containing modified tobacco (i.e., Quest 1® and Quest 3®) induced significantly less DNA damage (i.e., double strand DNA breaks) than that of a reference tobacco product (i.e., IM16). Accordingly, the modified tobacco products Quest 1®, and Quest 3® have a reduced potential to contribute to a tobacco related disease (i.e., Quest 1® and Quest 3® are reduced risk tobacco products, according to the double strand DNA break assay.

Figure 19:
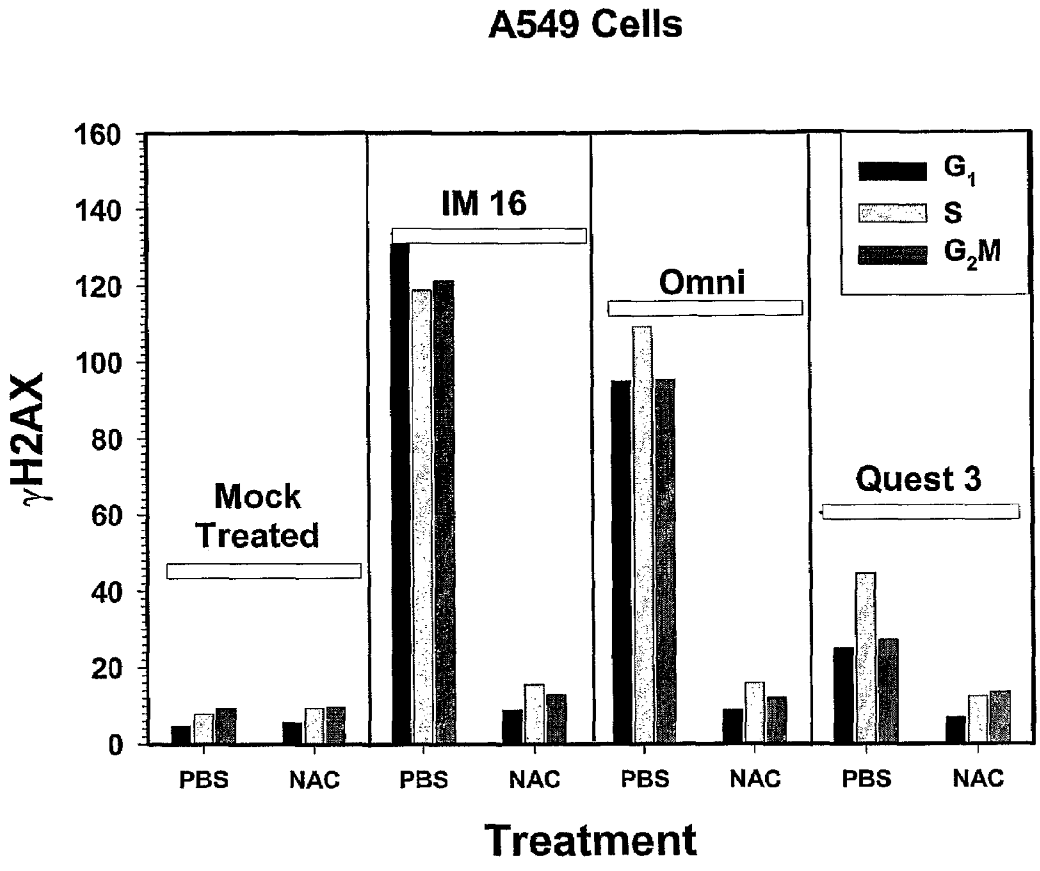
FIG. 19. Bar plot of results from Example 2 showing the increase (Δ) in mean γH2AX immunofluorescence of A549 cells exposed to smoke from IM 16, Omni® and Quest 3® in the presence of PBS or NAC, calculated for cells in particular phases of the cell cycle FIG. 20. An illustration of a QPTase inhibition construct comprising a QPTase inhibition cassette including full-length QPTase coding sequence and a GUS selection cassette.
Figure 27:
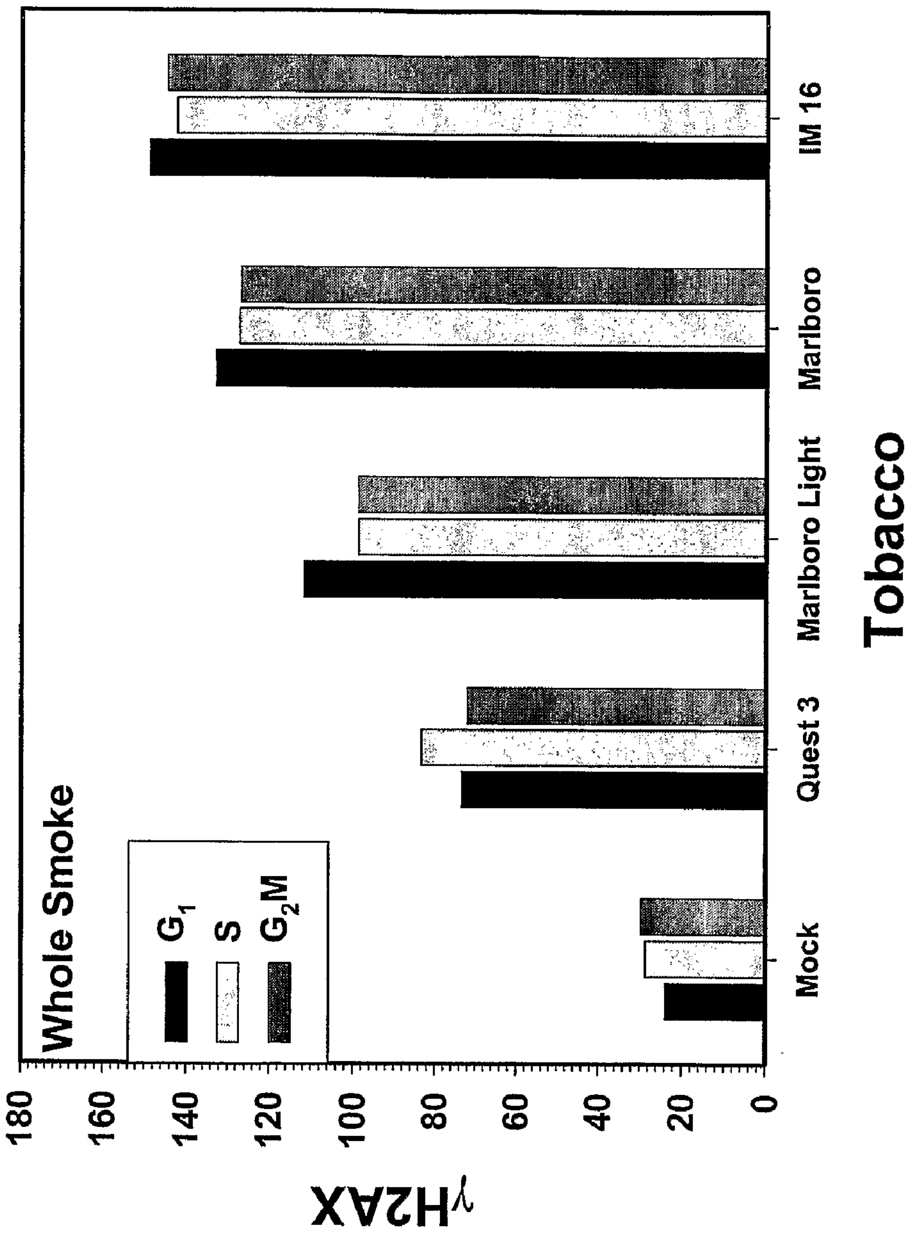
FIG. 27. Bar plot of results from Example 2 showing the increase (Δ) in mean γH2AX immunofluorescence of A549 cells exposed to smoke from IM 16, Marlboro®, Marlboro Light®, and Quest 3®, calculated for cells in particular phases of the cell cycle.
Figure 28:
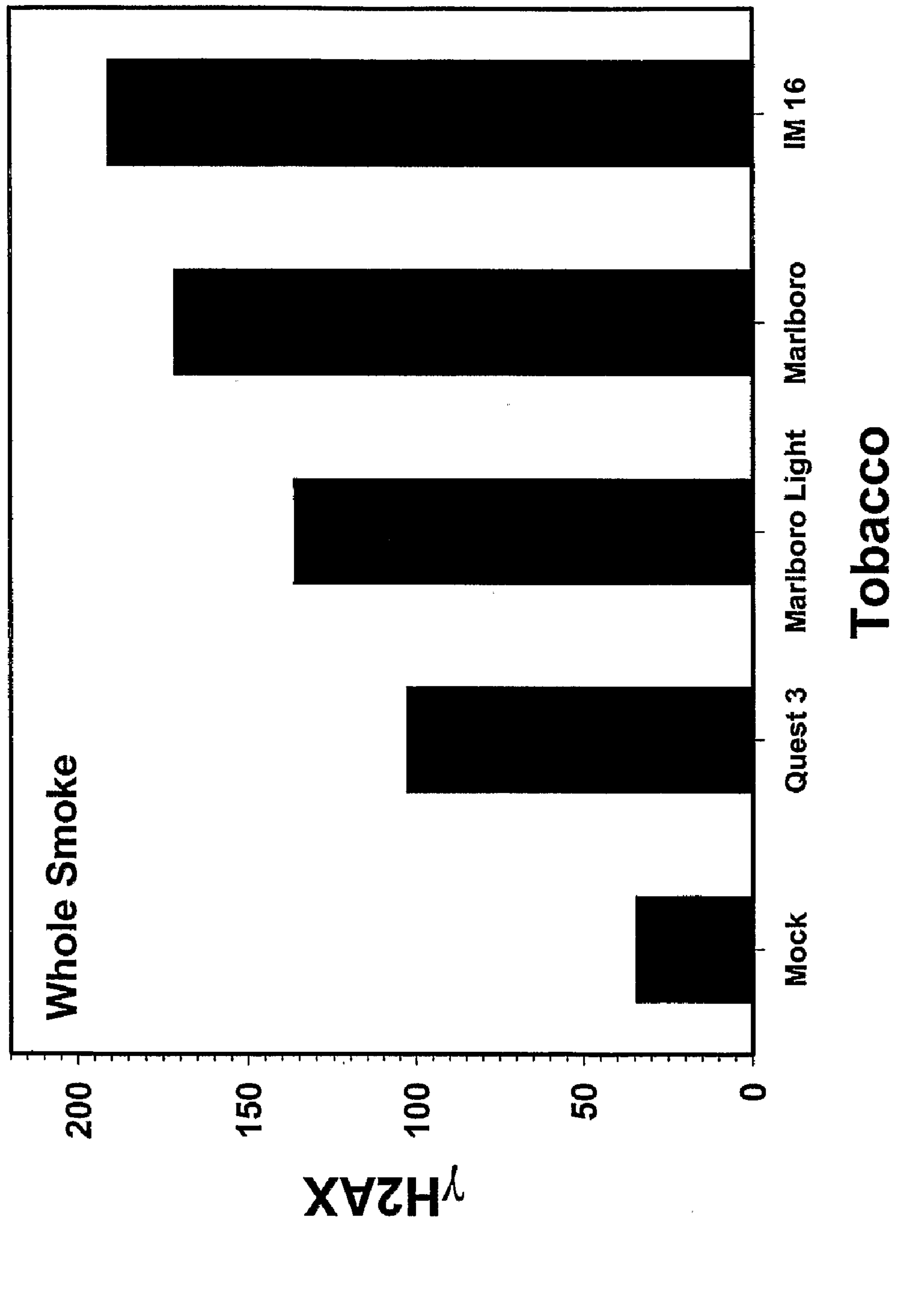
FIG. 28. Bar plot of results from FIG. 27 showing the increase (Δ) in mean γH2AX immunofluorescence of A549 cells exposed to smoke from IM 16, Marlboro®, Marlboro Light®, and Quest 3®, averaged for all cell cycles.

FIGS. 19, 27 and 28 show additional comparisons of reactions of A549 cells to smoke from various cigarettes, where the affect can vary for different cigarettes, and can vary according to the cell cycle of the cells, and can vary according to the presence of antioxidant.

Figure 26:
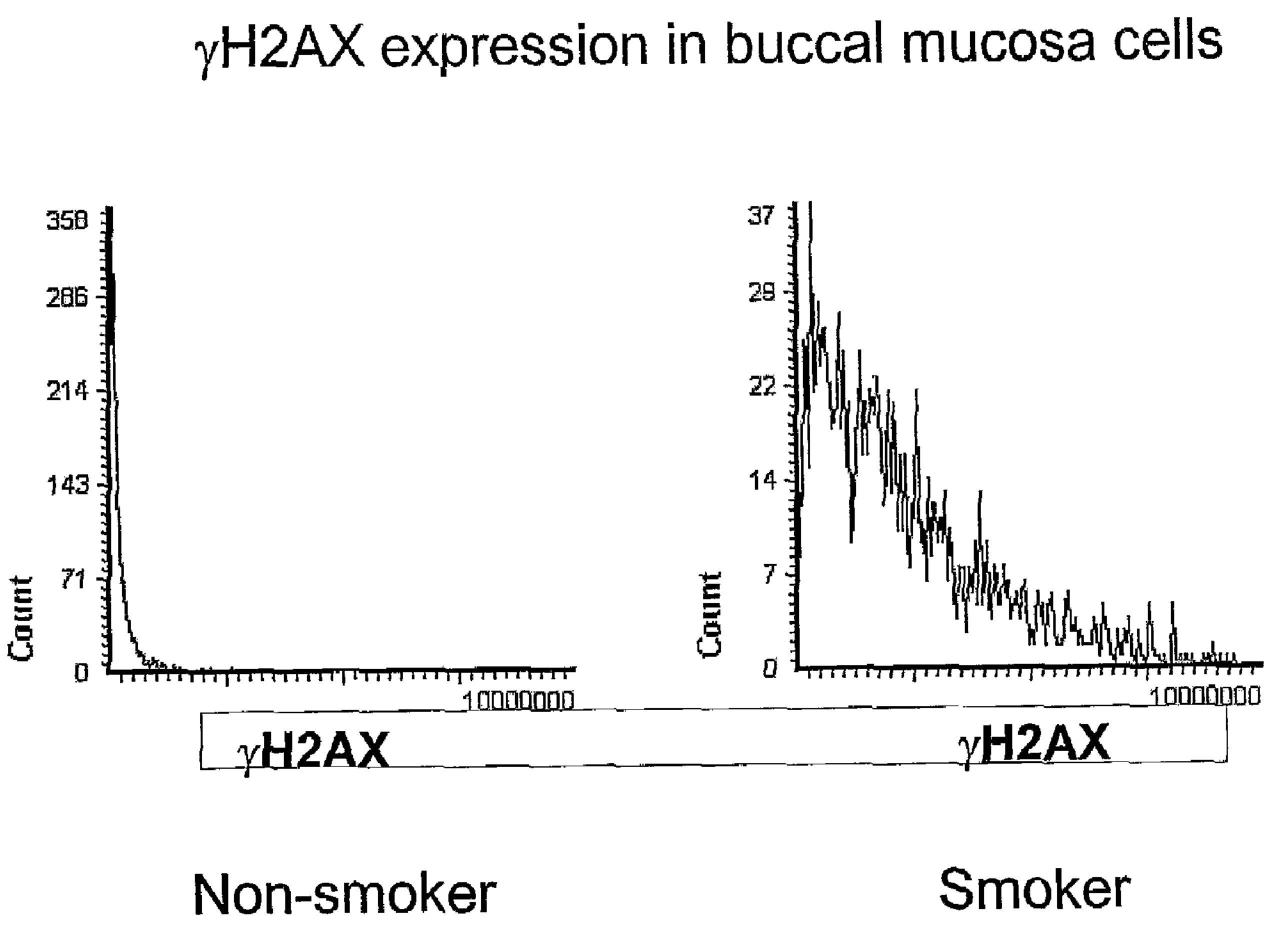
FIG. 26. Plot depicting γH2AX associated fluorescence (γH2AX; X-axis) and the number of cells having the corresponding γH2AX fluorescence level (Y axis), for buccal cells of a subject subsequent to smoking a cigarette (smoker) or a subject who did not smoke a cigarette (non-smoker).

Further performed was a test of double-strand DNA breaks in the cells of a human subject exposed to tobacco smoke. The level of γH2AX expression in the buccal mucosa of a smoker was compared to the level of γH2AX expression in the buccal mucosa of a nonsmoker. A cheek swab was collected from a subject (smoker) within 5 min completion of smoking a Marlboro light® cigarette, and a second check swab was collected from a subject that did not smoke a cigarette (non-smoker). Levels of γH2AX were then measured for both cell samples. As seen in FIG. 26 the X axis depicts γH2AX associated fluorescence (γH2AX), and the Y axis depicts the number of cells having the corresponding gH2AX fluorescence level. There were 358 cells with a very low value of γH2AX in the non-smoker sample, whereas the smoker sample had cells with γH2AX values spread over a wide range. Each histogram represents $3\times10^3$ cells. The buccal cells from the smoker showed a low number of cells having little or no γH2AX fluorescence signal, and showed a large number of cells with higher γH2AX fluorescence levels. In contrast, almost all cells of the non-smoker had little or no γH2AX fluorescence. Thus, human buccal cells exposed to tobacco smoke have an increased level of double strand DNA breaks relative to human buccal cells not exposed to tobacco smoke. These results parallel the in vitro results observed for A549 cells and for NHBE cells. Thus, the in vitro approaches described herein are predictive of in vivo responses.

Accordingly, the methods that were applied to A549 cells and NHBE cells for comparing different tobacco products, analyzing cells at different stages in cell cycle, and determining protection provided by the presence of an antioxidant, will be performed on human samples of buccal cells and it is expected, as shown in the in vitro experiments, that modified tobaccos, in particular genetically modified tobaccos that have a reduced amount of one or more compounds that contribute to a tobacco related disease (e.g., genetically modified tobacco having a reduced nicotine, TSNA, and/or sterol content) will induce fewer or a reduced amount of double strand DNA breaks in humans that are contacted with smoke from said modified tobaccos than will be observed in humans that are contacted with smoke from conventional tobacco products, reference tobacco products, or non-transgenic (wild-type tobacco of the same variety as the parental strain prior to genetic modification). The section that follows describes several methods for identifying a tobacco or tobacco products that modulate cell homeostasis.

Methods for Identifying a Tobacco or Tobacco Product that Modulates Cell Homeostasis Provided herein are methods for identifying a tobacco that modulates cell homeostasis by providing a tobacco, obtaining a tobacco composition from the tobacco, contacting a cell with the tobacco composition, and identifying the presence or absence of modulation of cell homeostasis after contact with the tobacco composition. In some embodiments, the methods provided herein can be used to identify a tobacco that modulates apoptosis or a tobacco that modulates cell proliferation. In some embodiments, the tobacco composition can be smoke or smoke condensate.

Also provided herein are methods of identifying a compound in tobacco that modulates cell homeostasis by providing a first tobacco, obtaining a tobacco composition from the first tobacco, contacting a first population of cells with the tobacco composition from the first tobacco, identifying the degree of modulation of cell homeostasis in the first population of cells after contact with the tobacco composition from the first tobacco, providing a second tobacco that has been modified to reduce a compound in the second tobacco, obtaining a tobacco composition from the second tobacco, contacting a second population of cells with the tobacco composition from the second tobacco, and identifying the degree of modulation of cell homeostasis after contact with the tobacco composition from the second tobacco, where an identification of a reduction in the degree of modulation of cell homeostasis after contact with the tobacco composition from the second tobacco identifies the compound as one that modulates cell homeostasis. In some embodiments, the methods provided herein can be used to identify a compound in tobacco that modulates apoptosis. In some embodiments, the methods provided herein can be used to identify a compound in tobacco that modulates cell proliferation. In some embodiments, the tobacco composition can be smoke or smoke condensate.

Also provided herein are methods of identifying a tobacco product that has a reduced potential to contribute to a tobacco-related disease by providing a first tobacco product, obtaining a tobacco composition from the first tobacco product, contacting a first population of cells with the tobacco composition from the first tobacco product, identifying the degree of modulation of cell homeostasis in the first population of cells after contact with the tobacco composition from the first tobacco product, providing a second tobacco product, obtaining a tobacco composition from the second tobacco product, contacting a second population of cells with the tobacco composition from the second tobacco product, and identifying the degree of modulation of cell homeostasis after contact with the tobacco composition from the second tobacco product, where an identification of a reduction in the degree of modulation of cell homeostasis after contact with the tobacco composition from the second tobacco product as compared to the degree of modulation of cell homeostasis after contact with the tobacco composition from the first tobacco product identifies the second tobacco product as one that has a reduced potential to contribute to a tobacco-related disease. In some embodiments, the second tobacco product has been modified to reduce a compound in the second tobacco. In some embodiments, the second tobacco product can be genetically modified to reduce the expression of at least one gene that regulates production of the compound. In some embodiments of the methods provided herein, the degree of modulation of cell homeostasis can be determined by identifying the degree of modulation of apoptosis. In some embodiments of the methods provided herein, the degree of modulation of cell homeostasis can be determined by identifying the degree of modulation of cell proliferation. In some embodiments, the tobacco composition can be smoke or smoke condensate.

Also provided herein are methods of making a tobacco product that has a reduced potential to contribute to a tobacco-related disease by providing a first tobacco, obtaining a tobacco composition from the first tobacco, contacting a first population of cells with the tobacco composition from the first tobacco, identifying the degree of modulation of cell homeostasis in the first population of cells after contact with the tobacco composition from the first tobacco, providing a second tobacco, obtaining a tobacco composition from the second tobacco, contacting a second population of cells with the tobacco composition from the second tobacco, identifying the degree of modulation of cell homeostasis after contact with the tobacco composition from the second tobacco product, where an identification of a reduction in the degree of modulation of cell homeostasis after contact with the tobacco composition from the second tobacco as compared to the degree of modulation of cell homeostasis after contact with the tobacco composition from the first tobacco identifies the second tobacco as one that has a reduced potential to contribute to a tobacco-related disease, and incorporating the second tobacco, which has a reduced potential to contribute to a tobacco-related disease, into a tobacco product. In some embodiments, the second tobacco has been modified to reduce a compound in the second tobacco. In some embodiments, the second tobacco can be genetically modified to reduce the expression of at least one gene that regulates production of the compound. In some embodiments of the methods provided herein, the degree of modulation of cell homeostasis can be determined by identifying the degree of modulation of apoptosis. In some embodiments of the methods provided herein, the degree of modulation of cell homeostasis can be determined by identifying the degree of modulation of cell proliferation. In some embodiments, the tobacco composition can be smoke or smoke condensate.

The methods provided herein can be used to determine the affect of a tobacco product or a compound from a tobacco product, on cell homeostasis. Cells of an organism contacted with a tobacco composition, e.g., mammalian epithelial cells, can undergo apoptosis and can proliferate at particular levels under “normal” conditions, where “normal” as used in this context refers to conditions in which cells are not contacted with tobacco or a tobacco composition and are not otherwise placed under atypical (e.g., stressful) environmental conditions. Environmental conditions, for example, contacting the cells with a tobacco composition, can modulate apoptosis of the contacted cells and also can modulate the proliferation of the contacted cells. Such modulation can result in processes that can directly lead to cellular events in tobacco-related disease (e.g., apoptosis can be decreased, which can lead to neoplastic cell growth) or can indirectly lead to cellular events in tobacco-related disease (e.g., apoptosis can be increased, which can trigger a cell growth response in an organism, which can lead to neoplastic cell growth). The methods provided herein can be used to examine the affect of a tobacco product or a compound from a tobacco product, on cell homeostasis by, for example, determining the affect of a tobacco or tobacco compound on apoptosis in a cell or a cell population, or, for example, determining the affect of a tobacco or tobacco compound on cell proliferation of a cell or a cell population. In some embodiments, a first tobacco that causes a lesser degree of modulation of cell homeostasis relative to a second tobacco can be characterized as a reduced risk tobacco. In some embodiments, a first tobacco that causes a lesser degree of inhibition of apoptosis relative to a second tobacco can be characterized as a reduced risk tobacco. In some embodiments, a first tobacco that causes a lesser degree of inhibition of cell proliferation relative to a second tobacco can be characterized as a reduced risk tobacco. Any of a variety of known methods for determining modulation of cell homeostasis by, for example, modulating apoptosis or modulating cell proliferation, as exemplified herein, can be used in the methods provided herein.

Also provided herein are methods for determining cell response to cell damage. Cells can be exposed to environmental input, such as a tobacco composition, that causes cell damage. The response of these cells to the environmental input-mediated damage can be indicative of the likelihood of the environmental input leading to an environmental input-related disease. In one embodiment, cells can be contacted with a tobacco composition, and the response of the cells to the contact by the tobacco composition can indicate the likelihood of the tobacco composition leading to a tobacco-related disease.

As provided herein, cells contacted by different environmental inputs, for example, different tobacco compositions, can respond differently to cell damage caused by the environmental input, where some cell responses are more indicative of leading to a disease state compared to other cell responses. Thus, contemplated herein, two or more tobacco compositions can be compared and characterized according to the cell responses in reaction to damage induced by exposure to the tobacco compositions. In such methods, exposure conditions can be manipulated such that the amount of damage to the cells is equivalent for each different tobacco composition, resulting in a determination of different characteristic cell responses to the same amount of cell damage.

Accordingly, methods are provided herein for comparing two or more tobacco compositions by contacting a first tobacco composition with a first population of cells, and contacting a second composition with a second population of cells, where the two different contacting steps are performed in such a manner that the first and second population of cells undergo equivalent amount of cell damage, and then determining the degree of modulation of cell homeostasis in the first and second populations of cells, where the tobacco composition that is characterized by the lowest degree of cell modulation can be identified as a tobacco with reduced likelihood of causing a tobacco-related disease. In such methods, damage to the cells caused by the tobacco compositions can be measured by, for example, measuring the degree of damage to the genetic material of the cells, in accordance with the methods provided herein or otherwise known in the art. Also in such methods, the degree of modulation of cell homeostasis can be determined by the degree of modulation of apoptosis or cell proliferation relative to cells not contacted by a tobacco composition or relative to cells contacted by a tobacco composition from a tobacco, such as a reduced risk tobacco with a known degree of modulation of cell homeostasis. The following section describes several methods to evaluate the ability of a tobacco or a tobacco product to modulate apoptosis in greater detail.

Modulation of Apoptosis

In some embodiments, modulation of cell homeostasis can be identified by determining a modulation of apoptosis. Thus, provided herein are methods of identifying a tobacco that modulates apoptosis by providing a tobacco, obtaining a tobacco composition from the tobacco, contacting a cell with the tobacco composition, and identifying a modulation of apoptosis in the cell after contact with the tobacco composition. Also provided herein are methods of identifying a compound in tobacco that modulates apoptosis, methods of identifying a tobacco product that has a reduced potential to contribute to a tobacco-related disease, and methods of making a tobacco product that has a reduced potential to contribute to a tobacco-related disease, in accordance with the methods of identifying a tobacco or tobacco compound that modulates cell homeostasis provided herein elsewhere. Also provided herein are methods of identifying a compound in tobacco that modulates apoptosis, methods of identifying a tobacco product that has a reduced potential to contribute to a tobacco-related disease, and methods of making a tobacco product that has a reduced potential to contribute to a tobacco-related disease, in conjunction with the methods of identifying a tobacco or tobacco compound that modulates cell proliferation provided herein.

Also provided herein are methods of comparing two or more tobacco products. In some embodiments, a tobacco or tobacco compound that induces a lower degree of apoptosis can be characterized as a tobacco that has a potential to contribute to a tobacco-related disease. In some embodiments, a first tobacco that induces a lower degree of apoptosis than a second tobacco can be characterized as a tobacco that has an increased potential to contribute to a tobacco-related disease. In some embodiments, a first tobacco that induces a higher degree of apoptosis than a second tobacco can be characterized as a tobacco that has a reduced potential to contribute to a tobacco-related disease. In some embodiments, a tobacco or tobacco compound that induces a higher degree of apoptosis can be characterized as a tobacco that has a potential to contribute to a tobacco-related disease. In some embodiments, a first tobacco that induces a higher degree of apoptosis than a second tobacco can be characterized as a tobacco that has an increased potential to contribute to a tobacco-related disease. In some embodiments, a first tobacco that induces a lesser degree of apoptosis than a second tobacco can be characterized as a tobacco that has a reduced potential to contribute to a tobacco-related disease. In some embodiments, the methods of identifying a tobacco that modulates apoptosis can be used to identify modified tobacco that modulates apoptosis as provided herein or otherwise known in the art.

Also provided herein are methods of comparing two or more tobacco products. In some embodiments, a tobacco or tobacco compound that inhibits apoptosis can be characterized as a tobacco that has a potential to contribute to a tobacco-related disease. In some embodiments, upon inducing the same degree of DNA damage (DSBs) a first tobacco that induces lesser degree of apoptosis than a second tobacco can be characterized as a tobacco that has an increased potential to contribute to a tobacco-related disease. In some embodiments, upon inducing the same degree of DNA damage (DSBs) a first tobacco that induces lesser degree of apoptosis than a second tobacco can be characterized as a tobacco that has a reduced potential to contribute to a tobacco-related disease. In some embodiments, a tobacco or tobacco compound that increases apoptosis can be characterized as a tobacco that has a potential to contribute to a tobacco-related disease. In some embodiments, a first tobacco that increases apoptosis to a greater degree than a second tobacco can be characterized as a tobacco that has an increased potential to contribute to a tobacco-related disease. In some embodiments, a first tobacco that increases apoptosis to a lesser degree than a second tobacco can be characterized as a tobacco that has a reduced potential to contribute to a tobacco-related disease. In some embodiments, the methods of identifying a tobacco that modulates apoptosis can be used to identify modified tobacco that modulates apoptosis as provided herein or otherwise known in the art.

As used herein, a tobacco or tobacco compound that induces a lower or higher degree of apoptosis refers to a tobacco or tobacco compound that causes a cell or cell population to decrease or increase, respectively, apoptosis in that cell or cell population relative to a cell or cell population that is not contacted by the tobacco or tobacco compound. Any of a variety of methods can be used to determine apoptosis in a cell or cell population, including those provided herein, and other methods known in the art.

While not intending to be limited by the following explanation, a decreased degree of apoptosis in cells may result in cells with damaged DNA that can survive and be tumorigenic rather than die and be eliminated. In other cellular functions, extensive apoptosis may induce compensatory stem cell proliferation and result in tumorigenesis. Accordingly, as contemplated herein an increase or decrease in apoptosis can lead to a tobacco-related disease.

Also provided herein are methods of comparing two or more tobacco products when the two or more tobacco products induce the same level of damage to cells. In some embodiments, a tobacco or tobacco compound that inhibits apoptosis can be characterized as a tobacco that has a potential to contribute to a tobacco-related disease. In some embodiments, upon inducing the same degree of DNA damage (DSBs) a first tobacco that induces lesser degree of apoptosis than a second tobacco can be characterized as a tobacco that has an increased potential to contribute to a tobacco-related disease. In some embodiments, upon inducing the same degree of DNA damage, a first tobacco that induces lesser degree of apoptosis than a second tobacco can be characterized as a tobacco that has a reduced potential to contribute to a tobacco-related disease. In some embodiments, upon inducing the same degree of DNA damage, a tobacco or tobacco compound that increases apoptosis can be characterized as a tobacco that has a potential to contribute to a tobacco-related disease. In some embodiments, upon inducing the same degree of DNA damage, a first tobacco that increases apoptosis to a greater degree than a second tobacco can be characterized as a tobacco that has an increased potential to contribute to a tobacco-related disease. In some embodiments, upon inducing the same degree of DNA damage, a first tobacco that increases apoptosis to a lesser degree than a second tobacco can be characterized as a tobacco that has a reduced potential to contribute to a tobacco-related disease. In some embodiments, the methods of identifying a tobacco that modulates apoptosis can be used to identify modified tobacco that modulates apoptosis as provided herein or otherwise known in the art.

The methods provided herein can include one or more steps of determining modulation of apoptosis. Typically, such methods include assays for modulation of apoptosis in a population of cells. Any of a variety of methods known in the art for assaying apoptosis can be used in the methods provided herein. Exemplary known assays include assays for activation of apoptosis-related proteins, assays for double-strand DNA breaks, and assays for membrane permeability.

In one exemplary method, modulation of apoptosis can be identified by determining caspase activation. Caspases are proteases involved in apoptosis. Activation of caspases can lead to apoptosis in the cell. Accordingly, measurement of activated caspases can be used to identify apoptosis in cells. Typically, caspases are activated by a cleavage reaction. Thus, activated caspase can be determined by detecting activated cleaved caspases. For example, caspase activation can be identified using an antibody or fragment thereof, which binds to activated caspase but not inactive caspase. There are a number of caspases that can be screened in accordance with the methods provided herein, including but not limited to, caspase 1, 3 and 9. In another example, activation of caspase by its catalytic activity can be determined. For example, caspase-3 has substrate selectivity for the amino acid sequence Asp-Glu-Val-Asp (DEVD) (SEQ. ID. NO. 1). A fluorogenic indicator such as Ac-DEVD-AMC can be used for fluorometric assay of caspase-3 activity. A variety of caspase activation assays are known in the art, as exemplified in Gown et al., J. Histochem. Cytochem. (2002) 50:449-54; Iordanov et al., Apoptosis (2005) 10:153-66; and Kahlenberg et al., J. Leukoc. Biol. (2004) 76:676-84, all of which are hereby expressly incorporated by reference in their entireties.

In another exemplary method, modulation of apoptosis can be identified by determining cleavage of the protein poly (ADP-ribose) polymerase (PARP). Enzymatic cleavage of the PARP occurs uniquely during apoptosis. Activation of caspases results in cleavage of PARP, which produces inactive PARP fragments. One inactive PARP fragment binds DNA and inhibits DNA repair. Thus, cleavage of PARP can be determined using an antibody specific to cleaved PARP fragments. Cleavage of PARP also can be determined by measuring decrease in PARP activity. PARP catalyzes the NAD-dependent addition of poly(ADP-ribose) to nuclear proteins such as histone. Thus, in one exemplary assay, incorporation of biotinylated poly(ADP-ribose) onto histone proteins can be measured as an indicator of PARP activity. Methods for determining PARP cleavage are known in the art, as exemplified in Mullen, Methods Mol. Med. (2004) 88:171-81; Yu et al., Science (2002) 297:259-63; and Saldani et al. Eur. J. Histochem. (2001) 45:389-92, all of which are hereby expressly incorporated by reference in their entireties.

In another exemplary method, modulation of apoptosis can be identified by determining annexin V binding. Annexin V binds to phosphotidylserine on the cell membrane, a phenomenon that occurs only in cells undergoing apoptosis. In one exemplary assay, fluorescently labeled annexin V can be added to cells, and presence of the fluorescent marker on the cells is indicative of annexin binding. In another example, antibodies specific for annexin V can be used to detect the presence of annexin V on the cell membrane. This technique is often combined with the use of fluorescent dyes that are normally not able to penetrate the cell membrane unless it is damaged these include dyes such as propidium iodide and acridine orange. Methods for determining annexin V binding are known in the art, as exemplified in U.S. Pat. No. 5,767,247, Vermes et al., J. Immunol. Methods (1995) 184:39-51; Wilkins et al., Cytometry (2002) 48:14-9; and Peng et al., Chin. Med. Sci. J. (2002) 17:17-21, all of which are hereby expressly incorporated by reference in their entireties.

In another exemplary method, modulation of apoptosis can be identified by determining chromatin condensation. Chromatin condensation is a well-established indicator of apoptosis. Chromatin condensation can be detected by a variety of methods, for example, detection by decreased forward angle light scatter or decreased right angle light scatter, and detection by presence of a specific dye such as Hoechst 33342. Methods for determining chromatin condensation are known in the art, as exemplified in Tounekti et al., Exp. Cell Res. (1995) 217:506-16 and Dobrucki et al., Micron (2001) 32:645-52, all of which are hereby expressly incorporated by reference in their entireties.

In another exemplary method, modulation of apoptosis can be identified by determining an increase sensitivity of chromatin in cells to acid or heat-induced denaturation. Sensitivity of chromatin in cells can be a marker of apoptosis. Chromatin sensitivity to acid or heat-induced denaturation can be detected by a variety of methods known in the art, such as detecting the altered binding of the metachromatic dye acridine orange. Methods for assaying chromatin sensitivity to denaturation are known in the art, as exemplified in Frankfurt et al., (1996) Exp. Cell Res. 226:387-397, Frankfurt et al., (2001) J. Histochem. Cytochem. 49:369-378, Frankfurt et al., (2001) J. Immunol. Methods. 253: 133-144, Groos et al., (2003) Anat. Rec. 272A:503-513, Zamzani et al., (1999) Nature 401:127-128, and Allera et al., (1997) J. Biol. Chem. 272:10817-10822, all of which are hereby expressly incorporated by reference in their entireties.

In another exemplary method, modulation of apoptosis can be identified by determining fractional DNA content. Under appropriate conditions, small molecular weight DNA fragments occurring as the result of the apoptotic process can be removed from cells, resulting in cells with decreased DNA content. Assays can be used to detect cells with decreased (fractional) DNA content by using, for example, DNA dyes in flow cytometry according to known methods. Methods for assaying fraction DNA content are known in the art, as exemplified in Mazur et al., Hum. Exp. Toxicol. (2002) 21:335-41 and Gorczyca, Endocrine-Related Cancer (1999) 6:17-19, all of which are hereby expressly incorporated by reference in their entireties.

In another exemplary method, modulation of apoptosis can be identified by determining TUNEL assay, as discussed herein elsewhere. TUNEL assay can detect DNA strand breaks occurring following activation of an apoptosis-specific nuclease. Incorporation of labeled nucleotides at the site of the double-strand breaks can be detected by, for example, binding of antibodies or other molecules (biotin-avidin) carrying a fluorescent tag.

An exemplary assay for cell apoptosis determination is provided in Example 1 for caspase-3 activation measurement. Briefly, cells were treated with smoke (i.e., A549) or smoke condensate (i.e., NHBE) and fixed as described above, then rinsed twice in PBS and immersed in 0.2% Triton X-100 (Sigma) in a solution of 1% (w/v) bovine serum albumin (BSA; Sigma) in PBS for 30 min to suppress non specific antibody binding. The cells were then incubated in 100 μl volume of 1% BSA containing 1:100 dilution of anti-cleaved (activated) caspase-3 rabbit polyclonal Ab (Cell Signaling Technology, Beverly, Mass.) overnight at 4° C., washed twice with PBS and incubated with 1:30 diluted FITC-conjugated F(ab')2 fragment of swine anti-rabbit immunoglobulin (DAKO, Carpinteria, Calif.) for 30 min in room temperature in the dark. The cells were then counterstained with 1 μg/ml 4,6-diamidino-2-phenylindole (DAPI, Molecular Probes, Eugene, Oreg.) in PBS for 5 min. Each experiment was performed with an IgG control in which cells were labeled only with secondary antibody, FITC-conjugated F(ab')2 fragment of goat anti-mouse immunoglobulins, without primary antibody incubation to estimate the extent of nonspecific binding of the secondary antibody to the cells. The following section describes several assays that can be used to evaluate the ability of a tobacco or a tobacco product to modulate cell proliferation.

Modulation of Cell Proliferation

In some embodiments, modulation of cell homeostasis can be identified by determining modulation of cell proliferation. Thus, provided herein are methods of identifying a tobacco that modulates cell proliferation by providing a tobacco, obtaining a tobacco composition from the tobacco, contacting a cell with the tobacco composition, and identifying a modulation of cell proliferation in the cell after contact with the tobacco composition. Also provided herein are methods of identifying a compound in tobacco that modulates cell proliferation, methods of identifying a tobacco product that has a reduced potential to contribute to a tobacco-related disease, and methods of making a tobacco product that has a reduced potential to contribute to a tobacco-related disease, in accordance with the methods of identifying a tobacco or tobacco compound that modulates cell homeostasis provided herein elsewhere. Also provided herein are methods of identifying a compound in tobacco that modulates cell proliferation, methods of identifying a tobacco product that has a reduced potential to contribute to a tobacco-related disease, and methods of making a tobacco product that has a reduced potential to contribute to a tobacco-related disease, in conjunction with the methods of identifying a tobacco or tobacco compound that modulates cell proliferation provided herein.

Also provided herein are methods of comparing two or more tobacco products. In some embodiments, a tobacco or tobacco compound that inhibits cell proliferation can be characterized as a tobacco that has a potential to contribute to a tobacco-related disease. In some embodiments, a first tobacco that inhibits cell proliferation to a greater degree than a second tobacco can be characterized as a tobacco that has an increased potential to contribute to a tobacco-related disease. In some embodiments, a first tobacco that inhibits cell proliferation to a lesser degree than a second tobacco can be characterized as a tobacco that has a reduced potential to contribute to a tobacco-related disease. In some embodiments, a tobacco or tobacco compound that increases cell proliferation can be characterized as a tobacco that has a potential to contribute to a tobacco-related disease. In some embodiments, a first tobacco that increases cell proliferation to a greater degree than a second tobacco can be characterized as a tobacco that has an increased potential to contribute to a tobacco-related disease. In some embodiments, a first tobacco that increases cell proliferation to a lesser degree than a second tobacco can be characterized as a tobacco that has a reduced potential to contribute to a tobacco-related disease.

In some embodiments, the methods of identifying a tobacco that modulates cell proliferation can be used to identify modified tobacco that modulates cell proliferation as provided herein or otherwise known in the art.

As used herein, a tobacco or tobacco compound that inhibits or increases cell proliferation refers to a tobacco or tobacco compound that causes a cell or cell population to proliferate at a decreased or increased rate, respectively, relative to a cell or cell population that is not contacted by the tobacco or tobacco compound. Any of a variety of methods can be used to determine cell proliferation in a cell or cell population, including those provided herein, and other methods known in the art.

Any of a variety of assays can be used that monitor alterations to the viability and growth potential of cells in vitro when challenged by exposure to a vast array of insults (e.g., ionizing radiation, ultraviolet radiation, drugs, toxins, carcinogens, CS, CSC, viruses, chemicals, free radicals, pollution, and the like). Assays that can be used in the methods provided herein can include assays that monitor proliferative rates (cell proliferation assays) and assays that monitor survivability and proliferation with time (e.g., clonogenic survival assay).

In one example, clonogenic survival can be monitored. The clonogenic survival assay can be used to study the ability of specific agents to impact the proliferation of cells. This assay is frequently employed in cancer research laboratories to determine the effect, if any, of a range of substances (e.g., drugs, radiation, chemicals, organic mixtures, etc), on the proliferation of tumor cells. The term "clonogenic" refers to the fact that these cells are clones of one another. Any of a variety of cell types can be used in such experiments. The cells used typically come from established cell lines, which have been well-studied and whose general characteristics are known. Typically, a clonogenic survival assay has four major steps: (1) inoculating cells into culture dishes and incubate the cells (e.g., 24-48 hours); (2) upon the cells reaching the logarithmic phase of growth, the treating the cells with a tobacco composition (e.g., contacting the cells with freshly prepared and diluted CS for different periods of time); (3) allowing the cells to recover for a set number of hours (e.g., up to 24 hours), then treating the cells and allowing the cells to grow further (e.g., trypsinizing the cells, replating the cells at specific dilutions, and allowing the cells to grow for 5-7 days); and (4) fixing, staining and counting the cells. Experimental specifics such as time of incubation and growth, number of cells to use for plating, and the like, can be readily determined by one skilled in the art according to the type of cell used. Typically, the number of surviving colonies of 25-50 cells is representative of the percentage of cells that survived the treatment. A graphical representation of survival versus exposure time to a tobacco composition can then be generated. The surviving fraction can be determined by dividing the number of colonies in the dish by the number of the colonies in the control (non-treated) dish.

In addition to clonogenic assays, any of a variety of cell proliferation assays can be used to monitor an increase or decrease in proliferative capacity and which can be used in context with exposure to a tobacco composition such as CS and/or CSCs.

In one example of cell proliferation assays, intake and conversion of a dye can be an indicator of cell proliferation. One example of such an assay is a resazurin-based assay. Resazurin is a redox dye which is not fluorescent, but upon reduction by metabolically active cells, is converted into a highly fluorescent product (resorufin). Living cells can readily reduce this non-toxic reagent and the resulting increase in fluorescence intensity is monitored using a fluorescence spectrophotometer or plate reader. Exemplary commercially available assays include alamarBlue™ reagent from BioSource International, Camarillo Calif.

Another example of dye intake and conversion-based cell proliferation assay is a tetrazolium salt-based assay. The tetrazolium salt assay is a colorimetric assay is based on the conversion of a tetrazolium salt (MTT, WST, or other) to formazan, a purple dye. This cellular reduction reaction involves the pyridine nucleotide cofactors NADH/NADPH and is only catalyzed by living cells. The formazan product has a low aqueous solubility and is present as purple crystals. Dissolving the resulting formazan with a solubilization buffer permits the convenient quantification of product formation. The intensity of the product color is directly proportional to the number of living cells in the culture. Exemplary commercially available assays include Quick Cell Proliferation Assay Kit from BioVision Inc., Mountain View, Calif.

In another example of cell proliferation assays, cells can be monitored for plasma membrane damage. Plasma membrane damage-based assays can be used to monitor cell death or cytotoxicity. Typical assays quantitate molecules released from damaged cells such as adenylate kinase and lactate dehydrogenase. Exemplary commercially available assays include LDH-Cytotoxicity Assay Kit from BioVision Inc., Mountain View, Calif.

In another example of cell proliferation assays, cells can be monitored for dye exclusion/dye uptake assays. Dye exclusion/uptake assays distinguish live from dead cells based on dyes which specifically stain either live or dead cells. Exemplary commercially available assays include trypan blue dye exclusion, Live-Dye™ (a cell-permeable green fluorescent dye that stains live cells) from BioVision Inc., Mountain View, Calif.

In another example of cell proliferation assays, cells can be monitored for ATP and ADP levels. ATP and ADP level-based assays utilize the phenomenon that increased levels of ATP and decreased levels of ADP have been recognized in proliferating cells. Exemplary commercially available assays include ApoSENSOR™ Cell Viability Assay Kit from MBL International, Woburn Mass.

In another example of cell proliferation assays, cells can be monitored for protein or DNA levels in the cells. Cell proliferation is associated with increased protein and DNA synthesis. DNA quantitation-based assays can use, for example, [3H]-thymidine incorporation, the fluorescence of a DNA-dye complex from lysed cells, or other known markers of DNA synthesis. Similarly, protein synthesis can be monitored for incorporation of labeled amino acids into the proteins. Exemplary commercially available assays include Quantos™ Cell Proliferation Assay Kit from Stratagene, La Jolla, Calif.

Working Example 3 herein provides one non-limiting specific example of the clonogenic survival assay methods provided herein. Variations of the assay method used in terms of materials, assay times, instrumentation and protocols would be apparent to the skilled artisan.

EXAMPLE 3

A clonogenic survival assay was used to study the ability of tobaccos and tobacco products to impact the proliferation of cells. The experiment involves four major steps: (1) inoculate cells into culture dishes and incubate for 24-48 hours; (2) upon reaching the logarithmic phase of growth, the treatment is applied; the treatment in this case is freshly prepared and diluted CS for increasing periods of time; (3) the cells are then allowed to recover for a set number of hours (up to 24), then the cells are trypsinized, replated at specific dilutions, and allowed to continue growing for 5-7 days; the number of cells used depends largely on the plating efficiency of the cell line and must be determined empirically prior to the experiment; and (4) at the conclusion of the experiment, the cells are fixed, stained, and counted. The primary measure is to count surviving colonies of 25-50 cells which is presented as the percentage of cells which survived the treatment. A graphical representation of survival versus exposure time to CS is then generated. The surviving fraction is determined by dividing the number of colonies in the dish by the number of the colonies in the control (non-treated) dish.

A549 cells were exposed to smoke as previously described (see above). Following smoke exposure the medium is aspirated and the cells rinsed refed with 37° C. BEGM and placed in a 37° C., 5% $CO_2$ humidified incubator for two to three hours. The cells are harvested by trypsinization with trypsin-EDTA (0.25% trypsin-0.38 mg/ml EDTA, Invitrogen). Cells are centrifuged at 260×g for 8 min. Cell pellets are resuspended in 1 ml of Ham's F-12K medium, 10% FBS (complete medium) per pellet and counted. Cells are serially diluted so that the mock treated have ~65 cells per well and smoke treated have ~300 cells per well when seeded onto 96-well flat bottom tissue culture plates; one plate per condition. The plates are incubated for five days in a 37° C., 5% $CO_2$ humidified incubator. The colonies of cells are fixed with 5% formaldehyde/PBS and colored with 0.8% crystal violet solution for visualization. The colonies are counted with the aid of a macroscopic dissecting microscope. The cloning efficiency results are expressed in relation to the mock exposed cells. Unless otherwise indicated, each bar in the graphs represents three replicate data points per experiment.

Figure 14:
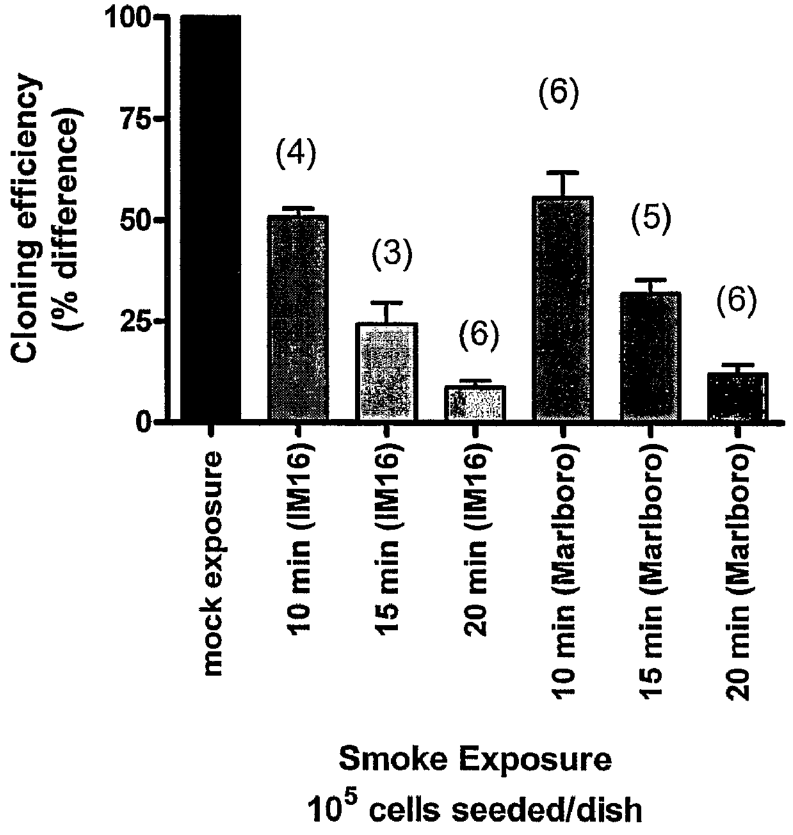
FIG. 14. Bar plot showing the relative percent cloning efficiency of A549 cells 5 days after exposure to smoke from IM 16 or Marlboro® for 10, 15 or 20 minutes.

A549 cells were exposed to whole smoke from IM16 or Marlboro® cigarettes for various lengths of time after which clonogenic assays were performed. FIG. 14 is a summary of multiple experiments. The numbers in parentheses indicate the number of experiments represented by each bar. The industry monitor reference cigarette IM16 shows an effect on viability essentially identical to that of the Marlboro® Red soft pack cigarettes. In both cases there was a linear decrease in cell viability with increasing smoke exposure.

Figure 15:
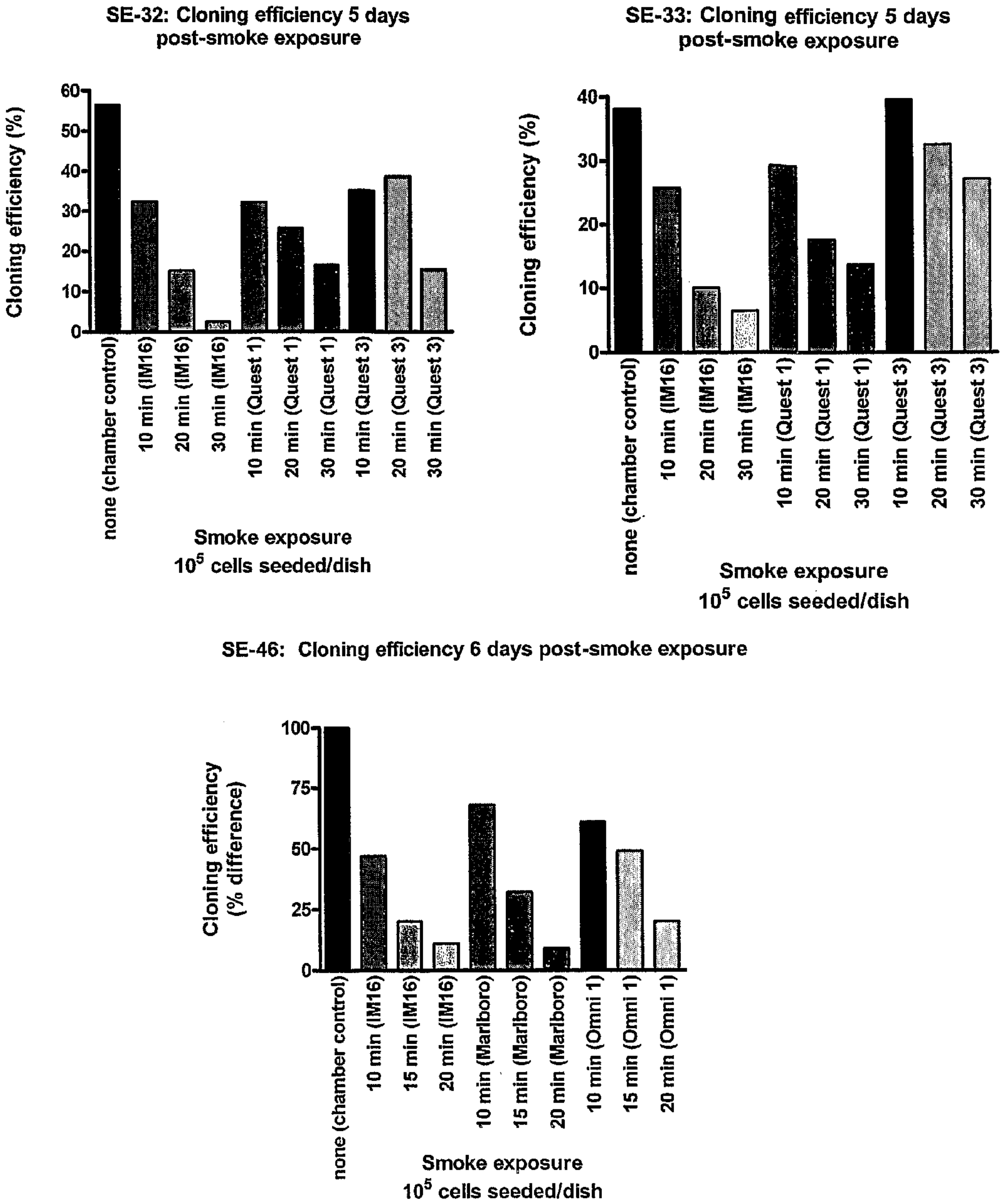
FIG. 15. Bar plots showing the relative percent cloning efficiency of A549 cells 5 days after exposure to smoke from IM 16, Quest 1® or Quest 3® for 10, 20 or 30 minutes (top two plots), or 6 days after (bottom plot) exposure to smoke from IM 16, Marlboro® or Omni®, for 10, 15 or 20 minutes.

In one set of experiments, A549 cells were exposed to smoke from various cigarettes for 20 min and clonogenic assays were performed. IM16, Omni®, Marlboro®, Quest 1®, or Quest 3® brand cigarettes were compared. Each graph of FIG. 15 represents a separate experiment. The assay distinguishes between the cigarettes, with Quest 3® treatment having the least impact on cell viability and IM 16 having the greatest. An overall ranking of the cigarettes in terms of impact on viability can be seen: Quest 3® < Quest 1® and Omni® < Marlboro® < IM16. Thus, the tobacco products containing modified tobacco (i.e., Omni®, Quest 1®, and Quest 3® had the an impact on cell viability that was significantly less than a reference tobacco product (i.e., IM16) and a conventional, commercially available, traditional tobacco product (i.e., Marlboro®). Accordingly, the modified tobacco products Omni®, Quest 1®, and Quest 3® have a reduced potential to contribute to a tobacco related disease (i.e., Omni®, Quest 1®, and Quest 3® are reduced risk tobacco products) according to the clonogenic assay.

Figure 16:
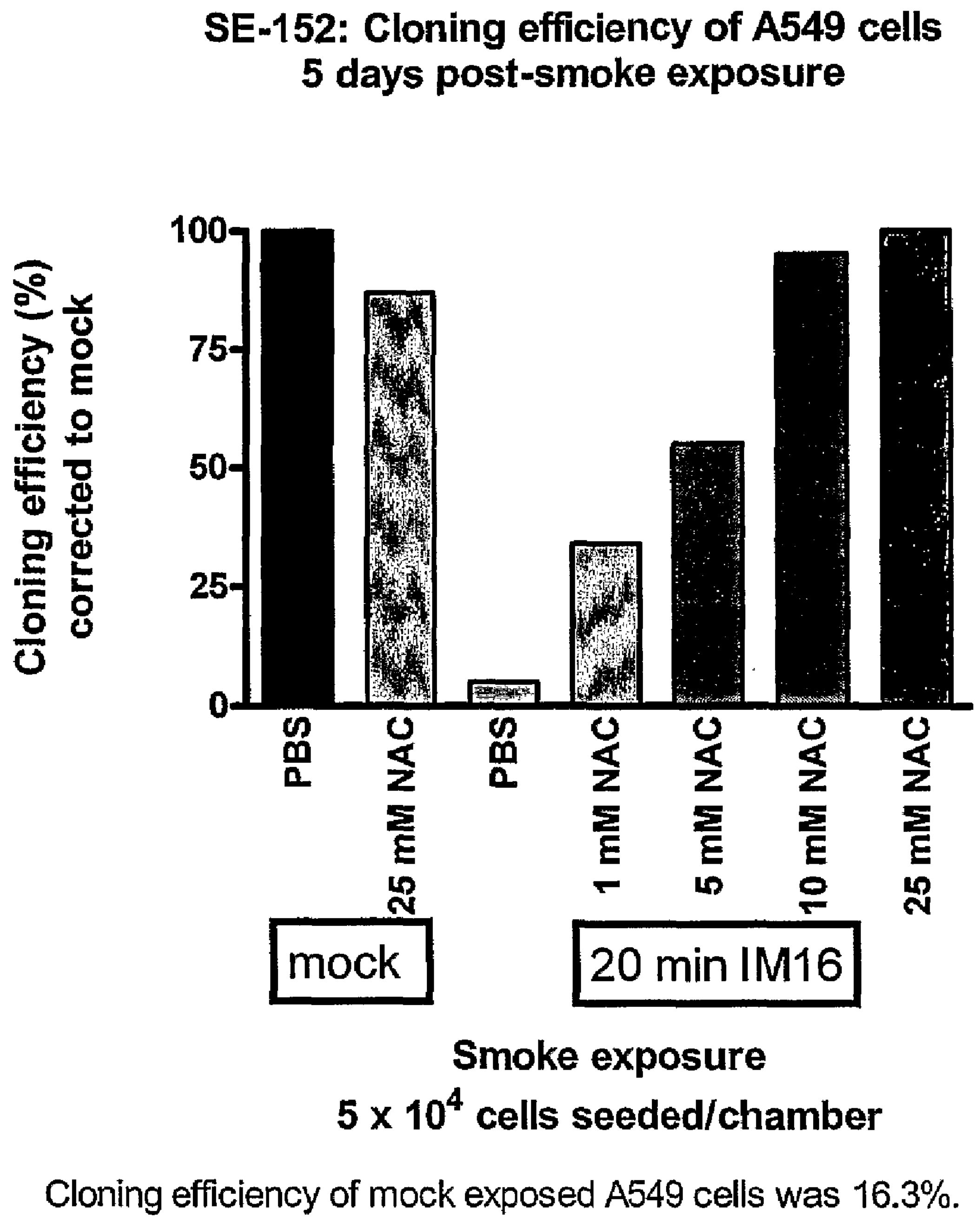
FIG. 16. Bar plot showing the relative percent cloning efficiency of A549 cells 5 days after exposure to smoke from IM 16 for 20 minutes in the presence of PBS or 1 mM, 5 mM, 10 mM or 25 mM NAC.

In a next set of experiments, the mitigation of the effect of whole smoke on cell viability by the presence of NAC was evaluated. A549 cells were exposed to 20 min IM16 smoke in the presence of various concentrations of the free radical scavenger N-acetylcysteine (NAC) and the clonogenic assay performed. NAC protected the viability of the cells in a dose-dependent manner. FIG. 16 shows the increasing degree of proliferation resulting from increasing concentrations of NAC.

Figure 17:
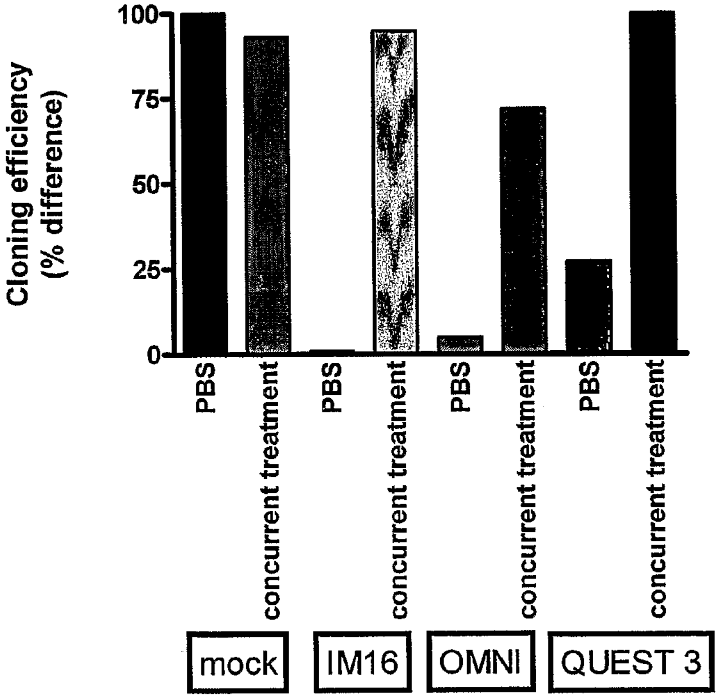
FIG. 17. Bar plot showing the relative percent cloning efficiency of A549 cells 5 days after exposure to smoke from IM 16, Omni® or Quest 3® for 20 minutes in the presence of PBS or 25 mM NAC.

In another series of experiments, the effect of NAC on the viability of cells contacted with whole smoke from different cigarettes was evaluated. A549 cells were exposed to smoke from various cigarettes for 20 min in the presence or absence of 25 mM NAC and the clonogenic assay performed. IM16, Omni®, and Quest 3® cigarettes were compared. NAC completely protected the cells exposed to Quest 3® smoke, and partially protected cells exposed to Omni® or IM16 (FIG. 17). Again, these data show that tobacco products containing modified tobacco (i.e., Omni® and Quest 3®) had the an impact on cell viability that was significantly less than a reference tobacco product (i.e., IM16). Accordingly, the modified tobacco products Omni® and Quest 3® have a reduced potential to contribute to a tobacco related disease (i.e., Omni® and Quest 3® are reduced risk tobacco products).

In yet another series of experiments, the effect of NAC on cell death caused by the VAPOR phase of smoke from different cigarettes was evaluated. A549 cells were exposed to the vapor phase of smoke for 20 min by inserting a Cambridge filter pad immediately after the cigarette in the smoking apparatus so as to filter out the particulate matter ("tar") and leave only the vapor phase. Three different cigarettes were used: IM16, Quest 1® and Quest 3®. Cells were exposed in the presence or absence of 25 mM NAC. The clonogenic assay was subsequently performed.

Figure 18:
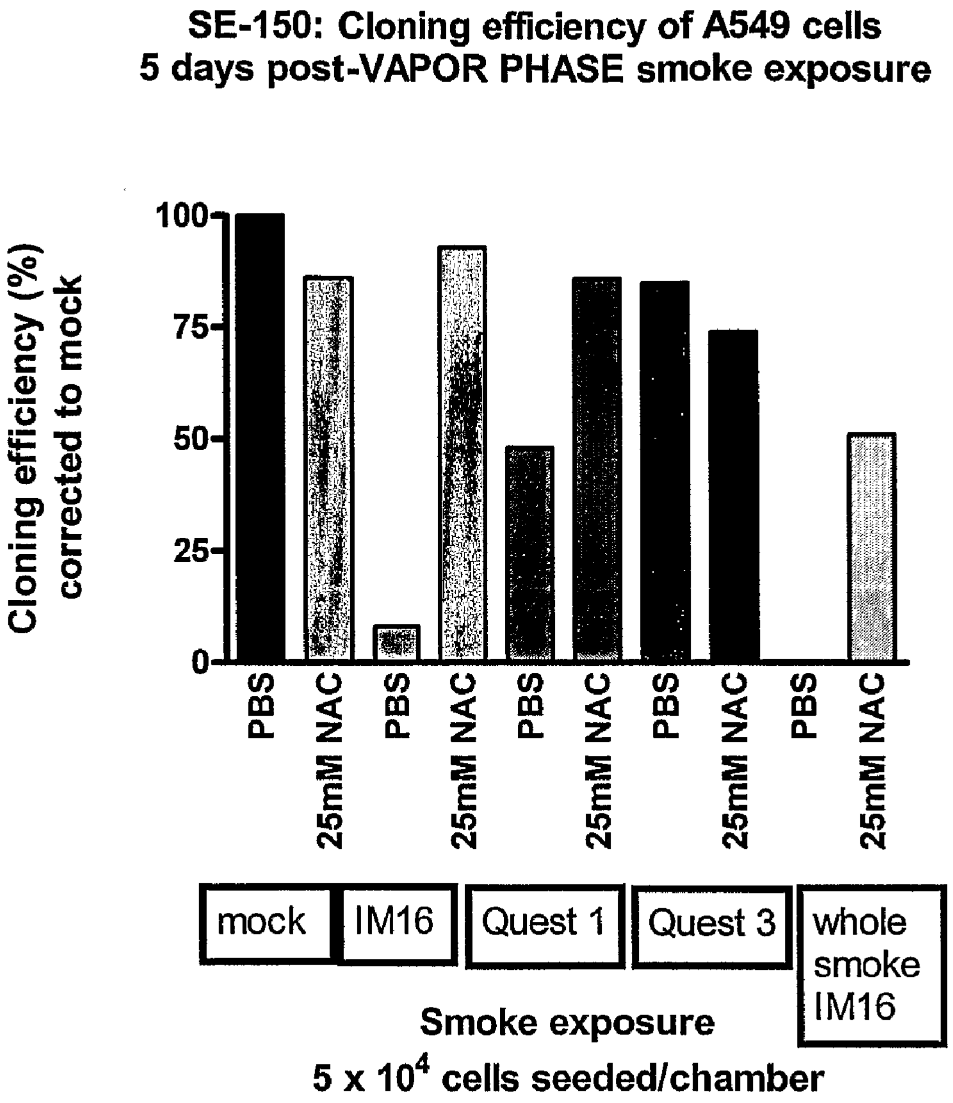
FIG. 18. Bar plot showing the relative percent cloning efficiency of A549 cells 5 days after exposure to vapor phase of smoke from IM 16, Quest 1® or Quest 3®, or smoke of IM 16 for 20 minutes in the presence of PBS or 25 mM NAC.

The vapor phase of all cigarettes showed less effect on cell viability than the corresponding whole smoke exposure, with Quest 3® exhibiting almost no effect (FIG. 18). The effect of various cigarette modifications on vapor phase toxicity can thus be selectively monitored. In all vapor phase exposures, the presence of the free radical scavenger NAC protected the cells against viability loss. These experiments provide more evidence that the tobacco products containing modified tobacco (i.e., Quest 1®, and Quest 3® had an impact on cell viability that was significantly less than a reference tobacco product (i.e., IM16) and, thus, Quest 1®, and Quest 3® have a reduced potential to contribute to a tobacco related disease (i.e., Quest 1® and Quest 3® are reduced risk tobacco products). The following section describes several epidemiological approaches to determine the potential of a tobacco or a tobacco product to contribute to a tobacco related disease.

Epidemiological Determinations

In still more embodiments, cells of the mouth, oral cavity, trachea, or lung (e.g., NHBE cells) from a plurality of individuals, preferably the same cell type, are independently contacted with a tobacco composition (e.g., CS) in an amount and for a time sufficient to induce damage of cellular genetic material or modulate cell homeostasis. The fact that CS, as well as various constituents of CS, can cause disruptions to the cell allows one to develop a set of relevant biomarkers that are useful for monitoring exposure to tobacco toxins, detecting pre-malignant disease, improving diagnosis and prognosis of current disease, developing new treatment options, and testing risk reduction strategies for current and former smokers. Accordingly, also provided herein are methods of detecting pre-malignant disease, improving diagnosis and prognosis of current disease, developing new treatment options, and testing risk reduction strategies for current and former smokers by determining the amount of induction of damage of cellular genetic material or modulation of cell homeostasis to the cells of a smoker or other tobacco consumer or a subject exposed to a tobacco composition. The cells of different individuals can respond differently to tobacco compositions and thereby have different levels of risk of developing a tobacco-related disease. The methods provided herein for determining the amount of induction of damage of cellular genetic material or modulation of cell homeostasis to cells contacted with a tobacco composition can be used to assess a subject's level of risk of developing a tobacco-related disease. Such methods can be generally performed in accordance with the methods provided herein, where the cells of the subject can be first contacted with smoke from the tobacco product in vivo (e.g., by the subject smoking a cigarette or side-stream smoke exposure), and then the cells can be harvested using known methods (e.g., lung lavage or cheek swab); alternatively, the cells of a subject can be first harvested and optionally cultured, and then contacted with smoke from the tobacco product in accordance with the methods provided herein.

For example, primary cultures of lung cells, bronchial cells, cells of the mouth, pharynx, larynx, and tongue can be generated from an individual to be tested and these cells are be contacted with a tobacco composition (e.g., CS from a tobacco product) so as to elucidate the individuals proclivity to acquire a tobacco related disease. Certain patterns of amount of induction of damage of cellular genetic material or modulation of cell homeostasis to tobacco compositions can be associated with individuals that do not develop a tobacco related disease and a different pattern of amount of induction of damage of cellular genetic material or modulation of cell homeostasis can be associated with individuals that have developed a tobacco-related disease. Analysis of the amount of induction of damage of cellular genetic material or modulation of cell homeostasis of many of such individuals allows the development of databases that provide an expected type and amount of induction of damage of cellular genetic material or modulation of cell homeostasis that is associated or not associated with a tobacco-related disease. That is, this information can be used to provide a baseline for an individual that is not likely to acquire a tobacco-related disease (e.g., a control level exemplified by non-tobacco users that do not develop a tobacco-related disease) and a baseline for an individual that is likely to acquire a tobacco related disease (e.g., a control level exemplified by tobacco users that have developed a tobacco-related disease). Accordingly, when a subject is analyzed for the predilection to develop a tobacco-related disease, the amount of induction of damage of cellular genetic material or modulation of cell homeostasis can be evaluated and, by comparing the determined values to that in one or both of the databases described above, the analyzed subject can be identified as having a predilection for developing a tobacco-related disease.

Additionally, a comparison of the induction of DNA damage induced by conventional tobacco products and a tobacco product containing a modified tobacco (e.g., a genetically modified tobacco) is contemplated. By one approach, a first set of biological samples (e.g., cells of the oral cavity (cheek or gum swab) or lung cells (lung lavage)) are obtained from individuals that are consumers of conventional tobacco products. These cells are analyzed for double strand DNA breaks using one of the assays described herein. Next, the individuals are provided a tobacco product comprising a modified tobacco to consume exclusively (i.e., in replacement for the conventional product). After a period of time has passed (e.g., 1, 2, 3, or 4 weeks or 1, 2, 3, 4, 5, 6, 7, 8, 9, 10, 11, or 12 months since the conversion from the conventional tobacco product to the tobacco product containing the modified tobacco), a second set of biological samples are taken from the individual and are analyzed for the presence of double strand DNA breaks. It will be determined that fewer double strand breaks will be observed in the second set of biological samples than the first set, which will provide evidence that the tobacco product comprising the modified tobacco has a reduced potential to contribute to a tobacco related disease (i.e., that said tobacco product comprising the modified tobacco is a reduced risk tobacco product).

Further provided herein are kits to be used in practicing the above methods. In various embodiments such kits can comprise an antibody that binds to phosphorylated but not unphosphorylated H2AX, a reference smoke product, a detectably labeled second antibody that specifically binds to the antibody that binds to phosphorylated H2AX, and suitable cells, as provided herein elsewhere.

Also provided herein are cells containing DNA having double-stranded breaks produced by exposure to a tobacco smoke product and, in particular, to genetically altered cells comprising cells prepared by a method comprising the steps of: (a) exposing a first cell population to a tobacco smoke product; (b) identifying cells containing a greater degree of phosphorylated H2AX relative to control cells; and (c) selectively collecting the cells identified in step (b) to form the composition of genetically altered cells. In preferred non-limiting embodiments, the cells having a higher degree of phosphorylated H2AX are identified by an immunofluorescence method and selectively collected, for example by fluorescence activated cell sorting. To permit the identification of genes associated with tobacco-induced diseases, also provided herein are libraries prepared by cloning a plurality of nucleic acid molecules prepared from the cells, the cells prepared according to methods provided for forming cells containing DNA having double-stranded breaks produced by exposure to a tobacco smoke product, herein into a plurality of vector molecules. The following section describes several types of modified tobacco that can be used with the methods described herein.

Modified Tobacco

The methods provided herein can be used to analyze traditional tobacco and/or modified tobacco. For example, the methods provided herein can be used to identify a modified tobacco, to identify a toxic compound in a modified tobacco, and to make a product containing a modified tobacco. Generally, the methods provided herein for analyzing modified tobacco can be performed in accordance with the methods of identifying tobacco and tobacco compounds, and methods of making a tobacco product, as provided elsewhere herein. Modified tobacco that can be used in the methods and tobacco products provided herein include chemically modified tobacco, expanded, extracted, or puffed tobacco, reconstituted tobacco, and genetically modified tobacco.

There is currently a great interest in developing approaches to decrease the levels of noxious, carcinogenic, or addictive substances including tar, nitrosamines, and nicotine in tobacco. Although researchers have developed several approaches to reduce some of these harmful compounds, many conventional techniques result in a product that has poor taste, fragrance, or smoking properties. Some processes, for example, reduce the nicotine content of tobacco by microbial enzymatic degradation, chemical extraction, or high pressure extraction. (See e.g., U.S. Pat. Nos. 4,557,280; 4,561,452; 4,848,373; 4,183,364; and 4,215,706, all of which are hereby expressly incorporated by reference in their entireties). More recently, techniques in genetic engineering and chemically-induced gene suppression have been employed to make reduced nicotine and/or TSNA tobacco. (See e.g., Conkling et al., WO98/56923; U.S. Pat. Nos. 6,586,661; 6,423,520; and U.S. patent application Ser. Nos. 09/963,340; 10/356,076; 09/941,042; 10/363,069; 10/729,121; 10/943,346; Timko et al., WO 00/67558, which designated the United States and was published in English, Nakatani et al., U.S. Pat. Nos. 5,684,241; 5,369,023; 5,260,205; and Roberts et al. 6,700,040, all of which are hereby expressly incorporated by reference in their entireties).

Any of a variety of chemically modified tobaccos can be included in the methods and tobacco products provided herein. For example, the chemical modification can include palladium, or can include an auxin, auxin analog, or jasmonate antagonist (see e.g., U.S. Pat. No. 6,789,548 and U.S. Pat. App. Pub. No. 20050072047, both of which are hereby expressly incorporated by reference in their entirety).

By one approach, a chemically modified tobacco is made as follows. A tobacco is provided and a casing solution is applied thereto. Thereafter, a plurality of metallic or carbonaceous catalytic particles having a mean average or a mode average particle size of less than about 20 microns is applied to the tobacco in a form separate from the casing solution. Next, a nitrate or nitrite source in a form separate from the casing solution and in a form separate from the plurality of metallic or carbonaceous catalytic particles is applied to the tobacco, before, after or simultaneously with applying the plurality of particles but after applying the casing solution, whereby a smoking composition is obtained. In some embodiments of this modified tobacco, a polyaromatic hydrocarbon, azaarene, carbazole, or a phenolic compound is reduced. Using this approach, the Omni® tobacco product was developed.

By another approach, a chemically modified tobacco is made by identifying a tobacco plant in a field for nicotine reduction; and contacting said tobacco plant with a composition selected from the group consisting of an auxin, auxin analog, and jasmonate antagonist from between about 21 days before topping to about 21 days after topping said tobacco plant, whereby the amount of nicotine in said topped tobacco plant contacted with said composition is below that of a topped tobacco plant of the same variety, grown under the same conditions, which has not been contacted with said composition.

In another example, the chemically modified tobacco can be extracted tobacco. By some approaches the chemically modified tobacco is extracted with an organic solvent and other processes use super-critical fluid extraction or carbon dioxide. In another example, the chemical modification can be a biotic modification. Microbes that ingest nitrates and alkaloids can be applied to tobacco so as to obtain a reduced nicotine tobacco; for example such a biotic modification can include bacteria. In another example, the tobacco is processed to remove the presence of a microbe. In another example the chemically modified tobacco can be sterilized, pasteurized, or radiated.

In another example, the chemically modified tobacco can have added thereto an exogenous component of tobacco or analog thereof. Tobacco can be modified to increase or decrease one or more compounds such as proteins, metabolites, nicotine-related compounds and sterols. In some methods provided herein, a tobacco which has been modified to produce lower levels of one or more compounds such as nicotine or a nicotine metabolite, or a sterol, can have exogenously added thereto, one of these lower-level compounds, one or more but not all lower-level compounds, or all lower-level compounds or an analog of the compound(s). Such tobaccos with one or more exogenously added compounds can be compared in accordance with the methods provided herein to the same tobacco to which no exogenous compound has been added, to which a different exogenous compound has been added, or to which a different level of the same exogenous compound has been added. For example, the methods provided herein can be used to compare a tobacco that has been genetically modified to produce reduced nicotine levels with the same tobacco to which exogenous nicotine or a nicotine analog has been added thereto. By performing such methods, the role of the exogenously added compound on cell damage or other response determined according to the methods provided herein (e.g., apoptosis or cell proliferation), can be determined.

In another example, the chemically modified tobacco has had added thereto a compound or composition containing antioxidants. Tobacco at any stage of its processing can have added thereto an antioxidant compound or a composition with antioxidant properties. Any of a variety of known antioxidant compounds can be added to the tobacco, including, but not limited to, lycopene, tocopherol, tocopherol metabolites, ascorbic acid, unsaturated fatty acids, N-acetyl cysteine, and other antioxidants known in the art. A composition with antioxidant properties can include a biological composition or extract that can neutralized oxidants, such as milk or milk proteins, tumeric or tumeric extracts, barley or barley extracts, alfalfa or alfalfa extracts. Other compounds that can be added to the tobacco include thiol-containing proteins, plant extracts, aromatic compounds (e.g., caffeine or pentoxyfyllen, which are contemplated to scavenge carcinogens).

Another form of modified tobacco is expanded or puffed tobacco. Included herein are methods to produce reduced-exposure tobacco products by utilizing the tobacco provided herein, deproteinized tobacco fiber, and freeze dried tobacco in any combination and in conjunction with expanded or puffed tobacco. More than 150 patents have been issued related to tobacco expansion (e.g., U.S. Pat. No. 3,991,772, herein expressly incorporated by reference in its entirety). "Expanded tobacco" is an important part of tobacco filler which is processed through expansion of suitable gases so that the tobacco is "puffed" resulting in reduced density and greater filling capacity. It reduces the weight of tobacco used in cigarettes. Advantageously, expanded tobacco reduces tar, nicotine and carbon monoxide deliveries and finds use, for example, in making low tar, low nicotine, and low carbon monoxide delivery cigarettes. Expanded tobacco is particularly useful in making low-tar delivery cigarettes. Carlton® cigarettes, which have had claims of being the lowest tar and nicotine delivery cigarette, are reportedly made with a very large percentage of expanded tobacco. However, use of expanded tobacco also results in reduced nicotine delivery, which can result in compensation.

Any method for expansion of tobacco known in the art can be used in the methods provided herein. The most common method used today incorporates liquid carbon dioxide (U.S. Pat. Nos. 4,340,073 and 4,336,814, herein expressly incorporated by reference in its entirety). Liquid propane has also been used for making commercial cigarettes, predominantly in Europe (U.S. Pat. No. 4,531,529, herein expressly incorporated by reference in its entirety). Liquid propane offers advantages over carbon dioxide since higher 3Q degrees of expansion are possible, in the range of 200%. Under pressure, the liquid carbon dioxide (or liquid propane) permeates the tobacco cell structure. When the tobacco is rapidly heated the carbon dioxide (or liquid propane) expands the cell back to its pre-cured size.

Another form of modified tobacco is reconstituted tobacco. Included herein are methods to produce reduced-exposure tobacco products by utilizing the tobacco provided herein, deproteinized tobacco fiber, and freeze dried tobacco in any combination and in conjunction with reconstituted tobacco. "Reconstituted tobacco" ("recon") is an important part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

The process to produce sheets of reconstituted tobacco ("recon") began during the 1950s. U.S. patents that describe such processes include: U.S. Pat. Nos. 3,499,454, 4,182,349 4,962,774, and 6,761,175, herein expressly incorporated by reference in its entirety. Recon is traditionally produced from tobacco stems and/or smaller leaf particles in a process that closely resembles a typical paper making process. The tar and nicotine yields of reconstituted tobacco are lower than those from equivalent quantities of whole tobacco leaf. This process entails processing the various tobacco portions that are to be made into Recon. After the Recon sheets are produced they are cut into a size and shape that resembles cut rag tobacco made from whole leaf tobacco. This cut recon then gets mixed with cut-rag tobacco and is ready for cigarette making.

Cigarettes can be manufactured with all recon, no recon, or any combination thereof. Most major brands have at least 10% of Recon in the Filler.

In another embodiment add nicotine can be added, or nicotine salts, to produce recon, which is made from reduced-nicotine transgenic tobacco or any non-tobacco plant material including but not limited to herbal blends so that when such reconstituted sheet is burned it yields substantially less tobacco-specific nitrosamines and other carcinogens produced from conventional cigarettes, yet satisfactory amounts are nicotine are present.

Processes of removing proteins from tobacco, thereby creating "deproteinized tobacco fiber" are known in the art, as exemplified in U.S. Pat. Nos. 4,289,147 and 4,347,324, herein expressly incorporated by reference in its entirety. Tobacco fiber is a major byproduct after removing protein. The fibrous remains from deproteinized tobacco can be included in any percentage as an ingredient of reconstituted tobacco. Cigarettes made from deproteinized tobacco have a different taste than conventional cigarettes. However, appropriate amounts of additives, including flavorings and nicotine, can be added to help alleviate this taste deficiency.

Cigarettes containing deproteinized tobacco have a significant advantage over conventional cigarettes since they produce reduced levels of carcinogens and harmful combustion products. "A 71% reduction in protein content of a flue-cured tobacco sheet resulted in an 81% reduction in the TA98 Ames mutagenicity" of the pyrolytic condensate" (Clapp, W. L., et al., "Reduction in Ames *Salmonella* mutagenicity of cigarette mainstream smoke condensate by tobacco protein removal", Mutation Research, 446, pg 167-174, 1999). Previous research in this area had determined that tobacco leaf protein might be the principal precursor of mutagens in TSC (Matsumoto, et al., "Mutagenicities of the pyrolysis of peptides and proteins", Mutation Research, 56, pg 281-288, 1978).

Extracting tobacco fiber from genetically modified reduced-nicotine tobacco effectively eliminates virtually all carcinogenic TSNAs such tobacco, since nitrosamines require relatively high concentrations of nicotine and other alkaloids to form at detectable levels.

Therefore, it can be advantageous to utilize reduced-nicotine tobacco in reduced-exposure cigarettes or other tobacco products to further reduce nitrosamines. Nicotine can be either left out or introduced later in the process, which can also be in the form of nicotine salts.

PAHs are formed from high temperature pyrolysis of amino acids, sugars, paraffins, terpenes, phytosterols, celluloses and other components of tobacco. Most of these components are greatly reduced in tobacco fiber, effectively reducing formation of PAHs. Catechols and phenols, recognized carcinogenic co-factors in CS, would also be reduced since low levels of soluble sugar are present in tobacco fiber.

Harmful gas phase compounds such as hydrogen cyanide, nitrogen oxides, and carbon monoxide are also reduced when cigarette containing only tobacco fiber is smoked compared to cigarettes made with whole-leaf tobacco. Hydrogen cyanide is formed from burning proteins and chlorophyll. Nitrogen oxides are formed from burning soluble protein, chlorophyll, nitrates, and alkaloids. These components would not be present in significant amounts in deproteinized tobacco. Tobacco fiber has approximately 85 percent less starches and cellulosic material thus reducing the major pyrolytic precursors of carbon monoxide.

In another embodiment, methods are provided to produce reconstituted tobacco that includes extracted tobacco fiber derived from conventional tobacco, reduced-nicotine transgenic tobacco, or increased-nicotine transgenic tobacco.

If the tobacco curing process is circumvented, virtually no TSNAs will be present in traditional tobacco products such as cigarettes, cigar filler or wrapper, roll-your-own tobacco for cigarettes, pipe tobacco, chewing tobacco, snuff, reconstituted tobacco and other preparations made with freeze-dried tobacco would contain virtually no TSNAs since traditional curing processes are eliminated.

In another embodiment TSNAs can be virtually eliminated through processing freshly harvested tobacco using lyophilization. This is accomplished by processing freshly harvested tobacco through freeze-drying units located near tobacco farms. Tobacco processed in this manner can be grown in a traditional fashion with spacing of plants or in a biomass setting. In addition to the economic advantages of eliminating the costs associated with the curing process, the tobacco can now be grown in a biomass fashion that can create hundreds of thousands of pounds of fresh tobacco per acre.

By growing tobacco in a biomass setting and immediately freeze drying the fresh tobacco for cigarettes, roll-your-own-tobacco, pipe tobacco, cigar filler or wrapper, chewing tobacco, snuff, and other versions of smokeless tobacco, labor is reduced not only by eliminating the transplant of each plant from greenhouse to the field but also by eliminating traditional harvesting and curing of the tobacco. Also, farmland needed for this purpose is greatly reduced. The yield of tobacco from one acre of tobacco grown in biomass is equivalent to approximately 100 acres of tobacco grown in a traditional manner.

"Tobacco biomass" is achieved by direct sowing an acre of land with copious quantities of tobacco seed within a few inches of each other in the field. Unlike tobacco planted with traditional spacing, individual plants can no longer be differentiated when tobacco is planted in a biomass fashion. An acre of tobacco biomass has the appearance of a continuous, dense, green carpet. U.S. Pub. Pat. App. No. 20020197688, herein expressly incorporated by reference in its entirety, describes such methods.

Lyophilization removes most of the water (−80%) from the weight of fresh harvested tobacco biomass. The result is Freeze Dried Tobacco ("FDT"). FDT is easily pulverized into fine particles suitable for processing into reconstituted tobacco sheet (recon). This recon can be cut and made into any type of tobacco product such as filler for cigarettes, roll-your-own-tobacco, pipe tobacco, cigar filler or wrapper, chewing tobacco, snuff, and other forms of smokeless tobacco. Flavorings and additives, including sugars, can be incorporated into the recon process.

Such recon can be made from 100 percent FDT or in any proportion that consumers prefer. The lyophilization process can have adverse affects on the taste of such tobacco products. Therefore, FDT can even be mixed in any percentage with traditional pulverized, cured tobacco so that the mixture can be made into reconstituted tobacco. Alternatively, FDT can be mixed in any percentages with any forms of traditional tobacco conducive for manufacturing cigarettes, roll-your-own tobacco, pipe tobacco, and cigar filler or wrapper, chewing tobacco, snuff and other versions of smokeless tobacco in order to satisfy the tastes of the mass market.

In another embodiment genetically modified reduced-nicotine tobacco can be used for reducing TSNAs as described above, thereby creating an additional benefit of such cigarettes, roll-your-own-tobacco, pipe tobacco, cigar filler or wrapper, chewing tobacco, snuff and other versions of smokeless tobacco being non-addictive and without any nitrosamines.

In another embodiment, nicotine can be added, in amounts that deliver the desired physiological response, back to the FDT for uses in cigarettes, cigar filler or wrapper, roll-your-own tobacco for cigarettes, pipe tobacco, chewing tobacco, snuff, and other versions of smokeless tobacco so that they will contain virtually no TSNAs. Cigarettes produced from tobacco fiber obtained from green leaf cured tobacco.

In another embodiment, *Nicotiana rustica* and/or increased-nicotine transgenic *Nicotiana tabacum* are freeze dried after harvest and are incorporated into recon. The benefits are that the high alkaloid content is preserved for low TNR cigarettes and that the tobacco curing step is saved. Also, the associated increase in TSNAs with high alkaloid tobaccos will not materialize. Preferred tobaccos for use with the methods described herein include genetically modified tobaccos as described in the following sections.

Genetically Modified Tobacco

In this application, several approaches to create genetically modified tobacco having a reduced amount of a harmful compound are described. Many embodiments concern nucleic acid constructs that inhibit the expression of a gene, which regulates production of a compound that is associated with a tobacco-related disease. Since these nucleic acid constructs efficiently reduce the presence of a compound that contributes to a tobacco-related disease, the genetically modified tobacco, prepared as described herein, can be used to create a tobacco product, such as a cigarette, which has a reduced potential to contribute to a tobacco-related disease. That is, aspects of the invention concern "reduced risk" tobacco products made from "reduced risk" transgenic tobacco created using the nucleic acid constructs described herein.

More specifically, aspects of the invention concern nucleic acid constructs that inhibit the expression of a number of genes involved in the synthesis and regulation of the production of nicotine, nornicotine, and/or sterols in tobacco. Alkaloids such as nicotine and nornicotine are precursors for a number of harmful compounds that contribute to tobacco-related disease (e.g., the tobacco specific nitrosamines (TSNAs): N'-nitrosonornicotine (NNN), N'-nitrosoanatabine (NAT), N'-nitrosoanabasine (NAB), 4-(N-nitrosomethylamino)-1-(3-pyridyl)-1-butanone (NNK), 4-(N-nitrosomethylamino)-4-(3-pyridyl)-1-butanal (NA)-4-N-nitrosomethylamino)-1-(3-pyridyl)-1-butanol (NNAL), 4-N-nitrosomethylamino)-4-(3-pyridyl)-1-butanol (iso-NNAL) and/or 4-(N-nitrosomethylamino)-4-(3-pyridyl)-butanoic acid (iso-NNAC) and acrolein). Sterols are precursors for a number of harmful compounds, which are generated by pyrolysis of tobacco, that also contribute to tobacco-related disease (e.g., polyaromatic hydrocarbons (PAHs), such as benz[a]pyrene (BAP), heterocyclic hydrocarbons, terpenes, paraffins, aromatic amines, and aldehydes).

Because the presence of these harmful compounds in tobacco contributes to tobacco-related disease, a transgenic or genetically modified tobacco that comprises a reduced amount of any one of these compounds, as compared to a reference tobacco (e.g., the industry standard reference tobacco IM16 (Philip Morris® USA) or the full-flavor low tar reference cigarette 2R4F or the ultra low tar cigarette 1R5F, which are Kentucky reference cigarettes that can be obtained from the Tobacco and Health Institute at the University of Kentucky), a conventional tobacco (e.g., a commercially available tobacco of the same class (e.g., "full-flavor" or "light" or "ultra-light")) or a non-transgenic tobacco (e.g., a tobacco of the same variety, such as Burley, Virginia Flue, or Oriental, or strain, such as LA Burley 21, K326, Tn90, Djebel174, as the transgenic tobacco prior to genetic modification) has a reduced potential to contribute to a tobacco-related disease. This "reduced risk" transgenic tobacco can then be processed, optionally, sterilized or otherwise made substantially-free of microbes, and said tobacco can be incorporated into tobacco products, preferably, cigarettes, optionally, by an aseptic approach so as to not introduce microbes (e.g., bacteria, mold, yeast, and fungi) into the products. Tobacco products comprising said transgenic tobacco can then be packaged, optionally, by an aseptic approach in air-tight or microbe-free packaging so as to not introduce microbes into the products.

In this manner, the conversion of alkaloid to TSNA, which results from microbial growth on the tobacco when microbes are introduced during processing, packaging, and storage, is significantly reduced. By using the embodied tobacco preparative methods, which may include several aseptic processing, manufacturing, and packaging procedures, one can maintain an amount of total TSNA (e.g., the collective content of NNN, NAT, NAB, and NNK) in a commercially available tobacco product of less than or equal to 0.5 μg/g (e.g., 0.05 μg/g, 0.1 μg, 0.2 μg/g, 0.3 μg/g, 0.4 μg/g, or 0.5 μg/g) for a period of at least 1 week, 1 month, or 1-5 years after packaging or incorporation of the tobacco into a tobacco product (e.g., at least 1-30 days, 30-90 days, 90-180 days, 180-270 days, 270 days-365 days, 1 year-1.5 years, 1.5-2.0 years, 2.0 years-2.5 years, 2.5 years-3.0 years, 3.0 years-4 years, and 4.0 years-5.0 years).

In some embodiments, a transgenic tobacco comprising a reduced amount of alkaloid (e.g., a reduced amount of nicotine, nornicotine, and/or TSNAs) and one or more of the isolated nucleic acids, nucleic acid cassettes, or nucleic acid constructs described herein is contacted with an exogenous nicotine so as to raise the level of nicotine in the contacted transgenic tobacco in a controlled fashion. By this approach, nicotine levels in transgenic tobacco that comprises a reduced amount of endogenous nicotine (i.e., nicotine that is produced by the transgenic plant from which the transgenic tobacco is obtained) can be selectively raised to levels that are commensurate with conventional full-flavor cigarettes, light cigarettes, or ultra-light cigarettes. (See e.g., WO 2005/018307, which designates the United States and was published in English, herein expressly incorporated by reference in its entirety). For example, transgenic tobacco comprising a reduced amount of endogenous nicotine and/or TSNAs can be contacted with an amount of exogenous nicotine that is at least, equal to, or more than 0.3 mg/g-20.0 mg/g (nicotine/gram of tobacco). That is, transgenic tobacco comprising a reduced amount of endogenous nicotine and/or TSNAs can be contacted with an amount of exogenous nicotine that is at least, equal to, or more than 0.3 mg/g, 0.4 mg/g, 0.5 mg/g, 0.6 mg/g, 0.7 mg/g, 0.8 mg/g, 0.9 mg/g, 1.0 mg/g, 1.1 mg/g, 1.2 mg/g, 1.3 mg/g, 1.4 mg/g, 1.5 mg/g, 1.6 mg/g, 1.7 mg/g, 1.8 mg/g, 1.9 mg/g, 2.0 mg/g, 2.1 mg/g, 2.2 mg/g, 2.3 mg/g, 2.4 mg/g, 2.5 mg/g, 2.6 mg/g, 2.7 mg/g, 2.8 mg/g, 2.9 mg/g, 3.0 mg/g, 3.1 mg/g, 3.2 mg/g, 3.3 mg/g, 3.4 mg/g, 3.5 mg/g, 3.6 mg/g, 3.7 mg/g, 3.8 mg/g, 3.9 mg/g, 4.0 mg/g, 4.1 mg/g, 4.2 mg/g, 4.3 mg/g, 4.4 mg/g, 4.5 mg/g, 4.6 mg/g, 4.7 mg/g, 4.8 mg/g, 4.9 mg/g, 5.0 mg/g, 5.1 mg/g, 5.2 mg/g, 5.3 mg/g, 5.4 mg/g, 5.5 mg/g, 5.6 mg/g, 5.7 mg/g, 5.8 mg/g, 5.9 mg/g, 6.0 mg/g, 6.1 mg/g, 6.2 mg/g, 6.3 mg/g, 6.4 mg/g, 6.5 mg/g, 6.6 mg/g, 6.7 mg/g, 6.8 mg/g, 6.9 mg/g, 7.0 mg/g, 7.1 mg/g, 7.2 mg/g, 7.3 mg/g, 7.4 mg/g, 7.5 mg/g, 7.6 mg/g, 7.7 mg/g, 7.8 mg/g, 7.9 mg/g, 8.0 mg/g, 8.1 mg/g, 8.2 mg/g, 8.3 mg/g, 8.4 mg/g, 8.5 mg/g, 8.6 mg/g, 8.7 mg/g, 8.8 mg/g, 8.9 mg/g, 9.0 mg/g, 9.1 mg/g, 9.2 mg/g, 9.3 mg/g, 9.4 mg/g, 9.5 mg/g, 9.6 mg/g, 9.7 mg/g, 9.8 mg/g, 9.9 mg/g, 10.0 mg/g, 10.1 mg/g, 10.2 mg/g, 10.3 mg/g, 10.4 mg/g, 10.5 mg/g, 10.6 mg/g, 10.7 mg/g, 10.8 mg/g, 10.9 mg/g, 11.0 mg/g, 11.1 mg/g, 11.2 mg/g, 11.3 mg/g, 11.4 mg/g, 11.5 mg/g, 11.6 mg/g, 11.7 mg/g, 11.8 mg/g, 11.9 mg/g, 12.0 mg/g, 12.1 mg/g, 12.2 mg/g, 12.3 mg/g, 12.4 mg/g, 12.5 mg/g, 12.6 mg/g, 12.7 mg/g, 12.8 mg/g, 12.9 mg/g, 13.0 mg/g, 13.1 mg/g, 13.2 mg/g, 13.3 mg/g, 13.4 mg/g, 13.5 mg/g, 13.6 mg/g, 13.7 mg/g, 13.8 mg/g, 13.9 mg/g, 14.0 mg/g, 14.1 mg/g, 14.2 mg/g, 14.3 mg/g, 14.4 mg/g, 14.5 mg/g, 14.6 mg/g, 14.7 mg/g, 14.8 mg/g, 14.9 mg/g, 15.0 mg/g, 15.1 mg/g, 15.2 mg/g, 15.3 mg/g, 15.4 mg/g, 15.5 mg/g, 15.6 mg/g, 15.7 mg/g, 15.8 mg/g, 15.9 mg/g, 16.0 mg/g, 16.1 mg/g, 16.2 mg/g, 16.3 mg/g, 16.4 mg/g, 16.5 mg/g, 16.6 mg/g, 16.7 mg/g, 16.8 mg/g, 16.9 mg/g, 17.0 mg/g, 17.1 mg/g, 17.2 mg/g, 17.3 mg/g, 17.4 mg/g, 17.5 mg/g, 17.6 mg/g, 17.7 mg/g, 17.8 mg/g, 17.9 mg/g, 18.0 mg/g, 18.1 mg/g, 18.2 mg/g, 18.3 mg/g, 18.4 mg/g, 18.5 mg/g, 18.6 mg/g, 18.7 mg/g, 18.8 mg/g, 18.9 mg/g, 19.0 mg/g, 19.1 mg/g, 19.2 mg/g, 19.3 mg/g, 19.4 mg/g, 19.5 mg/g, 19.6 mg/g, 19.7 mg/g, 19.8 mg/g, 19.9 mg/g, and 20.0 mg/g (nicotine/gram tobacco)). In some of the aforementioned embodiments, said transgenic tobacco comprises one or more of the isolated nucleic acids, isolated nucleic acid cassettes, or isolated nucleic acid constructs, described herein.

Nicotine-containing fractions, nicotine, or nicotine salts of organic acids are added to the reduced-nicotine transgenic tobacco by contacting said tobacco (e.g., spraying or additive application), with or without propylene glycol, solvent, flavoring, or water at any stage of the harvesting, curing, fermenting, aging, reconstituting, expanding, or otherwise processing of the tobacco, preferably at a stage that is post-cure, when flavorings and additives are provided. By "exogenous nicotine" is meant nicotine, nicotine derivatives, nicotine analogs, nicotine-containing fractions (e.g., extracts of *Nicotiana*), and nicotine salts of organic acids obtained from a source outside of the transgenic tobacco to which the exogenous nicotine is applied. In this manner, a transgenic tobacco with virtually any amount of nicotine can be obtained.

In some embodiments, the exogenous nicotine (e.g., commercially available nicotine salts, liquid, or a nicotine-containing extract prepared from a *Nicotiana* plant or portion thereof) is contacted with a reduced-alkaloid transgenic tobacco (e.g., a transgenic tobacco comprising a reduced amount of nicotine and/or TSNA as prepared as described herein) after the transgenic tobacco has been made substantially free of microbes (e.g., bacteria, yeast, mold, or fungi). The reduced alkaloid transgenic tobacco can be made substantially-free of microbes (e.g., an aseptic preparation) by employing sterilization, heat treatment, pasteurization, steam treatment, gas treatment, and radiation (e.g., gamma, microwave, and ultraviolet). The term "substantially-free of microbes" in some contexts can mean an amount of bacteria, mold, fungi, or yeast that is reduced to the point that the conversion of nicotine or total alkaloid to TSNA is negligible (e.g., the resultant concentration of total TSNA (e.g., NNN, NNK, NAT, and NAB in a tobacco or tobacco product is equal to or below 0.5 μg/g (e.g., 0.05 μg/g, 0.1 μg, 0.2 μg/g, 0.3 μg/g, 0.4 μg/g, or 0.5 μg/g) after prolonged storage (e.g., at least 1-30 days, 30-90 days, 90-180 days, 180-270 days, 270 days-365 days, 1 year-1.5 years, 1.5-2.0 years, 2.0 years-2.5 years, 2.5 years-3.0 years, 3.0 years-4 years, and 4.0 years-5.0 years)). The term "substantially-free of microbes" also includes the term "substantially-free of bacteria," which means in some contexts that the tobacco or tobacco product is substantially-free of *Arthrobacter, Proteus*, nicotine oxidizing bacteria, such as P-34*, Psuedomonas, Xantomonas*, or *Zoogloea* strains of bacteria. For example, a tobacco or tobacco product is substantially-free of bacteria or a particular strain of bacteria when said tobacco or tobacco product has less than or equal to 20% of the bacteria or a specific strain of bacteria normally present on the tobacco or tobacco product in the absence of application of a technique to rid the tobacco or tobacco product of bacteria (e.g., less than or equal to 1%, 2%, 3%, 4% 5%, 6%, 7%, 8%, 9%, 10%, 11%, 12%, 13%, 14%, 15%, 16%, 17%, 18%, 19%, or 20%). With respect to transgenic tobacco described herein, the term "substantially-free of bacteria" can refer to tobacco or a tobacco product containing said transgenic tobacco that has less than or equal to 20% of the bacteria normally present on the strain of tobacco prior to genetic modification and/or application of a technique to rid the tobacco or tobacco product of bacteria (e.g., less than or equal to 1%, 2%, 3%, 4% 5%, 6%, 7%, 8%, 9%, 10%, 11%, 12%, 13%, 14%, 15%, 16%, 17%, 18%, 19%, or 20%).

Once the exogenous nicotine has been contacted with the microbe-free transgenic tobacco, it is preferably processed and packaged aseptically and the tobacco product is maintained in an airtight container so as to not re-introduce microbes that convert the exogenous nicotine to TSNAs. By using the aseptic processing, manufacturing, and packaging procedures, described herein, one can maintain an amount of total TSNA (e.g., the collective content of NNN, NAT, NAB, and NNK) in a commercially available tobacco product, which comprises exogenous nicotine, of less than or equal to 0.5 μg/g (e.g., 0.05 μg/g, 0.1 μg, 0.2 μg/g, 0.3 μg/g, 0.4 μg/g, or 0.5 μg/g) for at least 1 week, 1 month, or 1-5 years after packaging (e.g., at least 1-30 days, 30-90 days, 90-180 days, 180-270 days, 270 days-365 days, 1 year-1.5 years, 1.5-2.0 years, 2.0 years-2.5 years, 2.5 years-3.0 years, 3.0 years-4 years, and 4.0 years-5.0 years). In some embodiments, the exogenous nicotine is contacted with a transgenic tobacco comprising one of the nucleic acid constructs described herein and a collective content of NNN, NAT, NAB, and NNN is less than or equal to 0.5 μg/g (e.g., 0.05 μg/g, 0.1 μg, 0.2 μg/g, 0.3 μg/g, 0.4 μg/g, or 0.5 μg/g). In some embodiments, a collective content of NNN, NAT, NAB, and NNN of less than or equal to 0.5 μg/g (e.g., 0.05 μg/g, 0.1 μg, 0.2 μg/g, 0.3 μg/g, 0.4 μg/g, or 0.5 μg/g) in a tobacco product containing said transgenic tobacco can be maintained for at least at least 1 week, 1 month, or 1-5 years after packaging (e.g., at least 1-30 days, 30-90 days, 90-180 days, 180-270 days, 270 days-365 days, 1 year-1.5 years, 1.5-2.0 years, 2.0 years-2.5 years, 2.5 years-3.0 years, 3.0 years-4 years, and 4.0 years-5.0 years). Accordingly, several embodiments of the invention address the problem of gradually increasing TSNA levels in alkaloid-containing tobacco products by employing processing, storage, and packaging methods that reduce the amount of microbial flora on the tobacco, limit the re-introduction of microbes during processing and maintain a reduced amount of microbes (e.g., bacteria) once the product is packaged, stored, and sold. Tobacco and tobacco products comprising transgenic tobacco having a reduced amount of endogenous nicotine and an amount of exogenous nicotine can be analyzed by various methods to confirm that said tobacco and said tobacco products are "reduced risk" or have less of a potential to contribute to a tobacco-related disease, as compared to the parent strain of tobacco having conventional amounts of endogenous nicotine or a reference tobacco, as described supra.

By using the constructs described herein, the amount of harmful compounds in tobacco, such as alkaloids and sterols, can be removed and a tobacco product comprising this genetically modified tobacco, with or without exogenous nicotine, will have a reduced potential to contribute to a tobacco-related disease. That is, genetically modified tobacco comprising the constructs described herein can be used to manufacture "reduced risk" tobacco products (e.g., a tobacco product comprising a reduced endogenous nicotine, reduced endogenous nornicotine, and/or reduced sterol tobacco), such as a cigarette, which may have exogenous nicotine incorporated therein.

Tobacco products that comprise a tobacco comprising one of the nucleic acid constructs described herein include "full-flavor," "lights," and "ultra light" cigarettes with both reduced levels of alkaloids and levels of alkaloids commensurate with a level of alkaloid common to the particular class of cigarette (i.e., a conventional amount of nicotine). The term "tobacco products" includes, but is not limited to, smoking materials (e.g., cigarettes, cigars, pipe tobacco), snuff, chewing tobacco, gum, and lozenges.

The term "reduced risk tobacco product" or "reduced risk tobacco" includes, but is not limited to, a tobacco product or tobacco comprising a genetically modified tobacco that has a reduced amount of a compound that contributes to a tobacco-related disease, such as nicotine, nornicotine, a sterol, or the metabolites thereof including, but not limited to, a TSNA, an acrolein, an aldehyde, or harmful compounds generated upon pyrolysis of tobacco, including but not limited to, PAH, BAP, a heterocyclic hydrocarbon, or an aromatic amine, as compared to the amount of these compounds in or generated by a reference tobacco or reference tobacco product (e.g., IM16, 1R5F, or 2R4F), a commercially available tobacco product of the same class (e.g., full-flavor, lights, and ultra-lights), or, preferably, a tobacco of the same variety (e.g., Burley, Virginia Flue, or Oriental) or strain (e.g., LA Burley 21, K326, Tn90, Djebel174) as the transgenic tobacco prior to genetic modification). In other contexts, a reduced risk tobacco or a reduced risk tobacco product refers to a transgenic tobacco or a tobacco product comprising transgenic tobacco that up-regulates fewer genes associated with a tobacco-related disease as compared to a reference tobacco or reference tobacco product (e.g., IM16, 1R5F, or 2R4F), a commercially available tobacco product of the same class (e.g., full-flavor, lights, and ultra-lights), or, preferably, a tobacco of the same variety (e.g., Burley, Virginia Flue, or Oriental) or strain (e.g., LA Burley 21, K326, Tn90, Djebel174) as the transgenic tobacco prior to genetic modification).

In some embodiments, it is desirable to confirm that the transgenic tobacco comprising the reduced amount of a harmful compound, in fact, has a reduced potential to contribute to a tobacco-related disease or that said transgenic tobacco is a reduced risk tobacco or tobacco product. Accordingly, this disclosure provides several assays that can be used to make this determination. Many of these assays have confirmed that embodiments of the transgenic tobaccos described herein have a reduced potential to contribute to a tobacco-related disease (i.e., that a reduced risk tobacco has been obtained).

That is, aspects of the invention concern methods to identify a tobacco or tobacco product that has a reduced potential to contribute to a tobacco-related disease (i.e., a reduced risk tobacco or tobacco product). By one approach, smoke or a smoke condensate from a transgenic tobacco comprising a reduced amount of a compound (e.g., nicotine, nornicotine, TSNA, or a sterol) is contacted with a first population of cells and the modulation (e.g., up-regulation or down-regulation) of the expression of a gene or a plurality of genes is compared with the expression of the same gene or plurality of genes in a second population of cells that are contacted with smoke or a smoke condensate from a reference tobacco or reference tobacco product (e.g., IM16, 1R5F, or 2R4F), a commercially available tobacco product of the same class (e.g., full-flavor, lights, and ultra-lights), or, preferably, a tobacco of the same variety (e.g., Burley, Virginia Flue, or Oriental) or strain (e.g., LA Burley 21, K326, Tn90, Djebel174) as the transgenic tobacco prior to genetic modification). A determination that said transgenic tobacco has a reduced potential to contribute to a tobacco-related disease (e.g., a determination that said transgenic tobacco is a reduced risk tobacco) is confirmed by the identification of a reduction in the expression of a gene that is associated with a tobacco-related disease or an increase in the expression of a gene that is associated with cell damage repair (e.g., repair of oxidative damage).

In still other contexts, a reduced risk tobacco or a reduced risk tobacco product refers to a transgenic tobacco or a tobacco product comprising transgenic tobacco that induces a down-regulation of fewer genes associated with the repair of tobacco-induced damage (e.g., oxidative damage), as compared to a reference tobacco or reference tobacco product (e.g., IM16, 1R5F, or 2R4F), a commercially available tobacco product of the same class (e.g., full-flavor, lights, and ultra-lights), or, preferably, a tobacco of the same variety (e.g., Burley, Virginia Flue, or Oriental) or strain (e.g., LA Burley 21, K326, Tn90, Djebel174) as the transgenic tobacco prior to genetic modification). In still more contexts, a reduced risk tobacco or a reduced risk tobacco product refers to a transgenic tobacco or a tobacco product comprising transgenic tobacco that induces a reduced level of inhibition of cell proliferation, as compared to a reference tobacco or reference tobacco product (e.g., IM16, 1R5F, or 2R4F), a commercially available tobacco product of the same class (e.g., full-flavor, lights, and ultra-lights), or, preferably, a tobacco of the same variety (e.g., Burley, Virginia Flue, or Oriental) or strain (e.g., LA Burley 21, K326, Tn90, Djebel174) as the transgenic tobacco prior to genetic modification). In some embodiments, a reduced risk tobacco product can comprise exogenous nicotine (e.g., transgenic tobacco comprising a reduced amount of endogenous nicotine and TSNAs, which has been contacted with exogenous nicotine and maintained under conditions that inhibit proliferation of microbes, such as bacteria).

Several assays are provided, which can be used to confirm that the transgenic tobacco created as described herein with or without exogenous nicotine has in fact, a lower potential to contribute to a tobacco-related disease (i.e., a reduced risk tobacco or tobacco product, as compared to conventional tobacco products, a reference tobacco product, or a tobacco product comprising the same). Some of the embodiments described herein compare the effects/damage (e.g., the extent of DNA damage, inhibition of apoptosis, or inhibition of cell proliferation) induced by smoke or smoke condensate generated from a transgenic tobacco or a tobacco product containing transgenic tobacco to a reference tobacco or reference tobacco product (e.g., IM16, 1R5F, or 2R4F), a commercially available tobacco product of the same class (e.g., full-flavor, lights, and ultra-lights), or, preferably, a tobacco of the same variety (e.g., Burley, Virginia Flue, or Oriental) or strain (e.g., LA Burley 21, K326, Tn90, Djebel174) without the genetic modification. In some embodiments, the transgenic tobacco or tobacco product comprising said transgenic tobacco also has incorporated therein an amount of exogenous nicotine and this product is compared to the parental strain of tobacco (i.e., tobacco of the same variety without genetic modification).

It should also be emphasized that the word "reduced," or the phrase "a reduced amount" is intended to refer to an amount of a harmful compound (e.g., total alkaloid, nicotine, nornicotine, a sterol, or the metabolites thereof including, but not limited to, a TSNA, an acrolein, an aldehyde, or compounds generated by pyrolysis including PAH, BAP, a heterocyclic hydrocarbon, or an aromatic amine) in a genetically modified tobacco plant, tobacco, or a tobacco product that is less than the amount of said harmful compound found, or generated preferably, in a tobacco plant, tobacco, or a tobacco product from the same class of tobacco product (e.g., full-flavor, light, ultra-light), same variety of tobacco (e.g. the parental strain of tobacco prior to genetic modification), or in comparison to a reference cigarette (e.g., IM16, 1R5F, or 2R4F), which has not been genetically modified. Thus, in some contexts and embodiments, wild-type tobacco of the same variety that has been grown and processed in the same manner as the genetically modified tobacco is used as a control by which to measure whether a reduction in a harmful compound has been obtained by the inventive methods described herein. In other embodiments, the determination of whether a reduced amount of a harmful compound in a transgenic tobacco or generated by a transgenic tobacco upon pyrolysis has been obtained is made by comparing the amount of a harmful compound in or generated from the transgenic tobacco to a commercially available cigarette and/or a reference cigarette (e.g., IM16, 1R5F, or 2R4F).

Accordingly, aspects of the invention concern genetically modified tobacco and tobacco products containing a tobacco that comprises a genetic modification, which have a reduced amount or are substantially free of a harmful compound including, but not limited to, nicotine, nornicotine, a sterol, an acrolein, an aldehyde, a TSNA selected from the group consisting of N'-nitrosonornicotine (NNN), 4-(N-nitrosomethylamino)-1-(3-pyridyl)-1-butanone (NNK), N'-nitrosoanatabine (NAT), and/or N'-nitrosoanabasine (NAB) or generate a reduced amount of a PAH, a BAP, a heterocyclic hydrocarbon, an aromatic amine upon pyrolysis, wherein this reduced risk genetically modified tobacco is made by lowering the expression of a gene in said tobaccos with one of the constructs described herein. Preferred embodiments include a transgenic tobacco and a tobacco product (e.g., cigarette) that comprises a cured tobacco comprising a genetic modification and a reduced amount of nicotine or total alkaloid (e.g., below a conventional level of nicotine or total alkaloid typical for the strain of plant, preferably, less than or equal to 3,000 ppm, 2000 ppm, 1000 ppm, or 500 ppm), wherein said genetic modification comprises an inhibition of a gene that regulates the production of nicotine and/or nornicotine, such as arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), or A622 using one or more of the constructs described herein.

Preferred embodiments also include a transgenic tobacco and a tobacco product (e.g., cigarette) that comprises a cured tobacco comprising a genetic modification and a reduced amount of a sterol (e.g., below a conventional level of said sterol typical for the strain of plant) wherein said genetic modification comprises an inhibition of a gene that regulates the production of a sterol in tobacco using one or more of the constructs described herein. Related embodiments include a transgenic tobacco and tobacco product made therefrom (e.g., a cigarette) that upon pyrolysis generates a reduced amount of a PAH, BAP, a heterocyclic hydrocarbon, or an aromatic amine, as compared to that generated by a reference tobacco or reference tobacco product (e.g., IM16, 1R5F, or 2R4F), a commercially available tobacco product of the same class (e.g., full-flavor, lights, and ultra-lights), or, preferably, a tobacco of the same variety (e.g., Burley, Virginia Flue, or Oriental) or strain (e.g., LA Burley 21, K326, Tn90, Djebel174) as the transgenic tobacco prior to genetic modification).

Preferred embodiments also include a transgenic tobacco and a tobacco product (e.g., cigarette) that comprises a cured tobacco comprising a genetic modification and a reduced amount of nicotine or total alkaloid and a sterol (e.g., below a conventional level of nicotine, total alkaloid, or sterol typical for the strain of plant) wherein said genetic modification comprises an inhibition of a gene that regulates the production of both nicotine and sterols in tobacco. That is, aspects of the invention concern isolated nucleic acids, isolated nucleic acid cassettes, and isolated nucleic acid constructs that inhibit the expression of a plurality of genes that regulate the production of nicotine and TSNAS, isolated nucleic acids, isolated nucleic acid cassettes, and isolated nucleic acid constructs that inhibit the expression of a plurality of genes that regulate the production of a sterol or sterols and, thus PAHs, and isolated nucleic acids, isolated nucleic acid cassettes, and isolated nucleic acid constructs that inhibit the expression of a plurality of genes that regulate the production of nicotine and TSNAS and sterols and, thus, PAHs (e.g., a double knockout of at least two different genes that regulate the production of at least two different harmful compounds in tobacco).

In some embodiments, the tobacco that is substantially free or comprises a reduced amount of nicotine, nornicotine, TSNAs, sterols, and/or produces a reduced amount of PAHs upon pyrolysis is made by exposing at least one tobacco cell of a selected variety (e.g., Burley, Virginia Flue, or Oriental) to an exogenous nucleic acid construct encoding an interfering RNA comprising an RNA duplex that comprises a first strand having a sequence that is substantially similar or identical to at least a portion of the coding sequence of a target gene and/or target gene product involved in nicotine biosynthesis or sterol biosynthesis, and a second strand that is complementary or substantially complementary to the first strand. In some embodiments, the nucleic acid construct further comprises a nucleotide sequence encoding the interfering RNA operably linked to a promoter operable in a plant cell. The tobacco cell is transformed with the nucleic acid construct, transformed cells are selected and at least one transgenic tobacco plant is regenerated from the transformed cells. The transgenic tobacco plants described herein can contain a reduced amount of anyone of nicotine, nornicotine, TSNAs and/or a sterol as compared to a control tobacco plant of the same variety. In some embodiments, nucleic acid constructs encoding interfering RNAs (RNAi) comprising a first strand having a sequence substantially similar or identical to the entire coding sequence of a target gene and/or target gene product involved in nicotine or sterol biosynthesis, and a second strand that is complementary or substantially complementary to the first strand, are contemplated.

In some embodiments, the gene product involved in nicotine biosynthesis is an enzyme. Such enzymes include, but are not necessarily limited to, putrescene N-methyltransferase (PMTase), N-methylputrescene oxidase, omithine decarboxylase, S-adenosylmethionine synthetase, NADH dehydrogenase, phosphoribosylanthranilate isomerase and quinolate phosphoribosyl transferase (QPTase). In preferred embodiments, the gene product that is inhibited using a construct described herein is QPTase, PMTase, and A622. In some embodiments, the tobacco that is made substantially free of nicotine and/or TSNAs (e.g., less than or equal to 0.5 mg/g nicotine and/or less than or equal to 0.5 μg/g collective content of NNN, NAT, NAB, and NNK) is prepared from a variety of Burley tobacco (e.g., Burley 21), Oriental tobacco (Djebal 174), or Virginia flue (Tn90 or K326) tobacco. It should be understood, however, that most tobacco varieties can be made to have reduced amounts of nicotine and/or TSNAs or can be made substantially free of nicotine and/or TSNAs by using the embodiments described herein. For example, plant cells of the variety Burley 21 are used as the host for the genetic engineering that results in the reduction of nicotine and/or TSNAs so that the resultant transgenic plants are a Burley 21 variety that has a reduced amount of nicotine and/or TSNAs.

Accordingly, some embodiments concern a tobacco that comprises a genetic modification comprising a reduced amount or a reduced level of expression of QPTase, PMTase, or A622, a reduced amount of nicotine or total alkaloid and/or a collective content of TSNA (e.g., NNN, NAT, NAB, or NNK) of less than or equal to 0.5 μg/g (e.g., 0.05 μg/g, 0.1 μg, 0.2 μg/g, 0.3 μg/g, 0.4 μg/g, or 0.5 μg/g). More embodiments concern a tobacco that comprises a reduced amount or a reduced level of expression of A622, a normal or conventional amount of nicotine (e.g., equal to, less than, or greater than 0.9 mg/g, 1.0 mg/g, 1.1 mg/g, 1.2 mg/g, 1.3 mg/g, 1.4 mg/g, 1.5 mg/g, 1.6 mg/g, 1.7 mg/g, 1.8 mg/g, 1.9 mg/g, and 2.0 mg/g), and a reduced amount of nornicotine (e.g., less than or equal to 0.5 μg/g, and/or a reduced amount of NNN (e.g., equal to or less than 0.05 μg/g, 0.1 μg, 0.2 μg/g, 0.3 μg/g, 0.4 μg/g, or 0.5 μg/g). That is, particular lines of transgenic tobacco containing the A622 inhibition cassette described herein were unexpectedly found to have a reduced level of nornicotine but conventional levels of nicotine. This finding is particularly important since nornicotine may be a more important precursor for NNN than nicotine. (See Carmella et al., Carcinogenesis, Vol. 21, No. 4, 839-843, (April 2000), herein expressly incorporated by reference in its entirety). In other transgenic lines, wherein the A622 gene was inhibited using one of the constructs described herein, it was found that both nicotine and nornicotine were effectively reduced (e.g., total alkaloids were less than or equal to 7,000 ppm, 5000 ppm, 3000 ppm, 1000 ppm, or 500 ppm).

Some of the nucleic acid constructs of the present invention employ interfering RNAs (e.g., siRNAs or dsRNAs) that comprise an RNA duplex wherein each RNA portion of the duplex is at least, greater than, or equal to 30, 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 750, 1000, 1500, 2000, 2500, or 5000 consecutive nucleotides complementary or substantially complementary to an mRNA that encodes a gene product or the entire coding sequence of the enzyme or complement thereof of an enzyme that regulates nicotine or sterol biosynthesis. In some embodiments, the RNA duplex comprises a first RNA strand that is complementary to an mRNA that encodes a gene product involved in nicotine or sterol biosynthesis and a second RNA stand that is complementary to said first strand. Some interfering RNAs of the present invention can comprise two separate RNA strands hybridized to each other by hydrogen bonding. Other interfering RNAs comprise a single RNA strand comprising a first and second regions of nucleotide sequence that are complementary to each other. In such embodiments, the first and second regions of nucleotide sequence are separated by a nucleotide sequence (e.g., a “linker”) that permits or, in the case of the FAD2 intron described herein, facilitates formation of a hairpin structure upon hybridization of the first and second regions. This “linker” that permits formation of a hairpin structure is preferably at least, greater than, or equal to 30, 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 800, 900, 1000 or more nucleotides in length. The section below provides more details on nitrosamines and TSNAs.

Nitrosamines and Tobacco-Specific Nitrosamines

The term nitrosamine generally refers to any of a class of organic compounds with the general formula $R_2NNO$ or RNHNO (where R denotes an amine-containing group). Nitrosamines are present in numerous foods and have been found to be carcinogenic in laboratory animals. These compounds are formed by nitrosation reactions of amines such as amino acids and alkaloids with nitrites and/or nitrous oxides. By themselves, nitrosamines are not carcinogenic substances, but in mammals nitrosamines undergo decomposition by enzymatic activation to form alkylating metabolites which appear to react with biopolymers to initiate their tumorogenic effect. Thus, by reducing the amount of nitrosamine intake, one has effectively reduced the carcinogenic potential in humans.

Nitrosamines have been identified in tobacco, tobacco products, and tobacco smoke (TS) by the use of techniques such as gas chromatography-thermal energy analysis (GC-TEA). Some of these nitrosamines have been identified as tobacco-specific nitrosamines (TSNAs). TSNAs are primarily formed by reactions between the two most abundant alkaloids, nicotine and nornicotine, with nitrous oxides (NOx), and they account proportionately for the highest concentration of nitrosamines in both tobacco products and in mainstream smoke. Of the TSNAs identified, and the subset that have been found to be present in CS, the most characterized is N-nitrosamine, 4-(methylnitrosamino)-1-(3-pyridyl)-1-butanone (N-nitrosamine-ketone), or NNK. When injected at relatively high doses, NNK is carcinogenic in rodents. Minimal amounts of TSNAs are found in green tobacco, indicating that TSNA formation may occur during processing steps such as curing, drying, fermentation, burning or storage of tobacco.

TSNA formation is attributed to chemical, enzymatic and bacterial influences during tobacco processing, particularly during curing, fermentation and aging. Nitrosation of nornicotine, anatabine, and anabasine gives the corresponding nitrosamines: N'-nitrosonornicotine (NNN), N'-nitrosoanatabine (NAT) and N'-nitrosoanabasine (NAB). Nitrosation of nicotine in aqueous solution affords a mixture of 4-(N-nitrosomethylamino)-1-(3-pyridyl)-1-butanone (NNK), NNN, and 4-(N-nitrosomethylamino)-4-(3-pyridyl)-1-butanal (NNA). Less commonly encountered TSNAs include NNAL (4-N-nitrosomethylamino)-1-(3-pyridyl)-1-butanol), iso-NNAL (4-N-nitrosomethylamino)-4-(3-pyridyl)-1-butanol, 11) and iso-NNAC (4-(N-nitrosomethylamino)-4-(3-pyridyl)-butanoic acid, 12). See, U.S. Pat. No. 6,135,121, the entire disclosure of which is hereby expressly incorporated by reference in its entirety.

TSNA levels are particularly high in chewing tobaccos and snuff. The partially anaerobic processes that occur during fermentation promote the formation of TSNAs from tobacco alkaloids by promoting increased nitrite levels; in particular, over-fermentation can increase TSNA levels in snuff by its effects on nitrate levels and microbial enzymatic activity. The reduction of the nitrosamine level in snuff in recent years has been achieved by maintaining a better control over the bacterial content in these products.

Since the nitrate level of tobacco is important for nitrosamine formation in cigarette smoke (CS), a significant reduction of nitrosamines in smoke can be achieved by low-nitrate leaf and stem blends. However, these methods may negatively impact the smokability or the taste of the tobacco. The nitrosamine content of mainstream smoke can be reduced by as much as 80% by cellulose acetate filters, and it can be reduced still further by filter ventilation.

Air-cured tobaccos such as burley and dark-fired may have higher levels of TSNAs than certain types of flue-cured bright, burley, or dark tobaccos apparently because the high temperatures associated with flue-curing can kill the microorganisms that transform the alkaloids into TSNAs. In air-cured types, nitrate (N—$NO_3$) is more abundant in the leaf (particularly in the leaf and stems) than in flue-cured tobacco and the alkaloid content is also much higher. This N—$NO_3$ is reduced to nitrite ($NO_2^-$) by microbes during curing and the $NO_2^-$ can be further reduced to NOx or react directly with alkaloids to form TSNAs.

It is contemplated that, in addition to the techniques described above, nitrate levels in tobacco (especially in the leaf) can be reduced by limiting exposure to nitrosating agents or conditions. Air-curing experiments at a higher temperature have shown that considerably higher levels of N-nitrosamines are formed at a curing temperature of 32° C. than at 16° C., which is associated with a rise of the nitrite level in the tobacco, and may also be associated with a rise in microbial enzymatic activity. Modified curing that involves faster drying from wider spacing or from more open curing structures has been shown to reduce TSNA levels in burley tobacco. The climatic conditions prevailing during curing exert a major influence on N-nitrosamine formation, and the relative humidity during air-curing can be of importance. Stalk curing results in higher TSNA levels in the smoke than primed-leaf curing. Sun-cured Oriental tobaccos have lower TSNA levels than Flue and air-cured dark tobaccos. Accelerated curing of crude tobaccos such as homogenized leaf curing limits the ability of bacteria to carry out the nitrosation reactions. However, many of the methods described above for reducing TSNAs in Burley tobacco can have undesirable effects on tobacco taste.

TSNA formation in flue-cured tobacco also results from exposure of the tobacco to combustion gases during curing, where nearly all of the TSNAs in flue-cured tobacco (e.g., Virginia Flue) result from a reaction involving NOx and nicotine. The predominant source of NOx is the mixture of combustion gases in direct-fired barns. At present, flue-cured tobacco is predominantly cured in commercial bulk barns. As a result of energy pressures in the U.S. during the 1960's, farmer-built “stick barns” with heat-exchanged flue systems were gradually replaced with more energy efficient bulk barns using direct-fired liquid propane gas (LPG) burners. These LPG direct-fired burner systems exhaust combustion gases and combustion by-products directly into the barn where contact is made with the curing tobacco. Studies indicate that LPG combustion by-products react with naturally occurring tobacco alkaloids to form TSNA.

In contrast to direct-fired curing, heat-exchange burner configurations completely vent combustion gases and combustion by-products to the external atmosphere rather than into the barn. The heat-exchange process precludes exposure of the tobacco to LPG combustion by-products, thereby eliminating an important source of nitrosating agent for TSNA formation, without degrading leaf quality or smoking quality. The use of heat exchangers reduces TSNA levels by about 90%. Steps are being taken to reduce TSNA levels in US tobacco by converting barns to indirect heat through the use of a heat exchanger, but these methods are very expensive. Although many of the approaches described in this section have significant drawbacks, it should be understood that any or all of these techniques can be used with other techniques, as described herein, to make tobacco and tobacco products having reduced nitrosamines. The section below provides more detail on nicotine and approaches to reduce nicotine in tobacco.

Nicotine

Nicotine is formed primarily in the roots of the tobacco plant and is subsequently transported to the leaves, where it is stored (Tso, Physiology and Biochemistry of Tobacco Plants, pp. 233-34, Dowden, Hutchinson & Ross, Stroudsburg, Pa. (1972)). Classical crop breeding techniques have produced tobacco with lower levels of nicotine, including varieties with as low as 8% of the amount of nicotine found in wild-type tobacco. The many methods described herein can be used with virtually any tobacco variety but are preferably used with Burley, Oriental or Flue (e.g., Virginia Flue) varieties.

Nicotine is produced in tobacco plants by the condensation of nicotinic acid and 4-methylaminobutanal. Two regulatory loci (Nic1 and Nic2) act as co-dominant regulators of nicotine production. Enzyme analyses of root tissue from single and double Nic mutants show that the activities of two enzymes, quinolate phosphoribosyl transferase ("QPTase") and putrescence methyl transferase (PMTase), are directly proportional to levels of nicotine biosynthesis. It has also been discovered, as reported in this application for the first time, that inhibition of A622 reduces the amount of nicotine in a tobacco plant. Accordingly, A622 encodes a gene product that regulates the production of nicotine.

An obligatory step in nicotine biosynthesis is the formation of nicotinic acid from quinolinic acid, a step that is catalyzed by QPTase. QPTase appears to be a rate-limiting enzyme in the pathway supplying nicotinic acid for nicotine synthesis in tobacco. (See, eg., Feth et al, *Planta,* 168, pp. 402-07 (1986) and Wagner et al., *Physiol. Plant.,* 68, pp. 667-72 (1986), herein expressly incorporated by reference in its entirety). A comparison of enzyme activity in tobacco tissues (root and callus) with different capacities for nicotine synthesis shows that QPTase activity is strictly correlated with nicotine content (Wagner and Wagner, Planta 165:532 (1985), herein expressly incorporated by reference in its entirety). In fact, Saunders and Bush (Plant Physiol 64:236 (1979), herein expressly incorporated by reference in its entirety), showed that the level of QPTase in the roots of low nicotine mutants is proportional to the level of nicotine in the leaves.

The modification of nicotine levels in tobacco plants by antisense regulation of putrescence methyl transferase (PMTase) expression has been proposed in U.S. Pat. Nos. 5,369,023 and 5,260,205, to Nakatani and Malik, and in PCT application WO 94/28142 to Wahad and Malik, which describe DNA encoding PMT and the use of sense and antisense PMT constructs, the entire disclosures of each of which are hereby expressly incorporated by reference in their entireties. Other genetic modifications proposed to reduce nicotine levels are described in PCT application WO 00/67558, to Timko, and WO 93/05646, to Davis and Marcum; the entire contents of each are hereby expressly incorporated by reference in their entireties. Although these investigators made significant contributions, there were significant drawbacks to their experimental design.

Most notably, it is presently revealed that there are several different PMT genes and each may play a role in nicotine biosynthesis. Knocking-out only one PMT gene creates a leaky system allowing the other genes to compensate for the reduction. Accordingly, the PMT constructs described herein were designed to inhibit a plurality of different PMT genes. That is, the PMT constructs described herein are designed to complement common regions to all five of the PMT genes so that inhibition of each of the PMT genes can be accomplished. Although many of the approaches described in this section have significant drawbacks, it should be understood that any or all of these techniques can be used with other techniques, as described herein, to make tobacco and tobacco products having reduced nicotine. The section below explains several approaches to reduce the amount of nicotine and sterols in tobacco and tobacco products.

Reducing the Amount of Nicotine and Sterols in Tobacco

As discussed above, TSNAs, nicotine, nornicotine, and sterols contribute significantly to tobacco-related disease, most notably the carcinogenic potential of tobacco and tobacco products. Thus, tobacco and tobacco products that have or produce reduced amounts of these compounds are reduced risk compositions (e.g., products that have a reduced potential to contribute to a tobacco-related disease). Without wishing to be bound by any particular theory, it is contemplated that the creation of tobacco plants, tobacco and tobacco products that have a reduced amount of nicotine will also have reduced amounts of TSNAs. That is, by removing nicotine from tobacco plants, tobacco and tobacco products, one effectively removes the most significant alkaloid substrate for TSNA formation. It was found that the reduction of nicotine in tobacco was directly related to the reduction of TSNAs. Similarly, it is contemplated that by removing sterols form tobacco, one can reduce the amount of PAHs generated from pyrolysis of the tobacco. Unexpectedly, the methods described herein not only produce tobacco with a reduced addictive potential but, concomitantly, produce a tobacco that have a reduced potential to contribute to a tobacco related disease.

It should be emphasized that the phrase "a reduced amount" is intended to refer to an amount of nicotine and/or TSNAs in a treated or transgenic tobacco plant, tobacco or a tobacco product that is less than what would be found in a tobacco plant, tobacco or a tobacco product from the same variety of tobacco, processed in the same manner, which has not been treated or was not made transgenic for reduced nicotine and/or TSNAs. Thus, in some contexts, wild-type tobacco of the same variety that has been processed in the same manner is used as a control by which to measure whether a reduction in nicotine, nornicotine, a sterol and/or TSNAs or PAHs has been obtained by the inventive methods described herein.

The amount of TSNAs (e.g., collective content of NNN, NAT, NAB, and NNK) and nicotine in wild-type tobacco varies significantly depending on the variety and the manner it is grown, harvested and cured. For example, a cured Burley tobacco leaf can have approximately 30,000 parts per million (ppm) nicotine and 8,000 parts per billion (ppb) TSNA (e.g., collective content of NNN, NAT, NAB, and NNK); a Flue-Cured leaf can have approximately 20,000 ppm nicotine and 300 ppb TSNA (e.g., collective content of NNN, NAT, NAB, and NNK); and an Oriental cured leaf can have approximately 10,000 ppm nicotine and 100 ppb TSNA (e.g., collective content of NNN, NAT, NAB, and NNK). Tobacco having a reduced amount of nicotine and/or TSNA, can have no detectable nicotine and/or TSNA (e.g., collective content of NNN, NAT, NAB, and NNK), or may contain some detectable amounts of one or more of the TSNAs and/or nicotine, so long as the amount of nicotine and/or TSNA is less than that found in tobacco of the same variety, grown under similar conditions, and cured and/or processed in the same manner. That is, cured Burley tobacco, as described herein, having a reduced amount of nicotine can have between 0 and 30,000 ppm nicotine and 0 and 8,000 ppb TSNA, desirably between 0 and 20,000 ppm nicotine and 0 and 6,000 ppb TSNA, more desirably between 0 and 10,000 ppm nicotine and 0 and 5,000 ppb TSNA, preferably between 0 and 5,000 ppm nicotine and 0 and 4,000 ppb TSNA, more preferably between 0 and 2,500 ppm nicotine and 0 and 2,000 ppb TSNA and most preferably between 0 and 1,000 ppm nicotine and 0 and 1,000 ppb TSNA. Embodiments of cured Burley leaf prepared by the methods described herein can also have between 0 and 1000 ppm nicotine and 0 and 500 ppb TSNA, 0 and 500 ppm nicotine and 0 and 250 ppb TSNA, 0 and 250 ppm nicotine and 0 and 100 ppb TSNA, 0 and 100 ppm nicotine and 0 and 50 ppb TSNA, 0 and 50 ppm nicotine and 0 and 5 ppb TSNA and some embodiments of cured Burley leaf described herein have virtually no detectable amount of nicotine or TSNA. In some embodiments above, the amount of TSNA refers to the collective content of NNN, NAT, NAB, and NNK.

Similarly, a cured Flue tobacco embodiment of the invention having a reduced amount of nicotine can have between 0 and 20,000 ppm nicotine and 0 and 300 ppb TSNA, desirably between 0 and 15,000 ppm nicotine and 0 and 250 ppb TSNA, more desirably between 0 and 10,000 ppm nicotine and 0 and 200 ppb TSNA, preferably between 0 and 5,000 ppm nicotine and 0 and 150 ppb TSNA, more preferably between 0 and 2,500 ppm nicotine and 0 and 100 ppb TSNA and most preferably between 0 and 1,000 ppm nicotine and 0 and 50 ppb TSNA. Embodiments of cured Flue tobacco, as described herein, can also have between 0 and 500 ppm nicotine and 0 and 25 ppb TSNA, 0 and 200 ppm nicotine and 0 and 10 ppb TSNA, 0 and 100 ppm nicotine and 0 and 5 ppb TSNA and some embodiments of cure Flue tobacco have virtually no detectable amount of nicotine or TSNA. In some embodiments above, the amount of TSNA refers to the collective content of NNN, NAT, NAB, and NNK.

Further, a cured Oriental tobacco embodiment having a reduced amount of nicotine can have between 0 and 10,000 ppm nicotine and 0 and 100 ppb TSNA, desirably between 0 and 7,000 ppm nicotine and 0 and 75 ppb TSNA, more desirably between 0 and 5,000 ppm nicotine and 0 and 50 ppb TSNA, preferably between 0 and 3,000 ppm nicotine and 0 and 25 ppb TSNA, more preferably between 0 and 1,500 ppm nicotine and 0 and 10 ppb TSNA and most preferably between 0 and 500 ppm nicotine and no detectable TSNA. Embodiments of cured Oriental tobacco can also have between 0 and 250 ppm nicotine and no detectable TSNA and some embodiments of cured Oriental tobacco have virtually no detectable amount of nicotine or TSNA. In some embodiments above, the amount of TSNA refers to the collective content of NNN, NAT, NAB, and NNK.

Some embodiments comprise cured tobaccos (e.g., Burley, Flue, or Oriental) with reduced amounts of nicotine as compared to control varieties, wherein the amount of nicotine is less than about 2 mg/g, 1 mg/g, 0.75 mg/g, 0.5 mg/g or desirably less than about 0.1 mg/g, and preferably less than 0.08 mg/g, 0.07 mg/g, 0.06 mg/g, 0.05 mg/g, 0.04 mg/g, 0.03 mg/g, 0.02 mg/g, 0.01 mg/g. Tobacco products made from these reduced nicotine and TSNA tobaccos are also embodiments. The term "tobacco products" include, but are not limited to, smoking materials (e.g., cigarettes, cigars, pipe tobacco), snuff, chewing tobacco, gum, and lozenges. As mentioned above, these reduced nicotine and nitrosamine tobaccos can be treated with exogenous nicotine so as to incrementally increase the amount of nicotine in the product and by employing aseptic processing and packaging techniques, the amounts of total TSNAs in the product can be kept at or below 0.5 ug/g for prolonged periods of time.

In some contexts, the phrase "reduced amount of nicotine and/or TSNAs" refers to the tobacco plants, cured tobacco, and tobacco products, as described herein, which have less nicotine and/or TSNAs (e.g., the collective content of NNN, NAT, NAB, and NNK) by weight than the same variety of tobacco grown, processed, and cured in the same way. For example, wild type cured tobacco can have has approximately 1-4% dry weight nicotine and approximately 0.2%-0.8% dry weight TSNA depending on the manner it was grown, harvested and cured. A typical cigarette has between 2-11 mg of nicotine and approximately 5.0 μg of TSNAs. Thus, the tobacco plants, tobacco and tobacco products of the invention can have, in dry weight for example, less than 0.01%, 0.015%, 0.02%, 0.025%, 0.03%, 0.035%, 0.04%, 0.045%, 0.05%, 0.055%, 0.06%, 0.065%, 0.07%, 0.075%, 0.08%, 0.085%, 0.09%, 0.095%, 0.1%, 0.15%, 0.175%, 0.2%, 0.225%, 0.25%, 0.275%, 0.3%, 0.325%, 0.35%, 0.375%, 0.4%, 0.425%, 0.45%, 0.475%, 0.5%, 0.55%, 0.6%, 0.65%, 0.7%, 0.75%, 0.8%, 0.85%, 0.9%, 0.95%, and 1.0% nicotine and less than 0.01%, 0.015%, 0.02%, 0.025%, 0.03%, 0.035%, 0.04%, 0.045%, 0.05%, 0.055%, 0.06%, 0.065%, 0.07%, 0.075%, and 0.08% TSNA (e.g., collective content of NNN, NAT, NAB, and NNK).

Alternatively, a cigarette of the invention can have, for example, less than 0.1 mg, 0.15 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, 1.0 mg, 1.1 mg, 1.15 mg, 1.2 mg, 1.25 mg, 1.3 mg, 1.35 mg, 1.4 mg, 1.45 mg, 1.5 mg, 1.55 mg, 1.6 mg, 1.65 mg, 1.7 mg, 1.75 mg, 1.8 mg, 1.85 mg, 1.9 mg, 1.95 mg, 2.0 mg, 2.1 mg, 2.15 mg, 2.2 mg, 2.25 mg, 2.3 mg, 2.35 mg, 2.4 mg, 2.45 mg, 2.5 mg, 2.55 mg, 2.6 mg, 2.65 mg, 2.7 mg, 2.75 mg, 2.8 mg, 2.85 mg, 2.9 mg, 2.95 mg, 3.0 mg, 3.1 mg, 3.15 mg, 3.2 mg, 3.25 mg, 3.3 mg, 3.35 mg, 3.4 mg, 3.45 mg, 3.5 mg, 3.55 mg, 3.6 mg, 3.65 mg, 3.7 mg, 3.75 mg, 3.8 mg, 3.85 mg, 3.9 mg, 3.95 mg, 4.0 mg, 4.1 mg, 4.15 mg, 4.2 mg, 4.25 mg, 4.3 mg, 4.35 mg, 4.4 mg, 4.45 mg, 4.4 mg, 4.45 mg, 4.5 mg, 4.55 mg, 4.6 mg, 4.65 mg, 4.7 mg, 4.75 mg, 4.8 mg, 4.85 mg, 4.9 mg, 4.95 mg, 5.0 mg, 5.5 mg, 5.7 mg, 6.0 mg, 6.5 mg, 6.7 mg, 7.0 mg, 7.5 mg, 7.7 mg, 8.0 mg, 8.5 mg, 8.7 mg, 9.0 mg, 9.5 mg, 9.7 mg, 10.0 mg, 10.5 mg, 10.7 mg, and 11.0 mg nicotine and less than 0.001 ug, 0.002 ug, 0.003 ug, 0.004 ug, 0.005 ug, 0.006 ug, 0.007 ug, 0.008 ug, 0.009 ug, 0.01 ug, 0.02 ug, 0.03 ug, 0.04 ug, 0.05 ug, 0.06 ug, 0.07 ug, 0.08 ug, 0.09 ug, 0.1 ug, 0.15 ug, 0.2 ug, 0.25 ug, 0.3 ug, 0.336 ug, 0.339 ug, 0.345 ug, 0.35 ug, 0.375 ug, 0.4 ug, 0.414 ug, 0.45 ug, 0.5 ug, 0.515 ug, 0.55 ug, 0.555 ug, 0.56 ug, 0.578 ug, 0.58 ug, 0.6 ug, 0.611 ug, 0.624 ug, 0.65 ug, 0.7 ug, 0.75 ug, 0.8 ug, 0.85 ug, 0.9 ug, 0.95 ug, 11.0 ug, 1.1 ug, 1.114 ug, 1.15 ug, 1.2 ug, 1.25 ug, 1.3 ug, 1.35 ug, 1.4 ug, 1.45 ug, 1.5 ug, 1.55 ug, 1.6 ug, 1.65 ug, 1.7 ug, 1.75 ug, 1.8 ug, 1.85 ug, 1.9 ug, 1.95 ug, 2.0 ug, 2.1 ug, 2.15 ug, 2.2 ug TSNA (e.g., collective content of NNN, NAT, NAB, and NNK).

Unexpectedly, it was discovered that several methods for reducing endogenous levels of nicotine in a plant are suitable for producing tobacco that is substantially free of nitrosamines, especially TSNAs. Any method that reduces levels of other alkaloids, including norniticotine, is likewise suitable for producing tobacco substantially free of nitrosamines, especially TSNAs. As described, embodiments of this invention comprise methods of reducing the carcinogenic potential of a tobacco product comprising providing a cured tobacco as described herein and preparing a tobacco product from said cured tobacco, whereby the carcinogenic potential of said tobacco product is thereby reduced.

In some embodiments that employed the A622 inhibition construct, it was found that transgenic tobacco that had conventional levels of nicotine but significantly reduced levels of nornicotine were produced. This particular line of tobacco is particularly useful because nornicotine may be the most significant precursor for NNN in tobacco. Accordingly, reduced risk conventional cigarettes and other tobacco products (e.g., snuff) comprising the A622 inhibition construct are embodiments.

Other embodiments of the invention include the use of the cured tobacco described herein for the preparation of a tobacco product that contains reduced amounts of carcinogens as compared to control varieties and/or that reduces the amount of a TSNA or TSNA metabolite in a human that uses tobacco. In some embodiments, for example, the tobacco smoking products described herein reduce the carcinogenic potential of side stream or main stream TS in humans exposed to said side stream or main stream TS. By providing the genetically modified cured tobacco described herein in a product that undergoes pyrolysis, for example, the side stream and/or main stream smoke produced by said product comprises a reduced amount of TSNAs and/or nicotine. Thus, the cured tobacco described herein can be used to prepare a tobacco smoking product that comprises a reduced amount of TSNAs in side stream and/or mainstream smoke.

In some embodiments, for example, the collective content of NNN, NAT, NAB, and NNK in the mainstream or side stream smoke from a tobacco product comprising the genetically modified tobacco described herein is between about 0-5.0 μg/g, 0-4.0 μg/g, 0-30 μg/g, 0-2.0 μg/g, 0-1.5 μg/g, 0-1.0 μg/g, 0-0.75 μg/g, 0-0.5 μg/g, 0-0.25 μg/g, 0-0.15 μg/g, 0-0.1 μg/g, 0-0.05 μg/g, 0-0.02 μg/g, 0-0.015 μg/g, 0-0.01 μg/g, 0-0.005 μg/g, 0-0.002 μg/g, or 0-0.001 μg/g. That is, some embodiments are genetically modified Burley tobacco, wherein the side stream or mainstream smoke produced from a tobacco product comprising said Burley tobacco has a collective content of NNN, NAT, NAB, and NNK in the mainstream or side stream smoke between about 0-5.0 μg/g, 0-4.0 μg/g, 0-3.0 μg/g, 0-2.0 μg/g, 0-1.5 μg/g, 0-1.0 μg/g, 0-0.75 μg/g, 0-0.5 μg/g, 0-0.25 μg/g, 0-0.15 μg/g, 0-0.1 μg/g, 0-0.05 μg/g, 0-0.02 μg/g, 0-0.015 μg/g, 0-0.01 μg/g, 0-0.005 μg/g, 0-0.002 μg/g, or 0-0.001 μg/g.

Other embodiments concern genetically modified Flue tobacco, wherein the sidestream or mainstream smoke produced from a tobacco product comprising said Flue tobacco has a collective content of NNN, NAT, NAB, and NNK in the mainstream or side stream smoke between about 0-5.0 μg/g, 0-4.0 μg/g, 0-3.0 μg/g, 0-2.0 μg/g, 0-1.5 μg/g, 0-1.0 μg/g, 0-0.75 μg/g, 0-0.5 μg/g, 0-0.25 μg/g, 0-0.15 μg/g, 0-0.1 μg/g, 0-0.05 μg/g, 0-0.02 μg/g, 0-0.015 μg/g, 0-0.01 μg/g, 0-0.005 μg/g, 0-0.002 μg/g, or 0-0.001 μg/g.

More embodiments concern genetically modified Oriental tobacco, wherein the sidestream or mainstream smoke produced from a tobacco product comprising said Oriental tobacco has a collective content of NNN, NAT, NAB, and NNK in the mainstream or side stream smoke between about 0-5.0 μg/g, 0-4.0 μg/g, 0-3.0 μg/g, 0-2.0 μg/g, 0-1.5 μg/g, 0-1.0 μg/g, 0-0.75 μg/g, 0-0.5 μg/g, 0-0.25 μg/g, 0-0.15 μg/g, 0-0.1 g/g, 0-0.05 μg/g, 0-0.02 μg/g, 0-0.015 μg/g, 0-0.01 μg/g, 0-0.005 μg/g, 0-0.002 μg/g, or 0-0.001 μg/g.

A preferred method of producing tobacco having a reduced amount of nicotine and TSNAs, involves genetic engineering directed at reducing the levels of nicotine and/or nornicotine or other alkaloids. Any enzyme involved in the nicotine synthesis pathway can be a suitable target for genetic engineering to reduce levels of nicotine and, optionally, levels of other alkaloids including nornicotine. Suitable targets for genetic engineering to produce tobacco having a reduced amount of nicotine and/or nitrosamines, especially TSNAs, include but are not limited to putrescene N-methyltransferase, N-methylputrescene oxidase, ornithine decarboxylase, S-adenosylmethionine synthetase, NADH dehydrogenase, phosphoribosylanthranilate isomerase, quinolate phosphoribosyl transferase (QPTase) or a combination of any of the above targets. Additionally, enzymes that regulate the flow of precursors into the nicotine or sterol synthesis pathway are suitable targets for genetic engineering to produce tobacco with a reduced amount of nicotine and nitrosamines, especially TSNAs, and tobaccos with reduced amounts of sterols, which produce a reduced amount of PAHs upon pyrolysis. Suitable methods of genetic engineering are known in the art and include, for example, the use of antisense and sense suppression technology to reduce or eliminate the production of enzymes, the use of interfering RNA molecules (gene silencing) as described herein to reduce or eliminate the expression of gene products, and the use of random or targeted mutagenesis to disrupt gene function, for example, using T-DNA insertion or EMS mutagenesis. The next section provides more description of these techniques.

Inhibition of Gene Expression Using Nucleic Acids

Inhibition of gene expression refers to the absence or observable reduction in the level of polypeptide and/or mRNA gene product. Some embodiments of the present invention relate to inhibiting the expression of one or more genes involved in the biosynthesis of nicotine, nornicotine, and/or sterols by genetically modifying a plant cell, such as a tobacco cell, by providing the cell with an inhibitory nucleic acid that reduces or eliminates the production of a gene product involved in nicotine or sterol biosynthesis. Inhibitory nucleic acids include, but are not limited to, interfering RNAs, antisense nucleic acids and catalytic RNAs. Some preferred embodiments of the present invention relate to interfering RNAs (RNAi).

RNA interference and gene silencing are terms that are used to describe a phenomenon by which the expression of a gene product is inhibited by an interfering RNA molecule. Interfering RNA molecules are double-stranded RNAs (dsRNA) that are expressed in or otherwise introduced into a cell. The dsRNA molecules may by of any length, however, short dsRNA constructs are commonly used. Such constructs are known as small interfering RNAs (siRNA), and are typically 21-23 bp in length.

RNA interference is exhibited by nearly every eukaryote and is thought to function by a highly conserved mechanism (Dillin, A. *PNAS,* 100:6289-91). As with antisense inhibition of gene expression, inhibition mediated by RNA interference is gene specific. However, in contrast to antisense-mediated inhibition, inhibition mediated by interfering RNA appears to be inherited (Dillin, A. *PNAS,* 100:6289-91). Without being bound by theory, it is believed that specificity is achieved through nucleotide sequence interaction between complementary portions of a target mRNA and the interfering RNA. The target mRNA is selected based on the specific gene to be silenced. In particular, the target mRNA, corresponds to the sense strand of the gene to be silenced. An interfering RNA, such as a dsRNA or an siRNA, comprises an RNA duplex, which includes a first strand that is substantially similar or identical to at least a portion of the nucleotide sequence of the target mRNA, and a second strand having a nucleotide sequence that is complementary or substantially complementary to the first strand.

When used herein with reference to an RNA duplex of the interfering RNA, it will be appreciated that the terms "first strand" and "second strand" are used in a relative sense. For example, the first strand of an RNA duplex can be selected to comprise either a nucleotide sequence substantially similar or identical to at least a portion of the nucleotide sequence of the target mRNA or a nucleotide sequence that is complementary or substantially complementary to at least a portion of the nucleotide sequence of the target mRNA. If the first strand is selected to be substantially similar or identical to at least a portion of the nucleotide sequence of the target mRNA, then the second strand will be complementary to at least a portion of the target mRNA because it is complementary to the first strand. If the first strand is selected to be complementary or substantially complementary to at least a portion of the target mRNA, then the second strand will be substantially similar or identical to at least a portion of the nucleotide sequence of the target mRNA because it is complementary to the first strand.

As used herein with reference to nucleic acids, "portion" means at least 5 consecutive nucleotides, at least 6 consecutive nucleotides, at least 7 consecutive nucleotides, at least 8 consecutive nucleotides, at least 9 consecutive nucleotides, at least 10 consecutive nucleotides, at least 11 consecutive nucleotides, at least 12 consecutive nucleotides, at least 13 consecutive nucleotides, at least 14 consecutive nucleotides, at least 15 consecutive nucleotides, at least 16 consecutive nucleotides, at least 17 consecutive nucleotides, at least 18 consecutive nucleotides, at least 19 consecutive nucleotides, at least 20 consecutive nucleotides, at least 21 consecutive nucleotides, at least 22 consecutive nucleotides, at least 23 consecutive nucleotides, at least 24 consecutive nucleotides, at least 25 consecutive nucleotides, at least 30 consecutive nucleotides, at least 35 consecutive nucleotides, at least 40 consecutive nucleotides, at least 45 consecutive nucleotides, at least 50 consecutive nucleotides, at least 60 consecutive nucleotides, at least 70 consecutive nucleotides, at least 80 consecutive nucleotides, at least 90 consecutive nucleotides, at least 100 consecutive nucleotides, at least 125 consecutive nucleotides, at least 150 consecutive nucleotides, at least 175 consecutive nucleotides, at least 200 consecutive nucleotides, at least 250 consecutive nucleotides, at least 300 consecutive nucleotides, at least 350 consecutive nucleotides, at least 400 consecutive nucleotides, at least 450 consecutive nucleotides, at least 500 consecutive nucleotides, at least 600 consecutive nucleotides, at least 700 consecutive nucleotides, at least 800 consecutive nucleotides, at least 900 consecutive nucleotides, at least 1000 consecutive nucleotides, at least 1200 consecutive nucleotides, at least 1400 consecutive nucleotides, at least 1600 consecutive nucleotides, at least 1800 consecutive nucleotides, at least 2000 consecutive nucleotides, at least 2500 consecutive nucleotides, at least 3000 consecutive nucleotides, at least 4000 consecutive nucleotides, at least 5000 consecutive nucleotides or greater than at least 5000 consecutive nucleotides. In some preferred embodiments, a portion of a nucleotide sequence is between 20 and 25 consecutive nucleotides. In other preferred embodiments, a portion of a nucleotide sequence is between 21 and 23 consecutive nucleotides. In some embodiments of the present invention, a portion of a nucleotide sequence includes the full-length coding sequence of the gene or the target mRNA.

Some preferred interfering RNAs that are described herein comprise an RNA duplex, which comprises a nucleotide sequence that is substantially similar or identical to at least a portion of the coding strand of a gene involved in nicotine or sterol biosynthesis. Although nucleic acid sequences that are substantially similar or identical to at least a portion of the coding strand of the target gene involved in nicotine biosynthesis are preferred, it will be appreciated that nucleotide sequences with insertions, deletions, and single point mutations relative to the target sequence are also effective for inhibition of gene expression. Sequence identity may determined by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the interfering RNA and a portion of the target gene is preferred. In especially preferred embodiments, at least about 21 to about 23 contiguous nucleotides in the target gene are greater than 90% identical to a sequence present in the interfering RNA.

In other embodiments of the present invention, the duplex region of the RNA may be defined functionally as including a nucleotide sequence that is capable of hybridizing with a portion of the target gene transcript. Exemplary hybridization conditions are 400 mM NaCl, 40 mM PIPES pH 6.4, 1 mM EDTA, 50° C. or 70° C. hybridization for 12-16 hours; followed by washing.

As described above, interfering RNAs disclosed herein comprise a sequence that is complementary to at least a portion of the sense strand of a gene encoding a target mRNA, which produces a polypeptide that is involved in nicotine biosynthesis. Preferred targets are the products of the quinolate phosphoribosyltransferase (QTPase) gene, the putrescene N-methyltransferase (PMTase) gene, and the A622 gene. However, it will be appreciated that interfering RNAs specific for other gene products or combinations of gene products involved in nicotine and nornicotine biosynthesis and/or sterol biosynthesis are contemplated. For example, additional gene products involved in nicotine biosynthesis include, but are not limited to, N-methylputrescene oxidase, ornithine decarboxylase, S-adenosylmethionine synthetase, NADH dehydrogenase, and phosphoribosylanthranilate isomerase. Additionally, it will be appreciated that interfering RNAs specific for other gene products or combinations of gene products involved in sterol biosynthesis include HMG-CoA reductase, 14alpha demethylase, squalene synthase, SMT2, SMT1, C14 sterol reductase, A8-A7-isomerase, and C4-demethylase.

Additionally, the interfering RNAs described herein can comprise a plurality nucleotide sequences that are each complementary to different portions of the sense strand of a gene involved in nicotine and/or sterol biosynthesis. Alternatively, the interfering RNAs described herein can comprise a plurality nucleotide sequences that are each complementary to at least a portion of the sense strands of different genes involved in nicotine and/or sterol biosynthesis. Still further, a single RNAi construct or inhibition cassette can be used to inhibit a plurality of genses involved in the regulation of the production of nicotine, nornicotine, or sterols. For example, as described below, it was found that the A622 inhibitory fragment and inhibition cassette (SEQ. ID. Nos. 5 and 26) efficiently reduced production of nicotine and nor nicotine in some lines of tobacco and in other lines of tobacco conventional levels of nicotine were maintained but the amount of nornicotine in said tobacco was 0.00 mg/g. Still further, the PMTase inhibitory sequence and PMTase inhibition cassette (SEQ. ID. Nos. 4 and 25) were designed to complement common regions of a plurality of PMTase genes so that the production of multiple gene products can be inhibited or reduced with a single construct.

In still more embodiments, it is contemplated that a single T-DNA containing construct be used to overexpress one gene and, in the same construct, inhibiting expression of a second gene. That is, some embodiments concern constructs, tobacco containing said constructs, and tobacco products containing said tobacco, wherein said constructs comprise an overexpression cassette that comprises a gene that regulates the production of a compound that improves the composition of the tobacco (e.g, overexpression of a gene encoding an antioxidant, such as glutathione or tocopherol) and, on the same construct, an inhibition cassette that comprises an inhibitory sequence that reduces the production of a compound that contributes to a tobacco related disease (e.g., nicotine, nornicotine, or a sterol).

In preferred embodiments, the interfering RNAs described herein comprise at least one region of double-stranded RNA (duplex RNA). This duplex RNA can range from about 10 bp in length to about 10,000 bp in length. In some embodiments, the duplex RNA ranges from about 15 bp in length to about 1500 bp in length. In other embodiments, the duplex RNA ranges from about 20 bp in length to about 1200 bp in length. In still other embodiments, the duplex RNA ranges from about 21 bp in length to about 23 bp in length. In a preferred embodiment, the duplex RNA has a length of 22 bps. Short regions of duplex RNA are often designated siRNA, whereas longer regions of RNA duplex are often termed dsRNA. In some embodiments of the present invention, the interfering RNA duplex region is a dsRNA. In other embodiments, the interfering RNA duplex region is an siRNA. In a preferred embodiment, the duplex region about the length of the coding sequence of a target mRNA encoding a polypeptide involved in nicotine biosynthesis.

Interfering RNAs described herein can be generated using a variety of techniques. For example, an interfering RNA can be generated in a host cell in vivo by providing the cell with one or more a nucleic acid constructs that comprise the nucleic acids necessary to encode the strands of a double-stranded RNA. Such constructs can be included in various types of vectors. Exemplary vectors contemplated herein include, but are not limited to, plasmids, viral vectors, viroids, replicable and nonreplicable linear DNA molecules, replicable and nonreplicable linear RNA molecules, replicable and nonreplicable circular DNA molecules and replicable and nonreplicable circular RNA molecules. Preferred vectors include plasmid vectors, especially vector systems derived from the *Agrobacterium* Ti plasmid, such as pCambia vectors and derivatives thereof.

In some embodiments, both strands of the double-stranded region of the interfering RNA can be encoded by a single vector. In such cases, the vector comprises a first promoter operably linked to a first nucleic acid which is substantially similar or identical to at least a portion of the target mRNA. The vector also comprises a second promoter operably linked to a second nucleic acid, which is complementary or substantially to the first nucleic acid.

Another type of single vector construct, which can be used to generate interfering RNA, encodes a double-stranded RNA hairpin. In such embodiments, the vector comprises a promoter operably linked to a nucleic acid that encodes both strands of the duplex RNA. The first nucleotide sequence, which encodes the strand that is substantially similar or identical to at least a portion of the target mRNA, is separated from the second nucleotide sequence, which encodes a strand complementary or substantially complementary to the first strand, by a region of nucleotide sequence that does not substantially hybridize with either of the strands. This nonhybridizing region permits the RNA sequence transcribed from the vector promoter to fold back on itself, thereby permitting the complementary RNA sequences to hybridize so as to produce an RNA hairpin. Vectors comprising a plurality of nucleic acids, each of which encode both strands of the duplex RNA are also contemplated.

Other embodiments of the present invention relate to multiple vector systems for the production of interfering RNA. In one example, a multiple vector system is used to produce a single interfering RNA that is specific for a single gene product involved in nicotine biosynthesis. In such embodiments, at least two vectors are used. The first vector comprises a promoter operably linked to a first nucleic acid that encodes a first strand of the RNA duplex that is present in the interfering RNA. The second vector comprises a promoter operably linked to a second nucleic acid that encodes the second strand of the RNA duplex, which is complementary to the first strand.

Other multiple vector systems are combinations of vectors, wherein each vector in the system encodes a different interfering RNA. Each of the interfering RNAs are specific for different gene products involved in nicotine biosynthesis. In some embodiments, the vectors in a multiple vector system can encode different interfering RNAs that are specific to different portions of a single gene product involved in nicotine biosynthesis.

It will be appreciated that the promoters used in the above-described vectors can either be constitutive or regulated. Constitutive promoters are promoters that are always expressed. The constitutive promoters selected for use in the above-described vectors can range from weak promoters to strong promoters depending on the desired amount of interfering RNA to be produced. Regulated promoters are promoters for which the desired level of expression can be controlled. An example of a regulated promoter is an inducible promoter. Using an inducible promoter in the above-described vector constructs permits expression of a wide range of concentrations of interfering RNA inside a cell.

It will also be appreciated that there is no requirement that the same or same types of promoters be used in vectors or multiple vector systems that comprise a plurality of promoters. For example, in some vectors or vector systems, a first promoter, which controls the expression of the first interfering RNA strand, can be an inducible promoter, whereas the second promoter, which controls the expression of the second RNA strand, can be a constitutive promoter. This same principal can also be illustrated in a multiple vector system. For example, a multiple vector system may have three vectors each of which includes one or more different types of promoters. Such a system can include, for example, a first vector having repressible promoter that controls the expression of an interfering RNA specific for a first gene product involved in nicotine biosynthesis, a second vector having a constitutive promoter that controls the expression of an interfering RNA specific for a second gene product involved in nicotine biosynthesis and a third vector having an inducible promoter that controls the expression of an interfering RNA specific for a third gene product involved in nicotine biosynthesis.

In other embodiments of the present invention, interfering RNAs can be produced synthetically and introduced into a cell by methods known in the art. Synthetic interfering RNAs can include a variety of RNA molecules, which include, but are not limited to, nucleic acids having at least one region of duplex RNA. The duplex RNA in such molecules can comprise, for example, two antiparallel RNA strands that form a double-stranded RNA having flush ends, two antiparallel RNA strands that form a double-stranded RNA having at least one end that forms a hair pin structure, or two antiparallel RNA strands that form a double-stranded RNA, wherein both ends form a hair pin structure. In some embodiments, synthetic interfering RNAs comprise a plurality of RNA duplexes.

The regions of RNA duplex in synthetic interfering RNAs can range from about 10 bp in length to about 10,000 bp in length. In some embodiments, the duplex RNA ranges from about 15 bp in length to about 1500 bp in length. In other embodiments, the duplex RNA ranges from about 20 bp in length to about 1200 bp in length. In still other embodiments, the duplex RNA ranges from about 21 bp in length to about 23 bp in length. In a preferred embodiment, the duplex RNA has a length of 22 bps. In preferred embodiments, synthetic interfering RNAs are siRNAs. In another preferred embodiment, the synthetic interfering RNA is an siRNA specific for the coding sequence of a target mRNA encoding a polypeptide involved in nicotine biosynthesis.

Some aspects of the present invention relate to interfering nucleic acids that are not comprised entirely of RNA. Still other aspects relate to interfering nucleic acids that do not comprise any RNA. Such interfering nucleic acids are synthetic interfering RNA analogs. These analogs substantially mimic the specificity and activity of interfering RNA from which they are modeled; however, they typically include additional properties which make their use desirable. For example, one or both strands of the interfering nucleic acid may contain one or more nonnatural nucleotide bases that improve the stability of the molecule, enhance that affinity of the molecule for the target mRNA and/or enhance cellular uptake of the molecule. Other modifications are also contemplated. For example, an interfering nucleic acid can include one or more nucleic acid strands composed of naturally-occurring nucleobases, sugars and covalent internucleoside (backbone) linkages as well as non-naturally-occurring nucleobases, sugars and covalent internucleoside linkages.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming nucleic acids, the phosphate groups covalently link adjacent nucleosides to one another to form a linear polymeric compound. In turn the respective ends of this linear polymeric structure can be further joined to form a circular structure. Within the nucleic acid structure, the phosphate groups are commonly referred to as forming the internucleoside backbone of the oligonucleotide. The normal linkage or backbone of RNA and DNA is a 3' to 5' phosphodiester linkage.

Specific examples of interfering nucleic acids useful in certain embodiments of this invention include one or more nucleic acid strands containing modified backbones or non-natural internucleoside linkages. As used herein, nucleic acids having modified backbones include those that retain a phosphorus atom in the backbone and those that do not have a phosphorus atom in the backbone.

In some embodiments, modified nucleic acid backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Certain nucleic acids having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

In some embodiments, modified nucleic acid backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other embodiments, the interfering nucleic acid can comprise one or more mimetic regions, wherein both the sugar and the internucleoside linkage, i.e., the backbone, of the nucleotide units are replaced with novel groups. In such embodiments, the base units are maintained for hybridization with an appropriate nucleic acid target compound. One such compound, a mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference in its entirety. Further teaching of PNA compounds can be found in Nielsen et al., Science, 1991, 254, 1497-1500.

In still other embodiments of the present invention, interfering nucleic acids may include nucleic acid strands having phosphorothioate backbones and/or heteroatom backbones. Modified interfering nucleic acids may also contain one or more substituted sugar moieties. In some embodiments, the interfering nucleic acids comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$ and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Another modification includes 2'-methoxyethoxy (2' $OCH_2CH_2OCH_3$, also known as 2'-O-(2-methoxyethyl) or 2'-MOE) (Martin et al., Helv. Chim. Acta, 1995, 78, 486-504).

An embodiment of the present invention includes the use of Locked Nucleic Acids (LNAs) to generate interfering nucleic acids having enhanced affinity and specificity for the target polynucleotide. LNAs are nucleic acid in which the 2'-hydroxyl group is linked to the 3' or 4' carbon atom of the sugar ring thereby forming a bicyclic sugar moiety. The linkage is preferably a methelyne ($—CH_2—$)n group bridging the 2' oxygen atom and the 4' carbon atom wherein n is 1 or 2. LNAs and preparation thereof are described in WO 98/39352 and WO 99/14226, the disclosures of which are incorporated herein by reference in their entireties.

Other modifications include 2'-methoxy (2'-O—$CH_3$), 2'-aminopropoxy (2'-$OCH_2CH_2CH_2NH_2$), 2'-allyl (2'-$CH_2$—CH═$CH_2$), 2'-O-allyl (2'-O—$CH_2$—CH═$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Interfering nucleic acids may also have sugar mimetics such as cyclobutyl moieties in place of the pentofuranosyl sugar.

The interfering nucleic acids contemplated herein may also include nucleobase (often referred to in the art simply as "base") modifications or substitutions. As used herein, "umnodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrimido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. ed., CRC Press, 1993, the disclosures of which are incorporated herein by reference in their entireties. Certain of these nucleobases are particularly useful for increasing the binding affinity of the interfering nucleic acids described herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Another modification of the interfering nucleic acids described herein involves chemically linking to at least one of the nucleic acid strands one or more moieties or conjugates which enhance the activity, cellular distribution or cellular uptake of the of the interfering nucleic acid. The interfering nucleic acids can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynarnic properties of nucleic acids, and groups that enhance the pharmacokinetic properties of such molecules. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve interfering nucleic acid uptake, enhance its resistance to degradation, and/or strengthen sequence-specific hybridization with target molecules. Groups that enhance the pharmacokinetic properties, in the context of this invention, include groups that improve the uptake, distribution, metabolism or excretion of the interfering nucleic acid. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., dihexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyloxycholesterol moiety (Crooke et al., J. Pharmacol. Exp. Ther., 1996, 277, 923-937).

As described above, it is not necessary for all positions in a given compound to be uniformly modified, and in fact, more than one of the aforementioned modifications may be incorporated in a single compound or even at a single nucleoside within an nucleic acid. The methods described herein also contemplate the use of interfering nucleic acids which are chimeric compounds. “Chimeric” interfering nucleic acid compounds or “chimeras,” as used herein, are interfering nucleic acid compounds, which contain two or more chemically distinct regions, each made up of at least one monomer unit, i.e., a nucleotide in the case of a nucleic acid compound. These interfering nucleic acids typically contain at least one region wherein the nucleic acid is modified so as to confer upon the interfering nucleic acid increased resistance to nuclease degradation, increased cellular uptake, and/or increased binding affinity for the target nucleic acid. An additional region of the nucleic acid may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby contributes further to the inhibition of gene expression by the interfering nucleic acid.

The above-described interfering nucleic acids may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare nucleic acids such as the phosphorothioates and alkylated derivatives.

The interfering nucleic acid compounds for use with the methods described herein encompass any pharmaceutically acceptable salts, esters, or salts of such esters, or any other compound.

Although terms, such as interfering RNA, dsRNA and siRNA, are used throughout the remainder of the specification, it will be appreciated that in the context of synthetically produced interfering nucleic acids, that such terms are meant to include interfering nucleic acids of all types, including those which incorporate modifications, such as those described above.

Some embodiments of the present invention relate to methods of reducing or eliminating the expression of one or more target genes involved in nicotine, nornicotine, and/or sterol biosynthesis. Target genes that are involved in nicotine, nornicotine, and/or sterol biosynthesis are expressed through the transcription a first gene product, the target mRNA, which is then translated to produce a second gene product, the target polypeptide. Thus, reduction or elimination of the expression of one or more target genes results in the reduction or elimination of one or more target mRNAs and/or target polypeptides. Target polypeptides involved in nicotine and nornicotine biosynthesis include, for example, putrescene N-methyltransferase, N-methylputrescene oxidase, ornithine decarboxylase, S-adenosylmethionine synthetase, NADH dehydrogenase, phosphoribosylanthranilate isomerase, and quinolate phosphoribosyl transferase (QPTase). In a preferred embodiment, the expression of the QPTase, PMTase, and A622 product is inhibited.

Reduction of the expression of one or more target genes and/or target gene products that are involved in nicotine, nornicotine, and/or sterol biosynthesis leads to a reduction in the amount of nicotine, sterols, and TSNAs produced in tobacco and PAHs upon pyrolysis of the tobacco. In certain embodiments, the expression of one or more target gene products involved in nicotine, nornicotine, and/or sterol biosynthesis is eliminated. Elimination of such target gene products can result in the elimination of nicotine, nornicotine, and/or sterol biosynthesis, thereby reducing the amount of nicotine, nornicotine, and/or sterol present in tobacco to levels below the detection limit of methods commonly used. Reduction of the amount of nicotine and nornicotine present in tobacco can lead to a reduction in the amount of TSNAs produced in the tobacco. In some embodiments, the amount of TSNA present in tobacco is reduced to levels below the detection limit of methods commonly used to detect TSNAs. Similarly, the reduction in the amount of sterol present in tobacco can lead to a reduction in the amount of PAH generated from the tobacco upon pyrolysis.

The reduction in or elimination of the expression of target genes or target gene products involved in nicotine, nornicotine, and/or sterol biosynthesis is achieved by providing an interfering RNA specific to one or more such target genes to a tobacco cell, thereby producing a genetically modified tobacco cell. The interfering RNA can be provided as a synthetic double-stranded RNA, or alternatively, as a nucleic acid construct capable of encoding the interfering RNA. Synthetic double-stranded interfering RNAs are taken up by the cell directly whereas interfering RNAs encoded by a nucleic acid construct are expressed from the construct subsequent to the entry of the construct inside the cell. The reduction in or elimination of the expression of the target genes and/or the target gene products is mediated by the presence of the interfering RNA inside the cell.

In general, the interfering RNAs that are produced inside the cell, whether expressed from a nucleic acid construct or provided as synthetic double-stranded RNA molecules, include an RNA duplex having a first and second strand. At least a portion the first strand of the duplex is substantially similar or identical to at least a portion of a target mRNA or a target gene involved in nicotine biosynthesis. Correspondingly, at least a portion of the second strand of the duplex is complementary or substantially complementary to the first strand, and thus, at least a portion of the second strand is complementary or substantially complementary to at least a portion of the mRNA encoded by the target gene. In some embodiments of the present invention, the interfering RNA can comprise a first strand that is substantially similar or identical to the entire coding sequence of the target gene or target mRNA involved in nicotine biosynthesis and a second strand complementary or substantially complementary to the first strand.

The reduction in or elimination of the expression of genes and/or gene products involved in nicotine, nornicotine, and/or sterol biosynthesis can be characterized by comparing the amount of nicotine, nornicotine, and/or sterol produced in genetically modified cells, with the amount of nicotine, nornicotine, and/or sterol produced in cells that have not been genetically modified. Alternatively, such reduction in or elimination of gene expression can be characterized by genetically analyzing plant cells so as to determine the level of mRNA present in the genetically modified plant cell as compared to a non-modified plant cell. Depending on the assay, quantitation of the amount of gene expression allows one to determine a degree of reduction in gene expression, which can be greater than 10%, 33%, 50%, 90%, 95% or 99% as compared to an untreated cell. As with nicotine and nornicotine, the reduction in or elimination of TSNA production in tobacco can be characterized by comparing the amount of TSNAs produced genetically modified cells, with the amount of TSNAs produced in cells that have not been genetically modified. The section below provides more description of the transgenic plants and cells of the invention.

Transgenic Plant Cells and Plants

Aspects of the present invention concern transgenic plant cells comprising one or more interfering RNAs that are capable of reducing or eliminating the expression of one or more target genes and/or target gene products involved in nicotine, nornicotine, and/or sterol biosynthesis. As described above, an appropriate interfering RNA comprises a duplex RNA that comprises a first strand that is substantially similar or identical to at least a portion of a target gene or target mRNA, which encodes a gene product involved in nicotine, nornicotine, and/or sterol biosynthesis. The RNA duplex also comprises a second strand that is complementary or substantially complementary to the first strand.

The interfering RNA or nucleic acid construct comprising the interfering RNA can be introduced into the plant cell in any suitable manner. Plant cells possessing stable interfering RNA activity, for example, by having a nucleic acid construct stably integrated into a chromosome, can be used to regenerate whole plants using methods known in the art. As such, some aspects of the present invention relate to plants, such as tobacco plants, transformed with one or more nucleic acid constructs and/or vectors which encode at least one interfering RNA that is capable of reducing or eliminating the expression of a gene product involved in nicotine biosynthesis. Transgenic tobacco cells and the plants described herein are characterized in that they have a reduced amount of nicotine, nornicotine, sterol and/or TSNA and/or generate a reduced amount of PAHs, as compared to unmodified or control tobacco cells and plants.

The tobacco plants described herein are suitable for conventional growing and harvesting techniques (e.g. topping or no topping, bagging the flowers or not bagging the flowers, cultivation in manure rich soil or without manure) and the harvested leaves and stems are suitable for use in any traditional tobacco product including, but not limited to, pipe, cigar and cigarette tobacco and chewing tobacco in any form including leaf tobacco, shredded tobacco or cut tobacco. It is also contemplated that the low nicotine and/or TSNA tobacco described herein can be processed and blended with conventional tobacco so as to create a wide-range of tobacco products with varying amounts of nicotine and/or nitrosamines. These blended tobacco products can be used in tobacco product cessation programs so as to slowly move a consumer from a high nicotine and/or sterol product to a low nicotine and sterol product. Some embodiments of the invention comprise a tobacco use cessation kit, comprising two or more tobacco products with different levels of nicotine. For example, a smoker can begin the program smoking blended cigarettes having 0.6 mg of nicotine, gradually move to smoking cigarettes with 0.3 mg of nicotine, followed by cigarettes having less than 0.1 mg nicotine until the consumer decides to quit smoking altogether. Accordingly, the blended cigarettes described herein provide the basis for an approach to reduce the exposure of a tobacco consumer to a tobacco related disease in a step-wise fashion. The components of the tobacco use cessation kit described herein may include other tobacco products, including but not limited to, smoking materials (e.g., cigarettes, cigars, pipe tobacco), snuff, chewing tobacco, gum, and lozenges.

Gene silencing has been employed in several laboratories to create transgenic plants characterized by lower than normal amounts of specific gene products. As used herein, "exogenous" or "heterologous" nucleic acids, including DNAs and/or RNAs, refer to nucleic acids that have been introduced into a cell (or the cell's ancestor) through the efforts of humans. The nucleic acid constructs that are used with the transgenic plants and the methods for producing the transgenic plants described herein encode one or more interfering RNA constructs comprising regulatory sequences, which include, but are not limited to, a transcription initiation sequence ("promoter") operable in the plant being transformed, and a polyadenylation/transcription termination sequence. Typically, the promoter is located upstream of the 5'-end of the nucleotide sequence to be expressed. The transcription termination sequence is generally located just downstream of the 3'-end of the nucleotide sequence to be transcribed.

In some preferred embodiments, the nucleic acid encoding the exogenous interfering RNA, which is transformed into a tobacco cell, comprises a first RNA strand that is identical to the an endogenous coding sequence of a gene encoding a gene product involved in nicotine biosynthesis. However, minor variations between the exogenous and endogenous sequences can be tolerated. It is preferred, but not necessarily required, that the exogenously-produced interfering RNA sequence, which is substantially similar to the endogenous gene coding sequence, be of sufficient similarity to the endogenous gene coding sequence, such that the complementary interfering RNA strand is capable of binding to the endogenous sequence in the cell to be regulated under stringent conditions as described below.

In some embodiments, the heterologous sequence utilized in the methods of the present invention may be selected so as to produce an interfering RNA product comprising a first strand that is substantially similar or identical to the entire QTPase mRNA sequence, or to a portion thereof, and a second strand that is complementary to the entire QPTase mRNA sequence, or to a portion thereof. The interfering RNA may be complementary to any contiguous sequence of the natural messenger RNA. For example, it may be complementary to the endogenous mRNA sequence proximal to the 5'-terminus or capping site, downstream from the capping site, between the capping site and the initiation codon and may cover all or only a portion of the non-coding region, may bridge the non-coding and coding region, be complementary to all or part of the coding region, complementary to the C-terminus of the coding region, or complementary to the 3'-untranslated region of the mRNA.

As used herein, the term "gene" refers to a DNA sequence that incorporates (1) upstream (5') regulatory signals including the promoter, (2) a coding region specifying the product, protein or RNA of the gene, (3) downstream regions including transcription termination and polyadenylation signals and (4) associated sequences required for efficient and specific expression. The DNA sequence of the present invention may consist essentially of the sequence provided herein, or equivalent nucleotide sequences representing alleles or polymorphic variants of these genes, or coding regions thereof. Use of the phrase "substantial sequence similarity" or "substantially similar" in the present specification and claims means that DNA, RNA or amino acid sequences which have slight and non-consequential sequence variations from the actual sequences disclosed and claimed herein are considered to be equivalent to the sequences of the present invention. In this regard, "slight and non-consequential sequence variations" mean that "similar" sequences (i.e., the sequences that have substantial sequence similarity with the DNA, RNA or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

As used herein, a "native nucleotide sequence" or "natural nucleotide sequence" means a nucleotide sequence that can be isolated from non-transgenic cells or tissue. Native nucleotide sequences are those which have not been artificially altered, such as by site-directed mutagenesis. Once native nucleotide sequences are identified, nucleic acid molecules having native nucleotide sequences may be chemically synthesized or produced using recombinant nucleic acid procedures as are known in the art. As used herein, a "native plant nucleotide sequence" is that which can be isolated from non-transgenic plant cells or tissue. As used herein, a "native tobacco nucleotide sequence" is that which can be isolated from non-transgenic tobacco cells or tissue. Use of the phrase "isolated" or "substantially pure" in the present specification and claims as a modifier of nucleic acids, polypeptides or proteins means that the nucleic acids, polypeptides or proteins so designated have been separated from their in vivo cellular environments through the efforts of human beings.

The nucleotide sequences provided herein, such as interfering RNAs or nucleic acids encoding interfering RNAs, can be transformed into a variety of host cells. As used herein, "transformation" refers to the introduction of exogenous nucleic acid into cells so as to produce transgenic cells stably transformed with the exogenous nucleic acid. A variety of suitable host cells, having desirable growth and handling properties, are readily available in the art.

Standard techniques, such as restriction mapping, Southern blot hybridization, polymerase chain reaction (PCR) and/or nucleotide sequence analysis can be employed to identify clones expressing the desired interfering RNA construct. Following the introduction and verification of the desired interfering RNA or nucleic acid construct encoding the desired interfering RNA, whole plants can be regenerated from successfully transformed cells using conventional techniques.

Nucleic acid constructs, or "transcription cassettes," encoding the interfering RNAs that are used to produce the transgenic cells and plants of the present invention include, 5' to 3' in the direction of transcription, a promoter as described herein, a nucleotide sequence as described herein operatively associated with the promoter, and, optionally, a termination sequence including stop signal for RNA polymerase and a polyadenylation signal. All of these regulatory regions should be capable of operating in the cells of the tissue to be transformed. Any suitable termination signal may be employed in carrying out the present invention, examples thereof including, but not limited to, the nopaline synthase (nos) terminator, the octapine synthase (ocs) terminator, the CaMV terminator or native termination signals, derived from the same gene as the transcriptional initiation region or derived from a different gene. (See, e.g., Rezian et al. (1988) supra, and Rodermel et al. (1988), supra).

The term "operatively associated," as used herein, refers to nucleotide sequences on a single nucleic acid molecule that are associated so that the function of one sequence is affected by the other. Thus, a promoter is operatively associated with a nucleotide sequence when it is capable of affecting the transcription of that sequence (i.e., the nucleic acid is under the transcriptional control of the promoter). The promoter is said to be "upstream" from the transcribed nucleotide sequence, which is in turn said to be "downstream" from the promoter.

In some embodiments, the transcription cassette may be provided in a DNA construct that also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide (such as antibiotics, toxins, heavy metals or the like), provide complementation by imparting prototrophy to an auxotrophic host and/or provide a visible phenotype through the production of a novel compound in the plant.

The various fragments comprising the various constructs, transcription cassettes, markers and the like may be introduced consecutively by restriction enzyme cleavage of an appropriate replication system and insertion of the particular construct or fragment into the available site. After ligation and cloning, the DNA construct may be isolated for further manipulation. All of these techniques are amply exemplified in the literature as demonstrated by J. Sambrook et al., Molecular Cloning, A Laboratory Manual (2d Ed. 1989) (Cold Spring Harbor Laboratory).

Vectors that may be used to transform plant tissue with nucleic acid constructs of the present invention include *Agrobacterium* and Transbacter vectors and ballistic vectors, as well as vectors suitable for DNA-mediated transformation. In this particular embodiment, the promoter is a region of a DNA sequence that incorporates the necessary signals for the efficient expression of the coding sequence. This region may include sequences to which an RNA polymerase binds, but is not limited to such sequences, and may include sequences to which other regulatory proteins bind along with sequences involved in the control of protein translation. Such regions may also include coding sequences.

Promoters employed in carrying out the invention may be constitutively active promoters. Numerous constitutively active promoters that are operable in plants are available. A preferred example is the Cauliflower Mosaic Virus (CaMV) 35S promoter, which is expressed constitutively in most plant tissues. As an alternative, the promoter may be a root-specific promoter or root cortex specific promoter, as explained in greater detail below.

Nucleic acid sequences have been expressed in transgenic tobacco plants utilizing the Cauliflower Mosaic Virus (CaMV) 35S promoter. (See, e.g., Cornelissen et al., "Both RNA Level and Translation Efficiency are Reduced by Anti-Sense RNA in Transgenic Tobacco", Nucleic Acids Res. 17, pp. 833-43 (1989); Rezaian et al., "Anti-Sense RNAs of Cucumber Mosaic Virus in Transgenic Plants Assessed for Control of the Virus", Plant Molecular Biology 11, pp. 463-71 (1988); Rodermel et al., "Nuclear-Organelle Interactions: Nuclear Antisense Gene Inhibits Ribulose Bisphosphate Carboxylase Enzyme Levels in Transformed Tobacco Plants", Cell 55, pp. 673-81 (1988); Smith et al., "Antisense RNA Inhibition of Polygalacturonase Gene Expression in Transgenic Tomatoes", Nature 334, pp. 724-26 (1988); Van der Krol et al., "An Anti-Sense Chalcone Synthase Gene in Transgenic Plants Inhibits Flower Pigmentation", Nature 333, pp. 866-69 (1988)).

Use of the CaMV 35S promoter for expression of interfering RNAs in the transformed tobacco cells and plants of this invention is preferred. Use of the CaMV promoter for expression of other recombinant genes in tobacco roots has been well described (Lam et al., "Site-Specific Mutations Alter In Vitro Factor Binding and Change Promoter Expression Pattern in Transgenic Plants", Proc. Nat. Acad. Sci. USA 86, pp. 7890-94 (1989); Poulsen et al. "Dissection of 5' Upstream Sequences for Selective Expression of the *Nicotiana plumbaginifolia* rbcS-8B Gene", Mol. Gen. Genet. 214, pp. 16-23 (1988)). Other promoters that are active only in root tissues (root specific promoters) are also particularly suited to the methods of the present invention. See, e.g., U.S. Pat. No. 5,459,252 to Conkling et al.; Yamamoto et al., The Plant Cell, 3:371 (1991). The TobRD2 root-cortex specific promoter may also be utilized. All patents cited herein are intended to be incorporated herein by reference in their entirety.

The recombinant interfering nucleic acid molecules and vectors used to produce the transformed tobacco cells and plants of this invention may further comprise a dominant selectable marker gene. Suitable dominant selectable markers for use in tobacco include, inter alia, antibiotic resistance genes encoding neomycin phosphotransferase (NPTII) and hygromycin phosphotransferase (HPT). Preferred selectable markers include the norflurazone resistance genes described in this disclosure. Other well-known selectable markers that are suitable for use in tobacco include a mutant dihydrofolate reductase gene that encodes methotrexate-resistant dihydrofolate reductase. DNA vectors containing suitable antibiotic resistance genes, and the corresponding antibiotics, are commercially available.

Transformed tobacco cells are selected out of the surrounding population of non-transformed cells by placing the mixed population of cells into a culture medium containing an appropriate concentration of the antibiotic (or other compound normally toxic to tobacco cells) against which the chosen dominant selectable marker gene product confers resistance. Thus, only those tobacco cells that have been transformed will survive and multiply. Additionally, the positive selection techniques described by Jefferson (e.g., WO 00055333; WO 09913085; U.S. Pat. Nos. 5,599,670; 5,432,081; and 5,268,463, hereby expressly incorporated by reference in their entireties) can be used.

Methods of making recombinant plants of the present invention, in general, involve first providing a plant cell capable of regeneration (the plant cell typically residing in a tissue capable of regeneration). The plant cell is then transformed with an interfering RNA or a nucleic acid construct encoding an interfering RNA comprising a transcription cassette of the present invention (as described above) and a recombinant plant is regenerated from the transformed plant cell. As explained below, the transforming step is carried out by techniques as are known in the art, including but not limited to bombarding the plant cell with microparticles carrying the transcription cassette, infecting the cell with an *Agrobacterium tumefaciens* containing a Ti plasmid carrying the transcription cassette or any other technique suitable for the production of a transgenic plant.

Numerous *Agrobacterium* vector systems useful in carrying out the present invention are known. For example, U.S. Pat. No. 4,459,355 discloses a method for transforming susceptible plants, including dicots, with an *Agrobacterium* strain containing the Ti plasmid. The transformation of woody plants with an *Agrobacterium* vector is disclosed in U.S. Pat. No. 4,795,855. Further, U.S. Pat. No. 4,940,838 to Schilperoort et al. discloses a binary *Agrobacterium* vector (i.e., one in which the *Agrobacterium* contains one plasmid having the vir region of a Ti plasmid but no T region, and a second plasmid having a T region but no vir region) useful in carrying out the present invention, all references are hereby expressly incorporated by reference in their entireties.

Microparticles suitable for the ballistic transformation of a plant cell, carrying a nucleic acid construct of the present invention, are also useful for making the transformed plants described herein. The microparticle is propelled into a plant cell to produce a transformed plant cell and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Christou et al., U.S. Pat. No. 5,015,580. When using ballistic transformation procedures, the transcription cassette may be incorporated into a plasmid capable of replicating in or integrating into the cell to be transformed. Examples of microparticles suitable for use in such systems include 1 to 5 μm gold spheres. The nucleic acid construct may be deposited on the microparticle by any suitable technique, such as by precipitation.

Plant species may be transformed with the interfering RNA or nucleic acid construct encoding an interfering RNA of the present invention by the nucleic acid-mediated transformation of plant cell protoplasts. Plants may be subsequently regenerated from the transformed protoplasts in accordance with procedures well known in the art. Fusion of tobacco protoplasts with nucleic acid-containing liposomes or with nucleic acid constructs via electroporation is known in the art. (Shillito et al., "Direct Gene Transfer to Protoplasts of Dicotyledonous and Monocotyledonous Plants by a Number of Methods, Including Electroporation", Methods in Enzymology 153, pp. 313-36 (1987)).

These inhibition constructs or RNAi constructs can be transferred to plant cells by any known method in the art. Preferably, *Agrobacterium*-mediated or Biolistic-mediated transformation are used, according to well-established protocols. It is also contemplated that Transbacter-mediated transformation can be used, as described below. (See Broothaerts et al., Nature 433, 629 (2005), herein expressly incorporated by reference in its entirety).

By this approach, first bacteria are prepared as follows. YM plus antibiotic plates (see below) are streaked with bacteria and the plates are incubated for 2-3 days at 28° C. Transformation is accomplished by measuring about 20 mL Minimal A medium for each bacterial strain. Scrapping or washing the Scrape or wash bacteria from plate with sterile loop and then suspending said bacteria in 20 mL of Minimal A medium. The cell density is adjusted to an OD600 0.9-1.0.

Next, the first healthy fully expanded leaves from 4-5 week old tissue culture grown tobacco plants are cut into 0.5 cm squares (or can use a cork borer, which is about 1.0 cm diameter) in deep Petri dish, under sterile RMOP liquid medium. The tissue pieces are stored in RMOP in a deep Petri dish. The leaf pieces (about 20 per transformation) are then transferred to a deep Petri dish containing bacterial suspension. To ensure that the bacteria have contacted a cut edge of the leaf, the suspension with leaf cutting is swirled and is left standing for 5 minutes. The leaf pieces are then removed from the suspension and blotted dry on filter paper or on the edge of the container. The leaf pieces are then placed with adaxial side (upper leaf surface) on solid RMOP at about 10 pieces per plate.

The plates are then incubated in the dark at 28° C. for: 2-3 days, if *A. tumefaciens* is used, 5 days if *S. meliloti* is used, 5 days *M. loti* is used, and 5-11 days if *Rhizobium* sp. NGR234 is used.

Over the next week, selection is performed. For the purposes of this example, hygromycin selection is performed. Accordingly, the leaf pieces are transferred onto solid RMOP-TCH, with abaxial surface (lower surface of leaf) in contact with media. The plates are incubated for 2-3 weeks in the light at 28° C., with 16 hours daylight per day. Subculture occurs every 2 weeks.

Plantlet formation is accomplished as follows. Once shoots appear, the plantlet is transferred to MST-TCH pots. The plantlets are grown with 16 hours daylight for 1-2 weeks. Once roots form the plants appear, the plants can be transferred to soil in the greenhouse.

Media and Solutions for Tobacco Transformation:

| YM Media (1 L) | |
|---|---|
| Mannitol | 10 g |
| Yeast extract | 0.4 g |
| $K2HPO_4$ (10% w/v stock) | 1 ml |
| $KH2PO_4$ (10% w/v stock) | 4 ml |
| NaCl (10% w/v stock) | 1 ml |
| $MgSO_4$•7H2O (10% w/v stock) | 2 ml |
| pH 6.8 | |
| Agar 15 g/L | |
| Autoclave | |

*When ready to pour add antibiotic selection if required Keep poured plates for 2 days at room temperature to visualize any contamination, then store at 4° C.

RMOP+RMOP-TCH Media (Svab, Z., et al., 1975. Transgenic tobacco plants by cocultivation of leaf disks with pPZP *Agrobacterium* binary vectors. In "Methods in Plant Molecular Biology—A Laboratory Manual", P. Maliga, D. Klessig, A. Cashmore, W. Gruissem and J. Varner, eds. Cold Spring Harbor Press: 55-77), herein expressly incorporated by reference in its entirety).

| 1 L Final conc. | |
|---|---|
| Sucrose 30 g | (3%) |
| Myo-inositol 100 mg | (0.1%) |
| MS Macro 10x 100 mL | (1x) |
| MS Micro 1000x 1 mL | (1x) |
| $Fe_2EDTA$ Iron 100x 10 mL | (1x) |
| Thiamine-HCl (10 mg/mL stock) | 100 μL (1 mg) |
| NAA (1 mg/mL stock) 100 μL | 0.1 mg) |
| BAP (1 mg/mL stock) 1 mL | (1 mg) |
| pH 5.8 | |
| Phytagel 2.5 g/L for solid | |
| autoclave | |

*for RMOP-TCH, when ready to pour add: Timentin (200 mg/mL stock) 1 mL, Claforan (250 mg/mL stock) 1 mL, and Hygromycin (50 mg/mL stock) 1 mL BAP (1 mg/ml) (6-Benzylaminopurine)

Add 1N KOH drop wise to 100 mg BAP until dissolved. Make up to 100 mL with Milli-Q H2O and store at 4° C.

NAA (1 mg/ml) (Naphthalene Acetic Acid)

Dissolve 100 mg NAA in 1 mL absolute ethanol. Add 3 mL 1N KOH. Make up to 80 mL with Milli-Q H2O. Adjust pH to 6.0 with 1N HCl, make up to 100 mL with Milli-Q H2O, and store at 4° C.

Cefotaxamine (250 mg/ml)

Add 8 ml sterile Milli-Q H2O to 2 g Claforan and store at 4° C. in dark

Timentin (200 mg/ml)

Add 15 ml sterile Milli-Q H2O to 3 g Timentin and store at 4° C.

MST+MST-TCH Media (Svab, Z., et al., 1975. Transgenic tobacco plants by cocultivation of leaf disks with pPZP *Agrobacterium* binary vectors. In "Methods in Plant Molecular Biology—A Laboratory Manual", P. Maliga, D. Klessig, A. Cashmore, W. Gruissem and J. Varner, eds. Cold Spring Harbor Press: 55-77), herein expressly incorporated by reference in its entirety).

| 1 L Final concentration | |
|---|---|
| Sucrose 30 g | (3%) |
| MS Macro 10x 100 mL | (1x) |
| MS Micro 1000x 1 mL | (1x) |
| $Fe_2EDTA$ Iron 100x 10 mL | (1x) |
| pH 5.8 | |
| Phytagel 2.5 g/L | |
| Autoclave | |
| For MST-TCH, when ready to pour add: | |
| Timentin (200 mg/mL stock) | (1 mL) |
| Cefotaxamine (250 mg/mL stock) | (1 mL) |
| Hygromycin (50 mg/mL stock) | (1 mL) |

MS Macro 10× ((Murashige and Skoog., *Phys. Plant.* 15: 473-497 (1962), herein expressly incorporated by reference in its entirety)).

| Final concentration 10x | (g/L) |
|---|---|
| $KNO_3$ | 19.0 |
| $NH4N0_3$ | 16.5 |
| $CaCl_2$•$2H_20$ | 4.4 |
| $MgS0_4$•$7H_20$ | 3.7 |
| $KH_2PO_4$ | 1.7 |
| Store 4° C. | |
| Substituting chemicals: | |
| $CaCl_2$ 3.3 g/L | |
| $MgS0_4$ 1.8 g/L | |

Substituting chemicals:

$CaCl_2$ 3.3 g/L $MgSO_4$ 1.8 g/L

MS Micro 1000×

(Murashige and Skoog., *Phys. Plant.* 15: 473-497 (1962), herein expressly incorporated by reference in its entirety).

| Final concentration 1000x | (g/L) |
|---|---|
| $MnS0_4$•$4H_20$ | 22.3 |
| $ZnS0_4$•$7H_20$ | 8.6 |
| $H_3BO_3$ | 6.2 |
| KI | 0.83 |
| $Na_2MoO_4$•$2H_20$ | 0.25 |
| $CuSO_4$•$5H_20$ | 25 mg |
| $CoCl_2$•$6H_20$ | 25 mg |
| Store 4° C. | |
| Substituting chemicals: | |
| $MnS0_4$•$H_20$ 16.9/L | |

-continued

| FeSO4EDTA Iron 100x | |
|---|---|
| | (g/1 L) |
| $FeSO_4 \cdot 7H_2O$ | 2.78 |
| $Na_2EDTA$ | 3.72 |
| Store 4° C. in dark bottle | |

Once the transformed cells are selected, by any of the approaches described above, they are induced to regenerate intact tobacco plants through application of tobacco cell and tissue culture techniques that are well known in the art. The method of plant regeneration is chosen so as to be compatible with the method of transformation. The stable presence of an interfering RNA or a nucleic acid encoding an interfering RNA in transgenic tobacco plants can be verified by Mendelian inheritance of the interfering RNA or a nucleic acid encoding an interfering RNA sequence, as revealed by standard methods of nucleic acid analysis applied to progeny resulting from controlled crosses. After regeneration of transgenic tobacco plants from transformed cells, the introduced nucleic acid sequence is readily transferred to other tobacco varieties through conventional plant breeding practices and without undue experimentation.

For example, to analyze the segregation of the transgene, regenerated transformed plants (TO) may be grown to maturity, tested for nicotine and/or TSNA levels, and selfed to produce $T_1$ plants. A percentage of $T_1$ plants carrying the transgene are homozygous for the transgene. To identify homozygous $T_1$ plants, transgenic $T_1$ plants are grown to maturity and selfed. Homozygous $T_1$ plants will produce $T_2$ progeny where each progeny plant carries the transgene; progeny of heterozygous $T_1$, plants will segregate 3:1.

Any plant tissue capable of subsequent clonal propagation, whether by organogenesis or embryogenesis, may be transformed with a nucleic acid embodiment of the present invention. Preferred plants for introduction of a nucleic acid embodiment, described herein, include *Nicotiana*. Preferred varieties of *Nicotana* for introduction of a nucleic acid embodiment as described herein include the *Nicotiana tabacum* varieties provided in Table 4.

TABLE 4

| Burley Varieties | Dark Varieties | Flu Cured | Other | Virginia | Hybrid | One Sucker | Newest Varieties | Oriental |
|---|---|---|---|---|---|---|---|---|
| KT 200 LC | BLACK MAMMOTH | K 149 | CU 748 | BROWN LEAF LIZARD | NBH 98 MS | OS400 | GL 350 | D174 |
| KT 204 LC | DF 485 | K 326 | GL 737 | TAIL ORNOCO LIZARD | 21 × KY 10 | KY 160 | | |
| KY | DF 911 | K 346 | OX 207 | TAIL TURTLE FOOT | MS 14 × KY L8 | | | |
| KY 10 | DT 508 | K 394 | PVH 03 | M and N | TN 97 | | | |
| KY 14 | DT 518 | K 730 | PVH 09 | SHIREY | KT 200 | | | |
| KY 17 | DT 592 | Coker 371 Gold | PVH 2040 | WALKER BROADLEAF | | | | |
| KY 907 | GREEN WOOD | CU 748 | RG 17 | | | | | |
| KY 907 LC | IMPROVED MADOLE | GL 737 | RG 81 | | | | | |
| KY 908 | KT-D4 LC | GL 939 | RGH 4 | | | | | |
| KY 908 | KY 160 | GL 973 | RGH 51 | | | | | |
| KY 910 MS | KY 171 | K 358 | RS 1410 | | | | | |
| Burley 21 × KY 10 | KY 171 | K 399 | Speight 168 | | | | | |
| MS KY14 × L8 | LITTLE CRITTENDEN | NC 102 | Speight 179 | | | | | |
| N 126 | LITTLE WOOD | NC 291 | Speight 190 | | | | | |
| N 777 | NARROW LEAF MADOLE | NC 297 | Speight 196 | | | | | |
| N 88 | NEWTON'S VH MADOLE | NC 55 | Speight 200A | | | | | |
| NBH 98 | NL MADOLE | NC 606 | Speight 210 | | | | | |
| TN 86 | TN D94 | NC 71 | Speight 218 | | | | | |
| TN 86 LC | TN D950 | NC 72 | Speight 220 | | | | | |
| TN 90 | TR MADOLE | NC 810 | Speight H-20 | | | | | |
| TN 90 LC | VA 309 | RGH 4 | Speight H-6 | | | | | |
| TN 97 LC | VA 312 | RGH 51 | Speight NF-3 | | | | | |
| VA 509 | VA 355 | | VA 119 NC 37 | | | | | |

TABLE 4-continued

| Burley Varieties | Dark Varieties | Flu Cured | Other | Virginia | Hybrid | One Sucker | Newest Varieties | Oriental |
|---|---|---|---|---|---|---|---|---|
| LA21 | VA 359 | | NF OX 414 NF Sp. G-172 | | | | | |

The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, callus tissue, existing meristematic tissue (e.g., apical meristems, axillary buds, and root meristems) and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the transcription cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or $T_1$) transformed plants may be selfed to give homozygous second generation (or $T_2$) transformed plants and the $T_2$ plants further propagated through classical breeding techniques. A dominant selectable marker (such as nptII) can be associated with the transcription cassette to assist in breeding.

As used herein, a crop comprises a plurality of plants of the present invention, and of the same genus, planted together in an agricultural field. By "agricultural field" is meant a common plot of soil or a greenhouse. Thus, the present invention provides a method of producing a crop of plants having reduced amounts of nicotine, nornicotine, and/or sterol, as compared to a similar crop of non-transformed plants of the same species and variety.

The modified tobacco plants described herein are suitable for conventional growing and harvesting techniques (e.g. topping or no topping, bagging the flowers or not bagging the flowers, cultivation in manure rich soil or without manure). The harvested tobacco leaves and stems are suitable for conventional methods of processing such as curing and blending. The modified tobacco is suitable for use in any traditional tobacco product including, but not limited to, pipe, cigar and cigarette tobacco, and chewing tobacco in any form including leaf tobacco, shredded tobacco, or cut tobacco.

Some embodiments concern the production and identification of particular lines of a transgenic Burley variety (Vector 21-41), which have very low levels of nicotine and TSNAs. The constructs used to create these particular lines of transgenic Burley tobacco are provided in Conkling et al., WO98/56923; U.S. Pat. Nos. 6,586,661; 6,423,520; and U.S. patent application Ser. Nos. 09/963,340; 10/356,076; 09/941,042; 10/363,069; 10/729,121; 10/943,346, all of which are hereby expressly incorporated by reference in their entireties. After the creation and analysis of nearly 2,000 lines of transgenic Burley tobacco, these particular lines of reduced nicotine and TSNA transgenic tobacco were identified. Tobacco harvested from these lines were incorporated into tobacco products (Quest 1®, Quest 2®, and Quest 3®) and were analyzed for their ability to reduce the potential to contribute to a tobacco-related disease, as described in the sections above. It was found that tobacco products comprising these lines of transgenic Burley tobacco, had a reduced potential to contribute to a tobacco-related disease (i.e., that these tobacco products are reduced risk tobacco products).

Several embodiments concern isolated nucleic acids that comprise, consist, or consist essentially of the nucleic acids described in the sequence listing (SEQ. ID. NOs.: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35) and fragments thereof at least 30 consecutive nucleotides in length. That is, embodiments of the invention include an isolated nucleic acid comprising, consisting of, consisting essentially of, any one or more of the sequences of SEQ. ID. NOs.: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35, or a fragment thereof (e.g., a fragment that is at least, less than or equal to or greater than 30, 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, or 9000 consecutive nucleotides of SEQ. ID. NOs.: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35.

In preferred embodiments, the target gene or target mRNA encodes QTPase, PMTase, or the A622 gene product. In preferred embodiments, an interfering RNA comprises, consists, or consists essentially of an RNA strand that is complementary to each least a portion (e.g., less than, greater than or equal to 30, 35, 40, 45, 50, 60, 75, 100, 150, 250, 500, 750, or 1000 consecutive nucleotides) of SEQ ID NOS: 2, 3, 4, or 5, and inhibits the production of QTPase, PMTase, A622, nicotine, nornicotine, NNN, NNK, NAT, or NAB in a tobacco. In related embodiments, the interfering RNA comprises, consists, or consists essentially of an RNA strand that is complementary to each least a portion (e.g., less than, greater than or equal to 30, 35, 40, 45, 50, 60, 75, 100, 150, 250, 500, 750, or 1000 consecutive nucleotides) of SEQ ID NO: 5, and inhibits production of nornicotine but not nicotine in a tobacco. In still more embodiments, the interfering RNA comprises, consists, or consists essentially of an RNA strand that is complementary to each least a portion (e.g., less than, greater than or equal to 30, 35, 40, 45, 50, 60, 75, 100, 150, 250, 500, 750, or 1000 consecutive nucleotides) of SEQ ID NO: 6, 7, 8, or 9, and inhibits production of at least one sterol (e.g., squalene synthase, HMG-CoA reductase, SMT2, or 14alpha demethylase) in a tobacco and a PAH upon pyrolysis of said tobacco.

Some of these nucleic acid embodiments comprise, consist, or consist essentially of fragments of the QPTase, PMTase, and A622 genes that were found to inhibit gene expression unexpectedly well in the RNAi constructs described herein, producing reduced alkaloid tobacco (below 7,000 ppm, 1,000 ppm, or 500 ppm). Some of these nucleic acids concern fragments of genes involved in sterol biosynthesis (e.g., squalene synthase, HMG-CoA reductase, SMT2, or 14alpha demethylase) and these fragments are particularly useful for inhibiting production of sterols in tobacco and PAHs when said tobacco undergoes pyrolysis.

Still more of the nucleic acid embodiments concern several phytoene desaturase (PDS) mutants (e.g., PDSM-1, PDSM-2, and PDSM-3, SEQ. ID. NOs.: 10, 11, or 12) that were developed to confer resistance to norflurazone, which allows both tissue-culture selection of cells transformed with the construct, as well as, field-based selection, wherein weeds and tobacco, which do not contain an herbicide resistance gene, are removed from the field or crop by spraying the herbicide norflurazone or an herbicide of the same class or activity (e.g., herbicides that contain $C_{12}H_9ClF_3N_3O$; (see U.S. Pat. No. 3,644,355, herein expressly incorporated by reference in its entirety)) but plants expressing PDSM-1, PDSM-2, or PDSM-3 survive the herbicide contact. That is, some embodiments include isolated nucleic acids that comprise, consist, or consist essentially of the PDS mutant sequences provided by SEQ. ID. NOs.:10, 11, or 12 and fragments thereof at least 30 nucleotides in length (e.g., less than, greater than or equal to 30, 35, 40, 45, 50, 60, 75, 100, 150, 250, 500, 750, 1000, 1100, 1200, 1300, 1400, 1500, 1600, 1700, or 1729 consecutive nucleotides) that include a mutation (e.g., T1478G, which encodes Val493Gly; G863C, which encodes Arg288Pro; and T1226C, which encodes Leu409Pro) that confers resistance to norflurazone). Preferably, the fragments of the PDS mutants described herein confer resistance to norflurazone, although fragments that do not confer resistance to the herbicide are also useful in the field in assays designed to follow the retention of constructs described herein in successive generations of transgenic plants. Approaches to develop more norflurazone-resistance genes are also provided herein.

Additional embodiments include isolated nucleic acids that comprise, consist, or consist essentially of root-specific promoters, constitutive promoters, and developmentally regulated promoters, which can be used interchangeably with the nucleic acid sequences described herein. Some embodiments, for example, include a root-specific promoter such as the truncated RD2 promoter (SEQ. ID NO. 13) or the Putrescene methyl transferase promoter (PMT-1) (SEQ. ID NO. 14). Constitutive promoters that can be used with embodiments described herein include the GapC promoter (SEQ. ID. NO.: 15), Actin 2 promoter (Act2P) (SEQ. ID NO. 16), the tobacco alcohol dehydrogenase promoter (ADP) (SEQ. ID NO. 17), and the *Arabidopsis* ribosomal protein L2 promoter (RPL2P) (SEQ. ID NO. 18). Developmentally regulated promoters that can be used with the nucleic acid sequences described herein include the cinnamyl alcohol dehydrogenase promoter (SEQ. ID NO. 19) and the metallothionein I promoter (SEQ. ID NO. 20). Additional embodiments also include isolated nucleic acids that comprise, consist, or consist essentially of the GAD2 terminator (SEQ. ID NO. 21), a FAD2 intron (provided by (SEQ. ID NO. 22), which was used as a spacer in several of the RNAi constructs, and the PAP1 intron (provided by nucleotides 6446-7625 of (SEQ. ID NO. 33). Because of the unique properties of the FAD2 intron, in particular the hair-pin secondary structure afforded by the interaction of splice sites in the sequence, it was found, unexpectedly, that transgenic tobacco could be made with various inhibitory sequences with nearly equivalent success (e.g., approximately 50% of the reduced nicotine lines created by multiple constructs were found to have less than 1,000 ppm total alkaloid). Accordingly, significantly improved RNAi constructs were generated using this spacer. That is, aspects of the invention concern the use of an intronic sequence comprising splicing recognition sequences (preferably FAD2 or PAP1 intron) to link or join a first RNA sequence to a second RNA sequence that is complementary to said first RNA sequence, wherein said first or second RNA sequence is complementary to a target RNA, which, preferably, regulates the production of a harmful compound in tobacco (e.g., nicotine, nornicotine, or a sterol).

Aspects of the invention also concern isolated nucleic acids that comprise, consist, or consist essentially of the inhibition and selection cassettes identified as SEQ. ID. Nos. 23, 24, 25, 26, 27, 28, 29, 30, 31, 32, 33, 34, or 35 and fragments thereof (e.g., a fragment that is at least, less than or equal to or greater than 30, 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, or 9000 consecutive nucleotides) of SEQ. ID. Nos. 23, 24, 25, 26, 27, 28, 29, 30, 31, 32, 33, 34, or 35).

Aspects of the invention also concern isolated nucleic acids that comprise, consist, or consist essentially a plurality of the nucleic acid sequences described herein. For example, a double knock-out construct comprising a portion of the A622 gene and a portion of the QPTase gene has been made and it is expected that this construct will efficiently reduce expression of at least two genes involved in the synthesis or regulation of the production of nicotine (SEQ. ID. No. 27). Another double knock-out construct comprises, consists of or consists essentially of a first isolated nucleic acid that inhibits nicotine biosynthesis (e.g., A622) and a second isolated nucleic acid that inhibits synthesis of at least one sterol (e.g., SMT2). (See (SEQ. ID. No. 33). Accordingly, aspects of the invention concern an isolated nucleic acid construct that inhibits the expression of a plurality of genes that regulate the production of more than one harmful compound in tobacco. In some aspects of these embodiments, said isolated nucleic acid construct inhibits the expression of at least two nicotine biosynthesis genes, a nicotine biosynthesis gene and a sterol biosynthesis gene, or two sterol biosynthesis genes. It should also be understood that aspects of the invention concern tobacco generated by crossing the transgenic tobaccos described herein. For example, some embodiments concern progeny of a cross between a transgenic tobacco having a reduced amount of nicotine and a transgenic tobacco having a reduced amount of a sterol. Crossings of the transgenic tobacco described herein and wild-type tobacco are also aspects of the invention.

The interfering RNAs used with the embodied nucleic acids can be expressed from nucleic acid construct that encodes one or more strands of the RNA duplex of the interfering RNA. In some embodiments, the nucleic acid construct is present on a vector. The vectors may be viral vectors, plasmids, or any other vehicles for nucleic acid delivery. In other embodiments, the interfering RNAs described herein can be generated synthetically by methods, such as direct synthesis or in vitro transcription. In some embodiments, synthetic interfering nucleic acids comprising modified nucleic acids are contemplated. Other embodiments of the present invention include multiple vector systems for producing an interfering RNA wherein a first vector encodes the first strand of the interfering RNA and a second vector encodes the second strand of the interfering RNA.

Still other embodiments of the present invention relate to tobacco cells comprising one or more of the nucleic acid constructs described herein, which encode an interfering RNA that is specific for a gene product involved in nicotine or sterol biosynthesis. In such embodiments, the interfering RNA reduces or eliminates the expression of such gene product. Additional embodiments relate to tobacco cells comprising one or more interfering RNAs that are specific for a gene product involved in nicotine biosynthesis. In certain embodiments, the interfering RNAs are synthetic interfering RNAs.

Certain embodiments of the present invention relate to tobacco plants and cured tobacco products having a reduced amount or nicotine, nornicotine, TSNAs, and/or sterols. In such embodiments, reduction in nicotine, nornicotine, TSNAs, and/or sterol amounts in the tobacco plants and cured tobacco products is mediated by an interfering RNA comprising an RNA duplex wherein at least 30 consecutive nucleotides (e.g., at least or equal to 30, 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 800, 900, 1000 consecutive nucleotides) of the RNA duplex are complementary or substantially complementary to a target mRNA that encodes a gene product involved in nicotine biosynthesis. Further aspects relate to a field or crop of tobacco plants comprising one or more of the constructs described herein. Still other aspects relate to a tobacco seed produced from one or more of the tobacco plants of the present invention.

Transgenic tobacco plants produced by the methods described herein can be cured by any of the tobacco curing techniques that are known in the art. As such, some embodiments of the present invention relate to cured tobacco and cure tobacco products made from the transgenic plants described herein. In some embodiments, the cured tobacco product is a blended tobacco product. In some embodiments, the cured tobacco product is processed in a microbe-free environment. In other embodiments, the cured tobacco is contacted with sterilizing vapor, heat, or radiation so as to prevent the conversion of alkaloid to TSNAs.

Some aspects of the present invention relate to methods of preparing a tobacco cell having a reduced nicotine and/or sterol content, wherein the method comprises providing a tobacco cell with one or more interfering RNAs or one or more nucleic acid constructs encoding an interfering RNA comprising an RNA duplex, which comprises a first strand having a sequence substantially similar or identical to at least a portion of the coding sequence of a target gene and/or target gene product involved in nicotine and/or sterol biosynthesis, and a second strand that is complementary or substantially complementary to the first strand. In a preferred embodiment, the target gene product involved in nicotine biosynthesis is QTPase, PMTase, or A622 and the target gene product involved in sterol biosynthesis is squalene synthase, HMG-CoA reductase, SMT2, or 14alpha demethylase.

Other aspects of the present invention relate to methods of preparing a tobacco plant having a reduced nicotine and/or sterol content comprising obtaining a tobacco cell in culture; providing to the tobacco cell one or more interfering RNAs or one or more nucleic acid constructs encoding an interfering RNA comprising an RNA duplex, which comprises a first strand having a sequence substantially similar or identical to at least a portion of the coding sequence of a target gene and/or target gene product involved in nicotine and/or sterol biosynthesis, and a second strand that is complementary or substantially complementary to the first strand; allowing expression of the interfering RNA, thereby reducing cellular nicotine and/or sterol content; and regenerating a tobacco plant from the tobacco cell. In some embodiments, the tobacco plants prepared by such method also have a reduced TSNA content and/or produce a reduced amount of PAHs upon pyrolysis, as compared to a conventional tobacco product of the same class, a reference tobacco product (e.g., IM16), or the same strain of tobacco prior to genetic modification.

As mentioned above, additional embodiments include tobacco products that have been carefully blended so that desired levels of nicotine, TSNAs, and/or sterols are obtained. For example, tobacco having a reduced level of nicotine and/or TSNAs, prepared as described above, can be blended with conventional tobacco so as to obtain virtually any amount of nicotine and/or sterols. Additionally, as mentioned above, exogenous nicotine can be added to the tobacco or tobacco product. Further, two or more varieties of tobacco (e.g., transgenic reduced alkaloid Burley, transgenic reduced alkaloid Flue-cured, and/or transgenic reduced alkaloid Oriental) can be blended so as to achieve a desired taste while maintaining nicotine levels at less than 7,000 ppm, 5,000 ppm, 3000 ppm, 2000 ppm, 1000 ppm, or 500 ppm and TSNA levels at 0.5 ug/g or less. Similarly, two or more varieties of transgenic tobacco having a reduced amount of sterols can be blended, as above, or varieties of sterol-reduced transgenic tobacco can be blended with varieties of nicotine reduced transgenic tobacco. In this manner, differences in variety, flavor, as well as amounts of nicotine and/or sterols can be incrementally adjusted. These blended tobaccos can be processed into tobacco products, which can be incorporated into tobacco use cessation kits (e.g., a multiple step nicotine reduction program, whereby a consumer's exposure to nicotine, TSNA, or PAH is gradually reduced over time by consumption of tobacco products that have increasingly smaller quantities of these compounds). Such kits and programs, are designed to reduce or eliminate nicotine dependence and reduce the potential to contribute to a tobacco related disease.

More embodiments concern methods to reduce the carcinogenic potential of tobacco products, including cigarettes, cigars, chewing tobacco, snuff and tobacco-containing gum and lozenges. Some methods, for example involve the use of the constructs described herein to obtain transgenic tobacco that comprises a reduced amount of nicotine, TSNAs, and/or sterols and the manufacture of tobacco products containing said tobacco. Accordingly, the transgenic tobacco plants, described above, are harvested, cured, and processed into tobacco products. These tobacco products have a reduced carcinogenic potential because they are prepared from tobacco that has a reduced amount of nicotine, TSNAs, and sterols. Smoke or smoke condensate generated from these tobaccos and tobacco products can also be evaluated using the assays provided above, which have been filed with this application and are herein expressly incorporated by reference in its entireties so as to confirm that said tobaccos and tobacco products have a reduced potential to contribute to a tobacco-related disease and that said tobaccos and tobacco products are reduced risk compositions.

Yet another aspect of the invention concerns the reduction of the amount of TSNAs, preferably NNN and NNK, and PAHs, preferably, BAP and metabolites thereof in humans who smoke, consume or otherwise ingest tobacco. This method is practiced by providing a tobacco product comprising a transgenic tobacco that comprises a reduced amount of nicotine and/or a sterol to said humans, thereby lowering the amount of TSNAs and/or PAHs in said humans exposed to said tobacco product. By one approach, for example, the carcinogenic potential of side stream or main stream TS in a human exposed to said side stream or main stream TS is reduced by providing the cured tobacco as described above in a product that undergoes pyrolysis, wherein pyrolysis of said product results in side stream or main stream smoke comprising a reduced amount of TSNAs and/or PAHs. The section below describes several preferred approaches to develop genetically modified tobaccos and tobacco products containing genetically modified tobacco that have a reduced amount of a compound that contributes to a tobacco related disease.

Preparation of Preferred Transgenic Tobaccos

A first generation of transgenic Burley tobacco was created using a full-length antisense QPTase construct. Tobacco of the variety Burley 21 LA was transformed with the binary *Agrobacterium* vector pYTY32 to produce a low nicotine tobacco variety, Vector 21-41. The binary vector pYTY32 carried the 2.0 kb NtQPT1 root-cortex-specific promoter driving antisense expression of the NtQPT1 cDNA (SEQ. ID. NO. 2) and the nopaline synthase (nos) 3' termination sequences from *Agrobacterium tumefaciens* T-DNA. The selectable marker for this construct was neomycin phosphotransferase (nptII) from *E. coli* Tn5 which confers resistance to kanamycin, and the expression nptII was directed by the nos promoter from *Agrobacterium tumefaciens* T-DNA. Transformed cells, tissues, and seedlings were selected by their ability to grow on Murashige-Skoog (MS) medium containing 300 μg/ml kanamycin. Burley 21 LA is a variety of Burley 21 with substantially reduced levels of nicotine as compared with Burley 21 (i.e., Burley 21 LA has 8% the nicotine levels of Burley 21, see Legg et al., *Can J Genet Cytol,* 13:287-91 (1971); Legg et al., *J Hered,* 60:213-17 (1969)).

One-hundred independent pYTY32 transformants of Burley 21 LA ($T_0$) were allowed to self. Progeny of the selfed plants ($T_1$) were germinated on medium containing kanamycin and the segregation of kanamycin resistance scored. $T_1$ progeny segregating 3:1 resulted from transformation at a single locus and were subjected to further analysis.

Nicotine levels of $T_1$ progeny segregating 3:1 were measured qualitatively using a micro-assay technique. Approximately ~200 mg fresh tobacco leaves were collected and ground in 1 ml extraction solution (Extraction solution: 1 ml Acetic acid in 100 ml $H_2O$). Homogenate was centrifuged for 5 min at 14,000×g and supernatant removed to a clean tube, to which the following reagents were added: 100 μL $NH_4OAC$ (5 g/100 ml $H_2O$+50 μL Brij 35); 500 μL Cyanogen Bromide (Sigma C-6388, 0.5 g/100 ml $H_2O$+50 μL Brij 35); 400 μL Aniline (0.3 ml buffered Aniline in 100 ml $NH_4OAC$+50 μL Brij 35). A nicotine standard stock solution of 10 mg/ml in extraction solution was prepared and diluted to create a standard series for calibration. Absorbance at 460 nm was read and nicotine content of test samples were determined using the standard calibration curve.

$T_1$ progeny that had less than 10% of the nicotine levels of the Burley 21 LA parent were allowed to self to produce $T_2$ progeny. Homozygous $T_2$ progeny were identified by germinating seeds on medium containing kanamycin and selecting clones in which 100% of the progeny were resistant to kanamycin (i.e., segregated 4:0; heterozygous progeny would segregate 3:1). Nicotine levels in homozygous and heterozygous $T_2$ progeny were qualitatively determined using the micro-assay and again showed levels less than 10% of the Burley 21 LA parent. Leaf samples of homozygous $T_2$ progeny were sent to the Southern Research and Testing Laboratory in Wilson, N.C. for quantitative analysis of nicotine levels using Gas Chromatography/Flame Ionization Detection (GC/FID). Homozygous $T_2$ progeny of transformant #41 gave the lowest nicotine levels (~70 ppm), and this transformant was designated as “Vector 21-41.”

Vector 21-41 plants were allowed to self-cross, producing $T_3$ progeny. $T_3$ progeny were grown and nicotine levels assayed qualitatively and quantitatively. $T_3$ progeny were allowed to self-cross, producing $T_4$ progeny. Samples of the bulked seeds of the $T_4$ progeny were grown and nicotine levels tested.

In general, Vector 21-41 is similar to Burley 21 LA in all assessed characteristics, with the exception of alkaloid content and total reducing sugars (e.g., nicotine and nor-nicotine). Vector 21-41 may be distinguished from the parent Burley 21 LA by its substantially reduced content of nicotine, nor-nicotine and total alkaloids. As shown below, total alkaloid concentrations in Vector 21-41 are significantly reduced to approximately relative to the levels in the parent Burley 21 LA, and nicotine and nor-nicotine concentrations show dramatic reductions in Vector 21-41 as compared with Burley 21 LA. Vector 21-41 also has significantly higher levels of reducing sugars as compared with Burley 21 LA.

Field trials of Vector 21-41 $T_4$ progeny were performed at the Central Crops Research Station (Clayton, N.C.) and compared to the Burley 21 LA parent. The design was three treatments (Vector 21-41, a Burley 21 LA transformed line carrying only the NtQPT1 promoter [Promoter-Control], and untransformed Burley 21 LA [Wild-type]), 15 replicates, 10 plants per replicate. The following agronomic traits were measured and compared: days from transplant to flowering; height at flowering; leaf number at flowering; yield; percent nicotine; percent nor-nicotine; percent total nitrogen; and percent reducing sugars.

Vector 21-41 was also grown on approximately 5000 acres by greater than 600 farmers in five states (Pennsylvania, Mississippi, Louisiana, Iowa, and Illinois). The US Department of Agriculture, Agriculture Marketing Service (USDA-AMS) quantified nicotine levels (expressed as percent nicotine per dry weight) using the FTC method of 2,701 samples taken from these farms. Nicotine levels ranged from 0.01% to 0.57%. The average percent nicotine level for all these samples was 0.09%, with the median of 0.07%. Burley tobacco cultivars typically have nicotine levels between 2% and 4% dry weight (Tso, T. C., 1972, *Physiology and Biochemistry of Tobacco Plants*. Dowden, Hutchinson, and Ross, Inc. Stroudsbury).

Figure 20:
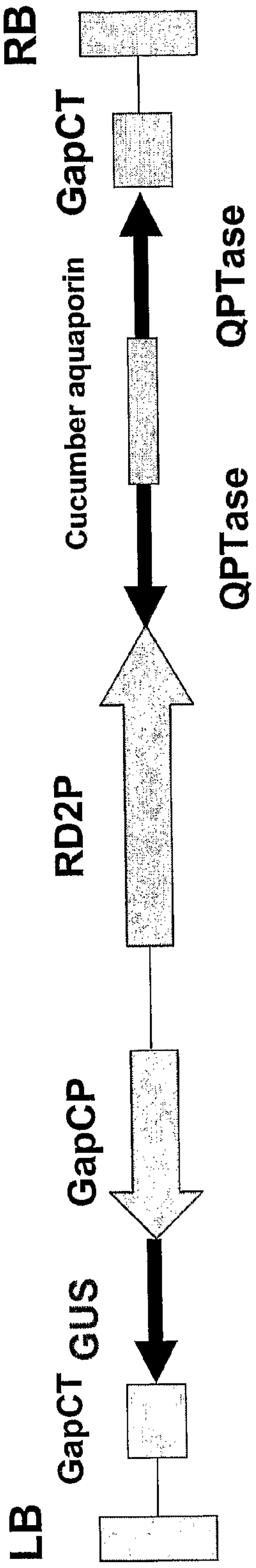

A transgenic Flue-cured tobacco with a reduced amount of nicotine and TSNAs was created using an RNAi approach. FIG. 20 illustrates an RNAi construct that was used to create a reduced nicotine tobacco, wherein the root-specific promoter RD2 (Bp 1-2010) was used to drive expression of an RNAi cassette comprising an antisense full-length QPTase cDNA (Bp 2011-3409) linked to a 382 bp fragment of the cucumber aquaporin gene (Bp 3410-3792), which is linked to a sense full-length QPTase cDNA (Bp 3793-5191) and the GapC terminator (Bp5192-5688) (see SEQ. ID. No. 23). This first RNAi construct also comprises a GUS-selection cassette comprising the GapC promoter (Bp 1-1291), which drives expression of the GUS gene (Bp 1292-3103), linked to the GapC terminator (Bp 3104-3600) (see SEQ. ID. No. 34). This first RNAi construct was ligated into a binary vector, pBin19 which was then introduced into *Agrobacterium tumefaciens*. Leaf disks from flue-cured variety K326 were then transformed with *Agrobacterium* that contained the RNAi construct comprising the RNAi cassette and the GUS selection cassette. GUS-based selection was then employed to select positively transformed plantlets (buds), which were then regenerated to plants. Leaf samples were then harvested and the alkaloid content was then determined. The alkaloid content of samples obtained from some of the transgenic lines created with this first RNAi construct was 6000 ppm. Since the total alkaloid content in tobacco is about 90% nicotine, it is understood by those skilled in the art that the transgenic Flue-cured tobacco created using the construct shown in FIG. 20 has significantly reduced levels of nicotine and TSNA, as compared to a conventional tobacco, a reference tobacco, or the parental strain of tobacco prior to genetic modification.

Figure 21:
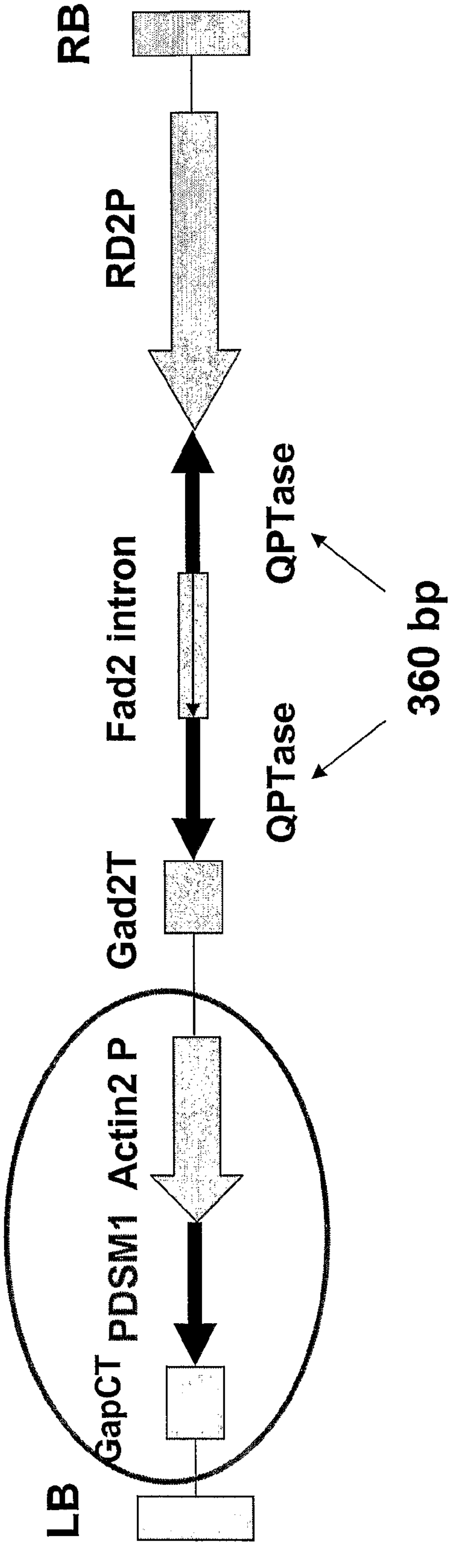
FIG. 21. An illustration of a QPTase inhibition construct comprising a QPTase inhibition cassette including a 360 bp fragment of the QPTase gene and a norflurazone resistance selection cassette including a mutant phytoene desaturase gene (PDSM-1).

FIG. 21 shows another RNAi construct that was used to generate several lines of reduced nicotine and TSNA tobacco. This RNAi construct has a QTPase inhibition cassette (SEQ. ID. No. 24) and a norflurazone selection cassette (SEQ. ID. No. 35). Starting from the right border (RB), the QPTase inhibition cassette comprises an RD2 promoter (Bp 1-2010) operably linked to an antisense fragment (360 bp) (Bp 2011-2370) of the QTPase gene, joined to a FAD2 intron (Bp 2371-3501), which is joined to a sense fragment of the QTPase gene (360 bp) (Bp 3502-3861), which is joined to the GAD2 terminator (Bp 3862-4134). The selection cassette comprises the Actin 2 promoter (Bp 1-1161) operably linked to a mutant phytoene desaturase gene (PDSM1) (Bp 1162-2890) joined to the GapC terminator (Bp 2891-3387) at the left border (LB).

Flue-cured tobacco was transformed with the construct shown in FIG. 21 using *Agrobacterium*-mediated transformation and 1,140 independent lines were selected, regenerated, and transplanted in the greenhouse. Of the 1,140 independent lines, 1,097 plants were harvested and tested for alkaloid content. A total of 608 lines were identified as having less than 1,000 ppm total alkaloid and 139 lines were identified as having less than 500 ppm total alkaloid. Accordingly, the transgenic Flue-cured tobacco created using the construct shown in FIG. 21 has significantly reduced levels of nicotine and TSNA, as compared to a conventional tobacco, a reference tobacco, or the parental strain of tobacco prior to genetic modification.

Burley tobacco was also transformed with the construct shown in FIG. 21 using *Agrobacterium*-mediated transformation and 385 independent lines were selected, regenerated, and transplanted in the greenhouse. Of the 385 independent lines, 350 lines of plants were harvested and tested for alkaloid content. A total of 142 lines were identified as having less than 1,000 ppm total alkaloid and 10 lines were identified as having less than 500 ppm total alkaloid. Accordingly, it is understood by those skilled in the art that the transgenic Burley tobacco created using the construct shown in FIG. 21 also has significantly reduced levels of nicotine and TSNA, as compared to a conventional tobacco, a reference tobacco, or the parental strain of tobacco prior to genetic modification.

Oriental tobacco will be transformed with the construct shown in FIG. 21 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Oriental tobacco that will be created using the construct shown in FIG. 21 will have significantly reduced levels of nicotine and TSNA, as compared to a conventional tobacco, a reference tobacco, or the parental strain of tobacco prior to genetic modification.

Figure 22:
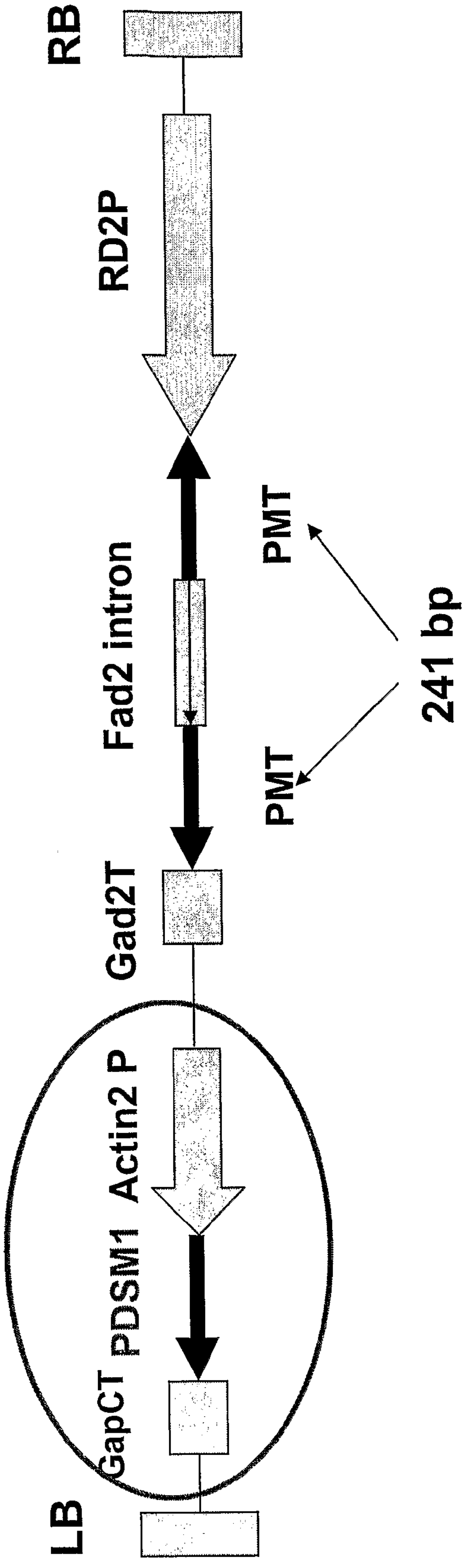
FIG. 22. An illustration of a PMTase inhibition construct comprising a PMTase inhibition cassette including a 241 bp fragment of the PMTase gene and a norflurazone resistance selection cassette including a mutant phytoene desaturase gene (PDSM-1).

FIG. 22 illustrates another RNAi construct that can be used to create a reduced nicotine and TSNA transgenic tobacco. This RNAi construct has a PMTase inhibition cassette (SEQ. ID. No. 25) and a norflurazone selection cassette (SEQ. ID. No. 35). Starting from the right border (RB), the PMTase inhibition cassette comprises an RD2 promoter (Bp 1-2010) operably linked to an antisense nucleic acid (241 bp) (Bp 2011-2251) of a PMTase gene, joined to a FAD2 intron (Bp 2252-3382), which is joined to a sense nucleic acid of the PMTase gene (241 bp) (Bp 3383-3623), which is joined to the GAD2 terminator (Bp 3624-3896). The selection cassette comprises the Actin 2 promoter (Bp 1-1161) operably linked to a mutant phytoene desaturase gene (PDSM1) (Bp 1162-2890) joined to the GapC terminator (Bp 2891-3387) at the left border (LB).

Flue-cured tobacco will be transformed with the construct shown in FIG. 22 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Flue-cured tobacco that will be created using the construct shown in FIG. 22 will have significantly reduced levels of nicotine and TSNA, as compared to a conventional tobacco, a reference tobacco, or the parental strain of tobacco prior to genetic modification.

Burley tobacco will be transformed with the construct shown in FIG. 22 using *Agrobacterium*-mediated, Transbacter-mediated (see e.g., Broothaerts et al., *Nature* 433:629 (2005), herein expressly incorporated by reference in its entirety) or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Burley tobacco that will be created using the construct shown in FIG. 22 will have significantly reduced levels of nicotine and TSNA, as compared to a conventional tobacco, a reference tobacco, or the parental strain of tobacco prior to genetic modification.

Oriental tobacco will also be transformed with the construct shown in FIG. 22 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Oriental tobacco that will be created using the construct shown in FIG. 22 will have significantly reduced levels of nicotine and TSNA, as compared to a conventional tobacco, a reference tobacco, or the parental strain of tobacco prior to genetic modification.

Figure 23:
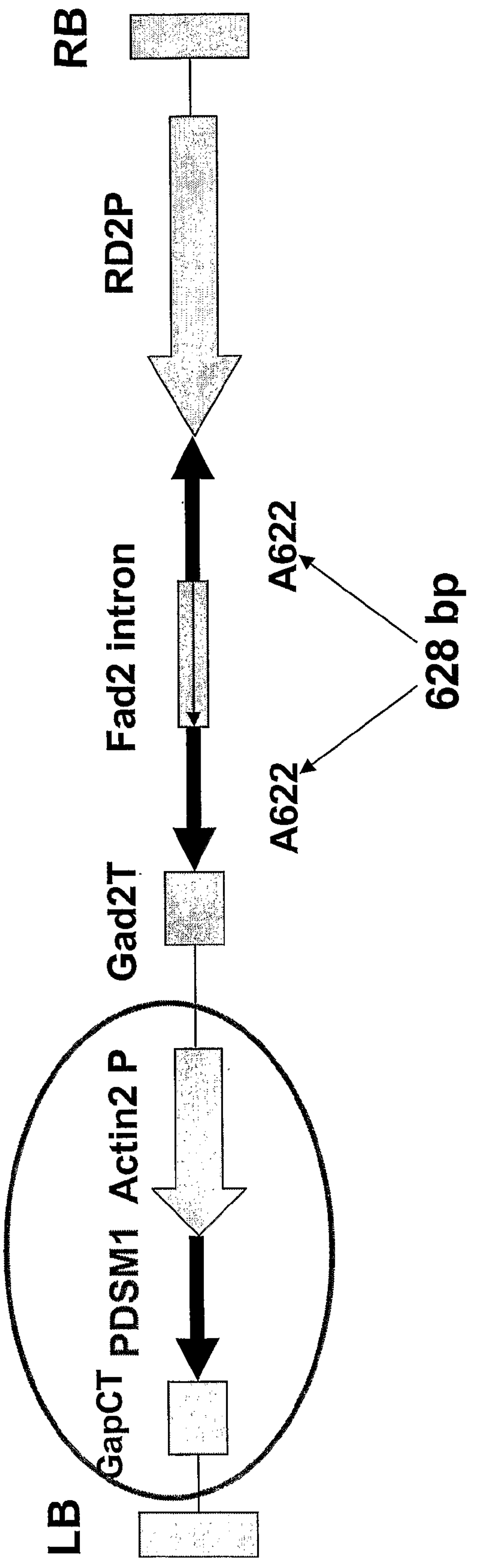
FIG. 23. An illustration of a A622 inhibition construct comprising a A622 inhibition cassette including a 628 bp fragment of the A622 gene and a norflurazone resistance selection cassette including a mutant phytoene desaturase gene (PDSM-1).

FIG. 23 illustrates another RNAi construct that was used to create a reduced nicotine and TSNA transgenic tobacco. This RNAi construct has a A622 inhibition cassette (SEQ. ID. No. 26) and a norflurazone selection cassette (SEQ. ID. No. 35). Starting from the right border (RB), the A622 inhibition cassette comprises an RD2 promoter (Bp 1-2010) operably linked to an antisense nucleic acid (628 bp) (Bp 2011-2638) of the A622 gene, joined to a FAD2 intron (Bp 2639-3769), which is joined to a sense nucleic acid of the A622 gene (628 bp) (Bp 3770-4397), which is joined to the GAD2 terminator (Bp 4398-4670). The selection cassette comprises the Actin 2 promoter (Bp 1-1161) operably linked to a mutant phytoene desaturase gene (PDSM1) (Bp 1162-2890) joined to the GapC terminator (Bp 2891-3387) at the left border (LB).

Flue-cured tobacco was transformed with the construct shown in FIG. 23 using *Agrobacterium*-mediated transformation and 270 independent lines were selected, regenerated, and transplanted in the greenhouse. Of the 270 independent lines, 259 plants were harvested and tested for alkaloid content. A total of 131 lines were identified as having less than 1,000 ppm total alkaloid and 45 lines were identified as having less than 500 ppm total alkaloid. Accordingly, it is understood by those skilled in the art that the transgenic Flue-cured tobacco created using the construct shown in FIG. 23 also has significantly reduced levels of nicotine and TSNA, as compared to a conventional tobacco, a reference tobacco, or the parental strain of tobacco prior to genetic modification.

Several lines that were transformed with this construct were unexpectedly found to have conventional levels of nicotine but a significantly reduced amount of nornicotine. That is, 9 lines were found to have nicotine levels ranging from 2.17 mg/g to 3.99 mg/g and nornicotine levels less than or equal to 0.00 to 0.06 mg/g (see Table 5).

TABLE 5

Transgenic tobacco having reduced nornicotine and conventional amounts of nicotine

| new I.D | Alkaloid (ppm) | Nornicotine (mg/g) | Nicotine (mg/g) |
|---|---|---|---|
| VDG 0 20 | 2486.53 | 0.00 | 2.30 |
| VDG 0 32 | 4683.01 | 0.00 | 3.48 |
| VDG 0 45 | 4490.79 | 0.00 | 3.94 |
| VDG 0 52 | 2855.58 | 0.00 | 2.61 |
| VDG 0 54 | 2291.89 | 0.00 | 2.17 |
| VDG 0 77 | 4857.86 | 0.06 | 3.99 |
| VDG 0 97 | 3072.40 | 0.00 | 2.58 |
| VDG 107 | 4921.31 | 0.03 | 3.59 |
| VDG 116 | 4960.64 | 0.00 | 3.56 |

TABLE 5-continued

Transgenic tobacco having reduced nornicotine and conventional amounts of nicotine

| new I.D | Alkaloid (ppm) | Nornicotine (mg/g) | Nicotine (mg/g) |
|---|---|---|---|
| Control-8 | 5005.22 | 0.28 | 4.02 |
| Control-20 | 5711.97 | 0.34 | 5.35 |
| Control-28 | 5196.25 | 0.24 | 4.52 |

*Highlighted entries show transgenic tobacco lines having a reduced amount of nornicotine and conventional amounts of nicotine.

Tobacco products containing the selectively reduced nornicotine transgenic tobacco described above are also embodiments of the invention. That is, tobacco products comprising a transgenic tobacco that comprises a conventional amount of nicotine (e.g., at least, less than, greater than, or equal to 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mg/g nicotine) and a reduced amount of nornicotine (e.g., 0.00, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or 0.2 mg/g), as compared to a conventional tobacco, a reference tobacco, or the parental strain of tobacco prior to genetic modification, are embodiments of the invention. Particularly preferred are transgenic tobacco and tobacco products made therefrom, which comprise a conventional amount of nicotine (e.g., at least, less than, greater than, or equal to 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mg/g nicotine) and a reduced amount of nornicotine (e.g., 0.00, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or 0.2 mg/g), as compared to a conventional tobacco, a reference tobacco, or the parental strain of tobacco prior to genetic modification, and an isolated fragment of the A622 gene, in particular, comprising, consisting of, or consisting essentially of an isolated nucleic acid of SEQ. ID. No. 5, or the cassette of SEQ. ID. No. 26.

Burley tobacco will be transformed with the construct shown in FIG. 23 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Burley tobacco that will be created using the construct shown in FIG. 23 will have significantly reduced levels of nicotine and TSNA, as compared to a conventional tobacco, a reference tobacco, or the parental strain of tobacco prior to genetic modification. It is also expected that some lines of tobacco created with the afore-mentioned nucleic acid construct will retain conventional amounts of nicotine but will comprise a reduced amount of nornicotine, as compared to a conventional tobacco, a reference tobacco, or the parental strain of tobacco prior to genetic modification.

Oriental tobacco will also be transformed with the construct shown in FIG. 23 using *Agrobacterium*-mediated, Transbacter-mediated, or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Oriental tobacco that will be created using the construct shown in FIG. 23 will have significantly reduced levels of nicotine and TSNA, as compared to a conventional tobacco, a reference tobacco, or the parental strain of tobacco prior to genetic modification. It is also expected that some lines of tobacco created with the afore-mentioned nucleic acid construct will retain conventional amounts of nicotine but will comprise a reduced amount of nornicotine, as compared to a conventional tobacco, a reference tobacco, or the parental strain of tobacco prior to genetic modification.

Figure 24:
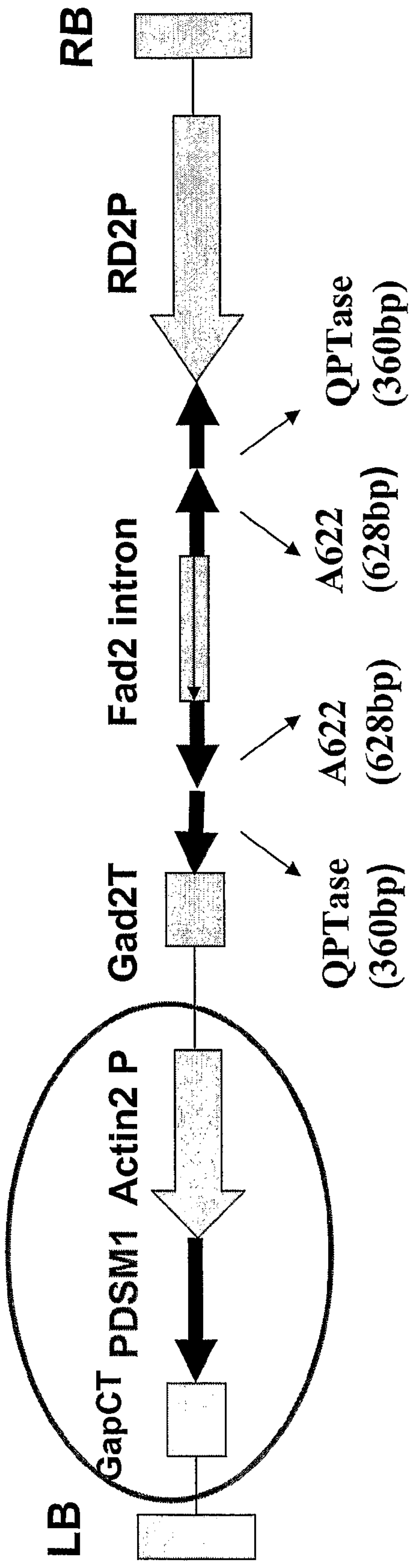
FIG. 24. An illustration of a QPTase/A622 double inhibition construct comprising a QPTase/A622 inhibition cassette including a 360 bp fragment of the QPTase gene and a 628 bp fragment of the A622 gene and a norflurazone resistance selection cassette including a mutant phytoene desaturase gene (PDSM-1).

FIG. 24 illustrates a double-knock-out RNAi construct, which has been created to develop a reduced nicotine and TSNA transgenic tobacco. This double-knock-out RNAi construct has a QPTase/A622 inhibition cassette (SEQ. ID. No.27) and a norflurazone selection cassette (SEQ. ID. No. 35). Starting from the right border (RB), the QPTase/A622 inhibition cassette comprises an RD2 promoter (Bp 1-2010) operably linked to a QPTase antisense nucleic acid (360 bp) (Bp 2011-2370) of a QPTase gene, which is joined to a A622 antisense nucleic acid (628 bp) (Bp 2371-2998) of a A622 gene, which is joined to a FAD2 intron (Bp 2999-4129), which is joined to a sense nucleic acid of the A622 gene (628 bp) (Bp 4130-4757), which is joined to a sense nucleic acid of the QPTase gene (360 bp) (Bp 4758-5117), which is joined to the GAD2 terminator (Bp 5118-5390). The selection cassette comprises the Actin 2 promoter (Bp 1-1161) operably linked to a mutant phytoene desaturase gene (PDSM1) (Bp 1162-2890) joined to the GapC terminator (Bp 2891-3387) at the left border (LB).

Flue-cured tobacco will be transformed with the construct shown in FIG. 24 using *Agrobacterium*-mediated, Transbacter-mediated, or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Flue-cured tobacco that will be created using the construct shown in FIG. 24 will have significantly reduced levels of nicotine and TSNA, as compared to a conventional tobacco, a reference tobacco, or the parental strain of tobacco prior to genetic modification.

Burley tobacco will be transformed with the construct shown in FIG. 24 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Burley tobacco that will be created using the construct shown in FIG. 24 will have significantly reduced levels of nicotine and TSNA, as compared to a conventional tobacco, a reference tobacco, or the parental strain of tobacco prior to genetic modification.

Oriental tobacco will also be transformed with the construct shown in FIG. 24 using *Agrobacterium*-mediated, Transbacter-mediated, or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Oriental tobacco that will be created using the construct shown in FIG. 24 will have significantly reduced levels of nicotine and TSNA, as compared to a conventional tobacco, a reference tobacco, or the parental strain of tobacco prior to genetic modification.

More embodiments concern an RNAi construct designed to reduce the amount of sterols in tobacco and thereby reduce production of a PAH upon pyrolysis of said transgenic tobacco. A first sterol-reducing RNAi construct has a 14alpha demethylase inhibition cassette (SEQ. ID. No. 28). The 14alpha demethylase inhibition cassette comprises a double (two promoters in tandem) 35S promoter (Bp 1-618) operably linked to an antisense 14alpha demethylase nucleic acid (Bp 619-1503), which is joined to a FAD2 intron (Bp 1504-2634), which is joined to a sense nucleic acid of the 14alpha demethylase gene (Bp 2635-3519), which is joined to the Nos terminator (Bp 3520-3773).

Flue-cured tobacco will be transformed with the 14alpha demethylase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Flue-cured tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Burley tobacco will be transformed with the 14alpha demethylase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Burley tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Oriental tobacco will be transformed with the 14alpha demethylase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Oriental tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

More embodiments concern another RNAi construct designed to reduce the amount of a sterol in tobacco and thereby reduce production of a PAH upon pyrolysis of said transgenic tobacco. A second sterol-reducing RNAi construct has a SMT2 inhibition cassette (SEQ. ID. No. 29). The SMT2 inhibition cassette comprises a double (two promoters in tandem) 35S promoter (Bp 1-618) operably linked to an antisense SMT2 nucleic acid (Bp 619-1398), which is joined to a FAD2 intron (Bp 1399-2529), which is joined to a sense nucleic acid of the SMT2 gene (Bp 2530-3309), which is joined to the Nos terminator (Bp 3310-3563).

Flue-cured tobacco will be transformed with the SMT2 inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Flue-cured tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Burley tobacco will be transformed with the SMT2 inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Burley tobacco that will be created using the construct above will have significantly reduced levels of sterols and will generate significantly less PAHs upon pyrolysis, as compared to a conventional tobacco, a reference tobacco, or the parental strain of tobacco prior to genetic modification.

Oriental tobacco will be transformed with the SMT2 inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Oriental tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

More embodiments concern another RNAi construct designed to reduce the amount of a sterol in tobacco and thereby reduce production of a PAH upon pyrolysis of said transgenic tobacco. A third sterol-reducing RNAi construct has a squalene synthase inhibition cassette (SEQ. ID. No. 30). The squalene synthase inhibition cassette comprises a double (two promoters in tandem) 35S promoter (Bp 1-618) operably linked to an antisense squalene synthase nucleic acid (Bp 619-1057), which is joined to a FAD2 intron (Bp 1058-2188), which is joined to a sense nucleic acid of the squalene synthase gene (Bp 2189-2627), which is joined to the Nos terminator (Bp 2628-2881).

Flue-cured tobacco will be transformed with the squalene synthase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Flue-cured tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Burley tobacco will be transformed with the squalene synthase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Burley tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Oriental tobacco will be transformed with the squalene synthase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Oriental tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

More embodiments concern yet another RNAi construct designed to reduce the amount of a sterol in tobacco and thereby reduce production of a PAH upon pyrolysis of said transgenic tobacco. A fourth sterol-reducing RNAi construct has a HMG-CoA reductase inhibition cassette (SEQ. ID. No. 31). The HMG-CoA reductase inhibition cassette comprises a double (two promoters in tandem) 35S promoter (Bp 1-618) operably linked to an antisense HMG-CoA reductase nucleic acid (Bp 619-1468), which is joined to a FAD2 intron (Bp 1469-2599), which is joined to a sense nucleic acid of the HMG-CoA reductase gene (Bp 2600-3449), which is joined to the Nos terminator (Bp 3450-3703).

Flue-cured tobacco (K326) was transformed with the HMG-CoA reductase inhibition cassette using *Agrobacterium*-mediated transformation and independent lines were selected, regenerated, and transplanted in the greenhouse. Several independent lines grown in the greenhouse were harvested and tested for the presence of various sterols (see Table 6). As shown in the table, several lines (e.g., HMGIR 1, HMGIR 2, HMGIR 3-2, HMGIR 4, HMGIR 7, HMGIR 11, HMGIR 13, HMGIR 16, HMGIR 18, HMGIR 19) were found to have significantly reduced levels of sterols, as compared to the parental strain of tobacco (i.e., tobacco of the same variety prior to genetic modification). Accordingly, embodiments include transgenic tobacco and tobacco products made therefrom comprising a reduced amount of sterols, as compared to a tobacco of the same variety, parental strain or a tobacco that has not been genetically modified. It is expected that the transgenic Flue-cured tobacco that was created using the construct above will generate significantly less PAHs upon pyrolysis, as compared to a conventional tobacco, a reference tobacco, or the parental strain of tobacco prior to genetic modification.

acid of the SMT2 gene (Bp 2956-3735), which is joined to the RuBisCo small subunit terminator (Bp 3736-4286).

Flue-cured tobacco will be transformed with the developmentally regulated SMT2 inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Flue-cured tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

TABLE 6

| | HmgCoa Reductase inhibition | | | | | | | | | | |
|---|---|---|---|---|---|---|---|---|---|---|---|
| | K326 cont | HMGIR 1 | HMGIR 2 | HMGIR 3-2 | HMGIR 4 | HMGIR 7 | HMGIR 11 | HMGIR 13 | HMGIR 16 | HMGIR 18 | HMGIR 19 |
| Squalene | 1 | 1.47 | 0.90 | 1.96 | 2.64 | 1.00 | 1.25 | 1.21 | 0.72 | 0.90 | 0.75 |
| Squalene | 1 | 1.48 | 0.88 | 2.13 | 2.78 | 0.94 | 1.14 | 1.12 | 0.97 | 0.73 | 0.96 |
| Tocopherol | 1 | 1.67 | 2.02 | 1.15 | 1.40 | 1.13 | 1.69 | 1.15 | 1.36 | 1.48 | 1.13 |
| Tocopherol | 1 | 1.73 | 2.08 | 1.33 | 1.34 | 0.84 | 1.54 | 0.88 | 1.05 | 1.11 | 0.87 |
| Campesterol | 1 | 0.74 | 1.13 | 0.47 | 0.60 | 0.76 | 0.75 | 0.83 | 0.90 | 1.20 | 1.21 |
| Stigmasterol | 1 | 0.45 | 1.00 | 0.34 | 0.30 | 0.50 | 0.55 | 0.65 | 0.85 | 1.42 | 1.27 |
| Sitosterol | 1 | 0.84 | 0.59 | 0.69 | 0.92 | 0.86 | 0.93 | 1.01 | 0.76 | 0.83 | 0.84 |

Burley tobacco will be transformed with the HMG-CoA reductase cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Burley tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Oriental tobacco will be transformed with the HMG-CoA reductase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Oriental tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

More embodiments concern still another RNAi construct designed to reduce the amount of a sterol in tobacco and thereby reduce production of a PAH upon pyrolysis of said transgenic tobacco. A fifth sterol-reducing RNAi construct has a developmentally regulated SMT2 inhibition cassette (SEQ. ID. No. 32). The developmentally regulated SMT2 inhibition cassette comprises a cinnamyl alcohol dehydrogenase promoter (Bp 1-995) operably linked to an antisense SMT2 nucleic acid (Bp 996-1775), which is joined to a PAP 1 intron (Bp 1776-2955), which is joined to a sense nucleic Burley tobacco will be transformed with the developmentally regulated SMT2 inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Burley tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Oriental tobacco will be transformed with the developmentally regulated SMT2 inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Oriental tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Figure 25:
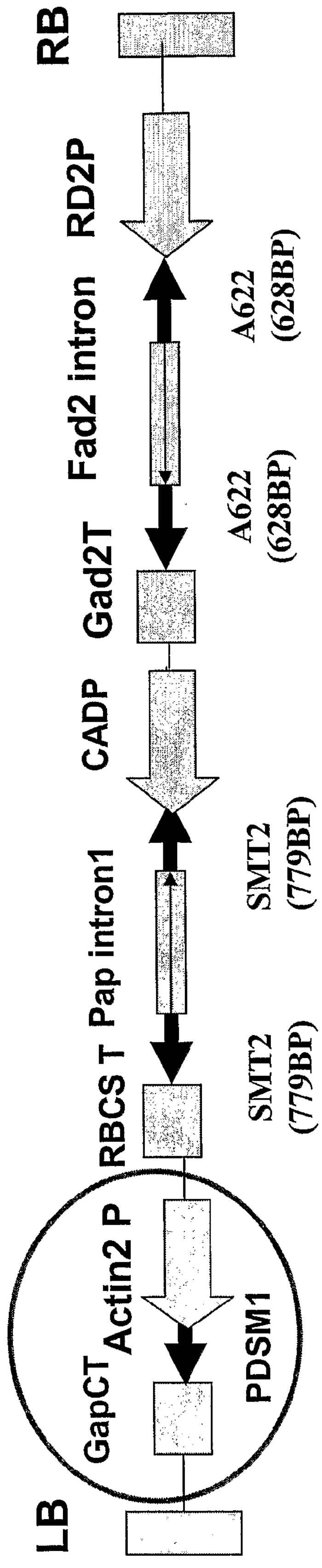
FIG. 25. An illustration of a SMT2/A622 double inhibition construct comprising a A622 inhibition cassette including a 628 bp fragment of the A622 gene, an SMT2 inhibition cassette including a 779 bp fragment of the SMT2 gene and a norflurazone resistance selection cassette including a mutant phytoene desaturase gene (PDSM-1).

FIG. 25 illustrates a double-knock-out RNAi construct that can be used to create a reduced nicotine, TSNA, sterol transgenic tobacco that generates a reduced amount of PAH upon pyrolysis. This double-knock-out RNAi construct has a A622/SMT2 inhibition cassette (SEQ. ID. No. 33) and a norflurazone selection cassette (SEQ. ID. No. 35). Starting from the right border (RB), the A622/SMT2 inhibition cassette comprises an RD2 promoter (Bp 1-2010) operably linked to a A622 antisense nucleic acid (628 bp) (Bp 2011-2638) of a A622 gene, which is joined to a FAD2 intron (Bp 2639-3769), which is joined to a sense nucleic acid of the A622 gene (628 bp) (Bp3770-4397), which is joined to the GAD2 terminator (Bp 4398-4670); which is joined to a cinnamyl alcohol dehydrogenase promoter (Bp 4671-5665) operably linked to an antisense SMT2 nucleic acid (Bp 5666-6445), which is joined to a PAP 1 intron (Bp 6446-7625), which is joined to a sense nucleic acid of the SMT2 gene (Bp 7626-8405), which is joined to the RuBisCo small subunit terminator (Bp 8406-8956).

Flue-cured tobacco will be transformed with the construct shown in FIG. 25 using *Agrobacterium*-mediated, Transbacter-mediated, or biolistic transformation and independent lines will be selected, regenerated, and transplanted in the greenhouse. Most of the independent lines grown in the greenhouse will be harvested and tested for alkaloid and sterol content. It is expected that approximately 50% of the lines tested will have less than 1,000 ppm total alkaloid and a reduced amount of sterols, as compared to the parental strain of tobacco, and approximately 10% of the lines tested will have less than 500 ppm total alkaloid and a reduced amount of sterols, as compared to the parental strain of tobacco. Accordingly, it is expected that the transgenic Flue-cured tobacco that will be created using the construct shown in FIG. 25 will have significantly reduced levels of nicotine, TSNA, sterol, and will generate significantly less PAHs upon pyrolysis, as compared to a conventional tobacco, a reference tobacco, or the parental strain of tobacco prior to genetic modification.

Burley tobacco will be transformed with the construct shown in FIG. 25 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid and sterol content. It is expected that approximately 50% of the lines tested will have less than 1,000 ppm total alkaloid and a reduced amount of sterols, as compared to the parental strain of tobacco, and approximately 10% of the lines tested will have less than 500 ppm total alkaloid and a reduced amount of sterols, as compared to the parental strain of tobacco. Accordingly, it is expected that the transgenic Burley tobacco that will be created using the construct shown in FIG. 25 will have significantly reduced levels of nicotine, TSNA, sterol, and will generate significantly less PAHs upon pyrolysis, as compared to a conventional tobacco, a reference tobacco, or the parental strain of tobacco prior to genetic modification.

Oriental tobacco will be transformed with the construct shown in FIG. 25 using *Agrobacterium*-mediated, Transbacter-mediated, or biolistic transformation and independent lines will be selected, regenerated, and transplanted in the greenhouse. Most of the independent lines grown in the greenhouse will be harvested and tested for alkaloid and sterol content. It is expected that approximately 50% of the lines tested will have less than 1,000 ppm total alkaloid and a reduced amount of sterols, as compared to the parental strain of tobacco, and approximately 10% of the lines tested will have less than 500 ppm total alkaloid and a reduced amount of sterols, as compared to the parental strain of tobacco. Accordingly, it is expected that the transgenic Oriental tobacco that will be created using the construct shown in FIG. 25 will have significantly reduced levels of nicotine, TSNA, sterol, and will generate significantly less PAHs upon pyrolysis, as compared to a conventional tobacco, a reference tobacco, or the parental strain of tobacco prior to genetic modification.

It should be emphasized that other promoters and terminators can be used with the nucleic acids of the invention interchangeably. Although RD2 (SEQ. ID. No. 13) is a preferred root-specific promoter, there are other root-specific promoters that can be used, as well. For example, the putrescene methyl transferase 1 promoter (PMT-1) (SEQ. ID. No. 14) is a root-specific promoter that can be used in place of the RD2 promoter in any of the constructs described above. Similarly, although the actin2 promoter (SEQ. ID. No. 16) is preferred for driving expression of a norflurazone resistance gene, other constitutive promoters such as the GapC promoter (SEQ. ID. No. 15), the tobacco alcohol dehydrogenase (ADP) (SEQ. ID. No. 17) and the *Arabidopsis* ribosomal protein L2 (RPL2P) (SEQ. ID. No. 18) can be used to drive expression of the norflurazone resistance gene. Additionally, developmentally regulatable promoters such as, cinnamyl alcohol dehydrogenase (SEQ. ID. No. 19) and metallothionein I promoter (SEQ. ID. No. 20) can be used interchangeable with the cassettes described herein.

Further, in some embodiments, a plurality of constitutive promoters, in tandem, can be used to drive expression of the norflurazone resistance gene. Additionally, a plurality of root-specific promoters can be used to drive expression one or more of the inhibition cassettes described above (e.g., the QTPase inhibition cassette, the PMTase inhibition cassette, the A622 inhibition cassette, a sterol inhibition cassette, or a double-knockout inhibition cassette). Developmentally regulatable promoters, a plurality of developmentally regulated promoters, constitutive promoters, or a plurality of constitutive promoters can also be used to drive expression of one or more of the inhibition or selection cassettes described above. Accordingly, any promoter operable in tobacco can be used to drive expression of any of the inhibition cassettes or the selection cassette described herein (e.g., nos, 35S, or CAMV). Terminators, such as GAD2 terminator (SEQ. ID. No. 21) and the FAD 2 (SEQ. ID. No. 22) or PAP1 introns can be used interchangeably, as well.

Other aspects of the invention concern the discovery of several mutants of the phytoene desaturase gene that confer resistance to the herbicide norflurazone (e.g., SEQ. ID. Nos.10, 11, and 12). These herbicide resistance genes were used as selectable markers in the transformations above. Typically, the selection was accomplished by introducing the transformed plant tissue to the norflurazone (e.g., 0.005 uM-0.1 uM conc.). That is, the concentration of norflurazone that can be used to select positive transformants containing a norflurazone resistance gene, as described herein can be at least, less than, greater than, or equal to 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0 uM. Preferably, less than or equal to 0.05 uM concentration of norflurazone is used when selecting transformants with Flue-cured tobacco and less than or equal to 0.0125 uM concentration norflurazone is used when selecting transformants with Burley tobacco. As the plantlet develops, selection was accomplished by differentiating the green shoots (positive transformants) from the yellow or white shoots (negative transformants). Once selection was made, the herbicide was removed and the plantlet was allowed to develop in the greenhouse.

The norflurazone resistant phytoene desaturase mutants (PDSM-1, PDSM-2, and PDSM-3) were generated by site-directed mutagenesis of particular regions of the gene believed to be involved in binding of the herbicide. Constructs carrying the various PDSM genes were then transferred to tobacco leaf disks by conventional *Agrobacterium* transformation and the resistance to norflurazone was analyzed at various concentrations. After several iterations, the mutants described as SEQ. ID. Nos. 10, 11, and 12, were identified as sequences that confer resistance to norflurazone. Accordingly, aspects of the invention concern the PDSM genes described herein, their use in plants as selectable markers to identify plant cells that contain a transformed gene, whether in tissue culture or in the field, and methods of identifying new PDSM genes that confer norflurazone resistance.

In a first selection construct, the *Arabidopsis* phytoene desaturase gene (PDS) (SEQ. ID. No. 36) was mutated using site-directed mutagenesis, such that a T to G mutation at position 1478, resulting in a Valine to Glycine change at amino acid residue 493 was created. To generate the norflurazone resistance gene, the open reading frame of the *Arabidopsis* phytoene desaturase gene was amplified and cloned into the TOPO vector (Invitrogen). A single base pair change from T-G at nucleotide position 1478, leading to a Valine to Glycine change at amino acid residue 493, was introduced using QuickChange Site-directed Mutagenisis Kit (Stratgene). The point mutation was verified by sequencing and the resultant mutant was named PDSM-1 (SEQ. ID. No. 10). The 1.729 Kb PDSM1 sequence was then amplified and ligated into the binary vector pWJ001, a pCambia derivative that contained the RNAi cassettes above, which was then introduced into *Agrobacterium tumefaciens*. A similar approach was used to generate the PDSM-2 and PDSM-3 mutants described in the sequence listing as SEQ. ID. NOs.11 and 12.

That is, in a second selection construct, the *Arabidopsis* phytoene desaturase gene (PDS) (SEQ. ID. No. 36) was mutated using site-directed mutagenesis, such that a G to C mutation at position 863, resulting in a Arginine to Proline change at amino acid residue 288 was created. To generate the norflurazone resistance gene, the open reading frame of the *Arabidopsis* phytoene desaturase gene was amplified and cloned into the TOPO vector (Invitrogen). A single base pair change was introduced using QuickChange Site-directed Mutagenisis Kit (Stratgene). The point mutation was verified by sequencing and the resultant mutant was named PDSM-2. The 1.729 Kb PDSM-2 sequence was then amplified and ligated into the binary vector pWJ001, a pCambia derivative that contained the RNAi cassettes above, which was then introduced into *Agrobacterium tumefaciens*

Further, in a third selection construct, the *Arabidopsis* phytoene desaturase gene (PDS) (SEQ. ID. No. 36) was mutated using site-directed mutagenesis, such that a T to C mutation at position 1226, resulting in a Leucine to Proline change at amino acid residue 409 was created. To generate the norflurazone resistance gene, the open reading frame of the *Arabidopsis* phytoene desaturase gene was amplified and cloned into the TOPO vector (Invitrogen). A single base pair change was introduced using QuickChange Site-directed Mutagenisis Kit (Stratgene). The point mutation was verified by sequencing and the resultant mutant was named PDSM-3. The 1.729 Kb PDSM-2 sequence was then amplified and ligated into the binary vector pWJ001, a pCambia derivative that contained the RNAi cassettes above, which was then introduced into *Agrobacterium tumefaciens*

Accordingly, aspects of the invention concern methods of identifying a mutation on a phytoene desaturase gene that confers resistance to an herbicide, preferably norflurazone. By one approach, a phytoene desaturase gene is provided, preferably SEQ. ID. No. 36, a nucleotide in said gene is mutated so as to generate a mutant phytoene desaturase gene, said mutant phytoene desaturase gene is transformed to a plant cell so as to generate a plant cell comprising said mutant phytoene desaturase gene, said plant cell comprising said mutant phytoene desaturase gene is then contacted with an herbicide, preferably norflurazone, and the presence or absence of a resistance to said herbicide is identified, whereby the presence of a resistance to said herbicide identifies said mutation as one that confers resistance to said herbicide. By one approach, the entire sequence of a phytoene desaturase gene (e.g., SEQ. ID. NO. 36) is mutated one residue at a time and each mutant is screened for resistance to the herbicide. Accordingly, aspects of the invention include compositions (e.g., nucleic acid constructs or cassettes, plant cells, plants, tobacco, or tobacco products) that comprise, consist, consist essentially of a mutant phytoene desaturase nucleic acid of SEQ. ID. NO. 10, 11, or 12 or fragment thereof at least or equal to 30, 50, 100, 200, 400, 500, 700, 900, 1000, 1200, 1400, 1600, or 1700 consecutive nucleotides of in length that confers resistance to an herbicide, in particular norflurazone. Aspects of the invention also include compositions (e.g., nucleic acid constructs or cassettes, plant cells, plants, tobacco, or tobacco products) comprising the mutant phytoene desaturase protein or fragments thereof (e.g., at least 15, 25, 50, 100, 200, 300, 400, 500 consecutive amino acids of a protein encoded by SEQ. ID. Nos. 10, 11, or 12) that confer resistance to an herbicide, in particular norflurazone.

The nucleic acid sequences, cassettes, and constructs described herein can also be altered by mutation such as substitutions, additions, or deletions that provide for sequences encoding functionally equivalent molecules. Due to the degeneracy of nucleotide coding sequences, other DNA sequences that encode substantially the same amino acid sequence can be used in some embodiments of the present invention. These include, but are not limited to, nucleic acid sequences comprising all or portions of the nucleic acid embodiments described herein that complement said sequences and have been altered by the substitution of different codons that encode a functionally equivalent amino acid residue within the sequence, thus producing a silent change. In some contexts, the phrase "substantial sequence similarity" in the present specification and claims means that DNA, RNA or amino acid sequences which have slight and non-consequential sequence variations from the actual sequences disclosed and claimed herein are considered to be equivalent to the sequences of the present invention. In this regard, "slight and non-consequential sequence variations" mean that "similar" sequences (i.e., the sequences that have substantial sequence similarity with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

Additional nucleic acid embodiments include sequences that are at least 80%, 81%, 82%, 83%, 84%, 85%, 86%, 87%, 88%, 89%, 90%, 91%, 92%, 93%, 94%, 95%, 96%, 97%, 98%, 99%, and 100% identical to the nucleic acids, nucleic acid constructs, and nucleic acid cassettes provided herein. Preferably these sequences also perform the functions of the particular nucleic acid embodiment (e.g., inhibition of nicotine, nornicotine, or sterol production or confer resistance to norflurazone). Determinations of sequence similarity are made with the two sequences aligned for maximum matching; gaps in either of the two sequences being matched are allowed in maximizing matching. Gap lengths of 10 or less are preferred, gap lengths of 5 or less are more preferred, and gap lengths of 2 or less still more preferred.

Additional nucleic acid embodiments also include nucleic acids that hybridize to the nucleic acid sequences disclosed herein under low, medium, and high stringency, wherein said additional nucleic acid embodiments also perform the function of the particular embodiment (e.g., inhibit nicotine, nornicotine, or sterol production or confer resistance to norflurazone). Identification of nucleic acids that hybridize to the embodiments described herein can be determined in a routine manner. (See J. Sambrook et al., Molecular Cloning, A Laboratory Manual (2d Ed. 1989) (Cold Spring Harbor Laboratory)). For example, hybridization of such sequences may be carried out under conditions of reduced stringency or even stringent conditions (e.g., conditions represented by a wash stringency of 0.3 M NaCl, 0.03 M sodium citrate, 0.1% SDS at 60 degrees C., or even 70 degrees C.). Preferably these sequences also perform the functions of the particular nucleic acid embodiment (e.g., inhibition of nicotine, nornicotine, or sterol production or confer resistance to norflurazone).

Accordingly aspects of the invention also include compositions comprising, consisting of, or consisting essentially of: (a) the nucleic acid sequences shown in the sequence listing (SEQ. ID. NOS. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36); (b) nucleotide sequences encoding the amino acid sequences encoded by the nucleic acids of the sequence listing (SEQ. ID. NOS. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36); (c) any nucleotide sequences that hybridizes to the complement of the sequences shown in the sequence listing (SEQ. ID. NOS. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) under stringent conditions, e.g., hybridization to filter-bound DNA in 0.5 M NaHPO4, 7.0% sodium dodecyl sulfate (SDS), 1 mM EDTA at 50 degrees C. and washing in 0.2.times.SSC/0.2% SDS at 50 degrees C.; and (d) any nucleotide sequence that hybridizes to the complement of the sequences shown in the sequence listing (SEQ. ID. NOS. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) under less stringent conditions (e.g., hybridization in 0.5 M NaHPO4, 7.0% sodium dodecyl sulfate (SDS), 1 mM EDTA at 37 degrees C. and washing in 0.2.times.SSC/0.2% SDS at 37 degrees C. Preferably these sequences also perform the functions of the particular nucleic acid embodiment (e.g., inhibition of nicotine, nornicotine, or sterol production or confer resistance to norflurazone). Aspects of the invention also include peptides encoded by the nucleic acid sequences of (a), (b), (c), or (d), above.

The examples described herein demonstrate that several different RNAi constructs can be used to effectively reduce the levels of nicotine, nornicotine, and sterols in tobacco. Additionally, these examples demonstrate that several mutant phytoene desaturase genes, which confer resistance to the herbicide norflurazone, have been created and that selection cassettes comprising these herbicide resistant nucleic acids can be used to determine the presence of a linked gene in transformed tobacco cells. Additionally, the norflurazone resistance nucleic acids described herein can be used in a general sense (e.g., in plants other than tobacco) to efficiently select positively transformed plant cells from plant cells that do not contain a construct comprising the norflurazone resistance gene. Thus, the norflurazone selection cassette or the norflurazone resistance gene described herein can be used to confer resistance to norflurazone in plants including, but not limited to, corn (*Zea mays*), canola (*Brassica napus, Brassica rapa* ssp.), alfalfa (*Medicago saliva*), rice (*Orya sativa*), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), duckweed (*Lemna*), oats, barley, vegetables, ornamentals, conifers, and turfgrasses (e.g., for ornamental, recreational or forage purposes). Vegetables include *Solanaceous* species (e.g., tomatoes; *Lycopersicon esculentum*), lettuce (e.g., *Lactuea sativa*), carrots (*Caucuis carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as Hubbard squash (*C. Hubbard*), Butternut squash (*C. moschtata*), Zucchini (*C. pepo*), Crookneck squash (*C. crookneck*), *C. argyrosperma, C. argyrosperma* ssp, *C. digitata, C. ecuadorensis, C. foetidissima, C. lundelliana*, and *C. martinezii*, and members of the genus *Cucumis* such as cucumber (*Cucumis sativus*), cantaloupe (*C. cantalupensis*), and musk melon (*C. melo*). Ornamental plants include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and chrysanthemum. Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies ainabilis*) and balsam fir (*Abies balsamea*); and cedars such as Western red cedar (*Thuja plicata*) and Alaska yellow-cedar (*Chamaecyparis nootkatensis*). Turf grass include but are not limited to zoysia grasses, bentgrasses, fescue grasses, bluegrasses, St. Augustine grasses, Bermuda grasses, buffalo grasses, ryegrasses, and orchard grasses. Also included are plants that serve primarily as laboratory models, e.g., *Arabidopsis*. Preferred plants for use in the present methods include (but are not limited to) legumes, solanaceous species (e.g., tomatoes), leafy vegetables such as lettuce and cabbage, turf grasses, and crop plants (e.g., tobacco, wheat, sorghum, barley, rye, rice, corn, soybean, cotton, cassaya, and the like), and laboratory plants (e.g., *Arabidopsis*). While any plant may be used to carry out this aspect of the invention, tobacco plants are particularly preferred.

Further, aspects of the invention concern the production of norflurazone-resistant or tolerant plants, which can be sprayed with the herbicide in the field. In this manner, weeds and non-transformed plants will die after contact with the herbicide but plants containing the construct harboring the norflurazone resistance gene will survive. In one embodiment, for example, a norflurazone-containing herbicide is applied to the plant comprising the DNA constructs of the present invention, and the plants are evaluated for tolerance to the herbicide. Any formulation of norflurazone can be used for testing plants comprising the DNA constructs of the present invention. The testing parameters for an evaluation of the norflurazone tolerance of the plant will vary depending on a number of factors. Factors would include, but are not limited to the type of norflurazone formulation, the concentration and amount of norflurazone used in the formulation, the type of plant, the plant developmental stage during the time of the application, environmental conditions, the application method, and the number of times a particular formulation is applied. For example, plants can be tested in a greenhouse environment using a spray application method. The testing range using norflurazone. can include, but is not limited to 0.5 oz/acre to 500 oz/acre. That is, the amount of herbicide that can be applied to transgenic plants containing a norflurazone-resistance gene in a field can be less than, equal to, or more than 0.5, 0.6, 0.7, 0.8, 0.9. 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, or 500 oz/acre. In some embodiments, the norflurazone application rate is 2.24 kg to 4.48 kg ai/hectare (2 to 4 lbs ai/acre) or 2.8 to 5.6 kg granules/hectare (2.5 to 5 lb/acre) or 234 L/hectare (25 gal/acre) in solution. Higher amounts are preferred for finer textured soils or when longer residual activity is desired.

The preferred commercially effective range can be from 25 oz/acre to 100 oz/acre of norflurazone, depending on the crop and stage of plant development. A crop can be sprayed with at least one application of a norflurazone. For testing in cotton an application of 32 oz/acre at the 3-leaf stage may be followed by additional applications at later stages in development. For wheat, corn, soybean, and tobacco an application of 32 oz/acre of norflurazone. at the 3-5 leaf stage can be used. The test parameters can be optimized for each crop in order to find the particular plant comprising the constructs of the present invention that confers the desired commercially effective norflurazone tolerance level. The section below describes typical curing methods which may be used to prepare the tobacco once it is harvested.

Curing

The curing process, which typically lasts about 1 week, brings out the flavor and aroma of tobacco. Several methods for curing tobacco may be used, and indeed many methods have been previously disclosed. For example, U.S. Pat. No. 4,499,911 to Johnson; U.S. Pat. No. 5,685,710 to Martinez Sagrera; U.S. Pat. No. 3,905,123 to Fowler; U.S. Pat. No. 3,840,025 to Fowler; and U.S. Pat. No. 4,192,323 to Home describe aspects of the tobacco curing process which may be used for some embodiments of the present invention. Conventionally, "sticks" that are loaded with tobacco are placed into bulk containers and placed into closed buildings having a heat source known as a curing barn. A flue is often used to control the smoke (thus earning the term "flue-cured"). The method of curing will depend, in some cases, on the type of tobacco-use cessation product desired, (i.e., snuff, cigarettes, or pipe tobacco may preferably utilize different curing methods) and preferred methods may vary from region to region and in different countries. In some approaches, the stems and midveins of the leaf are removed from the leaves prior to curing to yield a high quality, low nitrosamine tobacco product.

"Flue curing" is a popular method for curing tobacco in Virginia, North Carolina, and the Coastal Plains regions of the United States. This method is used mainly in the manufacture of cigarettes. Flue curing requires a closed building equipped with a system of ventilation and a source of heat. The heating can be direct or indirect (e.g., radiant heat). When heat and humidity are controlled, leaf color changes, moisture is quickly removed, and the leaf and stems dry. Careful monitoring of the heating and humidity can reduce the accumulation of nitrosamines.

Another curing method is termed "air curing". In this method, an open framework is prepared in which sticks of leaves (or whole plants) are hung so as to be protected from both wind and sun. Leaf color changes from green to yellow, as leaves and stems dry slowly.

"Fire curing" employs an enclosed barn similar to that used for flue curing. The tobacco is hung over low temperature fire so that the leaves cure in a smoke-laden atmosphere. This process uses lower temperatures, so the process may take up to a month, in contrast to flue curing, which takes about 6 to 8 days.

A further curing method, termed "sun curing" is the drying of uncovered sticks or strings of tobacco leaves in the sun. The best known sun-cured tobaccos are the so-called oriental tobaccos of Turkey, Greece, Yugoslavia, and nearby countries.

The curing process, and most particularly the flue-curing process, is generally divided into the following four stages:

A) Firing Up: During this step, the tobacco leaves turn bright lemon-orange in color. This is achieved by a gradual increase in temperature.

B) Leaf Yellowing: In this step any moisture is removed. This creates the "yellowing" of the tobacco. It also prepares the tobacco for drying in the next step.

C) Leaf Driving: Leaf drying, an important step in the curing process, requires much time for the tobacco to dry properly. Additionally, air flow is increased in this step to facilitate the drying process.

D) Stem Drying: The drying process continues, as the stem of the tobacco leaf becomes dried.

The cured tobacco may then be blended with other tobaccos or other materials to create the product to be used for the tobacco-use cessation method. The section below describes typical methods of blending and preparing a tobacco product of the invention.

Tobacco Blending

It may be desirable to blend tobacco of varying nicotine levels to create the cessation product having the desired level of nicotine. This blending process is typically performed after the curing process, and may be performed by conventional methods. Preferred tobacco blending approaches are provided below. In some embodiments, blending of the transgenic tobacco is conducted to prepare the tobacco so that it will contain specific amounts of nicotine, nornicotine, sterol and/or TSNA in specific products. Preferably, the blending is conducted so that tobacco products of varying amounts of nicotine are made in specific products.

A mixture that contains different types of tobacco is desirably substantially homogeneous throughout in order to avoid undesirable fluctuations in taste or nicotine levels. Typically, tobacco to be blended may have a moisture content between 30 and 75%. As an example, the tobacco is first cut or shredded to a suitable size, then mixed in a mixing device, such as a rotating drum or a blending box. One such known mixing device is a tumbling apparatus that typically comprises a rotating housing enclosing mixing paddles which are attached to and, therefore, rotate with the housing to stir the tobacco components together in a tumbling action as the drum turns.

After the desired tobaccos are thoroughly mixed, the resulting tobacco blend is removed from the mixing apparatus and bulked to provide a continuous, generally uniform quantity of the tobacco blend. The tobacco is then allowed to remain relatively undisturbed (termed the "bulking step") for the required period of time before subsequent operations are performed. The bulking step typically takes 30 minutes or less, and may be carried out on a conveyor belt. The conveyor belt allows the blended tobacco to remain in bulk form in an undisturbed condition while it is continuously moving the tobacco blend through the process from the mixing stage to the expansion stage.

The tobacco blend is typically expanded by the application of steam. The tobacco mixture is typically subjected to at least 0.25 pounds of saturated steam at atmospheric conditions per pound of blended tobacco for at least 10 seconds to provide an increase in moisture of at least 2 weight percent to the tobacco blend. After the tobacco blend has been expanded, it is dried. A typical drying apparatus uses heated air or superheated steam to dry the tobacco as the tobacco is conveyed by the heated air or steam stream through a drying chamber or series of drying chambers. Generally, the wet bulb temperature of the drying air may be from about 150 degrees F. to about 211 degrees F. The tobacco blend is typically dried to a moisture content of from about 60 percent to about 5 percent. The dried, expanded tobacco blend is then in a suitable mode to be processed into the tobacco-use cessation product as described below.

Some blending approaches begin with tobacco prepared from varieties that have extremely low amounts of nicotine, nornicotine, sterols and/or TSNAs. By blending prepared tobacco from a low nicotine/TSNA variety (e.g., undetectable levels of nicotine and/or TSNAs) with a conventional tobacco (e.g., Burley, which has 30,000 parts per million (ppm) nicotine and 8,000 parts per billion (ppb) TSNA; Flue-Cured, which has 20,000 ppm nicotine and 300 ppb TSNA; and Oriental, which has 10,000 ppm nicotine and 100 ppb TSNA), tobacco products having virtually any desired amount of nicotine and/or TSNAs can be manufactured. Other approaches blend only low nicotine/TSNA tobaccos (e.g., genetically modified Burley, genetically modified Virginia flue, and genetically modified Oriental tobaccos that contain reduced amounts of nicotine and/or TSNAs) and/or low sterol tobaccos (e.g., Burley, Flue-cured, and Oriental). Tobacco products having various amounts of nicotine and/or TSNAs can be incorporated into tobacco-use cessation kits and programs to help tobacco users reduce or eliminate their dependence on nicotine and reduce the carcinogenic potential.

By one approach, a step 1 tobacco product is comprised of approximately 25% low nicotine/TSNA tobacco and 75% conventional tobacco; a step 2 tobacco product can be comprised of approximately 50% low nicotine/TSNA tobacco and 50% conventional tobacco; a step 3 tobacco product can be comprised of approximately 75% low nicotine/TSNA tobacco and 25% conventional tobacco; and a step 4 tobacco product can be comprised of approximately 100% low nicotine/TSNA tobacco and 0% conventional tobacco. A tobacco-use cessation kit can comprise an amount of tobacco product from each of the aforementioned blends to satisfy a consumer for a single month program. That is, if the consumer is a one pack per day smoker, for example, a single month kit would provide 7 packs from each step, a total of 28 packs of cigarettes. Each tobacco-use cessation kit would include a set of instructions that specifically guide the consumer through the step-by-step process. Of course, tobacco products having specific amounts of nicotine and/or TSNAs would be made available in conveniently sized amounts (e.g., boxes of cigars, packs of cigarettes, tins of snuff, and pouches or twists of chew) so that consumers could select the amount of nicotine and/or TSNA they individually desire. There are many ways to obtain various low nicotine/low TSNA tobacco blends using the teachings described herein and the following is intended merely to guide one of skill in the art to one possible approach.

To obtain a step 1 tobacco product, which is a 25% low nicotine/TSNA blend, prepared tobacco from an approximately 0 ppm nicotine/TSNA tobacco can be mixed with conventional Burley, Flue-cured, or Oriental in a 25%/75% ratio respectively to obtain a Burly tobacco product having 22,500 ppm nicotine and 6,000 ppb TSNA, a Flue-cured product having 15,000 ppm nicotine and 225 ppb TSNA, and an Oriental product having 7,500 ppm nicotine and 75 ppb TSNA. Similarly, to obtain a step 2 product, which is 50% low nicotine/TSNA blend, prepared tobacco from an approximately 0 ppm nicotine/TSNA tobacco can be mixed with conventional Burley, Flue-cured, or Oriental in a 50%/50% ratio respectively to obtain a Burly tobacco product having 15,000 ppm nicotine and 4,000 ppb TSNA, a Flue-cured product having 10,000 ppm nicotine and 150 ppb TSNA, and an Oriental product having 5000 ppm nicotine and 50 ppb TSNA. Further, a step 3 product, which is a 75%/25% low nicotine/TSNA blend, prepared tobacco from an approximately 0 ppm nicotine/TSNA tobacco can be mixed with conventional Burley, Flue-cured, or Oriental in a 75%/25% ratio respectively to obtain a Burly tobacco product having 7,500 ppm nicotine and 2,000 ppb TSNA, a Flue-cured product having 5,000 ppm nicotine and 75 ppb TSNA, and an Oriental product having 2,500 ppm nicotine and 25 ppb TSNA.

By a preferred method, conventional Virginia flue tobacco was blended with genetically modified Burley (i.e., Burley containing a significantly reduced amount of nicotine and nitrosamine) to yield a blended tobacco that was incorporated into three levels of reduced nicotine cigarettes: a step 1 cigarette containing 0.6 mg nicotine, a step 2 cigarette containing 0.3 mg nicotine, and a step 3 cigarette containing less than 0.05 mg nicotine. The amount of total TSNA was found to range between approximately 0.17 μg/g-0.6 μg/g.

In some cigarettes, approximately, 28% of the blend was Virginia flue tobacco, approximately 29% of the blend was genetically modified (i.e., reduced nicotine Burley), approximately 14% of the blend was Oriental, approximately 17% of the blend was expanded flue-cured stem, and approximately 12% was standard commercial reconstituted tobacco. The amount of total TSNAs in cigarettes containing this blend was approximately 1.5 μg/g.

It should be appreciated that tobacco products are often a blend of many different types of tobaccos, which were grown in many different parts of the world under various growing conditions. As a result, the amount of nicotine and TSNAs will differ from crop to crop. Nevertheless, by using conventional techniques one can easily determine an average amount of nicotine and TSNA per crop used to create a desired blend. By adjusting the amount of each type of tobacco that makes up the blend one of skill can balance the amount of nicotine and/or TSNA with other considerations such as appearance, flavor, and smokability. In this manner, a variety of types of tobacco products having varying level of nicotine and/or nitrosamine, as well as, appearance, flavor and smokability can be created.

Nicotine Reduction and/or Tobacco-Use Cessation Programs Methods

It is also contemplated that the low nicotine and/or TSNA tobacco described herein can be processed and blended with conventional tobacco so as to create a wide-range of tobacco products with varying amounts of nicotine and/or nitrosamines. These blended tobacco products can be used in nicotine reduction and/or tobacco-use cessation programs so as to move a consumer from a high nicotine and TSNA product to a low nicotine and TSNA product.

In some embodiments of the invention, a stepwise nicotine reduction and/or tobacco-use cessation program can be established using the low nicotine, low TSNA products described above. As an example, the program participant initially determines his or her current level of nicotine intake. The program participant then begins the program at step 1, with a tobacco product having a reduced amount of nicotine, as compared to the tobacco product that was used prior to beginning the program. After a period of time, the program participant proceeds to step 2, using a tobacco product with less nicotine than the products used in step 1. The program participant, after another period of time, reaches step 3, wherein the program participant begins using a tobacco product with less nicotine than the products in step 2, and so on. Ultimately, the program participant uses a tobacco product having an amount of nicotine that is less than that which is sufficient to become addictive or to maintain an addiction. Thus, the nicotine reduction and/or tobacco-use cessation program limits the exposure of a program participant to nicotine and, concomitantly, the harmful effect of nicotine yet retains the secondary factors of addiction, including but not limited to, smoke intake, oral fixation, and taste.

For example, a smoker can begin the program smoking blended cigarettes having 5 mg of nicotine and 1.5 μg of nitrosamine, gradually move to smoking cigarettes with 3 mg of nicotine and 1 μg of nitrosamine, followed by cigarettes having 1 mg nicotine and 0.5 μg nitrosamine, followed by cigarettes having 0.5 mg nicotine and 0.25 μg nitrosamine, followed by cigarettes having less than 0.1 mg nicotine and less than 0.1 g TSNA until the consumer decides to smoke only the cigarettes having virtually no nicotine and nitrosamines or quitting smoking altogether. Preferably, a three-step program is followed whereby at step 1, cigarettes containing 0.6 mg nicotine and less than 2 μg/g TSNA are used; at step 2, cigarettes containing 0.3 mg nicotine and less than 1 μg/g TSNA are used; and at step 3, cigarettes containing less than 0.1 mg nicotine and less than 0.7 μg/g TSNA are used. More preferably, a three-step program is followed whereby at step 1, cigarettes containing 0.6 mg nicotine and less than 2 μg/g TSNA are used; at step 2, cigarettes containing 0.3 mg nicotine and less than 1 μg/g TSNA are used; and at step 3, cigarettes containing less than 0.05 mg nicotine and less than 0.7 μg/g TSNA are used. Accordingly, the blended cigarettes described herein provide the basis for an approach to reduce the carcinogenic potential in a human in a step-wise fashion.

The methods described herein facilitate tobacco-use cessation by allowing the individual to retain the secondary factors of addiction such as smoke intake, oral fixation, and taste, while gradually reducing the addictive nicotine levels consumed. Eventually, complete cessation is made possible because the presence of addiction for nicotine is gradually decreased while the individual is allowed to maintain dependence on the secondary factors, above.

Embodiments, for example, include stepwise blends of tobacco products, which are prepared with a variety of amounts of nicotine. These stepwise blends are made to have reduced levels of TSNAs and varying amounts of nicotine. As an example, cigarettes may contain, for example, 5 mg, 4, 3, 2, 1, 0.5, 0.1, or 0 mg of nicotine per cigarette. More preferably, blended cigarettes contain less than 0.01%, 0.02%, 0.03%, 0.04%, 0.05%, 0.06%, 0.07%, 0.08%, 0.09%, 0.1%, 0.2%, 0.3%, 0.4%, 0.5%, and 0.6% nicotine.

In another aspect of the invention, the cigarettes of varying levels of nicotine are packaged to clearly indicate the level of nicotine present, and marketed as a smoking cessation program. A preferred approach to produce a product for nicotine reduction and/or tobacco-use cessation program is provided below. Individuals may wish to step up the program by skipping gradation levels of nicotine per cigarette or staying at certain steps until ready to proceed to the next level. Significantly, aspects of the invention allow a consumer to individually select the amount of nicotine that is ingested by selection of a particular tobacco product described herein. Furthermore, because the secondary factors of addiction are maintained, dependence on nicotine can be reduced rapidly.

As an example, Virginia flue tobacco was blended with genetically modified Burley (i.e., Burley containing a significantly reduced amount of nicotine and nitrosamine) to yield a blended tobacco that was incorporated into three levels of reduced nicotine cigarettes: a step 1 cigarette containing 0.6 mg nicotine, a step 2 cigarette containing 0.3 mg nicotine, and a step 3 cigarette containing less than 0.05 mg nicotine. The stepwise packs of cigarettes are clearly marked as to their nicotine content, and the step in the stepwise nicotine reduction program is also clearly marked on the package. Each week, the user purchases packs containing cigarettes having the next lower level of nicotine, but limits himself to no more cigarettes per day than consumed previously. The user may define his/her own rate of nicotine reduction and/or smoking cessation according to individual needs by choosing a) the number of cigarettes smoked per day b) the starting nicotine levels c) the change in nicotine level per cigarette each week, and d) the final level of nicotine consumed per day. To keep better track of the program, the individual keeps a daily record of total nicotine intake, as well as the number of cigarettes consumed per day. Eventually, the individual will be consuming tobacco products with essentially no nicotine. Since the nicotine-free tobacco products of the final step are non-addictive, it should then be much easier to quit the use of the tobacco products altogether The nicotine reduction and/or tobacco-use cessation program limits the exposure of a program participant to nicotine while retaining the secondary factors of addiction. These secondary factors include but are not limited to, smoke intake, oral fixation, and taste. Because the secondary factors are still present, the program participant may be more likely to be successful in the nicotine reduction and/or tobacco-use cessation program than in programs that rely on supplying the program participant with nicotine but remove the above-mentioned secondary factors. Ultimately, the program participant uses a tobacco product having an amount of nicotine that is less than that which is sufficient to become addictive.

In another aspect of the invention, individuals would choose to obtain only cigarettes with less than 0.05 mg nicotine per cigarette. Some individuals, such as individuals needing to stop nicotine intake immediately (for example, individuals with medical conditions or individuals using drugs that interact with nicotine) may find this method useful. For some individuals, the mere presence of a cigarette in the mouth can be enough to ease withdrawal from nicotine addiction. Gradually, the addictive properties of smoking can decrease since there is no nicotine in the cigarettes. These individuals are then able to quit smoking entirely. More discussion on Smoking Cessation Programs that use reduced nicotine tobacco can be found in PCT/US2004/01695, which designates the United States and was published in English, hereby expressly incorporated by reference in its entirety.

In another aspect of the invention, packs of cigarettes containing the gradations of nicotine levels are provided as a "smoking cessation kit." An individual who wishes to quit smoking can buy the entire kit of cigarettes at the beginning of the program. Thus any temptation that may occur while buying cigarettes at the cigarette counter is avoided. Thus, the success of this method may be more likely for some individuals. A preferred example of such a kit is provided below.

Various nicotine reduction and/or smoking cessation kits are prepared, geared to heavy, medium, or light smokers. The kits provide all of the materials needed to quit smoking in either a two-week period (fast), a one-month period (medium) or in a two-month period (slow), depending on the kit. Each kit contains a set number of packs of cigarettes modified according the present invention, containing either step 1 cigarettes containing 0.6 mg nicotine, step 2 cigarettes containing 0.3 mg nicotine, and step 3 cigarettes containing less than 0.05 mg nicotine. For example, 1 pack a day smokers would receive 7 packs of cigarettes, each pack containing the above amounts of nicotine per each cigarette. Several weeks worth of additional cigarettes containing less than 0.05 mg nicotine/cigarette would also be provided in the kit, to familiarize the consumer with smoking no nicotine cigarettes. The kit would also contain a diary for keeping track of daily nicotine intake, motivational literature to keep the individual interested in continuing the cessation program, health information on the benefits of smoking cessation, and web site addresses to find additional anti-smoking information, such as chat groups, meetings, newsletters, recent publications, and other pertinent links. The table below describes the sequences referred to in the present disclosure.

SEQUENCES

```
Artificial Peptide (Caspase-3 binding peptide)
                                                   (SEQ ID No. 1)
DEVD

Nicotiana tabacum QPTase coding sequence
                                                   (SEQ ID No. 2)
atgtttagag ctattccttt cactgctaca gtgcatcctt atgcaattac agctccaagg    60
ttggtggtga aaatgtcagc aatagccacc aagaatacaa gagtggagtc attagaggtg   120
aaaccaccag cacacccaac ttatgattta aaggaagtta tgaaacttgc actctctgaa   180
gatgctggga atttaggaga tgtgacttgt aaggcgacaa ttcctcttga tatggaatcc   240
gatgctcatt ttctagcaaa ggaagacggg atcatagcag gaattgcact tgctgagatg   300
atattcgcgg aagttgatcc ttcattaaag gtggagtggt atgtaaatga tggcgataaa   360
gttcataaag gcttgaaatt tggcaaagta caaggaaacg cttacaacat tgttatagct   420
gagagggttg ttctcaattt tatgcaaaga atgagtggaa tagctacact aactaaggaa   480
atggcagatg ctgcacaccc tgcttacatg ttggagacta ggaaaactgc tcctggatta   540
cgtttggtgg ataaatgggc ggtattgatc ggtgggggga agaatcacag aatgggctta   600
tttgatatgg taatgataaa agacaatcac atatctgctg ctggaggtgt cggcaaagct   660
ctaaaatctg tggatcagta tttggagcaa aataaacttc aaataggggt tgaggttgaa   720
accaggacaa ttgaagaagt acgtgaggtt ctagactatg catctcaaac aaagacttcg   780
ttgactagga taatgctgga caatatggtt gttccattat ctaacggaga tattgatgta   840
tccatgctta aggaggctgt agaattgatc aatgggaggt ttgatacgga ggcttcagga   900
aatgttaccc ttgaaacagt acacaagatt ggacaaactg gtgttaccta catttctagt   960
ggtgccctga cgcattccgt gaaagcactt gacatttccc tgaagatcga tacagagctc  1020
gcccttgaag ttggaaggcg tacaaaacga gca tga

Nicotiana Tabacum QPTase inhibitory fragment
                                                   (SEQ ID No. 3)
ATGtttagagctattcctttcactgctacagtgcatccttatgcaattacagctccaaggttggtggtgaa
aatgtcagcaatagccaccaagaatacaagagtggagtcattagaggtgaaaccaccagcacacccaactt
atgatttaaaggaagttatgaaacttgcactctctgaagatgctgggaatttaggagatgtgacttgtaag
gcgacaattcctcttgatatggaatccgatgctcattttctagcaaaggaagacgggatcatagcaggaat
tgcacttgctgagatgatattcgcggaagttgatccttcattaaaggtggagtggtatgtaaatgatggcg
ataaa

Nicotiana tabacum Putrescene methyl transferase inhibitory fragment
                                                   (SEQ ID No. 4)
catttaccatctttcgccagaagtatgatcgagtctTAAtcaagtgaataatgaacactggtagtacaat
cattggaccaagatcgagtcttaatcaagtgaataaataagtgaaatgcgactattgtaggagaattctgc
agtaattatcataatttccaattcacaatcattgtaaaattctttctctgtggtgtttcgtactttaatat
aaattttcctgctgaagttttgaatcg

Nicotiana tabacum A622 inhibitory fragment
                                                   (SEQ ID No. 5)
tgatcaagtgaacatcatcaaagcaattaaagaagctggaaatatcaagagatttcttccttcagaatttg
gatttgatgtggatcatgctcgtgcaattgaaccagctgcatcactcttcgctctaaaggtaagaatcagg
aggatgatagaggcagaaggaattccatacacatatgtaatctgcaattggtttgcagatttcttcttgcc
caacttggggcagttagaggccaaaacccctcctagagacaaagttgtcatttttggcgatggaaatccca
aagcaatatatgtgaaggaagaagacatagcgacatacactatcgaagcagtagatgatccacggacattg
aataagactcttcacatgagaccacctgccaatattctatccttcaacgagatagtgtccttgtgggagga
caaaattgggaagaccctcgagaagttatatctatcagaggaagatattctccagattgtacaagagggac
```

-continued

| SEQUENCES |
|---|

ctctgccattaaggactaatttggccatatgccattcagttttgttaatggagattctgcaaactttgag
gttcagcctcctacaggtgtcgaagccactgagctatatccaaaagtgaaatacacaacc

*Nicotiana tabacum* Squalene synthase inhibitory fragment
(SEQ ID No. 6)
ccacattggggcttctgttactcaatgcttcataaggtttctcgtagctttgctctcgtcattcaacaact
tcccgtcgagcttcgtgacgccgtgtgcattttctatttggttcttcgagcacttgacactgttgaggatg
ataccagcattcccaccgatgttaaagtacctattctgatctcttttcatcagcatgtttatgatcgtgaa
tggcatttttcatgtggtacaaaagagtacaaggttctcatggaccagttccatcatgtttcaactgcttt
tctggagcttaggaaacattatcagcaggcaattgaggatattaccatgaggatgggtgcaggaatggcaa
aattcatatgcaaggaggtggaaacaactgatgattatgacgaatattgtcactatgtagctgggcttgtt
gggctaggattgt

*Nicotiana tabacum* HMG CoA reductase inhibitory fragment
(SEQ ID No. 7)
gaggctgtaaatgatggcaaagacctccatatttcagtaactatgccttctattgaggttggcacagttgg
tggtggaactcaacttgcatcacagtcagcttgcttgaacttattaggagtgaaaggtgcaaacagggagg
cagcagggtcaaatgcaaggctcttggccacaatagtagcaggttctgttcttgctggtgagttatctctc
atgtctgctatctcagcagggcagctggttaagagtcacatgaaatacaatagatctagcaaagatgttac
taagatttcctcttagtaaggaaaaagacaaatttattatcccaacatcgtgtacatcaccatcctttatg
gaccatcattattaaagaaatggattacaataaaagtaggaataaaatttttccaattaggggagcaataag
taaagggtagaccaaaaagttgaaaaagtgtaaggcattagtcatgtggagaaagatcaagaagaaaaaga
caagcaaatcaagggtggacgtggatctgtatgtagtgttgtattctttctatgaaggcatgtgaggaggt
agggtcgtatttttttctgagttcgtgtaaaaaaacctgcaaatatttggtgaagatctacgaaaggtgtt
aggtgggatggtgaccagtggggttaacttgtaattcaacatttggttaatttcattcatgcgccaaggaa
gataaccccttttttttaaataatcttttctgttgtactgtctttcgtttgtttgttaattgtgactaga
ttgtaatttagagagaaatggcatctcaaactctttatgtttgctcagaaagtttgcttttgtatatg

*Nicotiana tabacum* SMT2 inhibitory fragment
(SEQ ID No. 8)
agaagctacctgccatgcaccagatccattgggatgctataaagagatttaccgggtgctgaagcctggtc
aatgtttcgctgtgtatgagtggtgcatgaccgattcttacaaccccaataacgaagagcacaacaggatc
aaggccgaaattgagctcggaaatggcctccctgaggttagattgacaacacagtgcctcgaagcagccaa
accaagctggttttgaagttgtatgggacaaggatctggctgatgactcacctgttccatggtacttgcct
ttggatacgagtcacttctcgctcagtagcttccgcctaacagcagttggcagacttttcaccagaaatct
ggtttcggcgcttgaatacgtgggacttgctcctaaaggtagtcaaagggttcaagctttcttagagaaag
ctgcagaaggtcttgtcggtggtgccaagaaagggattttcacaccaatgtacttcttcgtggttcgcaag
cccatttcagactctcagTAAtatggagtttagtcacttagctttttgctttagctagcaaatctgtaaga
ttcttcgcacagaactttacacattgaatatgaccgccctaattaaggtgactacagtttttggagggcgt
tgtgggtggagggtttcttttctgtgttgcttgtctggcacaatttgatttcatgtcttgctatttttgc
cattgatgtccttgttctaagatatatacctattgacaagctcataaaggtgggcatttgctaatatatgg

*Nicotiana tabacum* 14alpha demethylase inhibitory fragment
(SEQ ID No. 9)
AAGAATATCACGTTCTTCGTTGGCCCAGAAGTGTCGGCCCATTTCTTTAAGGCCCCAGAAACCGATCTCAG
TCAACAAGAGGTTTATCAGTTCAATGTGCCTACTTTTGGCCCTGGTGTGGTTTTTGACGTTGATTATACTA
TCAGACAAGAGCAATTTAGGTTCTTTACTGAATCTTTGAGGGTAAATAAATTGAAGGGATATGTGGATCAG
ATGGTCATGGAAGCTGAGGAGTACTTCTCAAAATGGGGTGATAGTGGTGAAGTGGACTTGAAGTATGAACT
GGAGCATCTTATCATACTGACAGCTAGTAGATGTCTGTTGGGAGAAGAGGTTCGCAATAAACTCTTTGAGG
ATGTCTCTGCTCTCTTCCATGACCTGGACAATGGGATGCTTCCTATCAGTGTAATCTTTCCCTACCTTCCC
ATTCCAGCCCATCGCCGTCGTGACAATGCCCGCAAGAAGCTCGCGGAGATCTTTGCAAACATCATAGATTC
TAGAAAACGTACAGGCAAGGCGGAGAGCGATATGTTACAATGCTTCATTGACTCCAAGTACAAAGATGGGC
GGGCAACGACAGAGTCTGAGATCACAGGTCTTCTGATTGCTGCTCTTTTCGCTGGGCAACACACCAGTTCC
ATCACCTCCACTTGGGCAGGGGCATACCTTCTCTGCAACAACAAGTACATGTCTGCCGTCGTAGATGAACA
GAAGAATCTGATGAAGAAACATGGGAATAAGGTCGATCATGACATCCTTTCCGAGATGGAAGTCCTCTATA
GATGCATAAAGGAAGCCCTGAGACTCCATCCTCCACTGATAATGCTTCTACGTAGTCGCATAGTGATTTCA
CTGTTAAAACCAGGGAAGGAAAAGAGTATGAT

*Arab. thal.* Phytoene desaturase mutant-1 (PDSM-1)
(SEQ ID No. 10)
ATGGTTGTGTTTGGGAATGTTTCTGCGGCGAATTTGCCTTATCAAAACGGGTTTTTGGAGGCACTTTCATC
TGGAGGTTGTGAACTAATGGGACATAGCTTTAGGGTTCCCACTTCTCAAGCGCTTAAGACAAGAACAAGGA
GGAGGAGTACTGCTGGTCCTTTGCAGGTAGTTTGTGTGGATATTCCAAGGCCAGAGCTAGAGAACACTGTC
AATTTCTTGGAAGCTGCTAGTTTATCTGCATCCTTCCGTAGTGCTCCTCGTCCTGCTAAGCCTTTGAAAGT
TGTAATTGCTGGTGCTGGATTGGCTGGATTGTCAACTGCAAAGTACCTGGCTGATGCAGGCCACAAACCTC
TGTTGCTTGAAGCAAGAGATGTTCTTGGTGGAAAGATAGCTGCATGGAAGGATGAAGATGGGGACTGGTAT
GAGACTGGTTTACATATTTTCTTCGGTGCTTATCCGAATGTGCAGAATTTATTTGGAGAACTTGGGATCAA
TGATCGGTTGCAGTGGAAGGAACACTCCATGATTTTTGCTATGCCAAGTAAACCTGGAGAATTTAGTAGAT
TTGACTTCCCAGATGTCCTACCAGCACCCTTAAATGGTATTTGGGCTATTTTGCGGAACAACGAGATGCTG
ACATGGCCAGAGAAAATAAAGTTTGCTATTGGACTTTTGCCAGCCATGGTCGGCGGTCAGGCTTATGTTGA
GGCCCAAGATGGTTTATCAGTCAAAGAATGGATGGAAAAGCAGGGAGTACCTGAGCGCGTGACCGACGAGG
TGTTTATTGCCATGTCAAAGGCGCTAAACTTTATAAACCCTGATGAACTGTCAATGCAATGCATTTTGATA
GCTTTGAACCGGTTTCTTCAGGAAAAACATGGTTCCAAGATGGCATTCTTGGATGGTAATCCTCCGGAAAG
GCTTTGTATGCCAGTAGTGGATCATATTCGATCACTAGGTGGGGAAGTGCAACTTAATTCTAGGATAAAGA
AAATTGAGCTCAATGACGATGGCACGGTTAAGAGTTTCTTACTCACTAATGGAAGCACTGTCGAAGGAGAC
GCTTATGTGTTTGCCGCTCCAGTCGATATCCTGAAGCTCCTTTTACCAGATCCCTGGAAAGAAATACCGTA
CTTCAAGAAATTGGATAAATTAGTTGGAGTACCAGTTATTAATGTTCATATATGGTTTGATCGAAAACTGA -continued

SEQUENCES

AGAACACATATGATCACCTACTCTTTAGCAGAAGTAACCTTCTGAGCGTGTATGCCGACATGTCCTTAACT
TGTAAGGAATATTACGATCCTAACCGGTCAATGCTGGAGCTAGTATTTGCACCAGCAGAGGAATGGATATC
ACGGACTGATTCTGACATCATAGATGCAACAATGAAAGAACTTGAGAAACTCTTCCCTGATGAAATCTCAG
CTGACCAAAGCAAAGCTAAAATTCTGAAGTACCATGTCGTTAAGACTCCAAGATCTGGGTACAAGACCATC
CCAAACTGTGAACCATGTCGTCCTCTACAAAGATCACCTATTGAAGGATTCTACTTAGCTGGAGATTACAC
AAAACAGAAGTACTTAGCTTCCATGGAAGGCGCTGTCCTCTCTGGCAAATTCTGCTCTCAGTCTATTGTTC
AGGATTACGAGCTACTGGCTGCGTCTGGACCAAGAAAGTTGTCGGAGGCAACAGTATCATCATCATGA

*Arab. Thal.* Phytoene desaturase mutant-2 (PD SM-2)

(SEQ. ID. No. 11)

ATGGTTGTGTTTGGGAATGTTTCTGCGGCGAATTTGCCTTATCAAAACGGGTTTTTGGAGGCACTTTCATC
TGGAGGTTGTGAACTAATGGGACATAGCTTTAGGGTTCCCACTTCTCAAGCGCTTAAGACAAGAACAAGGA
GGAGGAGTACTGCTGGTCCTTTGCAGGTAGTTTGTGTGGATATTCCAAGGCCAGAGCTAGAGAACACTGTC
AATTTCTTGGAAGCTGCTAGTTTATCTGCATCCTTCCGTAGTGCTCCTCGTCCTGCTAAGCCTTTGAAAGT
TGTAATTGCTGGTGCTGGATTGGCTGGATTGTCAACTGCAAAGTACCTGGCTGATGCAGGCCACAAACCTC
TGTTGCTTGAAGCAAGAGATGTTCTTGGTGGAAAGATAGCTGCATGGAAGGATGAAGATGGGGACTGGTAT
GAGACTGGTTTACATATTTTCTTCGGTGCTTATCCGAATGTGCAGAATTTATTTGGAGAACTTGGGATCAA
TGATCGGTTGCAGTGGAAGGAACACTCCATGATTTTTGCTATGCCAAGTAAACCTGGAGAATTTAGTAGAT
TTGACTTCCCAGATGTCCTACCAGCACCCTTAAATGGTATTTGGGCTATTTTGCGGAACAACGAGATGCTG
ACATGGCCAGAGAAAATAAAGTTTGCTATTGGACTTTTGCCAGCCATGGTCGGCGGTCAGGCTTATGTTGA
GGCCCAAGATGGTTTATCAGTCAAAGAATGGATGGAAAAGCAGGGAGTACCTGAGCGCGTGACCGACGAGG
TGTTTATTGCCATGTCAAAGGCGCTAAACTTTATAAACCCTGATGAACTGTCAATGCAATGCATTTTGATA
GCTTTGAACCCGTTTCTTCAGGAAAAACATGGTTCCAAGATGGCATTCTTGGATGGTAATCCTCCGGAAAG
GCTTTGTATGCCAGTAGTGGATCATATTCGATCACTAGGTGGGGAAGTGCAACTTAATTCTAGGATAAAGA
AAATTGAGCTCAATGACGATGGCACGGTTAAGAGTTTCTTACTCACTAATGGAAGCACTGTCGAAGGAGAC
GCTTATGTGTTTGCCGCTCCAGTCGATATCCTGAAGCTCCTTTTACCAGATCCCTGGAAAGAAATACCGTA
CTTCAAGAAATTGGATAAATTAGTTGGAGTACCAGTTATTAATGTTCATATATGGTTTGATCGAAAACTGA
AGAACACATATGATCACCTACTCTTTAGCAGAAGTAACCTTCTGAGCGTGTATGCCGACATGTCCTTAACT
TGTAAGGAATATTACGATCCTAACCGGTCAATGCTGGAGCTAGTATTTGCACCAGCAGAGGAATGGATATC
ACGGACTGATTCTGACATCATAGATGCAACAATGAAAGAACTTGAGAAACTCTTCCCTGATGAAATCTCAG
CTGACCAAAGCAAAGCTAAAATTCTGAAGTACCATGTCGTTAAGACTCCAAGATCTGTGTACAAGACCATC
CCAAACTGTGAACCATGTCGTCCTCTACAAAGATCACCTATTGAAGGATTCTACTTAGCTGGAGATTACAC
AAAACAGAAGTACTTAGCTTCCATGGAAGGCGCTGTCCTCTCTGGCAAATTCTGCTCTCAGTCTATTGTTC
AGGATTACGAGCTACTGGCTGCGTCTGGACCAAGAAAGTTGTCGGAGGCAACAGTATCATCATCATGA

*Arab. Thal.* Phytoene desaturase mutant-2 (PDSM-3)

(SEQ. ID. No. 12)

ATGGTTGTGTTTGGGAATGTTTCTGCGGCGAATTTGCCTTATCAAAACGGGTTTTTGGAGGCACTTTCATC
TGGAGGTTGTGAACTAATGGGACATAGCTTTAGGGTTCCCACTTCTCAAGCGCTTAAGACAAGAACAAGGA
GGAGGAGTACTGCTGGTCCTTTGCAGGTAGTTTGTGTGGATATTCCAAGGCCAGAGCTAGAGAACACTGTC
AATTTCTTGGAAGCTGCTAGTTTATCTGCATCCTTCCGTAGTGCTCCTCGTCCTGCTAAGCCTTTGAAAGT
TGTAATTGCTGGTGCTGGATTGGCTGGATTGTCAACTGCAAAGTACCTGGCTGATGCAGGCCACAAACCTC
TGTTGCTTGAAGCAAGAGATGTTCTTGGTGGAAAGATAGCTGCATGGAAGGATGAAGATGGGGACTGGTAT
GAGACTGGTTTACATATTTTCTTCGGTGCTTATCCGAATGTGCAGAATTTATTTGGAGAACTTGGGATCAA
TGATCGGTTGCAGTGGAAGGAACACTCCATGATTTTTGCTATGCCAAGTAAACCTGGAGAATTTAGTAGAT
TTGACTTCCCAGATGTCCTACCAGCACCCTTAAATGGTATTTGGGCTATTTTGCGGAACAACGAGATGCTG
ACATGGCCAGAGAAAATAAAGTTTGCTATTGGACTTTTGCCAGCCATGGTCGGCGGTCAGGCTTATGTTGA
GGCCCAAGATGGTTTATCAGTCAAAGAATGGATGGAAAAGCAGGGAGTACCTGAGCGCGTGACCGACGAGG
TGTTTATTGCCATGTCAAAGGCGCTAAACTTTATAAACCCTGATGAACTGTCAATGCAATGCATTTTGATA
GCTTTGAACCGGTTTCTTCAGGAAAAACATGGTTCCAAGATGGCATTCTTGGATGGTAATCCTCCGGAAAG
GCTTTGTATGCCAGTAGTGGATCATATTCGATCACTAGGTGGGGAAGTGCAACTTAATTCTAGGATAAAGA
AAATTGAGCTCAATGACGATGGCACGGTTAAGAGTTTCTTACTCACTAATGGAAGCACTGTCGAAGGAGAC
GCTTATGTGTTTGCCGCTCCAGTCGATATCCTGAAGCTCCTTTTACCAGATCCCTGGAAAGAAATACCGTA
CTTCAAGAAATTGGATAAATTAGTTGGAGTACCAGTTATTAATGTTCATATATGGTTTGATCGAAAACTGA
AGAACACATATGATCACCCACTCTTTAGCAGAAGTAACCTTCTGAGCGTGTATGCCGACATGTCCTTAACT
TGTAAGGAATATTACGATCCTAACCGGTCAATGCTGGAGCTAGTATTTGCACCAGCAGAGGAATGGATATC
ACGGACTGATTCTGACATCATAGATGCAACAATGAAAGAACTTGAGAAACTCTTCCCTGATGAAATCTCAG
CTGACCAAAGCAAAGCTAAAATTCTGAAGTACCATGTCGTTAAGACTCCAAGATCTGTGTACAAGACCATC
CCAAACTGTGAACCATGTCGTCCTCTACAAAGATCACCTATTGAAGGATTCTACTTAGCTGGAGATTACAC
AAAACAGAAGTACTTAGCTTCCATGGAAGGCGCTGTCCTCTCTGGCAAATTCTGCTCTCAGTCTATTGTTC
AGGATTACGAGCTACTGGCTGCGTCTGGACCAAGAAAGTTGTCGGAGGCAACAGTATCATCATCATGA

*Nicotiana tabacum* Truncated RD2 promoter (SEQ. ID. No. 13)

aatatgaaaggaaacatattcaatacattgtagtttgctactcataatcgctagaatactttgtgccttgc
taataaagatacttgaaatagcttagtttaaatataaatagcataatagattttaggaattagtattttga
gtttaattacttattgacttgtaacagtttttataattccaaggcccatgaaaaatttaatgctttattag
ttttaaacttactatataaatttttcatatgtaaaatttaatcggtatagttcgatatttttttcaatttat
ttttataaaataaaaaacttaccctaattatcggtacagttatagatttatataaaaatctacggttcttc
agaagaaacctaaaaatcggttcggtgcggacggttcgatcggtttagtcgattttcaaatattcattgac
actcctagttgttgttataggtaaaaagcagttacagagaggtaaaatataacttaaaaaatcagttctaa
ggaaaaattgacttttatagtaaatgactgttatataaggatgttgttacagagaggtatgagtgtagttg
gtaaattatgttcttgacggtgtatgtcacatattatttattaaaactagaaaaaacagcgtcaaaactag
caaaaatccaacggacaaaaaaatcggctgaatttgatttggttccaacatttaaaaaagtttcagtgaga
aagaatcggtgactgttgatgatataaacaaagggcacattggtcaataaccataaaaaattatatgacag
ctacagttggtagcatgtgctcagctattgaacaaatctaaagaaggtacatctgtaaccggaacaccact
taaatgactaaattaccctcatcagaaagcagatggagtgctacaaataacacactattcaacaaccataa -continued

SEQUENCES ataaaacgtgttcagctactaaaacaaatataaataaatctatgtttgtaagcactccagccatgttaatg
gagtgctattgcctgttaactctcacttataaaatagtagtagaaaaaatatgaaccaaaacacaac

*Nicotiana tabacum* Putrescene methyl transferase-1 promoter (SEQ. ID. No. 14)

gaattcaatggagaaggaaaatatttccagtgtaaacacaagtgaatgaagagaagccaaaataatctcta
tcattcaagccttaggtggagattaaaaaaattatttactttcttatcaaagtaataggtgatcaacagct
ttcgtaaaacgtcattaggagaatattataatctcttttatgctgaagaacccacataaggaagatcataa
aatacatgactttcagatgacttcttggagctttatttttaaagagtggctagctggtcagcaaagaggtg
ctcgtcagatatcataaaattttactattatttgttttaagagggagatggggcacacatgcttgtgacaa
aagtaagaggaagaaaggagacagaagaggaaatagatttgggggggggggggggggtttcacaatcaaag
aaaattttaaaatggagagagaaatgagcacacacatatactaacaaaattttactaataattgcaccga
gacaaacttatattttagttccaaaatgtcagtctaaccctgcacgttgtaatgaattttaactattata
ttatatcgagttgcgccctccactcctcggtgtccaaattgtatttaaatgcatagatgtttattgggagt
gtacagcaagctttcggaaaatacaaaccataatactttctcttcttcaatttgtttagtttaattttg
aaa

*Nicotiana tabacum* GapC Promoter (SEQ. ID. No. 15)

TGCGTCAAATGGATAAACAAAAAAATAGCATAAGTTAGTTTTGTTACTCGAGAGTTATGTATTATAAGGTA
TAGGGAAATGACTCAAACATACCACTGAACTTAACGAAACGACGCATATATATACTACTTAACTTAACGAA
AAAGGGGTGAGAGTGGATGGGTGCTGGTAAATAATGAAGGGTTTATATAACGTCACGTGTCAAAATTCGAT
AGTAGTAGTTTCGTTAGTTGTAATAGCATATATGGCCCAAAGTTATAATATAGATAATATGTTTATGTCCA
ACTATTAACGAGTGACATAGACAGTTCATTTTGTGAAGTTCAATGACATATTTGAGCCCTTTCCCTTTTAT
TATCTCCTTTTATTTGTTCTAATAAAAGAATGGCATTTATTATGTACATAGACAAATAACTATTTTCTTTG
GAATATAATTTGTTTATATATTTTAAAATCATGTCTCAATTTAGTTTGTTTTGTGCATATTTCAACTATTC
AATTTTGTCCATATATTTATTACCTTCCCCCATTTACAAGCATTGAACCGCTTTGCTCACCAAAACTTATG
CACATTGCAAAAATATCATGTAAAGGTTTTATGTATGCTGTAATTAAGGTCTGAACTCATCGTGATTTTAT
TTTTAGGCTTCATTGACCACTACCAAACTCTTTGATGCTACATTTTCTAATTATATTGGAGTTCGATTATA
TCCGAATTCGCGTTGCGTAGGGCCCATTCGAGGGAAAACACTCCCTATCAAGGATTTTTTCATACCCAGAG
CTCGAACTCAAGACATCTGGTTAAGGGAAGAACAGTCTCATCCACTGCACCATATCCTTTTGTGGTCAACA
AGTAAATTTTATGTAGAACCAAAAACTATACTCGAATTGATAAAATAAATGGTGTAAAATATTGTTTTCTT
TCTTACATTTTGGACAGTAAATATGTAGGACAATAATAATTAGCGTGGGGTCTTAAGAAAATTAGCATAGA
TTTCCAGAAATTCCAAATCAACCGGCAGTTCCAGGTTTGAAAACTACAACTCATTCCGACGGTTCAAACTT
CAAACCATGCTTGCTGACTCGGCTTCTTCTTTCTTTTTCACCAAGACAGAGCAGTAGTCACGTGACACCCC
TCACGTGCCTCCCCCCTTTATATTTCAGACTGCAACCCTACACTTTCGCTACATTCACTACCATATTCTTT
TCACTAAGCAATTTTCTCTCCTACTTTTCTTTAAACCCCTTTTTTCTCCCCTAAGCCATGGCATCTAGATC

*Nicotiana tabacum* Actin2 Promoter (SEQ. ID. No. 16)

ATCTTATTGTATAAATATCCATAAACACATCATGAAAGACACTTTCTTTCACGGTCTGAATTAATTATGAT
ACAATTCTAATAGAAAACGAATTAAATTACGTTGAATTGTATGAAATCTAATTGAACAAGCCAACCACGAC
GACGACTAACGTTGCCTGGATTGACTCGGTTTAAGTTAACCACTAAAAAAACGGAGCTGTCATGTAACACG
CGGATCGAGCAGGTCACAGTCATGAAGCCATCAAAGCAAAAGAACTAATCCAAGGGCTGAGATGATTAATT
AGTTTAAAAATTAGTTAACACGAGGGAAAAGGCTGTCTGACAGCCAGGTCACGTTATCTTTACCTGTGGTC
GAAATGATTCGTGTCTGTCGATTTTAATTATTTTTTTGAAAGGCCGAAAATAAAGTTGTAAGAGATAAACC
CGCCtatataAATTCATATATTTTCTCTCCGCTTTGAATTGTCTCGTTGTCCTCCTCACTTTCATCGGCCG
TTTTTGAATCTCCGGCGACTTGACAGAGAAGAACAAGGAAGAAGACTAAGAGAGAAAGTAAGAGATAATCC
AGGAGATTCATTCTCCGTTTTGAATCTTCCTCAATCTCATCTTCTTCCGCTCTTTCTTTCCAAGGTAATAG
GAACTTTCTGGATCTACTTTATTTGCTGGATCTCGATCTTGTTTTCTCAATTTCCTTGAGATCTGGAATTC
GTTTAATTTGGATCTGTGAACCTCCACTAAATCTTTTGGTTTTACTAGAATCGATCTAAGTTGACCGATCA
GTTAGCTCGATTATAGCTACCAGAATTTGGCTTGACCTTGATGGAGAGATCCATGTTCATGTTACCTGGGA
AATGATTTGTATATGTGAATTGAAATCTGAACTGTTGAAGTTAGATTGAATCTGAACACTGTCAATGTTAG
ATTGAATCTGAACACTGTTTAAGTTAGATGAAGTTTGTGTATAGATTCTTCGAAACTTTAGGATTTGTAGT
GTCGTACGTTGAACAGAAAGCTATTTCTGATTCAATCAGGGTTTATTTGACTGTATTGAACTCTTTTTGTG
TGTTTGCAGCTCAT

*Nicotiana tabacum* alcohol dehydrogenase promoter (SEQ. ID. No. 17)

AAGCTTTTTATTTAGCTTTTTCCTCCCTATTTCAATATATAATGGCTCAATTTTTGTCAGATAGCAATAAA
ACCATACAAGAAAATAAAACAAATCACAAAATACAAAAAGAGGTTATATCTCCATGTATGCAATTTCATTA
TATGCATATAAGCATCTTACGTATAAAAAAAAAGAGGGAATCATGGACGTGTCTTTCTAATCCAAGTAGGG
TCAACTTTATAGGGTCGGTGTATGTGTAGTTTAATCGAAAAAGAATTCCATCATTAGGTAATTTACAATTA
GATCCTTAAATTATACAAATATATAAGGGTATAAAAGTTGATCAATATTTCAGGGATATTTTAGTCGTTCA
ACATTTAGTATAAATTATTCGTACTTTTATAATAATAAATAGATAGATAAACATAGATATAGATATAAATA
TAGATAGATAAATGGGGGATTTGCATCTATACCCACTTTTTGGGTCACGTTTTAATTTGTGCCCGCTTTGC
AAAAAAAATTGCAAGCGTACACACTTTTTCGCGTAACTTCAGCATACGGGGCTAAAGTAGCAAAGACAGTC
ACGCAAAACTTCAGCATACTTCAGTCTTTGCTACTTCAGCCCCGTATGCTGAAGTTATGCGAAAAGCGGGT
ATGCTTGTAATTTTTTTGCAAAGCGAGCATAAGTTAAAACGTGACACAAAAAGCGGGTATAGATACAAATG
GCCCTTTTTTTTCTAGCCAAATTTTATTCATTTTTTTGGAATACTTTTTCACTTTATTTTAAAATTAGTGT
TTGGTTATAAATTTTTAAATACAACTTGGAGTTGGACTCCAAAGTCTTTACATACTTATTTTTAGTTTTAT
TACCCTATTTTTTTTAACATGAGATATTTACTTTTACAGATCTAAAAATGATATTTTCTTAGTTTTAACAC
TATAAATAGCCATGAAGGCCCATTTCCTCCCTTTGCAAAAAGTATACCCAAACGCAACTCCGTCTTCACCT
CCAACTCCAACTTCATAATTTCAATTAAAGTGAAAATTATTTTAAGAGACCATTTGGACATGATAATTTTT
TCACTTTTTCCGAACTTTTTTTACTTTTTTTCAAATCAGTGTTTGGCCATAAAATTTTCATTTTTCACTT
GAAGTTGAATTTTTGAATTTTTCGAGAATTCGAAAAACCCCAGAAAGCTGTTTTTCAAAATTTTCACTCGG
ATCCTCACAAAACTTCCAAAATAACCCAAAATTATATTCATGTCCAACACAACTCTAATTTTCAAATACCA

-continued

SEQUENCES

TTTTCACTTGAAAAAGAAATTCACCTTTTTTTTTTTTTTGAACTTTACAATTCTTATGTCCAAACGCCCCC
TTCGAATCTACGGCCAACGTTTATTAAGTAAGGAAAGAAAAATGGCTATAATAATTATATCCCTTTTGAAG
TAAATATAATTCTACCAAATTAATTAATATGCTTAAAAACAATAAAAATAATCAAAATTGCTAGAGAGGAC
AACCAATTAGCCGAAGCATTGTCAAGATTGAGCAGGGCGCAGAATGAAGAAAGTAGTTTTTTATCTTTTGA
TGCCCTACGCCTTTTGTATTAAAATACTATATACAAGATTTGAAAAAGACGAGTTCCATTCAAAACAGTTC
CCTTGTCCCGAAATGTTCATTGATGAAGTAATATGCACTTTTAAAATTATTTTTTTCCAGTTTATCCTAAA
AAAAATATTATTTTTATAATCACATAGAAATAATATATATCAAATAACAAAGGGAAAAAGAAAGTAGGGAA
AGAAAATAATAATTGAAGTGGGCTGGGCTTTGACATGGAAAGGAATGGCTTAGTAATAATTGAAGTTAGCA
TCGGATCTATTTGAAGTGCCACTCATCCCTCAGAAAAACAGTGTTAGTATTTTCTCTCACAAATTGATTCT
GTGGTCCGAATTGGAGTTCCTAAATC

*Arab. thal.* ribosomal protein L2 promoter (RPL2P)

(SEQ. ID. No. 18)

TTCGTTGAAAAATCATCGAAATTTTCGACGGATTCCAATGATCAAAAATTCGTCAATAATTTCCAACGATA
TTCTGACTAAACTAAATCTGATGAAATATTTTTGACGGCTTTCCAACCAAAATATTTCGTTGTGACTTGTC
AAAAATCCGTTAGAATACTAAGCAACTTTTCGACAGATTTTCAGCAAAAATATTCGGTAATATAACGTGTT
AAAAATATGATAAAAAAAAAAACTTGATGAATCTACTAAAACTAAATTTTCAATCATATATATCTATTATT
CATATATTTCATTCATTTTATTATTTTTCTCTTAACAATTATTTAGTTATTCTGGTATCGTGTAATTATAT
TCATATGATTTATTCTGATATTGATTCGGTTAGCATCCGGATAAATCTGGGTTGGGCTTTTTAACTTGGTT
TTTCTAAGAAAAATTCTAATATGATTTGGTTAGCATCCGGATTAGTCTAGTTTGGTAGGCCTGCCTTTGTG
ATTCTTAACTCGGTCTTTTGTATGGGTTTGAACAATTACTACACCATTTAGATTCTTCTGACCCATATCAA
ATAAAGATCCACTTAGGCCCATTAGGGTTAGAACAAACATGAGGTTGCAGAATAAAAAGGGTTCATTTTCC
TCACTCTCAAGTTGGATCTCAAAACCCTAAtatctgaacttcgccgtcgag

*Arab. thal.* cinnamyl alcohol dehydrogenase promoter (SEQ. ID. No. 19)

ttctgttcgtatatttgtaactattatgtgtatttttatttgttagtattactaattcaagtggtttaag
ttgttgagactctttaaaatctaagcattttataaacaataatatataattattgtttaggctaaatttgt
cactaattaaggtttggatacatagtgtctaaactaagctaataatatcacttaacgtttacttgtaacgc
taggtgatgatgtcgtcaagtcaattggtacaaggaataaacgagtggtcatatgacattatgaccatatg
aattcaaactccagtaatccaatggtaattggattcaatgatcaagacttgaaccacgtaatccacccta
tccttagaagctcataaatatcactaaagggacaggcaacacttaaccagtagttgtccaataatttagtt
ttccaaaatgaaaaattattgttgtcatctattttaggtgttttagttcaatgtggattcctcgtcctaac
aaatacttgacgaatatatctagactataaaattggttatgagttctactttttttgtttgtgaaattat
caaaatttgttatatttatttatttattctcattaatttgagtactaattttaaattatttatactaaaa
acaattactaagatacaaaaatggataagagcatggtgtatagatatttaatgggatagaatatttcccat
aattgtatgtgtgtgagaggttttgttttcgtaaggaaagaaacaaaaaccatttgaccaaagaaaagcaa
aagaaggcaaggaatcaaacaacaaatgttgcaaggcagaaataatggacgttatgttaatgtagtgtcgt
cacacgtgacttaaaagagacgagtctgcgtgtcaaactaaaaatgtatgcaactataaaaatgggatttg
attatctttttagtaccgaagcctaccaaccacatgcacactaattctactcgccaaataaagtgaaaa
gag

*Arab. thal.* Metallothionein I promoter (SEQ. ID. No. 20)

aagtaacttttagaattgattcaatctttttagaatagatttttttttttttttttttggatttcgctga
ggttttaccatttgttactcagcatattttaacgatgttgcatttgtgtcccatatacgttattgttagt
gaaaaatataatgtaagaataatttatataactatcctactagcaaagctaacgcaaattttgaactcgaa
ctttagttaccgtgaatgaaaataacagacttgaactttataatactcgtagtatacgtaatttttgcttt
ttgcagatatgcttgccactaataaagtcataaattttatattttcataaactatagttatacacttttga
ctaaacaaacaaaatcggtttagcaaaagaaaaagttacttttctgatgaactaggataaggaattcggaa
ctgaattttgctacgttctctctggaccacacacactgaacacccttttaagatttctccttctcttttt
caacgtaatttatcttttgatcagaaacgacaaaaaagaagtctaacaatatcaaacaatttttttataga
tatttttagatatttttcctgctaattttatctagtgtagacaaacccaaatatacgattattataaaaac
acgaaataccaagtggacgactgaggttaatagatctagccgtagaataaagatctgcatgaaaggcggtg
agaatctaaacggtgataagaccataacacacggaacatcggtacgctctcgaacgtacaagaatcgacga
cacacaaacactccacaattatttgaacactggacaattattgaaccgacgtacgagaatcaatgcgctga
gggtaaagacgtaaatgaagaactagttttggagataagagcggagaaagattgcgacacatgtatggtca
atattaatctcatttagcttataaatttgggagcttcctctatcattaattttcattcataaatttttctt
caatttgaattttctcgagaaaa

*Arab. Thal.* Gad2 Terminator (SEQ. ID. No. 21)

gcaagtgtgttgcctttgtgtgGaAATGAAGAGGTACTTGCGAGGACTTTGCGTTTATCAGTTTATGTGTT
TGTATATCTATTTGATCCAGTTATTATGGATTATATACGCTTGAAACTCATTTTAAGCCATTGTTATTGAA
CGTTTATCAAATACTTTATTATGCCAAGCAAGTCAAACACATGCTTGTTGATTGAAATCAAGCTATAGAAA
TCTCTTCTTCACATACAGCAGTTTAGATTCACAATACAACAAGCGAAACGATAAAGTTTC

*Arab. Thal.* Fad2 Intron (SEQ. ID. No. 22)

gtccgtcgcttctcttccatttcttctcattttcgattttgattcttatttctttccagtagctcctgctc
tgtgaatttctccgctcacgatagatctgcttatactccttacattcaaccttagatctggtctcgattct
ctgtttctctgtttttttcttttggtcgagaatctgatgtttgtttatgttctgtcaccattaataataat
gaactctctcattcatacaatgattagtttctctcgtctacaaaacgatatgttgcattttcacttttctt
ctttttttctaagatgatttgctttgaccaatttgtttagatctttattttattttattttctggtgggtt
ggtggaaattgaaaaaaaaaaaaaacagcataaattgttatttgttaatgtattcatttttttggctatttgt
tctgggtaaaaatctgcttctactattgaatctttcctggatttttttactcctattgggtttttatagtaa
aaatacataataaaaggaaaacaaaagttttatagattctcttaaaccccttacgataaaagttggaatca -continued

| SEQUENCES |
|---|

aaataattcaggatcagatgctctttgattgattcagatgcgattacagttgcatggcaaattttctagat
ccgtcgtcacattttatttctgtttaaatatctaaatctgatatatgatgtcgacaaattctggtggctt
atacatcacttcaactgttttcttttggctttgtttgtcaacttggttttcaatacgatttgtgatttcga
tcgctgaattttaatacaagcaaactgatgttaaccacaagcaagagatgtgacctgccttattaacatc
gtattacttactactagtcgtattctcaacgcaatcgtttttgtatttctcacattatgccgcttctctac
tctttattccttttggtccacgcattttctatttgtggcaatccctttcacaacctgatttcccactttgg
atcatttgtctgaagactctcttgaatcgttaccacttgttcttgtgcatgctctgtttttttagaattaa
tgataaaactattccatagtcttgagttttcagcttgttgattcttttgcttttggttttctgcag QPTase (fill-length) inhibition cassette
(SEQ. ID. No. 23)
ctcgaggatctaaattgtgagttcaatctcttccctattggattgattatccttctttcttccaatttg
tgtttctttttgcctaatttattgtgttatcccctttatcctatttgtttcttacttatttatttgctt
ctatgtctttgtacaaagatttaaactctatggcacatatttaaagttgttagaaaataaattctttcaa
gattgatgaaagaacttttttaattgtagatatttcgtagattttattctcttactaccaatataacgcttg
aattgacgaaaatttgtgtccaaatatctagcaaaaaggtatccaatgaaaatatatcatatgtgatcttc
aaatcttgtgtcttatgcaagattgatactttgttcaatggaagagattgtgtgcatatttttaaaatttt
tattagtaataaagattctatatagctgttatagagggataatttttacaaagaacactataaatatgattg
ttgttgttagggtgtcaatggttcggttcgactggttattttataaaaattgtaccataccattttttttcg
atattctattttgtataaccaaaattagacttttcgaaatcgtcccaatcatgtcggtttcacttcggtat
cggtaccgttcggttaattttcattttttttaaatgtcattaaaattcactagtaaaaatagaatgcaat
aacatacgttcttttataggacttagcaaaagctctctagacatttttactgtttaaaggataatgaatta
aaaaacatgaaagatggctagagtatagatacacaactattcgacagcaacgtaaaagaaaccaagtaaaa
gcaaagaaaatataaatcacacgagtggaaagatattaaccaagttgggattcaagaataaagtctatatt
aaatattcaaaaagataaatttaaataatatgaaaggaaacatattcaatacattgtagtttgctactcat
aatcgctagaatactttgtgccttgctaataaagatacttgaaatagcttagtttaaatataaatagcata
atagattttaggaattagtattttgagtttaattacttattgacttgtaacagtttttataattccaaggc
ccatgaaaaatttaatgcttttattagttttaaacttactatataaatttttcatatgtaaaatttaatcgg
tatagttcgatatttttcaatttatttttataaaataaaaaacttaccctaattatcggtacagttatag
atttatataaaaatctacggttcttcagaagaaacctaaaaatcggttcggtgcggacggttcgatcggtt
tagtcgattttcaaatattcattgacactcctagttgttgttataggtaaaaagcagttacagagaggtaa
aatataacttaaaaaatcagttctaaggaaaaattgacttttatagtaaatgactgttatataaggatgtt
gttacagagaggtatgagtgtagttggtaaattatgttcttgacggtgtatgtcacatattatttattaaa
actagaaaaaacagcgtcaaaactagcaaaaatccaacggacaaaaaaatcggctgaatttgatttggttc
caacatttaaaaaagtttcagtgagaaagaatcggtgactgttgatgatataaacaaagggcacattggtc
aataaccataaaaaaattatatgacagctacagttggtagcatgtgctcagctattgaacaaatctaaagaa
ggtacatctgtaaccggaacaccacttaaatgactaaattaccctcatcagaaagcagatggagtgctaca
aataacacactattcaacaaccataaataaaacgtgttcagctactaaaacaaatataaataaatctatgt
ttgtaagcactccagccatgttaatggagtgctattgcctgttaactctcacttataaaatagtagtagaa
aaaatatgaaccaaaacacaacAACATCTCAAAATATTTGAAGTAACACAGAATTTTACATACACCAAACT
TATAAATCAAGTATTTTCATTGTAACAAATTCCATGAAACATGAAAACAAAGCTATAATGAAATTACCAAC
TCAAGCAATAAGGTTGGAAAAGAGCCATCTGAGATATTCCAGCAATTTACATCTTTTTGTTTGATTACACA
GTGAAGGATCTTTTGTTTGACAACTAGTAAAATGATTCTTATTTGCACCTTTCAGCTATTCAGCTGCTTTT
ACTCCAACCCTATAGCAGAAGTAATGGCGCTCATGCTCGTTTTGTACGCCTTCCAACTTCAAGGGCGAGCT
CTGTATCGATCTTCAGGGAAATGTCAAGTGCTTTCACGGAATGCGTCAGGGCACCACTAGAAATGTAGGTA
ACACCAGTTTGTCCAATCTTGTGTACTGTTTCAAGGGTAACATTTCCTGAAGCCTCCGTATCAAACCTCCC
ATTGATCAATTCTACAGCCTCCTTAAGCATGGATACATCAATATCTCCGTTAGATAATGGAACAACCATAT
TGTCCAGCATTATCCTAGTCAACGAAGTCTTTGTTTGAGATGCATAGTCTAGAACCTCACGTACTTCTTCA
ATTGTCCTGGTTTCAACCTCAACCCCTATTTGAAGTTTATTTTGCTCCAAATACTGATCCACAGATTTTAG
AGCTTTGCCGACACCTCCAGCAGCAGATATGTGATTGTCTTTTATCATTACCATATCAAATAAGCCCATTC
TGTGATTCTTCCCCCCACCGATCAATACCGCCCATTTATCCACCAAACGTAATCCAGGAGCAGTTTTCCTA
GTCTCCAAGATGTAAGCAGGGTGTGCAGCATCTGCCATTTCCTTAGTTAGTGTAGCTATTCCACTCATTCT
TTGCATAAAATTGAGAACAACCCTCTCAGCTATAACAATGTTGTAAGCGTTTCCTTGTACTTTGCCAAATT
TCAAGCCTTTATGAACTTTATCGCCATCATTTACATACCACTCCACCTTTAATGAAGGATCAACTTCCGCG
AATATCATCTCAGCAAGTGCAATTCCTGCTATGATCCCGTCTTCCTTTGCTAGAAAATGAGCATCGGATTC
CATATCAAGAGGAATTGTCGCCTTACAAGTCACATCTCCTAAATTCCCAGCATCTTCAGAGAGTGCAAGTT
TCATAACTTCCTTTAAATCATAAGTTGGGTGTGCTGGTGGTTTCACCTCTAATGACTCCACTCTTGTATTC
TTGGTGGCTATTGCTGACATTTTCACCACCAACCTTGGAGCTGTAATTGCATAAGGATGCACTGTAGCAGT
GAAAGGAATAGCTCTAAACATGGTTTTTTTTTGGGGGGGTTGTGAAATGAATTTTGTGGAAAATAGTTTTT
Ggggcacatcaatcctgcggtgacattcggaatgtttctaacaagaaagatatcgttggtccgagccttgc
tctacatcATAGCTCAGTGCATAGGGGCcctgtgcgggtgcgccttagtcaagacattgcagcgagatcat
tacaaccactatggcggtggcgctaaccagctcgttgatggttatagccgaggcactggccttgctgttga
gattatgggcacctttattcttctgtatactgtcttctccgccactgatcccaaacgcaatgctagagatt
cccatgttcctgtcttggctccactccccattggctttgctgtcttcattgttcacctcgccaccattccc
gtcaccggcactggcatcaacccagcgagCAAAAACTATTTTCCACAAAATTCATTTCACAACCCCCCCAA
AAAAAAACCATGTTTAGAGCTATTCCTTTCACTGCTACAGTGCATCCTTATGCAATTACAGCTCCAAGGTT
GGTGGTGAAAATGTCAGCAATAGCCACCAAGAATACAAGAGTGGAGTCATTAGAGGTGAAACCACCAGCAC
ACCCAACTTATGATTTAAAGGAAGTTATGAAACTTGCACTCTCTGAAGATGCTGGGAATTTAGGAGATGTG
ACTTGTAAGGCGACAATTCCTCTTGATATGGAATCCGATGCTCATTTTCTAGCAAAGGAAGACGGGATCAT
AGCAGGAATTGCACTTGCTGAGATGATATTCGCGGAAGTTGATCCTTCATTAAAGGTGGAGTGGTATGTAA
ATGATGGCGATAAAGTTCATAAAGGCTTGAAATTTGGCAAAGTACAAGGAAACGCTTACAACATTGTTATA
GCTGAGAGGGTTGTTCTCAATTTTATGCAAAGAATGAGTGGAATAGCTACACTAACTAAGGAAATGGCAGA
TGCTGCACACCCTGCTTACATCTTGGAGACTAGGAAAACTGCTCCTGGATTACGTTTGGTGGATAAATGGG
CGGTATTGATCGGTGGGGGAAGAATCACAGAATGGGCTTATTTGATATGGTAATGATAAAAGACAATCAC
ATATCTGCTGCTGGAGGTGTCGGCAAAGCTCTAAAATCTGTGGATCAGTATTTGGAGCAAAATAAACTTCA
AATAGGGGTTGAGGTTGAAACCAGGACAATTGAAGAAGTACGTGAGGTTCTAGACTATGCATCTCAAACAA
AGACTTCGTTGACTAGGATAATGCTGGACAATATGGTTGTTCCATTATCTAACGGAGATATTGATGTATCC -continued

SEQUENCES

ATGCTTAAGGAGGCTGTAGAATTGATCAATGGGAGGTTTGATACGGAGGCTTCAGGAAATGTTACCCTTGA
AACAGTACACAAGATTGGACAAACTGGTGTTACCTACATTTCTAGTGGTGCCCTGACGCATTCCGTGAAAG
CACTTGACATTTCCCTGAAGATCGATACAGAGCTCGCCCTTGAAGTTGGAAGGCGTACAAAACGAGCATGA
GCGCCATTACTTCTGCTATAGGGTTGGAGTAAAAGCAGCTGAATAGCTGAAAGGTGCAAATAAGAATCATT
TTACTAGTTGTCAAACAAAAGATCCTTCACTGTGTAATCAAACAAAAAGATGTAAATTGCTGGAATATCTC
AGATGGCTCTTTTCCAACCTTATTGCTTGAGTTGGTAATTTCATTATAGCTTTGTTTTCATGTTTCATGGA
ATTTGTTACAATGAAAATACTTGATTTATAAGTTTGGTGTATGTAAAATTCTGTGTTACTTCAAATATTTT
GAGATGTTgagctcgtgaaatggcctctttagtttttgattgaatcataggggtattagttttctatggcc
gggagtggtcttcttgcttaattgtaatggaataaccagagaggaactactgtgttatctttgaggaatgt
tgggctttttcgtttgaattatcatgaatgaaattttactttttcccaatacaagtttgttttcgtttct
tggtttttgttatcccttggtttatgtcttggtttggcttaaatgattgaagattacactacctatgtttc
tgctattcctgttgaagatcacatttgataataatgcatcgaatgcattaaagtttcttattggctctgtc
aaaagtattgaaggtggatttttctaattggcaagagaaagtattaaagaggtgatttattagtacttata
tttttctcagcatctctctttcagtgttggagcttcataaaattagcacttcagagtttcagtcgggagct
gaattcga bp1-2010: RD2 promoter
bp2011-3409: antisense QPTase full-length cDNA
bp3410-3792: cucumber aquaporin partial sequence
bp3793-5191: sense QPTase full-lenght cDNA
bp5192-5688: GapC terminator Qptase (fragment) inhibition cassette (SEQ. ID. No. 24)

ctcgaggatctaaattgtgagttcaatctcttccctattggattgattatcctttcttttcttccaatttg
tgtttctttttgcctaatttattgtgttatcccctttatcctattttgtttctttacttatttatttgctt
ctatgtctttgtacaaagatttaaactctatggcacatattttaaagttgttagaaaataaattctttcaa
gattgatgaaagaacttttttaattgtagatatttcgtagattttattctcttactaccaatataacgcttg
aattgacgaaaatttgtgtccaaatatctagcaaaaaggtatccaatgaaaatatatcatatgtgatcttc
aaatcttgtgtcttatgcaagattgatactttgttcaatggaagagattgtgtgcatattttttaaaatttt
tattagtaataaagattctatatagctgttatagagggataattttacaaagaacactataaatatgattg
ttgttgttagggtgtcaatggttcggttcgactggttattttataaaatttgtaccataccatttttttcg
atattctattttgtataaccaaaattagacttttcgaaatcgtcccaatcatgtcggtttcacttcggtat
cggtaccgttcggttaattttcattttttttttaaatgtcattaaaattcactagtaaaaatagaatgcaat
aacatacgttcttttataggacttagcaaaagctctctagacatttttactgtttaaaggataatgaatta
aaaaacatgaaagatggctagagtatagatacacaactattcgacagcaacgtaaaagaaaccaagtaaaa
gcaaagaaaatataaatcacacgagtggaaagatattaaccaagttgggattcaagaataaagtctatatt
aaatattcaaaaagataaatttaaataatatgaaaggaaacatattcaatacattgtagtttgctactcat
aatcgctagaatactttgtgccttgctaataaagatacttgaaatagcttagtttaaatataaatagcata
atagattttaggaattagtattttgagtttaattacttattgacttgtaacagtttttataattccaaggc
ccatgaaaaatttaatgctttattagttttaaacttactatataaatttttcatatgtaaaatttaatcgg
tatagttcgatatttttttcaatttatttttataaaataaaaaacttaccctaattatcggtacagttatag
atttatataaaaatctacggttcttcagaagaaacctaaaaatcggttcggtgcggacggttcgatcggtt
tagtcgattttcaaatattcattgacactcctagttgttgttataggtaaaaagcagttacagagaggtaa
aatataacttaaaaaatcagttctaaggaaaaattgacttttatagtaaatgactgttatataaggatgtt
gttacagagaggtatgagtgtagttggtaaattatgttcttgacggtgtatgtcacatattatttattaaa
actagaaaaaacagcgtcaaaactagcaaaaatccaacggacaaaaaaatcggctgaatttgatttggttc
caacatttaaaaaagtttcagtgagaaagaatcggtgactgttgatgatataaacaaagggcacattggtc
aataaccataaaaaattatatgacagctacagttggtagcatgtgctcagctattgaacaaatctaaagaa
ggtacatctgtaaccggaacaccacttaaatgactaaattaccctcatcagaaagcagatggagtgctaca
aataacacactattcaacaaccataaataaaacgtgttcagctactaaaacaaatataaataaatctatgt
ttgtaagcactccagccatgttaatggagtgctattgcctgttaactctcacttataaaatagtagtagaa
aaaatatgaaccaaaacacaacTTTATCGCCATCATTTACATACCACTCCACCTTTAATGAAGGATCAACT
TCCGCGAATATCATCTCAGCAAGTGCAATTCCTGCTATGATCCCGTCTTCCTTTGCTAGAAAATGAGCATC
GGATTCCATATCAAGAGGAATTGTCGCCTTACAAGTCACATCTCCTAAATTCCCAGCATCTTCAGAGAGTG
CAAGTTTCATAACTTCCTTTAAATCATAAGTTGGGTGTGCTGGTGGTTTCACCTCTAATGACTCCACTCTT
GTATTCTTGGTGGCTATTGCTGACATTTTCACCACCAACCTTGGAGCTGTAATTGCATAAGGATGCACTGT
AGCAGTGAAAGGAATAGCTCTAAACATgtccgtcgcttctcttccatttcttctcattttcgattttgatt
cttatttctttccagtagctcctgctctgtgaatttctccgctcacgatagatctgcttatactccttaca
ttcaaccttagatctggtctcgattctctgtttctctgtttttttcttttggtcgagaatctgatgtttgt
ttatgttctgtcaccattaataataatgaactctctcattcatacaatgattagtttctctcgtctacaaa
acgatatgttgcattttcacttttcttctttttttctaagatgatttgctttgaccaatttgtttagatct
ttattttattttattttctggtgggttggtggaaattgaaaaaaaaaaaaacagcataaattgttatttgt
taatgtattcatttttttggctatttgttctgggtaaaaatctgcttctactattgaatctttcctggattt
tttactcctattgggtttttatagtaaaaatacataataaaaggaaaacaaaagttttatagattctctta
aacccccttacgataaaagttggaatcaaaataattcaggatcagatgctctttgattgattcagatgcgat
tacagttgcatggcaaattttctagatccgtcgtcacatttattttctgtttaaatatctaaatctgata
tatgatgtcgacaaattctggtggcttatacatcacttcaactgttttcttttggctttgtttgtcaactt
ggttttcaatacgatttgtgatttcgatcgctgaattttaatacaagcaaactgatgttaaccacaagca
agagatgtgacctgccttattaacatcgtattacttactactagtcgtattctcaacgcaatcgtttttgt
atttctcacattatgccgcttctctactctttattccttttggtccacgcattttctatttgtggcaatcc
ctttcacaacctgatttcccactttggatcatttgtctgaagactctcttgaatcgttaccacttgtttct
tgtgcatgctctgtttttttagaattaatgataaaactattccatagtcttgagttttcagcttgttgattc
ttttgcttttggttttctgcagATGTTTAGAGCTATTCCTTTCACTGCTACAGTGCATCCTTATGCAATTA
CAGCTCCAAGGTTGGTGGTGAAAATGTCAGCAATAGCCACCAAGAATACAAGAGTGGAGTCATTAGAGGTG
AAACCACCAGCACACCCAACTTATGATTTAAAGGAAGTTATGAAACTTGCACTCTCTGAAGATGCTGGGAA
TTTAGGAGATGTGACTTGTAAGGCGACAATTCCTCTTGATATGGAATCCGATGCTCATTTTCTAGCAAAGG -continued

| SEQUENCES |
| --- |

AAGACGGGATCATAGCAGGAATTGCACTTGCTGAGATGATATTCGCGGAAGTTGATCCTTCATTAAAGGTG
GAGTGGTATGTAAATGATGGCGATAAAgcaagtgtgttgcctttgtgtggaaatgaagaggtacttgcgag
gactttgcgtttatcagtttatgtgtttgtatatctatttgatccagttattatggattatatacgcttga
aactcattttaagccattgttattgaacgtttatcaaatactttattatgccaagcaagtcaaacacatgc
ttgttgattgaaatcaagctatagaaatctcttcttcacatacagcagtttagattcacaatacaacaagc
gaaacgataaagtttc bp 1-2010: RD2P
bp 2011-2370: AS QPTase-IRA
bp 2371-3501: Fad2 intron
bp 3502-3861: SN QPTase-IRA
bp 3862-4134: Gad2T PMTase (fragment) inhibiton cassette
(SEQ. ID. No. 25)
ctcgaggatctaaattgtgagttcaatctcttccctattggattgattatccctttcttttcttccaatttg
tgtttctttttgcctaatttattgtgttatcccctttatcctattttgtttctttacttatttatttgctt
ctatgtctttgtacaaagatttaaactctatggcacatattttaaagttgttagaaaataaattctttcaa
gattgatgaaagaacttttttaattgtagatatttcgtagattttattctcttactaccaatataacgcttg
aattgacgaaaatttgtgtccaaatatctagcaaaaaggtatccaatgaaaatatatcatatgtgatcttc
aaatcttgtgtcttatgcaagattgatactttgttcaatggaagagattgtgtgcatattttttaaaatttt
tattagtaataaagattctatatagctgttatagagggataattttacaaagaacactataaatatgattg
ttgttgttagggtgtcaatggttcggttcgactggttattttataaaatttgtaccataccatttttttcg
atattctattttgtataaccaaaattagacttttcgaaatcgtcccaatcatgtcggtttcacttcggtat
cggtaccgttcggttaattttcatttttttttaaatgtcattaaaattcactagtaaaaatagaatgcaat
aacatacgttcttttataggacttagcaaaagctctctagacatttttactgtttaaaggataatgaatta
aaaaacatgaaagatggctagagtatagatacacaactattcgacagcaacgtaaaagaaaccaagtaaaa
gcaaagaaaatataaatcacacgagtggaaagatattaaccaagttgggattcaagaataaagtctatatt
aaatattcaaaaagataaatttaaataatatgaaaggaaacatattcaatacattgtagtttgctactcat
aatcgctagaatactttgtgccttgctaataaagatacttgaaatagcttagtttaaatataaatagcata
atagattttaggaattagtattttgagtttaattacttattgacttgtaacagtttttataattccaaggc
ccatgaaaaaatttaatgctttattagttttaaacttactatataaatttttcatatgtaaaatttaatcgg
tatagttcgatatttttcaatttatttttataaaataaaaaacttaccctaattatcggtacagttatag
atttatataaaatctacggttcttcagaagaaacctaaaaatcggttcggtgcggacggttcgatcggtt
tagtcgattttcaaatattcattgacactcctagttgttgttataggtaaaaagcagttacagagaggtaa
aatataacttaaaaaatcagttctaaggaaaaattgacttttatagtaaatgactgttatataaggatgtt
gttacagagaggtatgagtgtagttggtaaattatgttcttgacggtgtatgtcacatattatttattaaa
actagaaaaaacagcgtcaaaactagcaaaaatccaacggacaaaaaaatcggctgaatttgatttggttc
caacatttaaaaaagtttcagtgagaaagaatcggtgactgttgatgatataaacaaagggcacattggtc
aataaccataaaaaattatatgacagctacagttggtagcatgtgctcagctattgaacaaatctaaagaa
ggtacatctgtaaccggaacaccacttaaatgactaaattaccctcatcagaaagcagatggagtgctaca
aataacacactattcaacaaccataaataaaacgtgttcagctactaaaacaaatataaataaatctatgt
ttgtaagcactccagccatgttaatggagtgctattgcctgttaactctcacttataaaatagtagtagaa
aaaatatgaaccaaaacacaacCGATTCAAAACTTCAGCAGGAAAATTTATATTAAAGTACGAAACACCAC
AGAGAAAGAATTTTACAATGATTGTGAATTGGAAATTATGATAATTACTGCAGAATTCTCCTACAATACGT
CGCATTTCACTTATTTATTCACTTGATTAAGACTCGATCTTGGTCCAATGATTGTACTACCAGTGTTCATT
ATTCACTTGATTAAGACTCGATCATACTTCTGGCGAAAGATGGTAAAATGgtccgtcgcttctcttccatt
tcttctcatttcgatttgattcttatttctttccagtagctcctgctctgtgaatttctccgctcacga
tagatctgcttatactccttacattcaaccttagatctggtctcgattctctgtttctctgtttttttctt
ttggtcgagaatctgatgtttgtttatgttctgtcaccattaataataatgaactctctcattcatacaat
gattagtttctctcgtctacaaaacgatatgttgcattttcacttttcttctttttttctaagatgatttg
ctttgaccaatttgtttagatctttattttattttattttctggtgggttggtggaaattgaaaaaaaaaa
aaacagcataaattgttatttgttaatgtattcatttttttggctatttgttctgggtaaaaatctgcttct
actattgaatctttcctggatttttttactcctattgggtttttatagtaaaaatacataataaaaggaaaa
caaaagttttatagattctcttaaaccccttacgataaaagttggaatcaaaataattcaggatcagatgc
tctttgattgattcagatgcgattacagttgcatggcaaatttttctagatccgtcgtcacattttatttc
tgtttaaatatctaaatctgatatatgatgtcgacaaattctggtggcttatacatcacttcaactgtttt
cttttggctttgtttgtcaacttggttttcaatacgatttgtgatttcgatcgctgaatttttaatacaag
caaactgatgttaaccacaagcaagagatgtgacctgccttattaacatcgtattacttactactagtcgt
attctcaacgcaatcgtttttgtatttctcacattatgccgcttctctactctttattccttttggtccac
gcattttctatttgtggcaatccctttcacaacctgatttcccactttggatcatttgtctgaagactctc
ttgaatcgttaccacttgtttcttgtgcatgctctgtttttttagaattaatgataaaactattccatagtc
ttgagttttcagcttgttgattcttttgcttttggtttctgcagCATTTTACCATCTTTCGCCAGAAGTA
TGATCGAGTCTTAATCAAGTGAATAATGAACACTGGTAGTACAATCATTGGACCAAGATCGAGTCTTAATC
AAGTGAATAAATAAGTGAAATGCGACGTATTGTAGGAGAATTCTGCAGTAATTATCATAATTTCCAATTCA
CAATCATTGTAAAATTCTTTCTCTGTGGTGTTTCGTACTTTAATATAAATTTTCCTGCTGAAGTTTTGAAT
CGgcaagtgtgttgcctttgtgtggaaatgaagaggtacttgcgaggactttgcgtttatcagtttatgtg
tttgtatatctatttgatccagttattatggattatatacgcttgaaactcattttaagccattgttattg
aacgtttatcaaatactttattatgccaagcaagtcaaacacatgcttgttgattgaaatcaagctataga
aatctcttcttcacatacagcagtttagattcacaatacaacaagcgaaacgataaagtttc bp 1-2010: RD2 promoter
bp 2011-2251: AS PMT arm
bp 2252-3382: Fad2 intron -continued

SEQUENCES bp 3383-3623: SN PMT arm
bp 3624-3896: Gad2 terminator

A622 (fragment) inhibition Cassette (SEQ. ID. No. 26)

ctcgaggatctaaattgtgagttcaatctcttccctattggattgattatcctttcttttcttccaatttg
tgtttctttttgcctaatttattgtgttatcccctttatcctattttgtttctttacttatttatttgctt
ctatgtctttgtacaaagatttaaactctatggcacatattttaaagttgttagaaaataaattctttcaa
gattgatgaaagaacttttaattgtagatatttcgtagattttattctcttactaccaatataacgcttg
aattgacgaaaatttgtgtccaaatatctagcaaaaaggtatccaatgaaaatatatcatatgtgatcttc
aaatcttgtgtcttatgcaagattgatactttgttcaatggaagagattgtgtgcatattttaaaatttt
tattagtaataaagattctatatagctgttatagagggataattttacaaagaacactataaatatgattg
ttgttgttagggtgtcaatggttcggttcgactggttattttataaaatttgtaccataccatttttttcg
atattctattttgtataaccaaaattagacttttcgaaatcgtcccaatcatgtcggtttcacttcggtat
cggtaccgttcggttaattttcattttttttaaatgtcattaaaattcactagtaaaaatagaatgcaat
aacatacgttctttatatggacttagcaaaagctctctagacatttttactgtttaaaggataatgaatta
aaaaacatgaaagatggctagagtatagatacacaactattcgacagcaacgtaaaagaaaccaagtaaaa
gcaaagaaaatataaatcacacgagtggaaagatattaaccaagttgggattcaagaataaagtctatatt
aaatattcaaaaagataaatttaaataatatgaaaggaaacatattcaatacattgtagtttgctactcat
aatcgctagaatactttgtgccttgctaataaagatacttgaaatagcttagtttaaatataaatagcata
atagattttaggaattagtattttgagtttaattacttattgacttgtaacagtttttataattccaaggc
ccatgaaaaatttaatgctttattagttttaaacttactatataaatttttcatatgtaaaatttaatcgg
tatagttcgatatttttcaatttatttttataaaataaaaaacttaccctaattatcggtacagttatag
atttatataaaaatctacggttcttcagaagaaacctaaaaatcggttcggtgcggacggttcgatcggtt
tagtcgattttcaaatattcattgacactcctagttgttgttataggtaaaaagcagttacagagaggtaa
aatataacttaaaaaatcagttctaaggaaaaattgacttttatagtaaatgactgttatataaggatgtt
gttacagagaggtatgagtgtagttggtaaattatgttcttgacggtgtatgtcacatattatttattaaa
actagaaaaaacagcgtcaaaactagcaaaaatccaacggacaaaaaaatcggctgaatttgatttggttc
caacatttaaaaaagtttcagtgagaaagaatcggtgactgttgatgatataaacaaagggcacattggtc
aataaccataaaaaattatatgacagctacagttggtagcatgtgctcagctattgaacaaatctaaagaa
ggtacatctgtaaccggaacaccacttaaatgactaaattaccctcatcagaaagcagatggagtgctaca
aataacacactattcaacaaccataaataaaacgtgttcagctactaaaacaaatataaataaatctatgt
ttgtaagcactccagccatgttaatggagtgctattgcctgttaactctcacttataaaatagtagtagaa
aaaatatgaaccaaaacacaacGGTTGTGTATTTCACTTTTGGATATAGCTCAGTGGCTTCGACACCTGTA
GGAGGCTGAACCTCAAAGTTTGCAGAATCTCCATTAACAAAAACTGAATGGCATATGGCCAAATTAGTCCT
TAATGGCAGAGGTCCCTCTTGTACAATCTGGAGAATATCTTCCTCTGATAGATATAACTTCTCGAGGGTCT
TCCCAATTTTGTCCTCCCACAAGGACACTATCTCGTTGAAGGATAGAATATTGGCAGGTGGTCTCATGTGA
AGAGTCTTATTCAATGTCCGTGGATCATCTACTGCTTCGATAGTGTATGTCGCTATGTCTTCTTCCTTCAC
ATATATTGCTTTGGGATTTCCATCGCCAAAAATGACAACTTTGTCTCTAGGAGGGGTTTTGGCCTCTAACT
GCCCCAAGTTGGGCAAGAAGAAATCTGCAAACCAATTGCAGATTACATATGTGTATGGAATTCCTTCTGCC
TCTATCATCCTCCTGATTCTTACCTTTAGAGCGAAGAGTGATGCAGCTGGTTCAATTGCACGAGCATGATC
CACATCAAATCCAAATTCTGAAGGAAGAAATCTCTTGATATTTCCAGCTTCTTTAATTGCTTTGATGATGT
TCACTTGATCAgtccgtcgcttctcttccatttcttctcattttcgattttgattcttatttctttccagt
agctcctgctctgtgaatttctccgctcacgatagatctgcttatactccttacattcaaccttagatctg
gtctcgattctctgtttctctgtttttttcttttggtcgagaatctgatgtttgtttatgttctgtcacca
ttaataataatgaactctctcattcatacaatgattagtttctctcgtctacaaaacgatatgttgcattt
tcacttttcttctttttttctaagatgatttgctttgaccaatttgtttagatctttattttattttattt
tctggtgggttggtggaaattgaaaaaaaaaaaaacagcataaattgttatttgttaatgtattcattttt
tggctatttgttctgggtaaaaatctgcttctactattgaatctttcctggatttttttactcctattgggt
ttttatagtaaaaatacataataaaaggaaaacaaaagttttatagattctcttaaaccccttacgataaa
agttggaatcaaaataattcaggatcagatgctctttgattgattcagatgcgattacagttgcatggcaa
attttctagatccgtcgtcacatttattttctgtttaaatatctaaatctgatatatgatgtcgacaaat
tctggtggcttatacatcacttcaactgttttcttttggctttgtttgtcaacttggttttcaatacgatt
tgtgatttcgatcgctgaatttttaatacaagcaaactgatgttaaccacaagcaagagatgtgacctgcc
ttattaacatcgtattacttactactagtcgtattctcaacgcaatcgtttttgtatttctcacattatgc
cgcttctctactctttattccttttggtccacgcattttctatttgtggcaatccctttcacaacctgatt
tcccactttggatcatttgtctgaagactctcttgaatcgttaccacttgtttcttgtgcatgctctgttt
tttagaattaatgataaaactattccatagtcttgagttttcagcttgttgattcttttgcttttggtttt
ctgcagTGATCAAGTGAACATCATCAAAGCAATTAAAGAAGCTGGAAATATCAAGAGATTTCTTCCTTCAG
AATTTGGATTTGATGTGGATCATGCTCGTGCAATTGAACCAGCTGCATCACTCTTCGCTCTAAAGGTAAGA
ATCAGGAGGATGATAGAGGCAGAAGGAATTCCATACACATATGTAATCTGCAATTGGTTTGCAGATTTCTT
CTTGCCCAACTTGGGGCAGTTAGAGGCCAAAACCCCTCCTAGAGACAAAGTTGTCATTTTTGGCGATGGAA
ATCCCAAAGCAATATATGTGAAGGAAGAAGACATAGCGACATACACTATCGAAGCAGTAGATGATCCACGG
ACATTGAATAAGACTCTTCACATGAGACCACCTGCCAATATTCTATCCTTCAACGAGATAGTGTCCTTGTG
GGAGGACAAAATTGGGAAGACCCTCGAGAAGTTATATCTATCAGAGGAAGATATTCTCCAGATTGTACAAG
AGGGACCTCTGCCATTAAGGACTAATTTGGCCATATGCCATTCAGTTTTTGTTAATGGAGATTCTGCAAAC
TTTGAGGTTCAGCCTCCTACAGGTGTCGAAGCCACTGAGCTATATCCAAAAGTGAAATACACAACCgcaag
tgtgttgcctttgtgtggaaatgaagaggtacttgcgaggactttgcgtttatcagtttatgtgtttgtat
atctatttgatccagttattatggattatatacgcttgaaactcattttaagccattgttattgaacgttt
atcaaatactttattatgccaagcaagtcaaacacatgcttgttgattgaaatcaagctatagaaatctct
tcttcacatacagcagtttagattcacaatacaacaagcgaaacgataaagtttc bp 1-2010: RD2 promoter
bp 2011-2638: antisense A622
bp 2639-3769: Fad2 intron -continued

SEQUENCES bp 3770-4397: sense A622
bp 4398-4670: Gad2 terminator

A622/Qptase (fragments) Double inhibiton cassette
(SEQ. ID. No. 27)
ctcgaggatctaaattgtgagttcaatctcttccctattggattgattatccttcttttcttccaatttg
tgtttctttttgcctaatttattgtgttatcccctttatcctattttgtttctttacttatttatttgctt
ctatgtctttgtacaaagatttaaactctatggcacatattttaaagttgttagaaaataaattctttcaa
gattgatgaaagaacttttttaattgtagatatttcgtagattttattctcttactaccaatataacgcttg
aattgacgaaaatttgtgtccaaatatctagcaaaaaggtatccaatgaaaatatatcatatgtgatcttc
aaatcttgtgtcttatgcaagattgatactttgttcaatggaagagattgtgtgcatatttttaaaatttt
tattagtaataaagattctatatagctgttatagagggataatttacaaagaacactataaatatgattg
ttgttgttagggtgtcaatggttcggttcgactggttattttataaaatttgtaccatacccattttttcg
atattctattttgtataaccaaaattagacttttcgaaatcgtcccaatcatgtcggtttcacttcggtat
cggtaccgttcggttaattttcatttttttttaaatgtcattaaaattcactagtaaaaatagaatgcaat
aacatacgttcttttataggacttagcaaaagctctctagacatttttactgtttaaaggataatgaatta
aaaaacatgaaagatggctagagtatagatacacaactattcgacagcaacgtaaaagaaaccaagtaaaa
gcaaagaaaatataaatcacacgagtggaaagatattaaccaagttgggattcaagaataaagtctatatt
aaatattcaaaaagataaatttaaataatatgaaaggaaacatattcaatacattgtagtttgctactcat
aatcgctagaatactttgtgccttgctaataaagatacttgaaatagcttagtttaaatataaatagcata
atagattttaggaattagtattttgagtttaattacttattgacttgtaacagtttttataattccaaggc
ccatgaaaaatttaatgctttattagttttaaacttactatataaatttttcatatgtaaaatttaatcgg
tatagttcgatatttttcaatttatttttataaaataaaaaacttaccctaattatcggtacagttatag
atttatataaaatctacggttcttcagaagaaacctaaaaatcggttcggtgcggacggttcgatcggtt
tagtcgattttcaaatattcattgacactcctagttgttgttataggtaaaaagcagttacagagaggtaa
aatataacttaaaaaatcagttctaaggaaaaattgacttttatagtaaatgactgttatataaggatgtt
gttacagagaggtatgagtgtagttggtaaattatgttcttgacggtgtatgtcacatattatttattaaa
actagaaaaaacagcgtcaaaactagcaaaaatccaacggacaaaaaaatcggctgaatttgatttggttc
caacatttaaaaaagtttcagtgagaaagaatcggtgactgttgatgatataaacaaagggcacattggtc
aataaccataaaaaattatatgacagctacagttggtagcatgtgctcagctattgaacaaatctaaagaa
ggtacatctgtaaccggaacaccacttaaatgactaaattaccctcatcagaaagcagatggagtgctaca
aataacacactattcaacaaccataaataaaacgtgttcagctactaaaacaaatataaataaatctatgt
ttgtaagcactccagccatgttaatggagtgctattgcctgttaactctcacttataaaatagtagagaaa
aaatatgaaccaaaacacaacTTATCGCCATCATTTACATACCACTCCACCTTTAATGAAGGATCAACTT
CCGCGAATATCATCTCAGCAAGTGCAATTCCTGCTATGATCCCGTCTTCCTTTGCTAGAAAATGAGCATCG
GATTCCATATCAAGAGGAATTGTCGCCTTACAAGTCACATCTCCTAAATTCCCAGCATCTTCAGAGAGTGC
AAGTTTCATAACTTCCTTTAAATCATAAGTTGGGTGTGCTGGTGGTTTCACCTCTAATGACTCCACTCTTG
TATTCTTGGTGGCTATTGCTGACATTTTCACCACCAACCTTGGAGCTGTAATTGCATAAGGATGCACTGTA
GCAGTGAAAGGAATAGCTCTAAACATggttgtgtatttcacttttggatatagctcagtggcttcgacacc
tgtaggaggctgaacctcaaagtttgcagaatctccattaacaaaaactgaatggcatatggccaaattag
tccttaatggcagaggtccctcttgtacaatctggagaatatcttcctctgatagatataacttctcgagg
gtcttcccaatttgtcctcccacaaggacactatctcgttgaaggatagaatattggcaggtggtctcat
gtgaagagtcttattcaatgtccgtggatcatctactgcttcgatagtgtatgtcgctatgtcttcttcct
tcacatatattgctttgggatttccatcgccaaaaatgacaactttgtctctaggaggggttttggcctct
aactgccccaagttgggcaagaagaaatctgcaaaccaattgcagattacatatgtgtatggaattccttc
tgcctctatcatcctcctgattcttacctttagagcgaagagtgatgcagctggttcaattgcacgagcat
gatccacatcaaatccaaattctgaaggaagaaatctcttgatatttccagcttctttaattgctttgatg
atgttcacttgatcaGTCCGTCGCTTCTCTTCCATTTCTTCTCATTTTCGATTTTGATTCTTATTTCTTTC
CAGTAGCTCCTGCTCTGTGAATTTCTCCGCTCACGATAGATCTGCTTATACTCCTTACATTCAACCTTAGA
TCTGGTCTCGATTCTCTGTTTCTCTGTTTTTTTCTTTTGGTCGAGAATCTGATGTTTGTTTATGTTCTGTC
ACCATTAATAATAATGAACTCTCTCATTCATACAATGATTAGTTTCTCTCGTCTACAAAACGATATGTTGC
ATTTTCACTTTTCTTCTTTTTTTCTAAGATGATTTGCTTTGACCAATTTGTTTAGATCTTTATTTTATTTT
ATTTTCTGGTGGGTTGGTGGAAATTGAAAAAAAAAAAAACAGCATAAATTGTTATTTGTTAATGTATTCAT
TTTTTGGCTATTTGTTCTGGGTAAAAATCTGCTTCTACTATTGAATCTTTCCTGGATTTTTTACTCCTATT
GGGTTTTTATAGTAAAAATACATAATAAAAGGAAAACAAAAGTTTTATAGATTCTCTTAAACCCCTTACGA
TAAAAGTTGGAATCAAAATAATTCAGGATCAGATGCTCTTTGATTGATTCAGATGCGATTACAGTTGCATG
GCAAATTTTCTAGATCCGTCGTCACATTTATTTTCTGTTTAAATATCTAAATCTGATATATGATGTCGAC
AAATTCTGGTGGCTTATACATCACTTCAACTGTTTTCTTTTGGCTTTGTTTGTCAACTTGGTTTTCAATAC
GATTTGTGATTTCGATCGCTGAATTTTTAATACAAGCAAACTGATGTTAACCACAAGCAAGAGATGTGACC
TGCCTTATTAACATCGTATTACTTACTACTAGTCGTATTCTCAACGCAATCGTTTTTGTATTTCTCACATT
ATGCCGCTTCTCTACTCTTTATTCCTTTTGGTCCACGCATTTTCTATTTGTGGCAATCCCTTTCACAACCT
GATTTCCCACTTTGGATCATTTGTCTGAAGACTCTCTTGAATCGTTACCACTTGTTTCTTGTGCATGCTCT
GTTTTTTAGAATTAATGATAAAACTATTCCATAGTCTTGAGTTTTCAGCTTGTTGATTCTTTTGCTTTTGG
TTTTCTGCAGtgatcaagtgaacatcatcaaagcaattaaagaagctggaaatatcaagagatttcttcct
tcagaatttggatttgatgtggatcatgctcgtgcaattgaaccagctgcatcactcttcgctctaaaggt
aagaatcaggaggatgatagaggcagaaggaattccatacacatatgtaatctgcaattggtttgcagatt
tcttcttgcccaacttggggcagttagaggccaaaacccctcctagagacaaagttgtcatttttggcgat
ggaaatcccaaagcaatatatgtgaaggaagaagacatagcgacatacactatcgaagcagtagatgatcc
acggacattgaataagactcttcacatgagaccacctgccaatattctatccttcaacgagatagtgtcct
tgtgggaggacaaaattgggaagaccctcgagaagttatatctatcagaggaagatattctccagattgta
caagagggacctctgccattaaggactaatttggccatatgccattcagtttttgttaatggagattctgc
aaactttgaggttcagcctcctacaggtgtcgaagccactgagctatatccaaaagtgaaatacacaaccA
TGTTTAGAGCTATTCCTTTCACTGCTACAGTGCATCCTTATGCAATTACAGCTCCAAGGTTGGTGGTGAAA
ATGTCAGCAATAGCCACCAAGAATACAAGAGTGGAGTCATTAGAGGTGAAACCACCAGCACACCCAACTTA
TGATTTAAAGGAAGTTATGAAACTTGCACTCTCTGAAGATGCTGGGAATTTAGGAGATGTGACTTGTAAGG
CGACAATTCCTCTTGATATGGAATCCGATGCTCATTTTCTAGCAAAGGAAGACGGGATCATAGCAGGAATT
GCACTTGCTGAGATGATATTCGCGGAAGTTGATCCTTCATTAAAGGTGGAGTGGTATGTAAATGATGGCGA -continued

SEQUENCES

TAAAgcaagtgtgttgcctttgtgtggaaatgaagaggtacttgcgaggactttgcgtttatcagtttatg
tgtttgtatatctatttgatccagttattatggattatatacgcttgaaactcattttaagccattgttat
tgaacgtttatcaaatactttattatgccaagcaagtcaaacacatgcttgttgattgaaatcaagctata
gaaatctcttcttcacatacagcagtttagattcacaatacaacaagcgaaacgataaagtttc bp 1-2010: RD2 promoter
bp 2011-2370: AS QPTase
bp 2371-2998: antisense A622
bp 2999-4129: Fad2 intron
bp 4130-4757: sense A622
bp 4758-5117: sense QPTase
bp 5118-5390: Gad2 terminator 14alpha demethylase inhibition cassette (SEQ. ID. No. 28)

gacggtccgatgtgagacttttcaacaaagggtaatatccggaaacctcctcggattccattgcccagcta
tctgtcactttattgtgaagatagtggaaaaggaaggtggctcctacaaatgccatcattgcgataaagga
aaggccatcgttgaagatgcctctgccgacagtggtcccaaagatggacccccacccacgaggagcatcgt
ggaaaaagaagacgttccaaccacgtcttcaaagcaagtggattgatgtgatggtccgatgtgagactttt
caacaaagggtaatatccggaaacctcctcggattccattgcccagctatctgtcactttattgtgaagat
agtggaaaaggaaggtggctcctacaaatgccatcattgcgataaaggaaaggccatcgttgaagatgcct
ctgccgacagtggtcccaaagatggacccccacccacgaggagcatcgtggaaaaagaagacgttccaacc
acgtcttcaaagcaagtggattgatgtgatatctccactgacgtaagggatgacgcacaatcccactatcc
ttcgcaagacccttcctctatataaggaagttcatttcatttggagaggaATCATACTCTTTTCCTTCCCT
GGTTTTAACAGTGAAATCACTATGCGAACTACGTAGAAGCATTATCAGTGGAGGATGGAGTCTCAGGGCTT
CCTTTATGCATCTATAGAGGACTTCCATCTCGGAAAGGATGTCATGATCGACCTTATTCCCATGTTTCTTC
ATCAGATTCTTCTGTTCATCTACGACGGCAGACATGTACTTGTTGTTGCAGAGAAGGTATGCCCCTGCCCA
AGTGGAGGTGATGGAACTGGTGTGTTGCCCAGCGAAAAGAGCAGCAATCAGAAGACCTGTGATCTCAGACT
CTGTCGTTGCCCGCCCATCTTTGTACTTGGAGTCAATGAAGCATTGTAACATATCGCTCTCCGCCTTGCCT
GTACGTTTTCTAGAATCTATGATGTTTGCAAAGATCTCCGCGAGCTTCTTGCGGGCATTGTCACGACGGCG
ATGGGCTGGAATGGGAAGGTAGGGAAAGATTACACTGATAGGAAGCATCCCATTGTCCAGGTCATGGAAGA
GAGCAGAGACATCCTCAAAGAGTTTATTGCGAACCTCTTCTCCCAACAGACATCTACTAGCTGTCAGTATG
ATAAGATGCTCCAGTTCATACTTCAAGTCCACTTCACCACTATCACCCCATTTTGAGAAGTACTCCTCAGC
TTCCATGACCATCTGATCCACATATCCCTTCAATTTATTTACCCTCAAAGATTCAGTAAAGAACCTAAATT
GCTCTTGTCTGATAGTATAATCAACGTCAAAAACCACACCAGGGCCAAAAGTAGGCACATTGAACTGATAA
ACCTCTTGTTGACTGAGATCGGTTTCTGGGGCCTTAAAGAAATGGGCCGACACTTCTGGGCCAACGAAGAA
CGTGATATTCTTgtccgtcgcttctcttccatttcttctcattttcgattttgattcttatttctttccag
tagctcctgctctgtgaatttctccgctcacgatagatctgcttatactccttacattcaaccttagatct
ggtctcgattctctgtttctctgtttttttcttttggtcgagaatctgatgtttgtttatgttctgtcacc
attaataataatgaactctctcattcatacaatgattagtttctctcgtctacaaaacgatatgttgcatt
ttcacttttcttcttttttttctaagatgatttgctttgaccaatttgtttagatctttattttattttatt
ttctggtgggttggtggaaattgaaaaaaaaaaaaaacagcataaattgttatttgttaatgtattcatttt
ttggctatttgttctgggtaaaaatctgcttctactattgaatctttcctggatttttttactcctattggg
tttttatagtaaaaatacataataaaaggaaaacaaaagttttatagattctcttaaaccccttacgataa
aagttggaatcaaaataattcaggatcagatgctctttgattgattcagatgcgattacagttgcatggca
aattttctagatccgtcgtcacattttattttctgtttaaatatctaaatctgatatatgatgtcgacaaa
ttctggtggcttatacatcacttcaactgttttcttttggctttgtttgtcaacttggttttcaatacgat
ttgtgatttcgatcgctgaatttttaatacaagcaaactgatgttaaccacaagcaagagatgtgacctgc
cttattaacatcgtattacttactactagtcgtattctcaacgcaatcgtttttgtatttctcacattatg
ccgcttctctactctttattcctttttggtccacgcattttctatttgtggcaatccctttcacaacctgat
ttcccactttggatcatttgtctgaagactctcttgaatcgttaccacttgtttcttgtgcatgctctgtt
ttttagaattaatgataaaactattccatagtcttgagttttcagcttgttgattcttttgcttttggttt
tctgcagAAGAATATCACGTTCTTCGTTGGCCCAGAAGTGTCGGCCCATTTCTTTAAGGCCCCAGAAACCG
ATCTCAGTCAACAAGAGGTTTATCAGTTCAATGTGCCTACTTTTGGCCCTGGTGTGGTTTTTGACGTTGAT
TATACTATCAGACAAGAGCAATTTAGGTTCTTTACTGAATCTTTGAGGGTAAATAAATTGAAGGGATATGT
GGATCAGATGGTCATGGAAGCTGAGGAGTACTTCTCAAAATGGGGTGATAGTGGTGAAGTGGACTTGAAGT
ATGAACTGGAGCATCTTATCATACTGACAGCTAGTAGATGTCTGTTGGGAGAAGAGGTTCGCAATAAACTC
TTTGAGGATGTCTCTGCTCTCTTCCATGACCTGGACAATGGGATGCTTCCTATCAGTGTAATCTTTCCCTA
CCTTCCCATTCCAGCCCATCGCCGTCGTGACAATGCCCGCAAGAAGCTCGCGGAGATCTTTGCAAACATCA
TAGATTCTAGAAAACGTACAGGCAAGGCGGAGAGCGATATGTTACAATGCTTCATTGACTCCAAGTACAAA
GATGGGCGGGCAACGACAGAGTCTGAGATCACAGGTCTTCTGATTGCTGCTCTTTTCGCTGGGCAACACAC
CAGTTCCATCACCTCCACTTGGGCAGGGGCATACCTTCTCTGCAACAACAAGTACATGTCTGCCGTCGTAG
ATGAACAGAAGAATCTGATGAAGAAACATGGGAATAAGGTCGATCATGACATCCTTTCCGAGATGGAAGTC
CTCTATAGATGCATAAAGGAAGCCCTGAGACTCCATCCTCCACTGATAATGCTTCTACGTAGTTCGCATAG
TGATTTCACTGTTAAAACCAGGGAAGGAAAAGAGTATGATgatcgttcaaacatttggcaataaagtttct
taagattgaatcctgttgccggtcttgcgatgattatcatataatttctgttgaattacgttaagcatgta
ataattaacatgtaatgcatgacgttatttatgagatgggtttttatgattagagtcccgcaattatacat
ttaatacgcgatagaaaacaaaatatagcgcgcaaactaggataaattatcgcgcgcggtgtcatctatgt
tactagatcg bp 1-618: double 35S promoter
bp 619-1503: AS 14alpha demethylase IR arm
bp 1504-2634: Fad2 intron -continued

| SEQUENCES |
| --- |

```
bp 2635-3519: SN 14alpha demethylase IR arm
bp 3520-3773: NOS terminator

SMT2 inhibition cassette
                                                                    (SEQ ID. No. 29)
gacggtccgatgtgagacttttcaacaaagggtaatatccggaaacctcctcggattccattgcccagcta
tctgtcactttattgtgaagatagtggaaaaggaaggtggctcctacaaatgccatcattgcgataaagga
aaggccatcgttgaagatgcctctgccgacagtggtcccaaagatggacccccacccacgaggagcatcgt
ggaaaaagaagacgttccaaccacgtcttcaaagcaagtggattgatgtgatggtccgatgtgagactttt
caacaaagggtaatatccggaaacctcctcggattccattgcccagctatctgtcactttattgtgaagat
agtggaaaaggaaggtggctcctacaaatgccatcattgcgataaaggaaaggccatcgttgaagatgcct
ctgccgacagtggtcccaaagatggacccccacccacgaggagcatcgtggaaaaagaagacgttccaacc
acgtcttcaaagcaagtggattgatgtgatatctccactgacgtaagggatgacgcacaatcccactatcc
ttcgcaagacccttcctctatataaggaagttcatttcatttggagaggaCCATATATTAGCAAATGCCCA
CCTTTATGAGCTTGTCAATAGGTATATATCTTAGAACAAGGACATCAATGGCAAAAATAGCAAGACATGAA
ATCAAATTGTGCCAGACAAGCAACACAGAAAAAGAAACCCTCCACCCACAACGCCCTCCAAAAACTGTAGT
CACCTTAATTAGGGCGGTCATATTCAATGTGTAAAGTTCTGTGCGAAGAATCTTACAGATTTGCTAGCTAA
AGCAAAAAGCTAAGTGACTAAACTCCATATTACTGAGAGTCTGAAATGGGCTTGCGAACCACGAAGAAGTA
CATTGGTGTGAAAATCCCTTTCTTGGCACCACCGACAAGACCTTCTGCAGCTTTCTCTAAGAAAGCTTGAA
CCCTTTGACTACCTTTAGGAGCAAGTCCCACGTATTCAAGCGCCGAAACCAGATTTCTGGTGAAAAGTCTG
CCAACTGCTGTTAGGCGGAAGCTACTGAGCGAGAAGTGACTCGTATCCAAAGGCAAGTACCATGGAACAGG
TGAGTCATCAGCCAGATCCTTGTCCCATACAACTTCAAAACCAGCTTGTTTGGCTGCTTCGAGGCACTGTG
TTGTCAATCTAACCTCAGGGAGGCCATTTCCGAGCTCAATTTCGGCCTTGATCCTGTTGTGCTCTTCGTTA
TTGGGGTTGTAAGAATCGGTCATGCACCACTCATACACAGCGAAACATTGACCAGGCTTCAGCACCCGGTA
AATCTCTTTATAGCATCCCAATGGATCTGGTGCATGGCAGGTAGCTTCTgtccgtcgcttctcttccattt
cttctcattttcgattttgattcttatttctttccagtagctcctgctctgtgaatttctccgctcacgat
agatctgcttatactccttacattcaaccttagatctggtctcgattctctgtttctctgtttttttcttt
tggtcgagaatctgatgtttgtttatgttctgtcaccattaataataatgaactctctcattcatacaatg
attagtttctctcgtctacaaaacgatatgttgcattttcactttcttctttttttctaagatgatttgc
tttgaccaatttgtttagatctttattttattttatttctggtgggttggtggaaattgaaaaaaaaaa
aacagcataaattgttatttgttaatgtattcatttttttggctatttgttctgggtaaaaatctgcttcta
ctattgaatctttcctggatttttttactcctattgggtttttatagtaaaaatacataataaaaggaaaac
aaaagttttatagattctcttaaaccccttacgataaaagttggaatcaaaataattcaggatcagatgct
ctttgattgattcagatgcgattacagttgcatggcaaattttctagatccgtcgtcacattttattttct
gtttaaatatctaaatctgatatatgatgtcgacaaattctggtggcttatacatcacttcaactgttttc
ttttggctttgtttgtcaacttggttttcaatacgatttgtgatttcgatcgctgaatttttaatacaagc
aaactgatgttaaccacaagcaagagatgtgacctgccttattaacatcgtattacttactactagtcgta
ttctcaacgcaatcgtttttgtatttctcacattatgccgcttctctactctttattccttttggtccacg
cattttctatttgtggcaatccctttcacaacctgatttcccactttggatcatttgtctgaagactctct
tgaatcgttaccacttgtttcttgtgcatgctctgtttttttagaattaatgataaaactattccatagtct
tgagttttcagcttgttgattcttttgcttttggttttctgcagAGAAGCTACCTGCCATGCACCAGATCC
ATTGGGATGCTATAAAGAGATTTACCGGGTGCTGAAGCCTGGTCAATGTTTCGCTGTGTATGAGTGGTGCA
TGACCGATTCTTACAACCCCAATAACGAAGAGCACAACAGGATCAAGGCCGAAATTGAGCTCGGAAATGGC
CTCCCTGAGGTTAGATTGACAACACAGTGCCTCGAAGCAGCCAAACAAGCTGGTTTTGAAGTTGTATGGGA
CAAGGATCTGGCTGATGACTCACCTGTTCCATGGTACTTGCCTTTGGATACGAGTCACTTCTCGCTCAGTA
GCTTCCGCCTAACAGCAGTTGGCAGACTTTTCACCAGAAATCTGGTTTCGGCGCTTGAATACGTGGGACTT
GCTCCTAAAGGTAGTCAAAGGGTTCAAGCTTTCTTAGAGAAAGCTGCAGAAGGTCTTGTCGGTGGTGCCAA
GAAAGGGATTTTCACACCAATGTACTTCTTCGTGGTTCGCAAGCCCATTTCAGACTCTCAGTAATATGGAG
TTTAGTCACTTAGCTTTTTGCTTTAGCTAGCAAATCTGTAAGATTCTTCGCACAGAACTTTACACATTGAA
TATGACCGCCCTAATTAAGGTGACTACAGTTTTTGGAGGGCGTTGTGGGTGGAGGGTTTCTTTTTCTGTGT
TGCTTGTCTGGCACAATTTGATTTCATGTCTTGCTATTTTTGCCATTGATGTCCTTGTTCTAAGATATATA
CCTATTGACAAGCTCATAAAGGTGGGCATTTGCTAATATATGGgatcgttcaaacatttggcaataaagtt
tcttaagattgaatcctgttgccggtcttgcgatgattatcatataatttctgttgaattacgttaagcat
gtaataattaacatgtaatgcatgacgttatttatgagatgggtttttatgattagagtcccgcaattata
catttaatacgcgatagaaaacaaaatatagcgcgcaaactaggataaattatcgcgcgcggtgtcatcta
tgttactagatcg

bp 1-618: double 35S promoter
bp 619-1398: AS SMT2 (Sterol methyltransferase) IR arm
bp 1399-2529: Fad2 intron
bp 2530-3309: SN SMT2 IR arm
bp 3310-3563: NOS terminator

Squalene Synthase inhibition cassette
                                                                    (SEQ ID No. 30)
gacggtccgatgtgagacttttcaacaaagggtaatatccggaaacctcctcggattccattgcccagcta
tctgtcactttattgtgaagatagtggaaaaggaaggtggctcctacaaatgccatcattgcgataaagga
aaggccatcgttgaagatgcctctgccgacagtggtcccaaagatggacccccacccacgaggagcatcgt
ggaaaaagaagacgttccaaccacgtcttcaaagcaagtggattgatgtgatggtccgatgtgagactttt
caacaaagggtaatatccggaaacctcctcggattccattgcccagctatctgtcactttattgtgaagat
agtggaaaaggaaggtggctcctacaaatgccatcattgcgataaaggaaaggccatcgttgaagatgcct
ctgccgacagtggtcccaaagatggacccccacccacgaggagcatcgtggaaaaagaagacgttccaacc
acgtcttcaaagcaagtggattgatgtgatatctccactgacgtaagggatgacgcacaatcccactatcc
ttcgcaagacccttcctctatataaggaagttcatttcatttggagaggaACAATCCTAGCCCAACAAGCC
CAGCTACATAGTGACAATATTCGTCATAATCATCAGTTGTTTCCACCTCCTTGCATAGAATTTTGCCATTC
CTGCACCCATCCTCATGGTAATATCCTCAATTGCCTGCTGATAATGTTTCCTAAGCTCCAGAAAAGCAGTT
GAAACATGATGGAACTGGTCCATGAGAACCTTGTACTCTTTTGTACCACATGAAAAATGCCATTCACGATC
```

-continued

SEQUENCES

ATAAACATGCTGATGAAAAGAGATCAGAATAGGTACTTTAACATCGGTGGGAATGCTGGTATCATCCTCAA
CAGTGTCAAGTGCTCGAAGAACCAAATAGAAAATGCACACGGCGTCACGAAGCTCGACGGGAAGTTGTTGA
ATGACGAGAGCAAAGCTACGAGAAACCTTATGAAGCATTGAGTAACAGAAGCCCCAATGTGGgtccgtcgc
ttctcttccatttcttctcattttcgattttgattcttatttctttccagtagctcctgctctgtgaattt
ctccgctcacgatagatctgcttatactccttacattcaaccttagatctggtctcgattctctgtttctc
tgtttttttcttttggtcgagaatctgatgtttgtttatgttctgtcaccattaataataatgaactctct
cattcatacaatgattagtttctctcgtctacaaaacgatatgttgcattttcacttttcttcttttttc
taagatgatttgctttgaccaatttgtttagatctttattttattttattttctggtgggttggtggaaat
tgaaaaaaaaaaaaacagcataaattgttatttgttaatgtattcatttttggctatttgttctgggtaa
aaatctgcttctactattgaatctttcctggatttttactcctattgggtttttatagtaaaaatacata
ataaaaggaaaacaaaagttttatagattctcttaaaccccttacgataaaagttggaatcaaaataattc
aggatcagatgctctttgattgattcagatgcgattacagttgcatggcaaattttctagatccgtcgtca
cattttattttctgtttaaatatctaaatctgatatatgatgtcgacaaattctggtggcttatacatcac
ttcaactgttttcttttggctttgtttgtcaacttggttttcaatacgatttgtgatttcgatcgctgaat
ttttaatacaagcaaactgatgttaaccacaagcaagagatgtgacctgccttattaacatcgtattactt
actactagtcgtattctcaacgcaatcgtttttgtatttctcacattatgccgcttctctactctttattc
cttttggtccacgcattttctatttgtggcaatccctttcacaacctgatttcccactttggatcatttgt
ctgaagactctcttgaatcgttaccacttgtttcttgtgcatgctctgtttttttagaattaatgataaaac
tattccatagtcttgagttttcagcttgttgattcttttgcttttggttttctgcagCCACATTGGGGCTT
CTGTTACTCAATGCTTCATAAGGTTTCTCGTAGCTTTGCTCTCGTCATTCAACAACTTCCCGTCGAGCTTC
GTGACGCCGTGTGCATTTTCTATTTGGTTCTTCGAGCACTTGACACTGTTGAGGATGATACCAGCATTCCC
ACCGATGTTAAAGTACCTATTCTGATCTCTTTTCATCAGCATGTTTATGATCGTGAATGGCATTTTTCATG
TGGTACAAAAGAGTACAAGGTTCTCATGGACCAGTTCCATCATGTTTCAACTGCTTTTCTGGAGCTTAGGA
AACATTATCAGCAGGCAATTGAGGATATTACCATGAGGATGGGTGCAGGAATGGCAAAATTCATATGCAAG
GAGGTGGAAACAACTGATGATTATGACGAATATTGTCACTATGTAGCTGGGCTTGTTGGGCTAGGATTGTg
atcgttcaaacatttggcaataaagtttcttaagattgaatcctgttgccggtcttgcgatgattatcata
taatttctgttgaattacgttaagcatgtaataattaacatgtaatgcatgacgttatttatgagatgggt
ttttatgattagagtcccgcaattatacatttaatacgcgatagaaaacaaaatatagcgcgcaaactagg
ataaattatcgcgcgcggtgtcatctatgttactagatcg bp 1-618: double 35S promoter
bp 619-1057: AS squalene synthase IR arm
bp 1058-2188: Fad2 intron
bp 2189-2627: SN squalene synthase IR arm
bp 2628-2881: NOS terminator HMGCoA Reductase inhibition cassette (SEQ ID No 31)

gacggtccgatgtgagacttttcaacaaagggtaatatccggaaacctcctcggattccattgcccagcta
tctgtcactttattgtgaagatagtggaaaaggaaggtggctcctacaaatgccatcattgcgataaagga
aaggccatcgttgaagatgcctctgccgacagtggtcccaaagatggacccccacccacgaggagcatcgt
ggaaaaagaagacgttccaaccacgtcttcaaagcaagtggattgatgtgatggtccgatgtgagactttt
caacaaagggtaatatccggaaacctcctcggattccattgcccagctatctgtcactttattgtgaagat
agtggaaaaggaaggtggctcctacaaatgccatcattgcgataaaggaaaggccatcgttgaagatgcct
ctgccgacagtggtcccaaagatggacccccacccacgaggagcatcgtggaaaaagaagacgttccaacc
acgtcttcaaagcaagtggattgatgtgatatctccactgacgtaagggatgacgcacaatcccactatcc
ttcgcaagacccttcctctatataaggaagttcatttcatttggagaggaCATATACAAAAGCAAACTTTC
TGAGCAAACATAAAGAGTTTGAGATGCCATTTCTCTCTAAATTACAATCTAGTCACAATTAACAAACAAAC
GAAAGACAGTACAACAGAAAAGATTATTTAAAAAAAAAGGGGTTATCTTCCTTGGCGCATGAATGAAATTA
ACCAAATGTTGAATTACAAGTTAACCCCACTGGTCACCATCCCACCTAACACCTTTCGTAGATCTTCACCA
AATATTTGCAGGTTTTTTTACACGAACTCAGAAAAAAATACGACCCTACCTCCTCACATGCCTTCATAGAA
AGAATACAACACTACATACAGATCCACGTCCACCCTTGATTTGCTTGTCTTTTTCTTCTTGATCTTTCTCC
ACATGACTAATGCCTTACACTTTTTCAACTTTTTGGTCTACCCTTTACTTATTGCTCTCCCTAATTGGAAA
ATTTTATTCCTACTTTTATTGTAATCCATTTCTTTAATAATGATGGTCCATAAAGGATGGTGATGTACACG
ATGTTGGGATAATAAATTTGTCTTTTTCCTTACTAAGAGGAAATCTTAGTAACATCTTTGCTAGATCTATT
GTATTTCATGTGACTCTTAACCAGCTGCCCTGCTGAGATAGCAGACATGAGAGATAACTCACCAGCAAGAA
CAGAACCTGCTACTATTGTGGCCAAGAGCCTTGCATTTGACCCTGCTGCCTCCCTGTTTGCACCTTTCACT
CCTAATAAGTTCAAGCAAGCTGACTGTGATGCAAGTTGAGTTCCACCACCAACTGTGCCAACCTCAATAGA
AGGCATAGTTACTGAAATATGGAGGTCTTTGCCATCATTTACAGCCTCgtccgtcgcttctcttccatttc
ttctcattttcgattttgattcttatttctttccagtagctcctgctctgtgaatttctccgctcacgata
gatctgcttatactccttacattcaaccttagatctggtctcgattctctgtttctctgtttttttctttt
ggtcgagaatctgatgtttgtttatgttctgtcaccattaataataatgaactctctcattcatacaatga
ttagtttctctcgtctacaaaacgatatgttgcattttcacttttcttctttttttctaagatgatttgct
ttgaccaatttgtttagatctttattttattttattttctggtgggttggtggaaattgaaaaaaaaaaaa
acagcataaattgttatttgttaatgtattcatttttggctatttgttctgggtaaaaatctgcttctac
tattgaatctttcctggatttttactcctattgggtttttatagtaaaaatacataataaaaggaaaaca
aaagttttatagattctcttaaaccccttacgataaaagttggaatcaaaataattcaggatcagatgctc
tttgattgattcagatgcgattacagttgcatggcaaattttctagatccgtcgtcacattttattttctg
tttaaatatctaaatctgatatatgatgtcgacaaattctggtggcttatacatcacttcaactgttttct
tttggctttgtttgtcaacttggttttcaatacgatttgtgatttcgatcgctgaatttttaatacaagca
aactgatgttaaccacaagcaagagatgtgacctgccttattaacatcgtattacttactactagtcgtat
tctcaacgcaatcgtttttgtatttctcacattatgccgcttctctactctttattccttttggtccacgc
attttctatttgtggcaatccctttcacaacctgatttcccactttggatcatttgtctgaagactctctt
gaatcgttaccacttgtttcttgtgcatgctctgtttttttagaattaatgataaaactattccatagtctt
gagttttcagcttgttgattcttttgcttttggttttctgcagGAGGCTGTAAATGATGGCAAAGACCTCC
ATATTTCAGTAACTATGCCTTCTATTGAGGTTGGCACAGTTGGTGGTGGAACTCAACTTGCATCACAGTCA
GCTTGCTTGAACTTATTAGGAGTGAAAGGTGCAAACAGGGAGGCAGCAGGGTCAAATGCAAGGCTCTTGGC -continued

SEQUENCES

CACAATAGTAGCAGGTTCTGTTCTTGCTGGTGAGTTATCTCTCATGTCTGCTATCTCAGCAGGGCAGCTGG
TTAAGAGTCACATGAAATACAATAGATCTAGCAAAGATGTTACTAAGATTTCCTCTTAGTAAGGAAAAAGA
CAAATTTATTATCCCAACATCGTGTACATCACCATCCTTTATGGACCATCATTATTAAAGAAATGGATTAC
AATAAAAGTAGGAATAAAATTTTCCAATTAGGGAGAGCAATAAGTAAAGGGTAGACCAAAAAGTTGAAAAA
GTGTAAGGCATTAGTCATGTGGAGAAAGATCAAGAAGAAAAAGACAAGCAAATCAAGGGTGGACGTGGATC
TGTATGTAGTGTTGTATTCTTTCTATGAAGGCATGTGAGGAGGTAGGGTCGTATTTTTTTCTGAGTTCGTG
TAAAAAAACCTGCAAATATTTGGTGAAGATCTACGAAAGGTGTTAGGTGGGATGGTGACCAGTGGGGTTAA
CTTGTAATTCAACATTTGGTTAATTTCATTCATGCGCCAAGGAAGATAACCCCTTTTTTTTTAAATAATCT
TTTCTGTTGTACTGTCTTTCGTTTGTTTGTTAATTGTGACTAGATTGTAATTTAGAGAGAAATGGCATCTC
AAACTCTTTATGTTTGCTCAGAAAGTTTGCTTTTGTATATGgatcgttcaaacatttggcaataaagtttc
ttaagattgaatcctgttgccggtcttgcgatgattatcatataatttctgttgaattacgttaagcatgt
aataattaacatgtaatgcatgacgttatttatgagatgggtttttatgattagagtcccgcaattataca
tttaatacgcgatagaaaacaaaatatagcgcgcaaactaggataaattatcgcgcgcggtgtcatctatg
ttactagatcg bp 1-618: double 35S promoter
bp 619-1468: AS HMG-CoAR IR
bp 1469-2599: Fad2 intron
bp 2600-3449: SN HMG-CoAR IR
bp 3450-3703: Nos terminator Developmental-stage regulated SMT2 inhibition cassette
(SEQ. ID. No. 32)

TTCTGTTCGTATATTTGTAACTATTATGTGTATTTTTATTTTGTTAGTATTACTAATTCAAGTGGTTTAAG
TTGTTGAGACTCTTTAAAATCTAAGCATTTTATAAACAATAATATATAATTATTGTTTAGGCTAAATTTGT
CACTAATTAAGGTTTGGATACATAGTGTCTAAACTAAGCTAATAATATCACTTAACGTTTACTTGTAACGC
TAGGTGATGATGTCGTCAAGTCAATTGGTACAAGGAATAAACGAGTGGTCATATGACATTATGACCATATG
AATTCAAACTCCAGTAATCCAATGGTAATTGGATTCAATGATCAAGACTTGAACCACGTAATCCACCCTTA
TCCTTAGAAGCTCATAAATATCACTAAAGGGACAGGCAACACTTAACCAGTAGTTGTCCAATAATTTAGTT
TTCCAAAATGAAAAATTATTGTTGTCATCTATTTTAGGTGTTTTAGTTCAATGTGGATTCCTCGTCCTAAC
AAATACTTGACGAATATATCTAGACTATAAAATTGGTTATGAGTTCTACTTTTTTTTGTTTGTGAAATTAT
CAAAATTTGTTATATTTATTTATTTATTCTCATTAATTTGAGTACTAATTTTTAAATTATTTATACTAAAA
ACAATTACTAAGATACAAAAATGGATAAGAGCATGGTGTATAGATATTTAATGGGATAGAATATTTCCCAT
AATTGTATGTGTGTGAGAGGTTTTGTTTTCGTAAGGAAAGAAACAAAAACCATTTGACCAAAGAAAAGCAA
AAGAAGGCAAGGAATCAAACAACAAATGTTGCAAGGCAGAAATAATGGACGTTATGTTAATGTAGTGTCGT
CACACGTGACTTAAAAGAGACGAGTCTGCGTGTCAAACTAAAAATGTATGCAACTATAAAAATGGGATTTG
ATTATCTTTTTAGTACCGAAGCCTACCAACCACATGCACACTAATTCTACTCGCCAAATAAAGTGAAAAGA
Gccatatattagcaaatgcccacctttatgagcttgtcaataggtatatatcttagaacaaggacatcaat
ggcaaaaatagcaagacatgaaatcaaattgtgccagacaagcaacacagaaaaagaaaccctccacccac
aacgccctccaaaaactgtagtcaccttaattagggcggtcatattcaatgtgtaaagttctgtgcgaaga
atcttacagatttgctagctaaagcaaaaagctaagtgactaaactccatattactgagagtctgaaatgg
gcttgcgaaccacgaagaagtacattggtgtgaaaatccctttcttggcaccaccgacaagaccttctgca
gctttctctaagaaagcttgaaccctttgactacctttaggagcaagtcccacgtattcaagcgccgaaac
cagatttctggtgaaaagtctgccaactgctgttaggcggaagctactgagcgagaagtgactcgtatcca
aaggcaagtaccatggaacaggtgagtcatcagccagatccttgtcccatacaacttcaaaaccagcttgt
ttggctgcttcgaggcactgtgttgtcaatctaacctcagggaggccatttccgagctcaatttcggcctt
gatcctgttgtgctcttcgttattggggttgtaagaatcggtcatgcaccactcatacacagcgaaacatt
gaccaggcttcagcacccggtaaatctctttatagcatcccaatggatctggtgcatggcaggtagcttct
GTAAGTTCCTGTTTTCACCTGCACCATGAAAAATATACTATTACTATTATTTTTCATTTATTTGTGTGGTC
CATATTGCTATGTGTGAAATGAAAAAATATTTTTTTTCTCAAACTACAATATTGTCAGAAAGAAAGGAATT
AATATTCCGAATTTATACCAAAAAATTAATTTCTTTTTTCTCTTTGGTAAGCTGGATTCTGTTATTCTTTG
GTAAAACGGAGAATAATTTTGTTTATCAACTTCTGTTGATTTTATGAACAATTCTCAATTAATTGAAGGGG
TAGTTTAAGGCTGATGAATCTTTTGGATGAGTTACTTGAGCAGTATGGATTGACTCACATGACTAACTGCT
TCACTAGCTTCCAATATTTTTTAGTTATTACATGTTGTGTATGTTGATTATTGTGCTCTAAGCAATCGGAT
TCTCTTGTTAAATAAAAACTATCATAGTTTATTTATTCAATAATCGAGTTTGAGCTAACACTCCTGTCTAT
CTGGAATACAAAAGGAAAGATAATAAAAGTTTTTGGTACCTTGAAAACTAGAAGTATCAGGAAGGGGAGCC
TTGAACAAAGGTCAAGTTGTCTCCGTTTGACCTACATGTCATGTTCGAGCCATTGATGCTTGCATCAGGAT
AGACTGCCTACATCACCCCCTCTTGCGGTACGGCCCTTCCCCGGACCTGCGTGAACGCGGGATACTTTGTG
CACCGGAAAACTACAAGTATCCCTAACACATATCAGGATTTTAGTGATATCCCTTCACTGCCGTGTTCGAT
AAAGGTTACATAAAGTTTTAAATTTATGGGTGCTAAATATCACAGCTAAATATACACATTAAAGATATTAC
TGCATCCATATATGTTGCCATGACCATACATCAAGTATACATCCACCCCTAATTTTTGAGTGTTTTTGAGA
TGCAGCAAAGTTGAAGGAGATTATAATAGTTTGATGTGGAGAGACTAATTTTTTTTTTAACATCACTTTCT
AAGGGTGCTATCTTTTCACCACCATCACTGGTGGCTTGTTGATTTGTAGCTAATCATTATCTTTTGATGAA
AACAAGGACATTCTTTAGTGCACTAAGATTGTTAAACGTTCGTGCTTCATTGTAAATGTAATATACTCGCG
CTTGTTGGCATGAACACTTGGAATTGTTTACTGGAACACTGCAGagaagctacctgccatgcaccagatcc
attgggatgctataaagagatttaccgggtgctgaagcctggtcaatgtttcgctgtgtatgagtggtgca
tgaccgattcttacaaccccaataacgaagagcacaacaggatcaaggccgaaattgagctcggaaatggc
ctccctgaggttagattgacaacacagtgcctcgaagcagccaaacaagctggttttgaagttgtatggga
caaggatctggctgatgactcacctgttccatggtacttgcctttggatacgagtcacttctcgctcagta
gcttccgcctaacagcagttggcagacttttcaccagaaatctggtttcggcgcttgaatacgtgggactt
gctcctaaaggtagtcaaagggttcaagctttcttagagaaagctgcagaaggtcttgtcggtggtgccaa
gaaagggattttcacaccaatgtacttcttcgtggttcgcaagcccatttcagactctcagtaatatggag
tttagtcacttagctttttgctttagctagcaaatctgtaagattcttcgcacagaactttacacattgaa
tatgaccgccctaattaaggtgactacagtttttggagggcgttgtgggtggagggtttctttttctgtgt
tgcttgtctggcacaatttgatttcatgtcttgctatttttgccattgatgtccttgttctaagatatata
cctattgacaagctcataaaggtgggcatttgctaatatatggTTTCCCTTTGCTTTTGTGTAAACCTCAA
AACTTTATCCCCCATCTTTGATTTTATCCCTTGTTTTTCTGCTTTTTTCTTCTTTCTTGGGTTTTAATTTC -continued

SEQUENCES

CGGACTTAACGTTTGTTTTCCGGTTTGCGAGACATATTCTATCGGATTCTCAACTGTCTGATGAAATAAAT
ATGTAATGTTCTATAAGTCTTTCAATTTGATATGCATATCAACAAAAAGAAAATAGGACAATGCGGCTACA
AATATGAAATTTACAAGTTTAAGAACCATGAGTCGCTAAAGAAATCATTAAGAAAATTAGTTTCACATTCA
ATTCTTGTCACATGATTAACGAGCTTGAGAGGTTTAGAGTAACAATATCTTGAAGCAAAAGATGACCCACT
TGAAATCTAGTGATGGATACATAAGTGGACGTGCCTTGTTTAGGATAGGATTCTGGATAAGAGTCTCGAAT
ATTCATTTTTACCAAGTATATTCAAGGATCTTGTGGATCATATATTTCCTCAATCAAAGGGACTTGACCCA
AATTCACATAAAGATATTTTGGAGTC bp 1-995: A.t. cinnamyl alcohol dehydrogenase promoter
bp 996-1775: AS SMT2 IR arm
bp 1776-2955: N.t. pap intron 1
bp 2956-3735: SN SMT2 IR arm
bp 3736-4286: A.t. RBCS RuBisCO small subunit) terminator A622/SMT2 double inhibition cassette (SEQ. ID. No. 33)

ctcgaggatctaaattgtgagttcaatctcttccctattggattgattatcctttcttttcttccaatttg
tgtttctttttgcctaatttattgtgttatcccctttatcctattttgtttctttacttatttatttgctt
ctatgtctttgtacaaagatttaaactctatggcacatattttaaagttgttagaaaataaattctttcaa
gattgatgaaagaacttttttaattgtagatatttcgtagattttattctcttactaccaatataacgcttg
aattgacgaaaatttgtgtccaaatatctagcaaaaaggtatccaatgaaaatatatcatatgtgatcttc
aaatcttgtgtcttatgcaagattgatactttgttcaatggaagagattgtgtgcatattttttaaaatttt
tattagtaataaagattctatatagctgttatagagggataatttttacaaagaacactataaatatgattg
ttgttgttagggtgtcaatggttcggttcgactggttattttataaaatttgtaccataccattttttttcg
atattctattttgtataaccaaaattagacttttcgaaatcgtcccaatcatgtcggtttcacttcggtat
cggtaccgttcggttaattttcattttttttttaaatgtcattaaaattcactagtaaaaatagaatgcaat
aacatacgttcttttataggacttagcaaaagctctctagacatttttactgtttaaaggataatgaatta
aaaaacatgaaagatggctagagtatagatacacaactattcgacagcaacgtaaaagaaaccaagtaaaa
gcaaagaaaatataaatcacacgagtggaaagatattaaccaagttgggattcaagaataaagtctatatt
aaatattcaaaaagataaatttaaataatatgaaaggaaacatattcaatacattgtagtttgctactcat
aatcgctagaatactttgtgccttgctaataaagatacttgaaatagcttagtttaaatataaatagcata
atagattttaggaattagtattttgagtttaattacttattgacttgtaacagtttttataattccaaggc
ccatgaaaaatttaatgctttattagttttaaacttactatataaatttttcatatgtaaaatttaatcgg
tatagttcgatattttttcaatttatttttataaaataaaaaacttaccctaattatcggtacagttatag
atttatataaaaatctacggttcttcagaagaaacctaaaaatcggttcggtgcggacggttcgatcggtt
tagtcgattttcaaatattcattgacactcctagttgttgttataggtaaaaagcagttacagagaggtaa
aatataacttaaaaaatcagttctaaggaaaaattgacttttatagtaaatgactgttatataaggatgtt
gttacagagaggtatgagtgtagttggtaaattatgttcttgacggtgtatgtcacatattatttattaaa
actagaaaaaacagcgtcaaaactagcaaaaatccaacggacaaaaaaatcggctgaatttgatttggttc
caacatttaaaaaagtttcagtgagaaagaatcggtgactgttgatgatataaacaaagggcacattggtc
aataaccataaaaaattatatgacagctacagttggtagcatgtgctcagctattgaacaaatctaaagaa
ggtacatctgtaaccggaacaccacttaaatgactaaattaccctcatcagaaagcagatggagtgctaca
aataacacactattcaacaaccataaataaaacgtgttcagctactaaaacaaatataaataaatctatgt
ttgtaagcactccagccatgttaatggagtgctattgcctgttaactctcacttataaaatagtagtagaa
aaaatatgaaccaaaacacaacGGTTGTGTATTTCACTTTTGGATATAGCTCAGTGGCTTCGACACCTGTA
GGAGGCTGAACCTCAAAGTTTGCAGAATCTCCATTAACAAAAACTGAATGGCATATGGCCAAATTAGTCCT
TAATGGCAGAGGTCCCTCTTGTACAATCTGGAGAATATCTTCCTCTGATAGATATAACTTCTCGAGGGTCT
TCCCAATTTTGTCCTCCCACAAGGACACTATCTCGTTGAAGGATAGAATATTGGCAGGTGGTCTCATGTGA
AGAGTCTTATTCAATGTCCGTGGATCATCTACTGCTTCGATAGTGTATGTCGCTATGTCTTCTTCCTTCAC
ATATATTGCTTTGGGATTTCCATCGCCAAAAATGACAACTTTGTCTCTAGGAGGGGTTTTGGCCTCTAACT
GCCCCAAGTTGGGCAAGAAGAAATCTGCAAACCAATTGCAGATTACATATGTGTATGGAATTCCTTCTGCC
TCTATCATCCTCCTGATTCTTACCTTTAGAGCGAAGAGTGATGCAGCTGGTTCAATTGCACGAGCATGATC
CACATCAAATCCAAATTCTGAAGGAAGAAATCTCTTGATATTTCCAGCTTCTTTAATTGCTTTGATGATGT
TCACTTGATCAgtccgtcgcttctcttccatttcttctcatttcgattttgattcttatttctttccagt
agctcctgctctgtgaatttctccgctcacgatagatctgcttatactccttacattcaaccttagatctg
gtctcgattctctgtttctctgtttttttcttttggtcgagaatctgatgtttgtttatgttctgtcacca
ttaataataatgaactctctcattcatacaatgattagtttctctcgtctacaaaacgatatgttgcattt
tcacttttcttcttttttttctaagatgatttgctttgaccaatttgtttagatctttattttattttattt
tctggtgggttggtggaaattgaaaaaaaaaaaaacagcataaattgttatttgttaatgtattcattttt
tggctatttgttctgggtaaaaatctgcttctactattgaatctttcctggatttttttactcctattgggt
ttttatagtaaaaatacataataaaaggaaaacaaaagttttatagattctcttaaaccccttacgataaa
agttggaatcaaaataattcaggatcagatgctctttgattgattcagatgcgattacagttgcatggcaa
attttctagatccgtcgtcacattttattttctgtttaaatatctaaatctgatatatgatgtcgacaaat
tctggtggcttatacatcacttcaactgttttcttttggctttgtttgtcaacttggttttcaatacgatt
tgtgatttcgatcgctgaatttttaatacaagcaaactgatgttaaccacaagcaagagatgtgacctgcc
ttattaacatcgtattacttactactagtcgtattctcaacgcaatcgtttttgtatttctcacattatgc
cgcttctctactctttattccttttggtccacgcattttctatttgtggcaatccctttcacaacctgatt
tcccactttggatcatttgtctgaagactctcttgaatcgttaccacttgtttcttgtgcatgctctgttt
tttagaattaatgataaaactattccatagtcttgagttttcagcttgttgattcttttgcttttggtttt
ctgcagTGATCAAGTGAACATCATCAAAGCAATTAAAGAAGCTGGAAATATCAAGAGATTTCTTCCTTCAG
AATTTGGATTTGATGTGGATCATGCTCGTGCAATTGAACCAGCTGCATCACTCTTCGCTCTAAAGGTAAGA
ATCAGGAGGATGATAGAGGCAGAAGGAATTCCATACACATATGTAATCTGCAATTGGTTTGCAGATTTCTT
CTTGCCCAACTTGGGGCAGTTAGAGGCCAAAACCCCTCCTAGAGACAAAGTTGTCATTTTTGGCGATGGAA
ATCCCAAAGCAATATATGTGAAGGAAGAAGACATAGCGACATACACTATCGAAGCAGTAGATGATCCACGG
ACATTGAATAAGACTCTTCACATGAGACCACCTGCCAATATTCTATCCTTCAACGAGATAGTGTCCTTGTG
GGAGGACAAAATTGGGAAGACCCTCGAGAAGTTATATCTATCAGAGGAAGATATTCTCCAGATTGTACAAG
AGGGACCTCTGCCATTAAGGACTAATTTGGCCATATGCCATTCAGTTTTTGTTAATGGAGATTCTGCAAAC -continued

SEQUENCES

TTTGAGGTTCAGCCTCCTACAGGTGTCGAAGCCACTGAGCTATATCCAAAAGTGAAATACACAACCgcaag
tgtgttgcctttgtgtggaaatgaagaggtacttgcgaggactttgcgtttatcagtttatgtgtttgtat
atctatttgatccagttattatggattatatacgcttgaaactcattttaagccattgttattgaacgttt
atcaaatactttattatgccaagcaagtcaaacacatgcttgttgattgaaatcaagctatagaaatctct
tcttcacatacagcagtttagattcacaatacaacaagcgaaacgataaagtttcTTCTGTTCGTATATTT
GTAACTATTATGTGTATTTTTATTTTGTTAGTATTACTAATTCAAGTGGTTTAAGTTGTTGAGACTCTTTA
AAATCTAAGCATTTTATAAACAATAATATATAATTATTGTTTAGGCTAAATTTGTCACTAATTAAGGTTTG
GATACATAGTGTCTAAACTAAGCTAATAATATCACTTAACGTTTACTTGTAACGCTAGGTGATGATGTCGT
CAAGTCAATTGGTACAAGGAATAAACGAGTGGTCATATGACATTATGACCATATGAATTCAAACTCCAGTA
ATCCAATGGTAATTGGATTCAATGATCAAGACTTGAACCACGTAATCCACCCTTATCCTTAGAAGCTCATA
AATATCACTAAAGGGACAGGCAACACTTAACCAGTAGTTGTCCAATAATTTAGTTTTCCAAAATGAAAAAT
TATTGTTGTCATCTATTTTAGGTGTTTTAGTTCAATGTGGATTCCTCGTCCTAACAAATACTTGACGAATA
TATCTAGACTATAAAATTGGTTATGAGTTCTACTTTTTTTTGTTTGTGAAATTATCAAAATTTGTTATATT
TATTTATTTATTCTCATTAATTTGAGTACTAATTTTTAAATTATTTATACTAAAAACAATTACTAAGATAC
AAAAATGGATAAGAGCATGGTGTATAGATATTTAATGGGATAGAATATTTCCCATAATTGTATGTGTGTGA
GAGGTTTTGTTTTCGTAAGGAAAGAAACAAAAACCATTTGACCAAAGAAAAGCAAAAGAAGGCAAGGAATC
AAACAACAAATGTTGCAAGGCAGAAATAATGGACGTTATGTTAATGTAGTGTCGTCACACGTGACTTAAAA
GAGACGAGTCTGCGTGTCAAACTAAAAATGTATGCAACTATAAAAATGGGATTTGATTATCTTTTTAGTAC
CGAAGCCTACCAACCACATGCACACTAATTCTACTCGCCAAATAAAGTGAAAAGAGccatatattagcaaa
tgcccacctttatgagcttgtcaataggtatatatcttagaacaaggacatcaatggcaaaaatagcaaga
catgaaatcaaattgtgccagacaagcaacacagaaaaagaaaccctccacccacaacgccctccaaaaac
tgtagtcaccttaattagggcggtcatattcaatgtgtaaagttctgtgcgaagaatcttacagatttgct
agctaaagcaaaaagctaagtgactaaactccatattactgagagtctgaaatgggcttgcgaaccacgaa
gaagtacattggtgtgaaaatccctttcttggcaccaccgacaagaccttctgcagctttctctaagaaag
cttgaaccctttgactacctttaggagcaagtcccacgtattcaagcgccgaaaccagatttctggtgaaa
agtctgccaactgctgttaggcggaagctactgagcgagaagtgactcgtatccaaaggcaagtaccatgg
aacaggtgagtcatcagccagatccttgtcccatacaacttcaaaaccagcttgtttggctgcttcgaggc
actgtgttgtcaatctaacctcagggaggccatttccgagctcaatttcggccttgatcctgttgtgctct
tcgttattggggttgtaagaatcggtcatgcaccactcatacacagcgaaacattgaccaggcttcagcac
ccggtaaatctctttatagcatcccaatggatctggtgcatggcaggtagcttctGTAAGTTCCTGTTTTC
ACCTGCACCATGAAAAATATACTATTACTATTATTTTTCATTTATTTGTGTGGTCCATATTGCTATGTGTG
AAATGAAAAAATATTTTTTTTCTCAAACTACAATATTGTCAGAAAGAAAGGAATTAATATTCCGAATTTAT
ACCAAAAAATTAATTTCTTTTTTCTCTTTGGTAAGCTGGATTCTGTTATTCTTTGGTAAAACGGAGAATAA
TTTTGTTTATCAACTTCTGTTGATTTTATGAACAATTCTCAATTAATTGAAGGGGTAGTTTAAGGCTGATG
AATCTTTTGGATGAGTTACTTGAGCAGTATGGATTGACTCACATGACTAACTGCTTCACTAGCTTCCAATA
TTTTTTAGTTATTACATGTTGTGTATGTTGATTATTGTGCTCTAAGCAATCGGATTCTCTTGTTAAATAAA
AACTATCATAGTTTATTTATTCAATAATCGAGTTTGAGCTAACACTCCTGTCTATCTGGAATACAAAAGGA
AAGATAATAAAAGTTTTTGGTACCTTGAAAACTAGAAGTATCAGGAAGGGGAGCCTTGAACAAAGGTCAAG
TTGTCTCCGTTTGACCTACATGTCATGTTCGAGCCATTGATGCTTGCATCAGGATAGACTGCCTACATCAC
CCCCTCTTGCGGTACGGCCCTTCCCCGGACCTGCGTGAACGCGGGATACTTTGTGCACCGGAAAACTACAA
GTATCCCTAACACATATCAGGATTTTAGTGATATCCCTTCACTGCCGTGTTCGATAAAGGTTACATAAAGT
TTTAAATTTATGGGTGCTAAATATCACAGCTAAATATACACATTAAAGATATTACTGCATCCATATATGTT
GCCATGACCATACATCAAGTATACATCCACCCCTAATTTTTGAGTGTTTTTGAGATGCAGCAAAGTTGAAG
GAGATTATAATAGTTTGATGTGGAGAGACTAATTTTTTTTTTAACATCACTTTCTAAGGGTGCTATCTTTT
CACCACCATCACTGGTGGCTTGTTGATTTGTAGCTAATCATTATCTTTTGATGAAAACAAGGACATTCTTT
AGTGCACTAAGATTGTTAAACGTTCGTGCTTCATTGTAAATGTAATATACTCGCGCTTGTTGGCATGAACA
CTTGGAATTGTTTACTGGAACACTGCAGagaagctacctgccatgcaccagatccattgggatgctataaa
gagatttaccgggtgctgaagcctggtcaatgtttcgctgtgtatgagtggtgcatgaccgattcttacaa
ccccaataacgaagagcacaacaggatcaaggccgaaattgagctcggaaatggcctccctgaggttagat
tgacaacacagtgcctcgaagcagccaaacaagctggttttgaagttgtatgggacaaggatctggctgat
gactcacctgttccatggtacttgcctttggatacgagtcacttctcgctcagtagcttccgcctaacagc
agttggcagacttttcaccagaaatctggtttcggcgcttgaatacgtgggacttgctcctaaaggtagtc
aaagggttcaagctttcttagagaaagctgcagaaggtcttgtcggtggtgccaagaaagggattttcaca
ccaatgtacttcttcgtggttcgcaagcccatttcagactctcagtaatatggagtttagtcacttagctt
tttgctttagctagcaaatctgtaagattcttcgcacagaactttacacattgaatatgaccgccctaatt
aaggtgactacagtttttggagggcgttgtgggtggagggtttctttttctgtgttgcttgtctggcacaa
tttgatttcatgtcttgctatttttgccattgatgtccttgttctaagatatatacctattgacaagctca
taaaggtgggcatttgctaatatatggTTTCCCTTTGCTTTTGTGTAAACCTCAAAACTTTATCCCCCATC
TTTGATTTTATCCCTTGTTTTTCTGCTTTTTTCTTCTTTCTTGGGTTTTAATTTCCGGACTTAACGTTTGT
TTTCCGGTTTGCGAGACATATTCTATCGGATTCTCAACTGTCTGATGAAATAAATATGTAATGTTCTATAA
GTCTTTCAATTTGATATGCATATCAACAAAAAGAAAATAGGACAATGCGGCTACAAATATGAAATTTACAA
GTTTAAGAACCATGAGTCGCTAAAGAAATCATTAAGAAAATTAGTTTCACATTCAATTCTTGTCACATGAT
TAACGAGCTTGAGAGGTTTAGAGTAACAATATCTTGAAGCAAAAGATGACCCACTTGAAATCTAGTGATGG
ATACATAAGTGGACGTGCCTTGTTTAGGATAGGATTCTGGATAAGAGTCTCGAATATTCATTTTTACCAAG
TATATTCAAGGATCTTGTGGATCATATATTTCCTCAATCAAAGGGACTTGACCCAAATTCACATAAAGATA
TTTTGGAGTC bp 1-2010: RD2 promoter
bp 2011-2638: antisense A622
bp 2639-3769: Fad2 intron
bp 3770-4397: sense A622
bp 4398-4670: Gad2 terminator
bp 4671-5665: A.t. cinnamyl alcohol dehydrogenase promoter
bp 5666-6445: AS SMT2 IR arm -continued

SEQUENCES bp 6446-7625: N.t. pap intron 1
bp 7626-8405: SN SMT2 IR arm
bp 8406-8956: A.t. RBCS (RUBisCO small subunit) terminator GUS Selection Cassette (SEQ. ID. No. 34)

TCTAGAATGTTCGTGCGTCAAATGGATAAACAAAAAAATAGCATAAGTTAGTTTTGTTACTCGAGAGTTAT
GTATTATAAGGTATAGGGAAATGACTCAAACATACCACTGAACTTAACGAAACGACGCATATATATACTAC
TTAACTTAACGAAAAAGGGGTGAGAGTGGATGGGTGCTGGTAAATAATGAAGGGTTTATATAACGTCACGT
GTCAAAATTCGATAGTAGTAGTTTCGTTAGTTGTAATAGCATATATGGCCCAAAGTTATAATATAGATAAT
ATGTTTATGTCCAACTATTAACGAGTGACATAGACAGTTCATTTTGTGAAGTTCAATGACATATTTGAGCC
CTTTCCCTTTTATTATCTCCTTTTATTTGTTCTAATAAAAGAATGGCATTTATTATGTACATAGACAAATA
ACTATTTTCTTTGGAATATAATTTGTTTATATATTTTAAAATCATGTCTCAATTTAGTTTGTTTTGTGCAT
ATTTCAACTATTCAATTTTGTCCATATATTTATTACCTTCCCCCATTTACAAGCATTGAACCGCTTTGCTC
ACCAAAACTTATGCACATTGCAAAAATATCATGTAAAGGTTTTATGTATGCTGTAATTAAGGTCTGAACTC
ATCGTGATTTTATTTTTAGGCTTCATTGACCACTACCAAACTCTTTGATGCTACATTTTCTAATTATATTG
GAGTTCGATTATATCCGAATTCGCGTTGCGTAGGGCCCATTCGAGGGAAAACACTCCCTATCAAGGATTTT
TTCATACCCAGAGCTCGAACTCAAGACATCTGGTTAAGGGAAGAACAGTCTCATCCACTGCACCATATCCT
TTTGTGGTCAACAAGTAAATTTTATGTAGAACCAAAAACTATACTCGAATTGATAAAATAAATGGTGTAAA
ATATTGTTTTCTTTCTTACATTTTGGACAGTAAATATGTAGGACAATAATAATTAGCGTGGGGTCTTAAGA
AAATTAGCATAGATTTCCAGAAATTCCAAATCAACCGGCAGTTCCAGGTTTGAAAACTACAACTCATTCCG
ACGGTTCAAACTTCAAACCATGCTTGCTGACTCGGCTTCTTCTTTCTTTTTCACCAAGACAGAGCAGTAGT
CACGTGACACCCCTCACGTGCCTCCCCCCTTTATATTTCAGACTGCAACCCTACACTTTCGCTACATTCAC
TACCATATTCTTTTCACTAAGCAATTTTCTCTCCTACTTTTCTTTAAACCCCTTTTTTCTCCCCTAAGCCA
TGGCATCTAGATCatgttacgtcctgtagaaaccccaacccgtgaaatcaaaaaactcgacggcctgtggg
cattcagtctggatcgcgaaaactgtggaattgatcagcgttggtgggaaagcgcgttacaagaaagccgg
gcaattgctgtgccaggcagttttaacgatcagttcgccgatgcagatattcgtaattatgcgggcaacgt
ctggtatcagcgcgaagtctttataccgaaaggttgggcaggccagcgtatcgtgctgcgtttcgatgcgg
tcactcattacggcaaagtgtgggtcaataatcaggaagtgatggagcatcagggcggctatacgccattt
gaagccgatgtcacgccgtatgttattgccgggaaaagtgtacgtatcaccgtttgtgtgaacaacgaact
gaactggcagactatcccgccgggaatggtgattaccgacgaaaacggcaagaaaaagcagtcttacttcc
atgatttctttaactatgccggaatccatcgcagcgtaatgctctacaccacgccgaacacctgggtggac
gatatcaccgtggtgacgcatgtcgcgcaagactgtaaccacgcgtctgttgactggcaggtggtggccaa
tggtgatgtcagcgttgaactgcgtgatgcggatcaacaggtggttgcaactggacaaggcactagcggga
ctttgcaagtggtgaatccgcacctctggcaaccgggtgaaggttatctctatgaactgtgcgtcacagcc
aaaagccagacagagtgtgatatctacccgcttcgcgtcggcatccggtcagtggcagtgaagggcgaaca
gttcctgattaaccacaaaccgttctactttactggctttggtcgtcatgaagatgcggacttgcgtggca
aaggattcgataacgtgctgatggtgcacgaccacgcattaatggactggattggggccaactcctaccgt
acctcgcattacccttacgctgaagagatgctcgactgggcagatgaacatggcatcgtggtgattgatga
aactgctgctgtcggctttaacctctctttaggcattggtttcgaagcgggcaacaagccgaaagaactgt
acagcgaagaggcagtcaacggggaaactcagcaagcgcacttacaggcgattaaagagctgatagcgcgt
gacaaaaaccacccaagcgtggtgatgtggagtattgccaacgaaccggatacccgtccgcaaggtgcacg
ggaatatttcgcgccactggcggaagcaacgcgtaaactcgacccgacgcgtccgatcacctgcgtcaatg
taatgttctgcgacgctcacaccgataccatcagcgatctctttgatgtgctgtgcctgaaccgttattac
ggatggtatgtccaaagcggcgatttggaaacggcagagaaggtactggaaaaagaacttctggcctggca
ggagaaactgcatcagccgattatcatcaccgaatacggcgtggatacgttagccgggctgcactcaatgt
acaccgacatgtggagtgaagagtatcagtgtgcatggctggatatgtatcaccgcgtctttgatcgcgtc
agcgccgtcgtcggtgaacaggtatggaatttcgccgattttgcgacctcgcaaggcatattgcgcgttgg
cggtaacaagaaagggatcttcactcgcgaccgcaaaccgaagtcggcggcttttctgctgcaaaaacgct
ggactggcatgaacttcggtgaaaaaccgcagcagggaggcaaacaatgaGAGCTCGTGAAATGGCCTCTT
TAGTTTTTGATTGAATCATAGGGGTATTAGTTTTCTATGGCCGGGAGTGGTCTTCTTGCTTAATTGTAATG
GAATAACCAGAGAGGAACTACTGTGTTATCTTTGAGGAATGTTGGGCTTTTTTCGTTTGAATTATCATGAA
TGAAATTTTACTTTTTCCCAATACAAGTTTGTTTTCGTTTCTTGGTTTTTGTTATCCCTTGGTTTATGTCT
TGGTTTGGCTTAAATGATTGAAGATTACACTACCTATGTTTCTGCTATTCCTGTTGAAGATCACATTTGAT
AATAATGCATCGAATGCATTAAAGTTTCTTATTGGCTCTGTCAAAAGTATTGAAGGTGGATTTTTCTAATT
GGCAAGAGAAAGTATTAAAGAGGTGATTTATTAGTACTTATATTTTTCTCAGCATCTCTCTTTCAGTGTTG
GAGCTTCATAAAATTAGCACTTCAGAGTTTCAGTCGGGAGCTGAATTCGA bp1-1291: GapC Promoter
bp1292-3103: GUS coding sequence
bp3104-3600: GapCterminator Norflurazone resistance selection cassette (SEQ. ID. No. 35)

CGTTTTGACGAGTTCGGATGTAGTAGTAGCCATTATTTAATGTACATACTAATCGTGAATAGTGAATATGA
TGAAACATTGTATCTTATTGTATAAATATCCATAAACACATCATGAAAGACACTTTCTTTCACGGTCTGAA
TTAATTATGATACAATTCTAATAGAAAACGAATTAAATTACGTTGAATTGTATGAAATCTAATTGAACAAG
CCAACCACGACGACGACTAACGTTGCCTGGATTGACTCGGTTTAAGTTAACCACTAAAAAAACGGAGCTGT
CATGTAACACGCGGATCGAGCAGGTCACAGTCATGAAGCCATCAAAGCAAAAGAACTAATCCAAGGGCTGA
GATGATTAATTAGTTTAAAAATTAGTTAACACGAGGGAAAAGGCTGTCTGACAGCCAGGTCACGTTATCTT
TACCTGTGGTCGAAATGATTCGTGTCTGTCGATTTTAATTATTTTTTTGAAAGGCCGAAAATAAAGTTGTA
AGAGATAAACCCGCCTATATAAATTCATATATTTTCTCTCCGCTTTGAATTGTCTCGTTGTCCTCCTCACT
TTCATCGGCCGTTTTTGAATCTCCGGCGACTTGACAGAGAAGAACAAGGAAGAAGACTAAGAGAGAAAGTA
AGAGATAATCCAGGAGATTCATTCTCCGTTTTGAATCTTCCTCAATCTCATCTTCTTCCGCTCTTTCTTTC
CAAGGTAATAGGAACTTTCTGGATCTACTTTATTTGCTGGATCTCGATCTTGTTTTCTCAATTTCCTTGAG
ATCTGGAATTCGTTTAATTTGGATCTGTGAACCTCCACTAAATCTTTTGGTTTTACTAGAATCGATCTAAG
TTGACCGATCAGTTAGCTCGATTATAGCTACCAGAATTTGGCTTGACCTTGATGGAGAGATCCATGTTCAT

-continued

SEQUENCES

GTTACCTGGGAAATGATTTGTATATGTGAATTGAAATCTGAACTGTTGAAGTTAGATTGAATCTGAACACT
GTCAATGTTAGATTGAATCTGAACACTGTTTAAGTTAGATGAAGTTTGTGTATAGATTCTTCGAAACTTTA
GGATTTGTAGTGTCGTACGTTGAACAGAAAGCTATTTCTGATTCAATCAGGGTTTATTTGACTGTATTGAA
CTCTTTTTGTGTGTTTGCAGCTCATatggttgtgtttgggaatgtttctgcggcgaatttgccttatcaaa
acgggtttttggaggcactttcatctggaggttgtgaactaatgggacatagctttagggttcccacttct
caagcgcttaagacaagaacaaggaggaggagtactgctggtcctttgcaggtagtttgtgtggatattcc
aaggccagagctagagaacactgtcaatttcttggaagctgctagtttatctgcatccttccgtagtgctc
ctcgtcctgctaagcctttgaaagttgtaattgctggtgctggattggctggattgtcaactgcaaagtac
ctggctgatgcaggccacaaacctctgttgcttgaagcaagagatgttcttggtggaaagatagctgcatg
gaaggatgaagatggggactggtatgagactggtttacatattttcttcggtgcttatccgaatgtgcaga
atttatttggagaacttgggatcaatgatcggttgcagtggaaggaacactccatgatttttgctatgcca
agtaaacctggagaatttagtagatttgacttcccagatgtcctaccagcacccttaaatggtatttgggc
tattttgcggaacaacgagatgctgacatggccagagaaaataaagtttgctattggacttttgccagcca
tggtcggcggtcaggcttatgttgaggcccaagatggtttatcagtcaaagaatggatggaaaagcaggga
gtacctgagcgcgtgaccgacgaggtgtttattgccatgtcaaaggcgctaaactttataaaccctgatga
actgtcaatgcaatgcattttgatagctttgaaccggtttcttcaggaaaaacatggttccaagatggcat
tcttggatggtaatcctccggaaaggctttgtatgccagtagtggatcatattcgatcactaggtggggaa
gtgcaacttaattctaggataaagaaaattgagctcaatgacgatggcacggttaagagtttcttactcac
taatggaagcactgtcgaaggagacgcttatgtgtttgccgctccagtcgatatcctgaagctccttttac
cagatccctggaaagaaataccgtacttcaagaaattggataaattagttggagtaccagttattaatgtt
catatatggtttgatcgaaaactgaagaacacatatgatcacctactctttagcagaagtaaccttctgag
cgtgtatgccgacatgtccttaacttgtaaggaatattacgatcctaaccggtcaatgctggagctagtat
ttgcaccagcagaggaatggatatcacggactgattctgacatcatagatgcaacaatgaaagaacttgag
aaactcttccctgatgaaatctcagctgaccaaagcaaagctaaaattctgaagtaccatgtcgttaagac
tccaagatctgggtacaagaccatcccaaactgtgaaccatgtcgtcctctacaaagatcacctattgaag
gattctacttagctggagattacacaaaacagaagtacttagcttccatggaaggcgctgtcctctctggc
aaattctgctctcagtctattgttcaggattacgagctactggctgcgtctggaccaagaaagttgtcgga
ggcaacagtatcatcatcatgagaaaagggcgaattcgttaaccgcagacGAGCTCGTGAAATGGCCTCTT
TAGTTTTTGATTGAATCATAGGGGTATTAGTTTTCTATGGCCGGGAGTGGTCTTCTTGCTTAATTGTAATG
GAATAACCAGAGAGGAACTACTGTGTTATCTTTGAGGAATGTTGGGCTTTTTTCGTTTGAATTATCATGAA
TGAAATTTTACTTTTTCCCAATACAAGTTTGTTTTCGTTTCTTGGTTTTTGTTATCCCTTGGTTTATGTCT
TGGTTTGGCTTAAATGATTGAAGATTACACTACCTATGTTTCTGCTATTCCTGTTGAAGATCACATTTGAT
AATAATGCATCGAATGCATTAAAGTTTCTTATTGGCTCTGTCAAAAGTATTGAAGGTGGATTTTTCTAATT
GGCAAGAGAAAGTATTAAAGAGGTGATTTATTAGTACTTATATTTTTCTCAGCATCTCTCTTTCAGTGTTG
GAGCTTCATAAAATTAGCACTTCAGAGTTTCAGTCGGGAGCTGAATTCGA bp 1-1161 Actin 2 Promter
bp 1162-2890 PDSM-1
bp 2891-3387 GapC terminator Phytoene desaturase (wild-type - *Arabidopsis*)

SEQ ID. No. 36

ATGGTTGTGTTTGGGAATGTTTCTGCGGCGAATTTGCCTTATCAAAACGGGTTTTTGGAGGCACTTTCATC
TGGAGGTTGTGAACTAATGGGACATAGCTTTAGGGTTCCCACTTCTCAAGCGCTTAAGACAAGAACAAGGA
GGAGGAGTACTGCTGGTCCTTTGCAGGTAGTTTGTGTGGATATTCCAAGGCCAGAGCTAGAGAACACTGTC
AATTTCTTGGAAGCTGCTAGTTTATCTGCATCCTTCCGTAGTGCTCCTCGTCCTGCTAAGCCTTTGAAAGT
TGTAATTGCTGGTGCTGGATTGGCTGGATTGTCAACTGCAAAGTACCTGGCTGATGCAGGCCACAAACCTC
TGTTGCTTGAAGCAAGAGATGTTCTTGGTGGAAAGATAGCTGCATGGAAGGATGAAGATGGGGACTGGTAT
GAGACTGGTTTACATATTTTCTTCGGTGCTTATCCGAATGTGCAGAATTTATTTGGAGAACTTGGGATCAA
TGATCGGTTGCAGTGGAAGGAACACTCCATGATTTTTGCTATGCCAAGTAAACCTGGAGAATTTAGTAGAT
TTGACTTCCCAGATGTCCTACCAGCACCCTTAAATGGTATTTGGGCTATTTTGCGGAACAACGAGATGCTG
ACATGGCCAGAGAAAATAAAGTTTGCTATTGGACTTTTGCCAGCCATGGTCGGCGGTCAGGCTTATGTTGA
GGCCCAAGATGGTTTATCAGTCAAAGAATGGATGGAAAAGCAGGGAGTACCTGAGCGCGTGACCGACGAGG
TGTTTATTGCCATGTCAAAGGCGCTAAACTTTATAAACCCTGATGAACTGTCAATGCAATGCATTTTGATA
GCTTTGAACCGGTTTCTTCAGGAAAAACATGGTTCCAAGATGGCATTCTTGGATGGTAATCCTCCGGAAAG
GCTTTGTATGCCAGTAGTGGATCATATTCGATCACTAGGTGGGGAAGTGCAACTTAATTCTAGGATAAAGA
AAATTGAGCTCAATGACGATGGCACGGTTAAGAGTTTCTTACTCACTAATGGAAGCACTGTCGAAGGAGAC
GCTTATGTGTTTGCCGCTCCAGTCGATATCCTGAAGCTCCTTTTACCAGATCCCTGGAAAGAAATACCGTA
CTTCAAGAAATTGGATAAATTAGTTGGAGTACCAGTTATTAATGTTCATATATGGTTTGATCGAAAACTGA
AGAACACATATGATCACCTACTCTTTAGCAGAAGTAACCTTCTGAGCGTGTATGCCGACATGTCCTTAACT
TGTAAGGAATATTACGATCCTAACCGGTCAATGCTGGAGCTAGTATTTGCACCAGCAGAGGAATGGATATC
ACGGACTGATTCTGACATCATAGATGCAACAATGAAAGAACTTGAGAAACTCTTCCCTGATGAAATCTCAG
CTGACCAAAGCAAAGCTAAAATTCTGAAGTACCATGTCGTTAAGACTCCAAGATCTGTGTACAAGACCATC
CCAAACTGTGAACCATGTCGTCCTCTACAAAGATCACCTATTGAAGGATTCTACTTAGCTGGAGATTACAC
AAAACAGAAGTACTTAGCTTCCATGGAAGGCGCTGTCCTCTCTGGCAAATTCTGCTCTCAGTCTATTGTTC
AGGATTACGAGCTACTGGCTGCGTCTGGACCAAGAAAGTTGTCGGAGGCAACAGTATCATCATCATGA
end The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein. Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein. Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto. All references cited herein are hereby expressly incorporated by reference.

What is claimed is:

1. A method of identifying a tobacco that induces a double-strand DNA break comprising:

(a) providing a tobacco;

(b) obtaining whole smoke from said tobacco;

(c) contacting a cell with said whole smoke; and (d) identifying the presence of a double strand DNA break in said cell after contact with said whole smoke.

2. The method of claim 1, wherein said tobacco comprises a genetic modification.

3. The method of claim 2, wherein said genetic modification reduces the amount of alkaloid in said tobacco to 500 ppm or less.

4. The method of claim 3, wherein said genetic modification reduces the expression of a gene encoding a quinolate phosphoribosyl transferase, a putrescene methyl transferase, or an A622 protein.

5. The method of claim 1, wherein said tobacco comprises a chemical modification.

6. The method of claim 5, wherein said chemical modification comprises palladium.

7. The method of claim 5, wherein said chemical modification comprises an auxin, auxin analog, or jasmonate antagonist.

8. The method of claim 1, wherein said tobacco is reconstituted tobacco.

9. The method of claim 1, wherein said tobacco is extracted tobacco.

10. The method of claim 1, wherein said tobacco is processed to remove the presence of a microbe.

11. The method of claim 1, wherein the presence of a phosphorylation of histone H2AX is identified.

12. The method of claim 1, wherein the presence of a double strand DNA break is determined by a method selected from the group consisting of; Comet assay; TUNEL assay; sister chromatid exchange assay; and detection of a chromosomal translocation.

13. The method of claim 1, wherein said tobacco is provided in a cigarette and said whole smoke is obtained from said cigarette.

14. The method of claim 13, wherein said whole smoke is obtained from said cigarette after passing through a filter attached to said cigarette.

15. The method of claim 14, wherein said filter comprises an antioxidant or a radical scavenger.

16. The method of claim 1, wherein a plurality of cells are contacted with said whole smoke and the presence of a double strand break in said plurality of cells is identified by detecting phosphorylation of histone H2AX.

17. The method of claim 16, wherein said plurality of cells are at least, greater than, or equal to a 50%, 60%, 70%, 75%, 80%, 85%, 90%, 95%, or a 100% population of cells in $G_0$, $G_1$, S, $G_2$, or M phase.

18. The method of claim 1, wherein said cell is obtained from a human.

19. The method of claim 18, wherein said cell is of the oral mucosa of said human.

20. The method of claim 19, wherein said cell is a cheek cell.

21. The method of claim 19, wherein said cell is obtained from a human after said human consumes a cigarette.

22. The method of claim 18, wherein said cell is of the pulmonary system of said human.

23. The method of claim 22, wherein said cell is a lung or bronchial cell.

24. The method of claim 22, wherein said cell is obtained from a human after said human consumes a cigarette.

25. The method of claim 1, wherein said cell is a A549 cell, a NHBE cell, or a cell obtained from a human primary culture.

26. The method of claim 1, further comprising the step of identifying said tobacco to be provided as a tobacco for an analysis of the potential to induce a double strand DNA break.

27. The method of claim 1, further comprising measuring the amount of double strand DNA breaks induced after exposure of said cell to said whole smoke.

28. The method of claim 27, wherein double strand DNA breaks are measured by detection of phosphorylated histone H2AX.

29. The method of claim 28, wherein said detection is performed by immunofluorescence or immuno-chromogenic methodology.

30. The method of claim 29, wherein said detection is quantitatively estimated using: flow cytometry, laser scanning cytometry, fluorescence image analysis, chromogenic product imaging, fluorescence microscopy or transmission microscopy.

31. A method of identifying a tobacco that induces an inhibition of apoptosis comprising:

(a) providing a tobacco;

(b) obtaining smoke or a smoke condensate from said tobacco;

(c) contacting a cell with said smoke or smoke condensate; and (d) identifying an inhibition of apoptosis in said cell after contact with said smoke or smoke condensate.

32. The method of claim 31, wherein said tobacco comprises a genetic modification.

33. The method of claim 32, wherein said genetic modification reduces the amount of alkaloid in said tobacco to 500 ppm or less.

34. The method of claim 32, wherein said genetic modification reduces the expression of a gene encoding a quinolate phosphoribosyl transferase, a putrescene methyl transferase, or an A622 protein.

35. The method of claim 31, wherein said tobacco comprises a chemical modification.

36. The method of claim 35, wherein said chemical modification comprises palladium.

37. The method of claim 35, wherein said chemical modification comprises an auxin, auxin analog, or jasmonate antagonist.

38. The method of claim 31, wherein said tobacco is reconstituted tobacco.

39. The method of claim 31, wherein said tobacco is extracted tobacco.

40. The method of claim 31, wherein said tobacco is processed to remove the presence of a microbe.

41. The method of claim 31, wherein whole smoke is obtained from said tobacco, said whole smoke is contacted with said cell, and said inhibition of apoptosis in said cell is measured after contact with said whole smoke.

42. The method of claim 41, wherein said tobacco is provided in a cigarette and said whole smoke is obtained from said cigarette.

43. The method of claim 41, wherein said whole smoke is obtained from said cigarette after passing through a filter attached to said cigarette.

44. The method of claim 43, wherein said filter comprises an antioxidant or a radical scavenger.

45. The method of claim 31, wherein the presence of caspase activation is identified.

46. The method of claim 31, wherein apoptosis is determined by a method selected from the group consisting of detection of caspase activation; detection of cleavage of the protein poly(ADP-ribose) polymerase; detection of annexin V binding to the cell membrane; detection of chromatin condensation; detection of an increase sensitivity of chromatin in cells to acid or heat-induced denaturation; detection of fractional DNA content; and TUNEL assay.

47. The method of claim 31, wherein said tobacco is provided in a cigarette and said smoke or smoke condensate is obtained from said cigarette.

48. The method of claim 31, wherein said smoke or smoke condensate is obtained from said cigarette after passing though a filter attached to said cigarette.

49. The method of claim 48, wherein said filter comprises an antioxidant or a radical scavenger.

50. The method of claim 31, wherein a plurality of cells are contacted with whole smoke and the presence of an inhibition of apoptosis is identified.

51. The method of claim 50, wherein said plurality of cells are at least, greater than, or equal to a 50%, 60%, 70%, 75%, 80%, 85%, 90%, 95%, or a 100% population of cells in $G_0$, $G_1$, S, $G_2$, or M phase.

52. The method of claim 31, wherein said cell is obtained from a human.

53. The method of claim 52, wherein said cell is of the oral mucosa of said human.

54. The method of claim 53, wherein said cell is a cheek cell.

55. The method of claim 52, wherein said cell is of the pulmonary system of said human.

56. The method of claim 55, wherein said cell is a lung or bronchial cell.

57. The method of claim 52, wherein said cell is obtained from a human after said human consumes a cigarette.

58. The method of claim 31, wherein said cell is a A549 cell, a NHBE cell, or a cell obtained from a human primary culture.

59. The method of claim 31, further comprising identifying said tobacco to be provided as a tobacco for an analysis of the potential to inhibit or to induce apoptosis.

60. The method of claim 31, further comprising measuring the amount of inhibition of apoptosis after exposure of said cell to said smoke or smoke condensate.

61. A method of comparing cigarettes that induce double-strand DNA breaks comprising:

(a) providing a first cigarette;

(b) obtaining whole smoke from said first cigarette;

(c) contacting a first plurality of cells with said whole smoke from said first cigarette;

(d) determining the amount of double strand DNA breaks or a marker of double strand DNA breaks in said first plurality of cells after contact with said whole smoke from said first cigarette;

(e) providing a second cigarette;

(f) obtaining whole smoke from said second cigarette;

(g) contacting a second plurality of cells with said whole smoke obtained from said second cigarette;

(h) determining the amount of double strand DNA breaks or a marker of double strand DNA breaks in said second plurality of cells after contact with said whole smoke from said second cigarette; and (i) comparing the amount of double strand DNA breaks or a marker of double strand DNA breaks in said first plurality of cells after contact with said whole smoke from said first cigarette with the amount of double strand DNA breaks or a marker of double strand DNA breaks in said second plurality of cells after contact with said whole smoke from said second cigarette.

62. The method of claim 61, wherein said first cigarette or said second cigarette comprises an attached filter and said whole smoke from said first cigarette or said whole smoke from said second cigarette is passed through the attached filter.

63. The method of claim 62, wherein said wherein said cell is an A549 cell, a NHBE cell, or a cell obtained from a human primary culture.

64. The method of claim 61, wherein said cell is an A549 cell, a NHBE cell, or a cell obtained from a human primary culture.

65. A method of comparing cigarettes that induce an inhibition of apoptosis or prevent induction of apoptosis comprising:

(a) providing a first cigarette;

(b) obtaining whole smoke from said first cigarette;

(c) contacting a first plurality of cells with said whole smoke from said first cigarette;

(d) determining the amount of inhibition of apoptosis or the amount of induction of apoptosis in said first plurality of cells or the amount of a marker of the inhibition or the induction of apoptosis in said first plurality of cells after contact with said whole smoke from said first cigarette;

(e) providing a second cigarette;

(f) obtaining whole smoke from said second cigarette;

(g) contacting a second plurality of cells with said whole smoke obtained from said second cigarette;

(h) determining the amount of inhibition of apoptosis or the amount of induction of apoptosis in said second plurality of cells or the amount of a marker of the inhibition or the induction of apoptosis in said second plurality of cells after contact with said whole smoke from said second cigarette; and (i) comparing the amount determined in step (d) with the amount determined in step (h) to identify whether the first cigarette induces less of an inhibition of apoptosis or prevents less of an induction of apoptosis than the second cigarette.

66. The method of claim 65, wherein said first cigarette or said second cigarette comprises an attached filter and said whole smoke from said first cigarette or said whole smoke from said second cigarette is passed through the attached filter.

67. The method of claim 66, wherein said wherein said cell is an A549 cell, a NHBE cell, or a cell obtained from a human primary culture.

68. The method of claim 65, wherein said cell is an A549 cell, a NHBE cell, or a cell obtained from a human primary culture.

69. A method of comparing cigarettes that induce double-strand DNA breaks comprising:

(a) providing a first cigarette;

(b) obtaining whole smoke from said first cigarette;

(c) contacting a first plurality of cells with said whole smoke from said first cigarette;

(d) performing an assay that detects double strand DNA breaks in said first plurality of cells after contact with said whole smoke from said first cigarette;

(e) providing a second cigarette;

(f) obtaining whole smoke from said second cigarette;

(g) contacting a second plurality of cells with said whole smoke obtained from said second cigarette;

(h) performing an assay that detects double strand DNA breaks in said second plurality of cells after contact with said whole smoke from said second cigarette; and (i) comparing the results of the assay performed in (d) with the results of the assay performed in (h) to identify whether the first cigarette induces less DNA damage than the second cigarette.

70. The method of claim 69, wherein said first cigarette or said second cigarette comprises an attached filter and said whole smoke from said first cigarette or said whole smoke from said second cigarette is passed through the attached filter.

71. The method of claim 70, wherein said cell is an A549 cell, a NHBE cell, or a cell obtained from a human primary culture.

72. The method of claim 69, wherein said assay that detects double strand DNA breaks is an assay that detects phosphorylation of histone H2AX.

73. The method of claim 69, wherein said assay that detects double strand DNA breaks is a Comet assay.

74. The method of claim 69, wherein said cell is an A549 cell, a NHBE cell, or a cell obtained from a human primary culture.

* * * * *

UNITED STATES PATENT AND TRADEMARK OFFICE

CERTIFICATE OF CORRECTION

PATENT NO. : 7,662,565 B2
APPLICATION NO. : 11/596088
DATED : February 16, 2010
INVENTOR(S) : Albino et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 150 days.

Signed and Sealed this

Twenty-eighth Day of December, 2010

David J. Kappos
*Director of the United States Patent and Trademark Office*